(12) United States Patent
Kühn

(10) Patent No.: US 9,410,134 B2
(45) Date of Patent: Aug. 9, 2016

(54) PROTEIN HAVING NUCLEASE ACTIVITY, FUSION PROTEINS AND USES THEREOF

(75) Inventor: Ralf Kühn, Berlin (DE)

(73) Assignee: Helmholtz Zentrum München—Deutsches Forschungszentrum für Gesundheit und Umwelt, Neuherberg (DE)

(*) Notice: Subject to any disclaimer, the term of this patent is extended or adjusted under 35 U.S.C. 154(b) by 0 days.

(21) Appl. No.: 14/124,117

(22) PCT Filed: Jun. 6, 2012

(86) PCT No.: PCT/EP2012/060711
§ 371 (c)(1),
(2), (4) Date: Mar. 18, 2014

(87) PCT Pub. No.: WO2012/168304
PCT Pub. Date: Dec. 13, 2012

(65) Prior Publication Data
US 2014/0298505 A1    Oct. 2, 2014

(30) Foreign Application Priority Data
Jun. 7, 2011    (EP) .................................... 11004635

(51) Int. Cl.
| C07H 21/04 | (2006.01) |
| C12N 9/16 | (2006.01) |
| A01K 67/027 | (2006.01) |
| C12N 15/62 | (2006.01) |
| C12N 15/85 | (2006.01) |
| C12N 15/90 | (2006.01) |
| C12N 9/22 | (2006.01) |

(52) U.S. Cl.
CPC .............. *C12N 9/16* (2013.01); *A01K 67/0275* (2013.01); *C12N 9/22* (2013.01); *C12N 15/62* (2013.01); *C12N 15/8509* (2013.01); *C12N 15/907* (2013.01); *C12Y 301/21004* (2013.01); *A01K 2207/05* (2013.01); *A01K 2217/075* (2013.01); *A01K 2227/105* (2013.01); *A01K 2267/03* (2013.01); *C07K 2319/80* (2013.01); *C12N 2999/007* (2013.01)

(58) Field of Classification Search
None
See application file for complete search history.

(56) References Cited

PUBLICATIONS

Brown et al. Mole Microbiol 1994;14:411-26.*
Ward et al. Direct submission to EMBL/GeneBank/DDBJ databases Feb. 2009, sequence search result.*
Database UniProt [Online], May 26, 2009, retrieved from accession No. UniProt:C1IBI5, 1 page.
Li et al., "TAL nucleases (TALNs): hybrid proteins composed of TAL effectors and FokI DNA-cleavage domain," Neucleic Acids Research, vol. 39, No. 1, Jan. 2011, p. 1-14.
Mahfouz et al., "De novo-engineered transcription activator-like effector (TALE) hybrid nuclease with novel DNA binding specificity creates double-strand breaks," Proceedings of the National Academy of Sciences, vol. 108, No. 6, Feb. 8, 2011, pp. 2623-2628.
Christian et al., "Targeting DNA Double-Strand Breaks with TAL Effector Nucleases," Genetics, vol. 186, No. 2, Oct. 1, 2010, pp. 757-761.
Cermak et al., "Efficient design and assembly of custom TALEN and other TAL effector-based constructs for DNA targeting," Nucleic Acids Research, vol. 39, No. 12, Apr. 14, 2011, pp. 1-11.
Geurts et al., "Knockout Rats via Embryo Microinjection of Zinc-Finger Nucleases," Science, vol. 325, No. 5939, Jul. 24, 2009, p. 433.
Geurts et al., "Supporting Online Material for Knockout Rats via Embryo Microinjection of Zinc-Finger Nucleases," Science, vol. 325, No. 5939, Jul. 24, 2009, pp. 1-15.
Moehle et al. "Targeted gene addition into a specified location in the human genome using designed zinc finger nucleases," Proceedings of the National Academy of Sciences, vol. 104, No. 9, Feb. 1, 2007, pp. 3055-3060.
International Search Report and Written Opinion of PCT/EP2012/060711 mailed Sep. 9, 2012.

* cited by examiner

*Primary Examiner* — Janice Li
(74) *Attorney, Agent, or Firm* — Briggs and Morgan, P.A.; Audrey J. Babcock

(57) ABSTRACT

The present invention relates to a nucleic acid molecule encoding (I) a polypeptide having the activity of an endonuclease, which is (a) a nucleic acid molecule encoding a polypeptide comprising or consisting of the amino acid sequence of SEQ ID NO: 1; (b) a nucleic acid molecule comprising or consisting of the nucleotide sequence of SEQ ID NO: 2; (c) a nucleic acid molecule encoding an endonuclease, the amino acid sequence of which is at least 70% identical to the amino acid sequence of SEQ ID NO: 1; (d) a nucleic acid molecule comprising or consisting of a nucleotide sequence which is at least 50% identical to the nucleotide sequence of SEQ ID NO: 2; (e) a nucleic acid molecule which is degenerate with respect to the nucleic acid molecule of (d); or (f) a nucleic acid molecule corresponding to the nucleic acid molecule of any one of (a) to (e) wherein T is replaced by U; (II) a fragment of the polypeptide of (I) having the activity of an endonuclease. Also, the present invention relates to a vector comprising the nucleic acid molecule and a protein encoded by said nucleic acid molecule. Further, the invention relates to a method of modifying the genome of a eukaryotic cell and a method of producing a non-human vertebrate or mammal.

12 Claims, 14 Drawing Sheets

Figure 13

Figure 1:
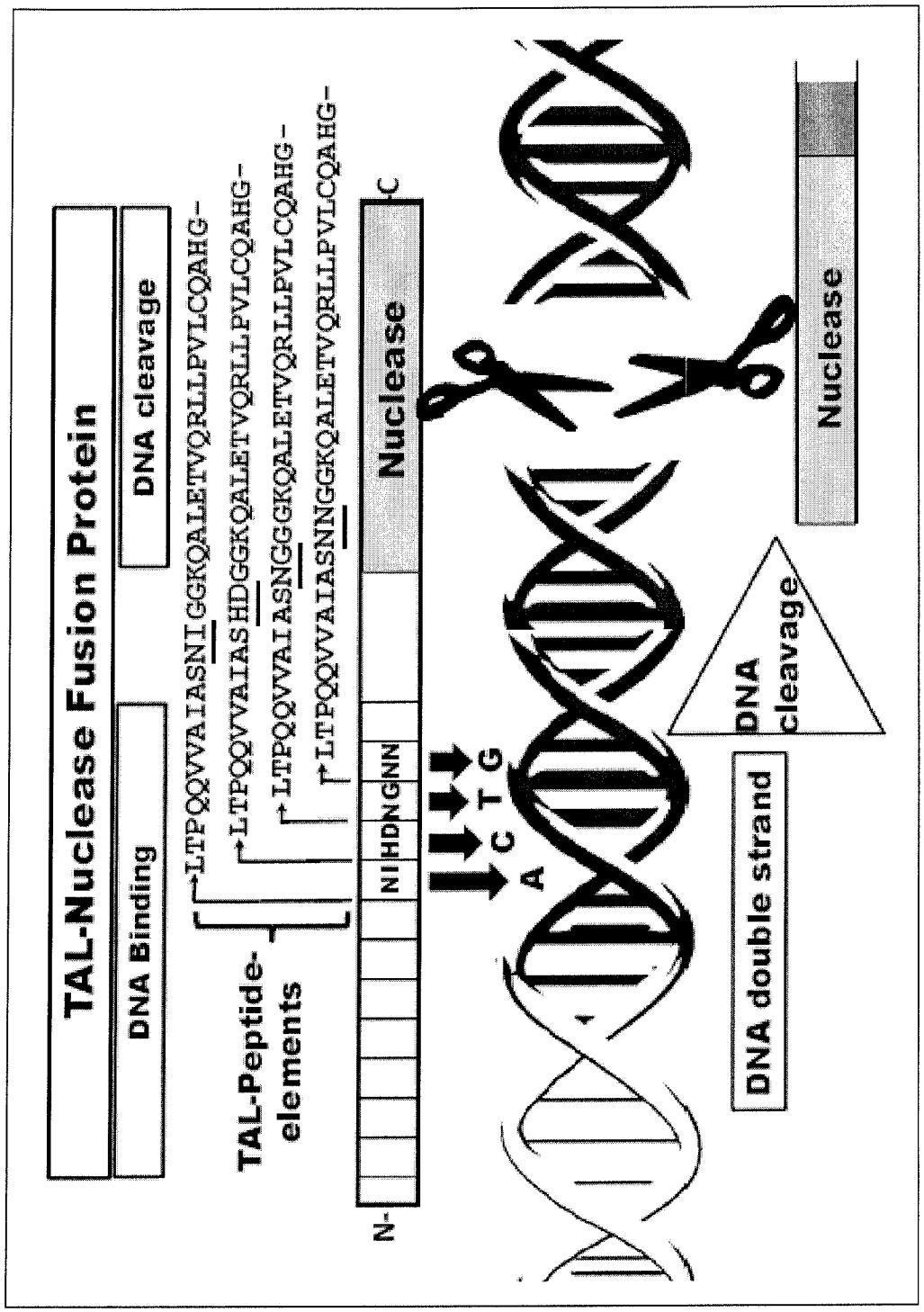

EGIKSNISLL KDELRGQISH ISHEYLSLID LAFDSKQNRL FEMKVLELLV
NEYGFKGRHL GGSRKPDGIV YSTTLEDNFG IIVDTKAYSE GYSLPISQAD
EMERYVRENS NRDEEVNPNK WWENFSEEVK KYYFVFISGS FKGKFEEQLR
RLSMTTGVNG SAVNVVNLLL GAEKIRSGEM TIEELERAMF NNSEFILKY

SEQUENCE LISTING

```
<160> NUMBER OF SEQ ID NOS: 67

<210> SEQ ID NO 1
<211> LENGTH: 199
<212> TYPE: PRT
<213> ORGANISM: Clostridium spec. 7_2_43 FAA

<400> SEQUENCE: 1

Glu Gly Ile Lys Ser Asn Ile Ser Leu Leu Lys Asp Glu Leu Arg Gly
1               5                   10                  15

Gln Ile Ser His Ile Ser His Glu Tyr Leu Ser Leu Ile Asp Leu Ala
            20                  25                  30

Phe Asp Ser Lys Gln Asn Arg Leu Phe Glu Met Lys Val Leu Glu Leu
        35                  40                  45

Leu Val Asn Glu Tyr Gly Phe Lys Gly Arg His Leu Gly Gly Ser Arg
    50                  55                  60

Lys Pro Asp Gly Ile Val Tyr Ser Thr Thr Leu Glu Asp Asn Phe Gly
65                  70                  75                  80

Ile Ile Val Asp Thr Lys Ala Tyr Ser Glu Gly Tyr Ser Leu Pro Ile
                85                  90                  95

Ser Gln Ala Asp Glu Met Glu Arg Tyr Val Arg Glu Asn Ser Asn Arg
            100                 105                 110

Asp Glu Glu Val Asn Pro Asn Lys Trp Trp Glu Asn Phe Ser Glu Glu
        115                 120                 125

Val Lys Lys Tyr Tyr Phe Val Phe Ile Ser Gly Ser Phe Lys Gly Lys
    130                 135                 140

Phe Glu Glu Gln Leu Arg Arg Leu Ser Met Thr Thr Gly Val Asn Gly
145                 150                 155                 160

Ser Ala Val Asn Val Val Asn Leu Leu Leu Gly Ala Glu Lys Ile Arg
                165                 170                 175

Ser Gly Glu Met Thr Ile Glu Glu Leu Glu Arg Ala Met Phe Asn Asn
            180                 185                 190

Ser Glu Phe Ile Leu Lys Tyr
            195

<210> SEQ ID NO 2
<211> LENGTH: 597
<212> TYPE: DNA
```

<213> ORGANISM: Clostridium spec. 7_2_43 FAA

<400> SEQUENCE: 2

```
gaaggcatca aaagcaacat ctccctcctg aaagacgaac tccggggca gattagccac        60
attagtcacg aatacctctc cctcatcgac ctggctttcg atagcaagca gaacaggctc       120
tttgagatga aagtgctgga actgctcgtc aatgagtacg ggttcaaggg tcgacacctc       180
ggcggatcta ggaaaccaga cggcatcgtg tatagtacca cactggaaga caactttggg       240
atcattgtgg ataccaaggc atactctgag ggttatagtc tgcccatttc acaggccgac       300
gagatggaac ggtacgtgcg cgagaactca aatagagatg aggaagtcaa ccctaacaag       360
tggtgggaga acttctctga ggaagtgaag aaatactact tcgtctttat cagcgggtcc       420
ttcaaggta aatttgagga acagctcagg agactgagca tgactaccgg cgtgaatggc       480
agcgccgtca acgtggtcaa tctgctcctg ggcgctgaaa agattcggag cggagagatg       540
accatcgaag agctggagag ggcaatgttt aataatagcg agtttatcct gaaatac         597
```

<210> SEQ ID NO 3
<211> LENGTH: 5866
<212> TYPE: DNA
<213> ORGANISM: Artificial sequence
<220> FEATURE:
<223> OTHER INFORMATION: pCAG-TAL-nuclease

<400> SEQUENCE: 3

```
ggcgcgccgg attcgacatt gattattgac tagttattaa tagtaatcaa ttacggggtc        60
attagttcat agcccatata tggagttccg cgttacataa cttacggtaa atggcccgcc       120
tggctgaccg cccaacgacc cccgcccatt gacgtcaata atgacgtatg ttcccatagt       180
aacgccaata gggactttcc attgacgtca atgggtggag tatttacggt aaactgccca       240
cttggcagta catcaagtgt atcatatgcc aagtacgccc cctattgacg tcaatgacgg       300
taaatggccc gcctggcatt atgcccagta catgacctta tgggactttc ctacttggca       360
gtacatctac gtattagtca tcgctattac catggtcgag gtgagcccca cgttctgctt       420
cactctcccc atctccccc cctccccacc cccaattttg tatttattta ttttttaatt       480
attttgtgca gcgatggggg cggggggggg ggggggcgc gcgccaggcg ggcggggcg       540
gggcgagggg cggggcgggg cgaggcggag aggtgcggcg gcagccaatc agagcggcgc       600
gctccgaaag tttcctttta tggcgaggcg gcggcggcgg cggccctata aaaagcgaag       660
cgcgcggcgg gcgggagtcg ctgcgcgctg ccttcgcccc gtgccccgct ccgccgccgc       720
ctcgcgccgc ccgccccggc tctgactgac cgcgttactc ccacaggtga gcgggcggga       780
cggcccttct cctccgggct gtaattagcg cttggtttaa tgacggcttg tttcttttct       840
gtggctgcgt gaaagccttg aggggctccg ggagggccct ttgtgcgggg gggagcggct       900
cggggggtgc gtgcgtgtgt gtgtgcgtgg ggagcgccgc gtgcggctcc gcgctgcccg       960
gcggctgtga gcgctgcggg cgcggcgcgg gctttgtgc gctccgcagt gtgcgcgagg      1020
ggagcgcggc cggggcggt gccccgcggt gcgggggggg ctgcgagggg aacaaaggct      1080
gcgtgcgggg tgtgtgcgtg gggggtgag caggggtgt gggcgcgtcg gtcggctgc      1140
aaccccccct gcacccccct ccccgagttg ctgagcacgg cccggcttcg ggtgcgggc      1200
tccgtacggg gcgtggcgcg gggctcgccg tgccggcgg ggggtggcgg caggtgggg      1260
tgccgggcg ggcggggccg cctcgggccg ggagggctc gggggagggg cgcggcggcc      1320
cccggagcgc cggcggctgt cgaggcgcgg cgagccgcag ccattgcctt ttatggtaat      1380
```

```
cgtgcgagag ggcgcaggga cttcctttgt cccaaatctg tgcggagccg aaatctggga    1440
ggcgccgccg caccccctct agcgggcgcg gggcgaagcg gtgcggcgcc ggcaggaagg    1500
aaatgggcgg ggagggcctt cgtgcgtcgc cgcgccgccg tccccttctc cctctccagc    1560
ctcggggctg tccgcggggg gacggctgcc ttcgggggg acggggcagg gcggggttcg     1620
gcttctggcg tgtgaccggc ggctctagag cctctgctaa ccatgttcat gccttcttct    1680
ttttcctaca gatccttaat taataatacg actcactata ggggccgcca ccatgggacc    1740
taagaaaaag aggaaggtgg cggccgctga ctacaaggat gacgacgata accaggtgg    1800 cggaggtagt ggcggaggtg gggtacccgc cagtccagca gcccaggtgg atctgagaac    1860
cctcggctac agccagcagc agcaggagaa gatcaaacca aggtgcggt ccaccgtcgc     1920 tcagcaccat gaagcactgg tggggcacgg tttcacacac gcccatattg tggctctgtc    1980
tcagcatccc gctgcactcg ggactgtggc cgtcaaatat caggacatga tcgccgctct    2040
gcctgaggca acccacgaag ccattgtggg cgtcggaaag cagtggagcg gtgccagagc    2100
actcgaagca ctcctcaccg tcgccgggga actgcggggt ccaccactcc agtccggact    2160
ggacactgga cagctgctga agatcgctaa acgcggcgga gtgacagctg tggaagctgt    2220
gcacgcttgg aggaatgctc tgacaggagc cccactgaat cttatgagac gacgtctcac    2280
ggcctgaccc cacagcaggt cgtcgctatt gcttctaatg gcggagggcg gcctgctctg    2340
gagagcattg tggctcagct gtccaggccc gatcctgccc tggctagatc cgcactcact    2400
aacgatcatc tggtcgctct cgcttgcctc ggtggacggc ccgctctgga cgcagtcaaa    2460
aagggtctcc cccatgctcc cgcactgatc aagagaacca caggagaat tcctgaggga    2520 tccgatcgtt taaacgatca cgcgtaaatg attgcagatc cactagttct agaattccag    2580
ctgagcgccg gtcgctacca ttaccagttg gtctggtgtc aaaaataata ataaccgggc    2640
aggggggatc tgcatggatc tttgtgaagg aaccttactt ctgtggtgtg acataattgg    2700
acaaactacc tacagagatt taaagctcta aggtaaatat aaaattttta agtgtataat    2760
gtgttaaact actgattcta attgtttgtg tattttagat tccaacctat ggaactgatg    2820
aatgggagca gtggtggaat gccagatcca gacatgataa gatacattga tgagtttgga    2880
caaaccacaa ctagaatgca gtgaaaaaaa tgctttattt gtgaaatttg tgatgctatt    2940
gctttatttg taaccattat aagctgcaat aaacaagtta acaacaacaa ttgcattcat    3000
tttatgtttc aggttcaggg ggaggtgtgg gaggttttt aaagcaagta aaacctctac     3060
aaatgtggta tggctgatta tgatctgcgg ccgccactgg ccgtcgtttt acaacgtcgt    3120
gactgggaaa accctggcgt tacccaactt aatcgccttg cagcacatcc ccctttcgcc    3180
agctggcgta atagcgaaga ggcccgcacc gatcgccctt ccaacagtt gcgcagcctg    3240 aatggcgaat ggaacgcgcc ctgtagcggc gcattaagcg cggcgggtgt ggtggttacg    3300
cgcagcgtga ccgctacact tgccagcgcc ctagcgcccg ctcctttcgc tttcttccct    3360
tcctttctcg ccacgttcgc cggctttccc cgtcaagctc taaatcgggg gctcccttta    3420
gggttccgat ttagtgcttt acggcacctc gaccccaaaa aacttgatta gggtgatggt    3480
tcacgtagtg ggccatcgcc ctgatagacg gttttcgcc ctttgacgtt ggagtccacg     3540
ttctttaata gtggactctt gttccaaact ggaacaacac tcaaccctat ctcggtctat    3600
tcttttgatt tataagggat tttgccgatt tcggcctatt ggttaaaaaa tgagctgatt    3660
taacaaaaat ttaacgcgaa ttttaacaaa atattaacgc ttacaattta ggtggcactt    3720
```

-continued

```
ttcggggaaa tgtgcgcgga acccctattt gtttattttt ctaaatacat tcaaatatgt    3780
atccgctcat gagacaataa ccctgataaa tgcttcaata atattgaaaa aggaagagta    3840
tgagtattca acatttccgt gtcgcccttt ttccctttt tgcggcattt tgccttcctg    3900
tttttgctca cccagaaacg ctggtgaaag taaaagatgc tgaagatcag ttgggtgcac    3960
gagtgggtta catcgaactg gatctcaaca gcggtaagat ccttgagagt tttcgccccg    4020
aagaacgttt tccaatgatg agcactttta aagttctgct atgtggcgcg gtattatccc    4080
gtattgacgc cgggcaagag caactcggtc gccgcataca ctattctcag aatgacttgg    4140
ttgagtactc accagtcaca gaaaagcatc ttacggatgg catgacagta agagaattat    4200
gcagtgctgc cataaccatg agtgataaca ctgcggccaa cttacttctg acaacgatcg    4260
gaggaccgaa ggagctaacc gcttttttgc acaacatggg gatcatgta actcgccttg    4320
atcgttggga accggagctg aatgaagcca taccaaacga cgagcgtgac accacgatgc    4380
ctgtagcaat ggcaacaacg ttgcgcaaac tattaactgg cgaactactt actctagctt    4440
cccggcaaca attaatagac tggatggagg cggataaagt tgcaggacca cttctgcgct    4500
cggcccttcc ggctggctgg tttattgctg ataaatctgg agccggtgag cgtgggtctc    4560
gcggtatcat tgcagcactg gggccagatg gtaagccctc ccgtatcgta gttatctaca    4620
cgacggggag tcaggcaact atggatgaac gaaatagaca gatcgctgag ataggtgcct    4680
cactgattaa gcattggtaa ctgtcagacc aagtttactc atatatactt tagattgatt    4740
taaaacttca ttttaatt aaaaggatct aggtgaagat cctttttgat aatctcatga    4800
ccaaaatccc ttaacgtgag ttttcgttcc actgagcgtc agaccccgta gaaaagatca    4860
aaggatcttc ttgagatcct ttttttctgc gcgtaatctg ctgcttgcaa acaaaaaaac    4920
caccgctacc agcggtggtt tgtttgccgg atcaagagct accaactctt tttccgaagg    4980
taactggctt cagcagagcg cagataccaa atactgtcct tctagtgtag ccgtagttag    5040
gccaccactt caagaactct gtagcaccgc ctacatacct cgctctgcta atcctgttac    5100
cagtggctgc tgccagtggc gataagtcgt gtcttaccgg gttggactca agacgatagt    5160
taccggataa ggcgcagcgg tcgggctgaa cggggggttc gtgcacacag cccagcttgg    5220
agcgaacgac ctacaccgaa ctgagatacc tacagcgtga gctatgagaa agcgccacgc    5280
ttcccgaagg gagaaaggcg gacaggtatc cggtaagcgg cagggtcgga acaggagagc    5340
gcacgaggga gcttccaggg ggaaacgcct ggtatcttta tagtcctgtc gggtttcgcc    5400
acctctgact tgagcgtcga ttttgtgat gctcgtcagg gggcggagc ctatggaaaa    5460
acgccagcaa cgcggccttt ttacggttcc tggcctttg ctggcctttt gctcacatgt    5520
tctttcctgc gttatcccct gattctgtgg ataaccgtat taccgccttt gagtgagctg    5580
ataccgctcg ccgcagccga acgaccgagc gcagcgagtc agtgagcgag gaagcggaag    5640
agcgcccaat acgcaaaccg cctctccccg cgcgttggcc gattcattaa tgcagctggc    5700
acgacaggtt cccgactgg aaagcgggca gtgagcgcaa cgcaattaat gtgagttagc    5760
tcactcatta ggcaccccag gctttacact ttatgcttcc ggctcgtatg ttgtgtggaa    5820
ttgtgagcgg ataacaattt cacacaggaa acagctatga ccatga           5866
```

<210> SEQ ID NO 4
<211> LENGTH: 176
<212> TYPE: PRT
<213> ORGANISM: Artificial sequence
<220> FEATURE:
<223> OTHER INFORMATION: N-terminal peptide

<400> SEQUENCE: 4

```
Met Gly Pro Lys Lys Arg Lys Val Ala Ala Asp Tyr Lys Asp
1               5                   10                  15

Asp Asp Asp Lys Pro Gly Gly Gly Ser Gly Gly Gly Gly Val Pro
                20                  25                  30

Ala Ser Pro Ala Ala Gln Val Asp Leu Arg Thr Leu Gly Tyr Ser Gln
            35                  40                  45

Gln Gln Gln Glu Lys Ile Lys Pro Lys Val Arg Ser Thr Val Ala Gln
    50                  55                  60

His His Glu Ala Leu Val Gly His Gly Phe Thr His Ala His Ile Val
65                  70                  75                  80

Ala Leu Ser Gln His Pro Ala Ala Leu Gly Thr Val Ala Val Lys Tyr
                85                  90                  95

Gln Asp Met Ile Ala Ala Leu Pro Glu Ala Thr His Glu Ala Ile Val
            100                 105                 110

Gly Val Gly Lys Gln Trp Ser Gly Ala Arg Ala Leu Glu Ala Leu Leu
        115                 120                 125

Thr Val Ala Gly Glu Leu Arg Gly Pro Pro Leu Gln Ser Gly Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175
```

<210> SEQ ID NO 5
<211> LENGTH: 78
<212> TYPE: PRT
<213> ORGANISM: Artificial sequence
<220> FEATURE:
<223> OTHER INFORMATION: C-terminal peptide

<400> SEQUENCE: 5

```
Leu Thr Pro Gln Gln Val Val Ala Ile Ala Ser Asn Gly Gly Gly Arg
1               5                   10                  15

Pro Ala Leu Glu Ser Ile Val Ala Gln Leu Ser Arg Pro Asp Pro Ala
                20                  25                  30

Leu Ala Arg Ser Ala Leu Thr Asn Asp His Leu Val Ala Leu Ala Cys
            35                  40                  45

Leu Gly Gly Arg Pro Ala Leu Asp Ala Val Lys Lys Gly Leu Pro His
        50                  55                  60

Ala Pro Ala Leu Ile Lys Arg Thr Asn Arg Arg Ile Pro Glu
65                  70                  75
```

<210> SEQ ID NO 6
<211> LENGTH: 408
<212> TYPE: PRT
<213> ORGANISM: Artificial sequence
<220> FEATURE:
<223> OTHER INFORMATION: ArtTal1

<400> SEQUENCE: 6

```
Leu Thr Pro Glu Gln Val Val Ala Ile Ala Ser Asn Ile Gly Gly Lys
1               5                   10                  15

Gln Ala Leu Glu Thr Val Gln Arg Leu Leu Pro Val Leu Cys Gln Ala
                20                  25                  30

His Gly Leu Thr Pro Gln Gln Val Val Ala Ile Ala Ser Asn Gly Gly
            35                  40                  45
```

Gly Lys Gln Ala Leu Glu Thr Val Gln Arg Leu Leu Pro Val Leu Cys
50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
130                 135                 140

Ile Ala Ser Asn Gly Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Asn Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Asn Gly Gly Lys Gln Ala Leu Glu
210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285

Gln Ala Leu Glu Thr Val Gln Arg Leu Leu Pro Val Leu Cys Gln Ala
290                 295                 300

His Gly Leu Thr Pro Gln Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Asn Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
370                 375                 380

Ser Asn Gly Gly Gly Lys Gln Ala Leu Glu Thr Val Gln Arg Leu Leu
385                 390                 395                 400

Pro Val Leu Cys Gln Ala His Gly
                405

<210> SEQ ID NO 7
<211> LENGTH: 7067
<212> TYPE: DNA
<213> ORGANISM: Artificial sequence
<220> FEATURE:
<223> OTHER INFORMATION: pCAG-ArtTal1-nuclease

<400> SEQUENCE: 7

-continued

```
gacattgatt attgactagt tattaatagt aatcaattac ggggtcatta gttcatagcc      60
catatatgga gttccgcgtt acataactta cggtaaatgg cccgcctggc tgaccgccca     120
acgaccccg cccattgacg tcaataatga cgtatgttcc catagtaacg ccaataggga     180
ctttccattg acgtcaatgg gtggagtatt tacggtaaac tgcccacttg gcagtacatc     240
aagtgtatca tatgccaagt acgcccccta ttgacgtcaa tgacggtaaa tggcccgcct     300
ggcattatgc ccagtacatg accttatggg actttcctac ttggcagtac atctacgtat     360
tagtcatcgc tattaccatg gtcgaggtga gccccacgtt ctgcttcact ctccccatct     420
cccccccctc cccaccccca attttgtatt tatttatttt ttaattattt tgtgcagcga     480
tgggggcggg gggggggggg gggcgcgcgc caggcggggc ggggcggggc gaggggcggg     540
gcggggcgag gcgagaggt gcggcggcag ccaatcagag cggcgcgctc cgaaagtttc     600
ctttttatggc gaggcggcgg cggcggcggc cctataaaaa gcgaagcgcg cggcgggcgg     660
gagtcgctgc gcgctgcctt cgcccgtgc cccgctccgc cgccgcctcg cgccgcccgc     720
cccggctctg actgaccgcg ttactcccac aggtgagcgg gcgggacggc ccttctcctc     780
cgggctgtaa ttagcgcttg gtttaatgac ggcttgtttc ttttctgtgg ctgcgtgaaa     840
gccttgaggg gctccgggag ggcccctttgt gcgggggga cggctcggg gggtgcgtgc     900
gtgtgtgtgt gcgtggggag cgccgcgtgc ggctccgcgc tgcccggcgg ctgtgagcgc     960
tgcgggcgcg gcgcggggct ttgtgcgctc cgcagtgtgc gcgaggggag cgcggccggg    1020
ggcggtgccc cgcggtgcgg ggggggctgc gagggaaca aaggctgcgt gcggggtgtg    1080
tgcgtgggg ggtgagcagg gggtgtgggc gcgtcggtcg ggctgcaacc ccccctgcac    1140
ccccctcccc gagttgctga gcacggcccg gcttcgggtg cggggctccg tacggggcgt    1200
ggcgcggggc tcgccgtgcc gggcggggg tgcggcagg tgggggtgcc gggcggggcg    1260
gggccgcctc gggccgggga gggctcgggg gaggggcgcg gcggccccg gagcgccggc    1320
ggctgtcgag gcgcggcgag ccgcagccat tgccttttat ggtaatcgtg cgagagggcg    1380
cagggacttc ctttgtccca aatctgtgcg gagccgaaat ctgggaggcg ccgccgcacc    1440
ccctctagcg ggcgcgggc gaagcggtgc ggcgccggca ggaaggaaat gggcggggag    1500
ggccttcgtg cgtcgccgcg ccgccgtccc cttctccctc tccagcctcg ggctgtccg    1560
cggggggacg gctgccttcg gggggacgg ggcagggcgg ggttcggctt ctggcgtgtg    1620
accggcggct ctagagcctc tgctaaccat gttcatgcct tcttcttttt cctacagatc    1680
cttaattaat aatacgactc actatagggg ccgccaccat gggacctaag aaaaagagga    1740
aggtggcggc cgctgactac aaggatgacg acgataaacc aggtggcgga ggtagtggcg    1800
gaggtggggt acccgccagt ccagcagccc aggtggatct gagaaccctc ggctacagcc    1860
agcagcagca ggagaagatc aaaccaaagg tgcggtccac cgtcgctcag caccatgaag    1920
cactggtggg gcacggtttc acacacgccc atattgtggc tctgtctcag catcccgctg    1980
cactcgggac tgtggccgtc aaatatcagg acatgatcgc cgctctgcct gaggcaaccc    2040
acgaagccat tgtgggcgtc ggaaagcagt ggagcggtgc cagagcactc gaagcactcc    2100
tcaccgtcgc cggggaactg cggggtccac cactccagtc cggactggac actgacagc    2160
tgctgaagat cgctaaacgc ggcggagtga cagctgtgga agctgtgcac gcttggagga    2220
atgctctgac aggagcccca ctgaatctta ctccagaaca ggtcgtcgca atcgcaagta    2280
acatcggcgg aaaacaggcc ctcgaaaccg tccagagact cctccccgtg ctgtgccagg    2340
```

```
cccacggact gaccccacag caggtggtcg ccatcgctag caacggcgga gggaagcagg    2400
ctctggagac cgtgcagagg ctgctccccg tcctgtgcca ggcacatggg ctcacacctc    2460
agcaggtggt cgcaattgcc tccaatggtg gcggaaaaca ggccctggaa actgtgcaga    2520
gactgctccc cgtgctgtgc caggctcacg gtctcacacc ccagcaggtg gtcgctatcg    2580
catctcatga cgggggcaag caggcactgg agacagtgca gcggctgctc cctgtcctgt    2640
gccaggccca cggactcact cctcagcagg tcgtcgccat tgctagtaac ggcggaggga    2700
aacaggctct ggaaaccgtg cagcgcctgc tccccgtgct gtgccaagcc cacggcctga    2760
ccccccagca ggtggtcgca atcgcctcaa acaatggtgg caagcaggcc ctggagactg    2820
tgcagcgact gctcccagtg ctgtgccagg cccatggact cacaccacag caggtcgtcg    2880
ctattgcaag caacaatgga gggaaacagg cactggaaac agtccagagg ctgctccccg    2940
tgctgtgcca agcgcatgga ctcactcccc agcaggtcgt cgccatcgct tccaataacg    3000
gcggcaagca ggccctggag accgtccaga gactgctccc cgtgctgtgc caagctcacg    3060
gactcacacc tgagcaggtc gtggcaatcg cctctaacat tggagggaaa caggccctgg    3120
aaactgtaca gcggctgctc cccgtgctgt gccaagcaca cggactcact ccacagcagg    3180
tcgtggccat tgcaagtcat gacgaggca agcaggccct ggaaacagtg cagcgcctgc    3240
tccctgtgct gtgccaggct catggtctga ctcctcagca ggtggtggcc atcgcttcca    3300
acaatggagg gaagcaggcc ctggagaccg tacagagact gctccccgtg ctgtgccaag    3360
cgcacggtct gaccccctcag caggtcgtcg caatcgccag caatggcggg ggcaagcagg    3420
ctctcgaaac cgtccagcgg ctcctcccag tcctctgtca ggctcacggc ctgaccccac    3480
agcaggtcgt cgctattgct tctaatggcg gagggcggcc tgctctggag agcattgtgg    3540
ctcagctgtc caggcccgat cctgccctgg ctagatccgc actcactaac gatcatctgg    3600
tcgctctcgc ttgcctcggt ggacggcccg ctctggacgc agtcaaaaag ggtctccccc    3660
atgctcccgc actgatcaag agaaccaaca ggagaattcc tgagggatcc gatcgtttaa    3720
acgatcacgc gtaaatgatt gcagatccac tagttctaga attccagctg agcgccggtc    3780
gctaccatta ccagttggtc tggtgtcaaa aataataata accgggcagg gggatctgc    3840 atggatcttt gtgaaggaac cttacttctg tggtgtgaca taattggaca aactacctac    3900
agagatttaa agctctaagg taaatataaa atttttaagt gtataatgtg ttaaactact    3960
gattctaatt gtttgtgtat tttagattcc aacctatgga actgatgaat gggagcagtg    4020
gtggaatgcc agatccagac atgataagat acattgatga gtttggacaa accacaacta    4080
gaatgcagtg aaaaaaatgc tttatttgtg aaatttgtga tgctattgct ttatttgtaa    4140
ccattataag ctgcaataaa caagttaaca acaacaattg cattcatttt atgtttcagg    4200
ttcaggggga ggtgtgggag gttttttaaa gcaagtaaaa cctctacaaa tgtggtatgg    4260
ctgattatga tctgcggccg ccactggccg tcgttttaca acgtcgtgac tgggaaaacc    4320
ctggcgttac ccaacttaat cgccttgcag cacatccccc tttcgccagc tggcgtaata    4380
gcgaagaggc ccgcaccgat cgcccttccc aacagttgcg cagcctgaat ggcgaatgga    4440
acgcgccctg tagcggcgca ttaagcgcgg cgggtgtggt ggttacgcgc agcgtgaccg    4500
ctacacttgc cagcgcccta gcgcccgctc ctttcgcttt cttcccttcc tttctcgcca    4560
cgttcgccgg ctttccccgt caagctctaa atcgggggct ccctttaggg ttccgattta    4620
gtgctttacg gcacctcgac cccaaaaaac ttgattaggg tgatggttca cgtagtgggc    4680
catcgccctg atagacggtt tttcgccctt tgacgttgga gtccacgttc tttaatagtg    4740
```

```
gactcttgtt ccaaactgga acaacactca accctatctc ggtctattct tttgatttat    4800
aagggatttt gccgatttcg gcctattggt taaaaaatga gctgatttaa caaaaattta    4860
acgcgaattt taacaaaata ttaacgctta caatttaggt ggcacttttc ggggaaatgt    4920
gcgcggaacc cctatttgtt tattttcta aatacattca aatatgtatc cgctcatgag     4980
acaataaccc tgataaatgc ttcaataata ttgaaaaagg aagagtatga gtattcaaca    5040
tttccgtgtc gcccttattc cctttttgc ggcattttgc cttcctgttt ttgctcaccc     5100
agaaacgctg gtgaaagtaa aagatgctga agatcagttg ggtgcacgag tgggttacat    5160
cgaactggat ctcaacagcg gtaagatcct tgagagtttt cgccccgaag aacgttttcc    5220
aatgatgagc acttttaaag ttctgctatg tggcgcggta ttatcccgta ttgacgccgg    5280
gcaagagcaa ctcggtcgcc gcatacacta ttctcagaat gacttggttg agtactcacc    5340
agtcacagaa aagcatctta cggatggcat gacagtaaga gaattatgca gtgctgccat    5400
aaccatgagt gataacactg cggccaactt acttctgaca acgatcggag gaccgaagga    5460
gctaaccgct tttttgcaca acatggggga tcatgtaact cgccttgatc gttgggaacc    5520
ggagctgaat gaagccatac caaacgacga gcgtgacacc acgatgcctg tagcaatggc    5580
aacaacgttg cgcaaactat taactggcga actacttact ctagcttccc ggcaacaatt    5640
aatagactgg atggaggcgg ataaagttgc aggaccactt ctgcgctcgg cccttccggc    5700
tggctggttt attgctgata atctggagc cggtgagcgt gggtctcgcg gtatcattgc     5760
agcactgggg ccagatggta agccctcccg tatcgtagtt atctacacga cggggagtca    5820
ggcaactatg gatgaacgaa atagacagat cgctgagata ggtgcctcac tgattaagca    5880
ttggtaactg tcagaccaag tttactcata tatactttag attgatttaa aacttcattt    5940
ttaatttaaa aggatctagg tgaagatcct ttttgataat ctcatgacca aaatccctta    6000
acgtgagttt tcgttccact gagcgtcaga ccccgtagaa aagatcaaag gatcttcttg    6060
agatcctttt tttctgcgcg taatctgctg cttgcaaaca aaaaaaccac cgctaccagc    6120
ggtggtttgt ttgccggatc aagagctacc aactcttttt ccgaaggtaa ctggcttcag    6180
cagagcgcag ataccaaata ctgtccttct agtgtagccg tagttaggcc accacttcaa    6240
gaactctgta gcaccgccta catacctcgc tctgctaatc ctgttaccag tggctgctgc    6300
cagtggcgat aagtcgtgtc ttaccgggtt ggactcaaga cgatagttac cggataaggc    6360
gcagcggtcg ggctgaacgg ggggttcgtg cacacagccc agcttggagc gaacgaccta    6420
caccgaactg agatacctac agcgtgagct atgagaaagc gccacgcttc ccgaagggag    6480
aaaggcggac aggtatccgg taagcggcag ggtcggaaca ggagagcgca cgagggagct    6540
tccaggggga aacgcctggt atctttatag tcctgtcggg tttcgccacc tctgacttga    6600
gcgtcgattt ttgtgatgct cgtcaggggg gcggagccta tggaaaaacg ccagcaacgc    6660 ggcctttttta cggttcctgg ccttttgctg gccttttgct cacatgttct ttcctgcgtt    6720
atcccctgat tctgtggata accgtattac cgcctttgag tgagctgata ccgctcgccg    6780
cagccgaacg accgagcgca gcgagtcagt gagcgaggaa gcggaagagc gcccaatacg    6840
caaaccgcct ctccccgcgc gttggccgat tcattaatgc agctggcacg acaggtttcc    6900
cgactggaaa gcgggcagtg agcgcaacgc aattaatgtg agttagctca ctcattaggc    6960
accccaggct ttacacttta tgcttccggc tcgtatgttg tgtggaattg tgagcggata    7020
acaatttcac acaggaaaca gctatgacca tgaggcgcgc cggattc                 7067
```

<210> SEQ ID NO 8
<211> LENGTH: 476
<212> TYPE: PRT
<213> ORGANISM: Artificial sequence
<220> FEATURE:
<223> OTHER INFORMATION: TalRab2

<400> SEQUENCE: 8

```
Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Asn Gly Gly Lys Gln Ala Leu Glu Thr Val Gln Arg Leu Leu
        115                 120                 125

Pro Val Leu Cys Gln Ala His Gly Leu Thr Pro Gln Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser His Asp Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Gln Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Asn Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Gly Gly Gly Lys Gln Ala Leu Glu Thr Val Gln Arg Leu Leu Pro Val
        355                 360                 365
```

-continued

```
Leu Cys Gln Ala His Gly Leu Thr Pro Glu Gln Val Val Ala Ile Ala
370                 375                 380

Ser Asn Ile Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
                405                 410                 415

Ile Ala Ser Asn Asn Gly Gly Lys Gln Ala Leu Glu Thr Val Gln Arg
                420                 425                 430

Leu Leu Pro Val Leu Cys Gln Ala His Gly Leu Thr Pro Gln Gln Val
                435                 440                 445

Val Ala Ile Ala Ser Asn Gly Gly Gly Lys Gln Ala Leu Glu Thr Val
            450                 455                 460

Gln Arg Leu Leu Pro Val Leu Cys Gln Ala His Gly
465                 470                 475

<210> SEQ ID NO 9
<211> LENGTH: 7271
<212> TYPE: DNA
<213> ORGANISM: Artificial sequence
<220> FEATURE:
<223> OTHER INFORMATION: pCAG-TalRab2-nuclease

<400> SEQUENCE: 9
ggcgcgccgg attcgacatt gattattgac tagttattaa tagtaatcaa ttacggggtc      60
attagttcat agcccatata tggagttccg cgttacataa cttacggtaa atggcccgcc     120
tggctgaccg cccaacgacc cccgcccatt gacgtcaata atgacgtatg ttcccatagt     180
aacgccaata gggactttcc attgacgtca atgggtggag tatttacggt aaactgccca     240
cttggcagta catcaagtgt atcatatgcc aagtacgccc cctattgacg tcaatgacgg     300
taaatggccc gcctggcatt atgcccagta catgacctta tgggactttc ctacttggca     360
gtacatctac gtattagtca tcgctattac catggtcgag gtgagcccca cgttctgctt     420
cactctcccc atctcccccc cctccccacc cccaattttg tatttattta ttttttaatt     480
attttgtgca gcgatggggg cggggggggg gggggggcgc gcgccaggcg gggcggggcg     540
gggcgagggg cggggcgggg cgaggcggag aggtgcggcg gcagccaatc agagcggcgc     600
gctccgaaag tttccttttta tggcgaggcg cggcggcgg cggccctata aaaagcgaag     660
cgcgcggcgg gcgggagtcg ctgcgcgctg ccttcgcccc gtgccccgct ccgccgccgc     720
ctcgcgccgc ccgccccggc tctgactgac cgcgttactc ccacaggtga gcgggcggga     780
cggcccttct cctccgggct gtaattagcg cttggtttaa tgacggcttg tttcttttct     840
gtggctgcgt gaaagccttg agggctccg gagggccct ttgtgcgggg gggagcggct     900
cggggggtgc gtgcgtgtgt gtgtgcgtgg ggagcgccgc gtgcggctcc gcgctgcccg     960
gcggctgtga gcgctgcggg cgcggcgcgg ggctttgtgc gctccgcagt gtgcgcgagg    1020
ggagcgcggc cggggcggt gccccgcggt gcggggggg ctgcgagggg aacaaaggct    1080
gcgtgcgggg tgtgtgcgtg ggggggtgag caggggtgt gggcgcgtcg gtcgggctgc    1140
aaccccccct gcaccccccct ccccgagttg ctgagcacgg cccggcttcg ggtgcgggc    1200 tccgtacggg gcgtggcgcg gggctcgccg tgccggcgg ggggtggcgg caggtggggg    1260
tgccgggcgg ggcggggccg cctcgggccg ggaggggctc gggggagggg cgggcggcc    1320 cccggagcgc cggcggctgt cgaggcgcgg cgagccgcag ccattgcctt ttatggtaat    1380
cgtgcgagag ggcgcaggga cttccttttgt cccaaatctg tgcggagccg aaatctggga    1440
```

-continued

```
ggcgccgccg caccccctct agcgggcgcg gggcgaagcg gtgcggcgcc ggcaggaagg    1500
aaatgggcgg ggagggcctt cgtgcgtcgc cgcgccgccg tccccttctc cctctccagc    1560
ctcggggctg tccgcggggg gacggctgcc ttcgggggg acggggcagg gcggggttcg     1620
gcttctggcg tgtgaccggc ggctctagag cctctgctaa ccatgttcat gccttcttct    1680
ttttcctaca gatccttaat taataatacg actcactata ggggccgcca ccatgggacc    1740
taagaaaaag aggaaggtgg cggccgctga ctacaaggat gacgacgata aaccaggtgg    1800
cggaggtagt ggcggaggtg gggtacccgc cagtccagca gcccaggtgg atctgagaac    1860
cctcggctac agccagcagc agcaggagaa gatcaaacca aaggtgcggt ccaccgtcgc    1920
tcagcaccat gaagcactgg tggggcacgg tttcacacac gcccatattg tggctctgtc    1980
tcagcatccc gctgcactcg ggactgtggc cgtcaaatat caggacatga tcgccgctct    2040
gcctgaggca acccacgaag ccattgtggg cgtcggaaag cagtggagcg gtgccagagc    2100
actcgaagca ctcctcaccg tcgccgggga actgcggggt ccaccactcc agtccggact    2160
ggacactgga cagctgctga agatcgctaa acgcggcgga gtgacagctg tggaagctgt    2220
gcacgcttgg aggaatgctc tgacaggagc cccactgaat ctgacacccc agcaggtggt    2280
ggccattgct agcaacaatg ggggcaagca ggctctggag acagtgcagc gcctgctgcc    2340
tgtgctgtgc caggctcacg gactgactcc acagcaggtg gtggccatcg cttccaacaa    2400
tggagggaaa caggctctgg aaacagtgca gaggctgctg cccgtgctgt gccaggctca    2460
tggactgaca cctcagcagg tcgtcgccat tgcttctaac ggcggaggga agcaggctct    2520
ggagactgtg cagagactgc tgccagtgct gtgccaggcc catggactga cccctcagca    2580
ggtcgtggct atcgctagta acaatggcgg aaaacaggct ctggaaactg tgcagcggct    2640
gctccccgtg ctgtgccagg cccacggcct cactccacag caggtcgtcg ctatcgcctc    2700
taataacggg ggcaagcagg ctctggagac agtacagcgc ctgttacccg tgctgtgcca    2760
ggcacacggc ctcacacctc agcaggtcgt ggcaatcgct tcccatgacg agggaaaca    2820 ggctctggaa acggtccaga ggctgctccc cgtgctgtgc aagctcacg gcctcacccc    2880 tcagcaggtg tcgctattg cttctcatga tggcggaaag caggctctgg agaccgtgca    2940
gagactgctc cctgtgctgt gccaagccca cggcctgact ccacagcagg tcgtggccat    3000
cgctagtcat gacgggggca acaggctct ggaaacagta cagcggctgt acccgtgct    3060 gtgccaagcc catggcctca cacctcagca agtcgtcgct atcgctagca acaatggagg    3120
gaagcaggct ctggagacgg tgcagcgcct gctcccagtg ctgtgccaag ctcatggcct    3180 caccctcag caagtcgtcg caattgcttc caataacggc ggaaaacagg ctctggaaac    3240
cgtccagagc tgctgcccg tgctgtgcca agcacatggc ttaactccac agcaagtggt    3300
ggccattgct tctaatgggg gcggaaagca ggccctggag acagtccaga gactgttgcc    3360
cgtgctgtgc caagcgcatg gactgacacc tgaacaggtc gtcgctatcg ctagtaatat    3420
tgggggcaaa caggccctgg aaacagtgca gcggctgctt cccgtgctgt gccaggcgca    3480
tggactcaca ccccagcagg tcgtcgcaat cgcctctaat aacggaggga agcaggccct    3540
ggaaaccgtg cagagactgt acctgtgct gtgccaggca catggtctga caccacagca    3600
ggtggtcgca attgctagca atggcggagg gaagcaggcc ctggagactg tccagagact    3660 gctaccgtg ctgtgccaag cgcacggcct gaccccacag caggtcgtcg ctattgcttc    3720
taatggcgga gggcggcctg ctctggagag cattgtggct cagctgtcca ggcccgatcc    3780
tgccctggct agatccgcac tcactaacga tcatctggtc gctctcgctt gcctcggtgg    3840
```

```
acggcccgct ctggacgcag tcaaaaaggg tctcccccat gctcccgcac tgatcaagag    3900
aaccaacagg agaattcctg agggatccga tcgtttaaac gatcacgcgt aaatgattgc    3960
agatccacta gttctagaat tccagctgag cgccggtcgc taccattacc agttggtctg    4020
gtgtcaaaaa taataataac cgggcagggg ggatctgcat ggatctttgt gaaggaacct    4080
tacttctgtg gtgtgacata attggacaaa ctacctacag agatttaaag ctctaaggta    4140
aatataaaat ttttaagtgt ataatgtgtt aaactactga ttctaattgt ttgtgtattt    4200
tagattccaa cctatggaac tgatgaatgg gagcagtggt ggaatgccag atccagacat    4260
gataagatac attgatgagt ttggacaaac cacaactaga atgcagtgaa aaaaatgctt    4320
tatttgtgaa atttgtgatg ctattgcttt atttgtaacc attataagct gcaataaaca    4380
agttaacaac aacaattgca ttcattttat gtttcaggtt caggggagg tgtgggaggt    4440 ttttaaagc aagtaaaacc tctacaaatg tggtatggct gattatgatc tgcggccgcc    4500
actggccgtc gttttacaac gtcgtgactg ggaaaaccct ggcgttaccc aacttaatcg    4560
ccttgcagca catccccctt tcgccagctg gcgtaatagc gaagaggccc gcaccgatcg    4620
cccttcccaa cagttgcgca gcctgaatgg cgaatggaac gcgccctgta gcggcgcatt    4680
aagcgcggcg ggtgtggtgg ttacgcgcag cgtgaccgct acacttgcca gcgccctagc    4740
gcccgctcct ttcgctttct tcccttcctt tctcgccacg ttcgccggct ttccccgtca    4800
agctctaaat cggggggctcc ctttagggtt ccgatttagt gctttacggc acctcgaccc    4860
caaaaaactt gattagggtg atggttcacg tagtgggcca tcgccctgat agacggtttt    4920
tcgccctttg acgttggagt ccacgttctt taatagtgga ctcttgttcc aaactggaac    4980
aacactcaac cctatctcgg tctattcttt tgatttataa gggattttgc cgatttcggc    5040
ctattggtta aaaaatgagc tgatttaaca aaaatttaac gcgaatttta acaaaatatt    5100
aacgcttaca atttaggtgg cacttttcgg ggaaatgtgc gcggaacccc tatttgttta    5160 ttttttctaaa tacattcaaa tatgtatccg ctcatgagac aataaccctg ataaatgctt    5220
caataatatt gaaaaaggaa gagtatgagt attcaacatt tccgtgtcgc ccttattccc    5280
ttttttgcgg cattttgcct tcctgttttt gctcacccag aaacgctggt gaaagtaaaa    5340
gatgctgaag atcagttggg tgcacgagtg ggttacatcg aactggatct caacagcggt    5400
aagatccttg agagttttcg ccccgaagaa cgttttccaa tgatgagcac ttttaaagtt    5460
ctgctatgtg gcgcggtatt atcccgtatt gacgccgggc aagagcaact cggtcgccgc    5520
atacactatt ctcagaatga cttggttgag tactcaccag tcacagaaaa gcatcttacg    5580
gatggcatga cagtaagaga attatgcagt gctgccataa ccatgagtga taacactgcg    5640
gccaacttac ttctgacaac gatcggagga ccgaaggagc taaccgcttt tttgcacaac    5700 atggggatc atgtaactcg ccttgatcgt tgggaaccgg agctgaatga agccatacca    5760
aacgacgagc gtgacaccac gatgcctgta gcaatggcaa caacgttgcg caaactatta    5820
actggcgaac tacttactct agcttcccgg caacaattaa tagactggat ggaggcggat    5880
aaagttgcag gaccacttct gcgctcggcc cttccggctg gctggtttat tgctgataaa    5940
tctggagccg gtgagcgtgg gtctcgcggt atcattgcag cactggggcc agatggtaag    6000
ccctcccgta tcgtagttat ctacacgacg gggagtcagg caactatgga tgaacgaaat    6060
agacagatcg ctgagatagg tgcctcactg attaagcatt ggtaactgtc agaccaagtt    6120
tactcatata tactttagat tgatttaaaa cttcatttt aatttaaaag gatctaggtg    6180
```

-continued

```
aagatccttt ttgataatct catgaccaaa atcccttaac gtgagttttc gttccactga    6240
gcgtcagacc ccgtagaaaa gatcaaagga tcttcttgag atcctttttt tctgcgcgta    6300
atctgctgct tgcaaacaaa aaaaccaccg ctaccagcgg tggtttgttt gccggatcaa    6360
gagctaccaa ctctttttcc gaaggtaact ggcttcagca gagcgcagat accaaatact    6420
gtccttctag tgtagccgta gttaggccac cacttcaaga actctgtagc accgcctaca    6480
tacctcgctc tgctaatcct gttaccagtg gctgctgcca gtggcgataa gtcgtgtctt    6540
accgggttgg actcaagacg atagttaccg gataaggcgc agcggtcggg ctgaacgggg    6600
ggttcgtgca cacagcccag cttggagcga acgacctaca ccgaactgag atacctacag    6660
cgtgagctat gagaaagcgc cacgcttccc gaagggagaa aggcggacag gtatccggta    6720
agcggcaggg tcggaacagg agagcgcacg agggagcttc cagggggaaa cgcctggtat    6780
ctttatagtc ctgtcgggtt tcgccacctc tgacttgagc gtcgattttt gtgatgctcg    6840
tcagggggc ggagcctatg gaaaaacgcc agcaacgcgg cctttttacg gttcctggcc    6900
ttttgctggc cttttgctca catgttcttt cctgcgttat ccctgattc tgtggataac    6960
cgtattaccg cctttgagtg agctgatacc gctcgccgca gccgaacgac cgagcgcagc    7020
gagtcagtga gcgaggaagc ggaagagcgc ccaatacgca aaccgcctct ccccgcgcgt    7080
tggccgattc attaatgcag ctggcacgac aggtttcccg actggaaagc gggcagtgag    7140
cgcaacgcaa ttaatgtgag ttagctcact cattaggcac cccaggcttt acactttatg    7200
cttccggctc gtatgttgtg tggaattgtg agcggataac aatttcacac aggaaacagc    7260
tatgaccatg a                                                          7271
```

<210> SEQ ID NO 10
<211> LENGTH: 583
<212> TYPE: PRT
<213> ORGANISM: Flavobacterium okeanokoites

<400> SEQUENCE: 10

```
Met Phe Leu Ser Met Val Ser Lys Ile Arg Thr Phe Gly Trp Val Gln
 1               5                   10                  15

Asn Pro Gly Lys Phe Glu Asn Leu Lys Arg Val Val Gln Val Phe Asp
            20                  25                  30

Arg Asn Ser Lys Val His Asn Glu Val Lys Asn Ile Lys Ile Pro Thr
        35                  40                  45

Leu Val Lys Glu Ser Lys Ile Gln Lys Glu Leu Val Ala Ile Met Asn
    50                  55                  60

Gln His Asp Leu Ile Tyr Thr Tyr Lys Glu Leu Val Gly Thr Gly Thr
65                  70                  75                  80

Ser Ile Arg Ser Glu Ala Pro Cys Asp Ala Ile Ile Gln Ala Thr Ile
                85                  90                  95

Ala Asp Gln Gly Asn Lys Lys Gly Tyr Ile Asp Asn Trp Ser Ser Asp
            100                 105                 110

Gly Phe Leu Arg Trp Ala His Ala Leu Gly Phe Ile Glu Tyr Ile Asn
        115                 120                 125

Lys Ser Asp Ser Phe Val Ile Thr Asp Val Gly Leu Ala Tyr Ser Lys
    130                 135                 140

Ser Ala Asp Gly Ser Ala Ile Glu Lys Glu Ile Leu Ile Glu Ala Ile
145                 150                 155                 160

Ser Ser Tyr Pro Pro Ala Ile Arg Ile Leu Thr Leu Leu Glu Asp Gly
                165                 170                 175
```

```
Gln His Leu Thr Lys Phe Asp Leu Gly Lys Asn Leu Gly Phe Ser Gly
            180                 185                 190

Glu Ser Gly Phe Thr Ser Leu Pro Glu Gly Ile Leu Leu Asp Thr Leu
        195                 200                 205

Ala Asn Ala Met Pro Lys Asp Lys Gly Glu Ile Arg Asn Asn Trp Glu
    210                 215                 220

Gly Ser Ser Asp Lys Tyr Ala Arg Met Ile Gly Gly Trp Leu Asp Lys
225                 230                 235                 240

Leu Gly Leu Val Lys Gln Gly Lys Lys Glu Phe Ile Ile Pro Thr Leu
                245                 250                 255

Gly Lys Pro Asp Asn Lys Glu Phe Ile Ser His Ala Phe Lys Ile Thr
            260                 265                 270

Gly Glu Gly Leu Lys Val Leu Arg Arg Ala Lys Gly Ser Thr Lys Phe
        275                 280                 285

Thr Arg Val Pro Lys Arg Val Tyr Trp Glu Met Leu Ala Thr Asn Leu
    290                 295                 300

Thr Asp Lys Glu Tyr Val Arg Thr Arg Arg Ala Leu Ile Leu Glu Ile
305                 310                 315                 320

Leu Ile Lys Ala Gly Ser Leu Lys Ile Glu Gln Ile Gln Asp Asn Leu
                325                 330                 335

Lys Lys Leu Gly Phe Asp Glu Val Ile Glu Thr Ile Glu Asn Asp Ile
            340                 345                 350

Lys Gly Leu Ile Asn Thr Gly Ile Phe Ile Glu Ile Lys Gly Arg Phe
        355                 360                 365

Tyr Gln Leu Lys Asp His Ile Leu Gln Phe Val Ile Pro Asn Arg Gly
    370                 375                 380

Val Thr Lys Gln Leu Val Lys Ser Glu Leu Glu Glu Lys Lys Ser Glu
385                 390                 395                 400

Leu Arg His Lys Leu Lys Tyr Val Pro His Glu Tyr Ile Glu Leu Ile
                405                 410                 415

Glu Ile Ala Arg Asn Ser Thr Gln Asp Arg Ile Leu Glu Met Lys Val
            420                 425                 430

Met Glu Phe Phe Met Lys Val Tyr Gly Tyr Arg Gly Lys His Leu Gly
        435                 440                 445

Gly Ser Arg Lys Pro Asp Gly Ala Ile Tyr Thr Val Gly Ser Pro Ile
450                 455                 460

Asp Tyr Gly Val Ile Val Asp Thr Lys Ala Tyr Ser Gly Gly Tyr Asn
465                 470                 475                 480

Leu Pro Ile Gly Gln Ala Asp Glu Met Gln Arg Tyr Val Glu Glu Asn
                485                 490                 495

Gln Thr Arg Asn Lys His Ile Asn Pro Asn Glu Trp Trp Lys Val Tyr
            500                 505                 510

Pro Ser Ser Val Thr Glu Phe Lys Phe Leu Phe Val Ser Gly His Phe
        515                 520                 525

Lys Gly Asn Tyr Lys Ala Gln Leu Thr Arg Leu Asn His Ile Thr Asn
    530                 535                 540

Cys Asn Gly Ala Val Leu Ser Val Glu Glu Leu Leu Ile Gly Gly Glu
545                 550                 555                 560

Met Ile Lys Ala Gly Thr Leu Thr Leu Glu Glu Val Arg Arg Lys Phe
                565                 570                 575

Asn Asn Gly Glu Ile Asn Phe
            580
```

<210> SEQ ID NO 11
<211> LENGTH: 558
<212> TYPE: PRT
<213> ORGANISM: Acinetobacter lwoffii

<400> SEQUENCE: 11

Met Ser Thr Trp Leu Leu Gly Asn Thr Thr Val Arg Ser Pro Phe Arg
1               5                   10                  15

Leu Ile Asp Gly Leu Lys Val Phe Ala Leu Thr Asn Gly Asp Ile Arg
            20                  25                  30

Gly Thr Lys Glu Lys Glu Leu Val Phe Cys Lys Ala Leu Val Glu Gly
        35                  40                  45

Gly Ile Ile Ser Ala Ser Phe Glu Ala Glu Asp Thr Ser Gly Phe Ser
    50                  55                  60

Asp Thr Thr Tyr Ser Val Gly Arg Lys Trp Arg Ser Ala Leu Glu Lys
65                  70                  75                  80

Leu Gly Phe Ile Glu Gln Phe Asn Gln Ile Tyr Ile Leu Thr Glu Asn
                85                  90                  95

Gly Arg Asn Leu Leu Asn Ser Gln Thr Leu Gln Ser Asp Gln Glu Cys
            100                 105                 110

Tyr Leu Arg Ser Leu Ile Leu Tyr Ser Tyr Lys Ala Glu Asn Ser Asp
        115                 120                 125

Asn Pro Gly Gly Phe Phe Ser Pro Leu Met Leu Thr Leu His Ile Met
    130                 135                 140

Lys Glu Leu Glu Ile Arg Thr Gly Ser Ser Arg Ile Ser Phe Gln Glu
145                 150                 155                 160

Met Ala Ala Val Ile Gln Leu Thr Phe Ser Tyr Leu Asp Ile Asn Gln
                165                 170                 175

Ser Val Asn Glu Ile Leu Thr Ile Arg Ser Asn Arg Gln Ala Ser Leu
            180                 185                 190

Ser Lys Lys Lys Phe Asp Arg Glu Leu Tyr Glu Ser Lys Ser Ser Lys
        195                 200                 205

Ala Lys Ile Lys Ala Pro Ser Ile Lys Asp Tyr Ala Asp Thr Asn Leu
    210                 215                 220

Arg Tyr Leu Lys Ser Thr Gly Leu Phe Thr Ala Ser Gly Lys Gly Ile
225                 230                 235                 240

Cys Phe Ile Asp Asp Lys Lys Ile Val Ile Asp Lys Leu Ile Ala Met
                245                 250                 255

Tyr Gly Thr Phe Asp Ile Ser Gln Ser Asp Leu Lys Ile Gln Lys Gly
            260                 265                 270

Ala Pro Leu Pro Thr Asp His Lys Glu Thr Asn Ile Leu Leu Val Glu
        275                 280                 285

Gln Leu Glu Glu Thr Leu Asn Arg Asn Arg Ile Leu Phe Glu Lys Asn
    290                 295                 300

Ser Ser Ile Ala Gln Ala Pro Ile Gly Glu Ile Lys Asn Tyr Arg Tyr
305                 310                 315                 320

His Leu Glu Glu Leu Leu Phe Glu Asn Asn Glu Lys Lys Phe Ala Glu
                325                 330                 335

Asn Gln Lys Asn Glu Trp Asp Glu Ile Leu Ala Tyr Met Asp Leu Leu
            340                 345                 350

Ile Ser Pro Lys Pro Ile Ser Ile Glu Ile Ala Asp Lys Glu Ile Ser
        355                 360                 365

Ile Pro Ser Gly Glu Arg Pro Ala Tyr Phe Glu Trp Val Leu Trp Arg
    370                 375                 380

```
Ala Phe Leu Ala Leu Asn His Leu Ile Ile Glu Pro Gln Gln Cys Arg
385                 390                 395                 400

Arg Phe Lys Val Asp Gln Asp Phe Lys Pro Ile His Asn Ala Pro Gly
            405                 410                 415

Gly Gly Ala Asp Val Ile Phe Glu Tyr Glu Asn Phe Lys Ile Leu Gly
            420                 425                 430

Glu Val Thr Leu Thr Ser Asn Ser Arg Gln Glu Ala Ala Glu Gly Glu
        435                 440                 445

Pro Val Arg Arg His Ile Ala Val Glu Thr Val Asn Thr Pro Asp Lys
    450                 455                 460

Asp Val Tyr Gly Leu Phe Leu Ala Leu Thr Ile Asp Thr Asn Thr Ala
465                 470                 475                 480

Glu Thr Phe Arg His Gly Ala Trp Tyr His Gln Glu Leu Met Asp
            485                 490                 495

Val Lys Ile Leu Pro Leu Thr Leu Glu Ser Phe Lys Lys Tyr Leu Glu
            500                 505                 510

Ser Leu Arg Lys Lys Asn Gln Val Glu Thr Gly Ile Phe Asp Leu Lys
        515                 520                 525

Lys Met Met Asp Glu Ser Leu Lys Leu Arg Glu Thr Leu Thr Ala Pro
530                 535                 540

Gln Trp Lys Asn Glu Ile Thr Asn Lys Phe Ala Arg Pro Ile
545                 550                 555

<210> SEQ ID NO 12
<211> LENGTH: 556
<212> TYPE: PRT
<213> ORGANISM: Micrococcus lylae

<400> SEQUENCE: 12

Met Ala Ser Leu Ser Lys Thr Lys His Leu Phe Gly Phe Thr Ser Pro
1               5                   10                  15

Arg Thr Ile Glu Lys Ile Ile Pro Glu Leu Asp Ile Leu Ser Gln Gln
            20                  25                  30

Phe Ser Gly Lys Val Trp Gly Glu Asn Gln Ile Asn Phe Phe Asp Ala
        35                  40                  45

Ile Phe Asn Ser Asp Phe Tyr Glu Gly Thr Thr Tyr Pro Gln Asp Pro
50                  55                  60

Ala Leu Ala Ala Arg Asp Arg Ile Thr Arg Ala Pro Lys Ala Leu Gly
65                  70                  75                  80

Phe Ile Gln Leu Lys Pro Val Ile Gln Leu Thr Lys Ala Gly Asn Gln
            85                  90                  95

Leu Val Asn Gln Lys Arg Leu Pro Glu Leu Phe Thr Lys Gln Leu Leu
        100                 105                 110

Lys Phe Gln Leu Pro Ser Pro Tyr His Thr Gln Ser Pro Thr Val Asn
    115                 120                 125

Phe Asn Val Arg Pro Tyr Leu Glu Leu Leu Arg Leu Ile Asn Glu Leu
130                 135                 140

Gly Ser Ile Ser Lys Thr Glu Ile Ala Leu Phe Leu Gln Leu Val
145                 150                 155                 160

Asn Tyr Asn Lys Phe Asp Glu Ile Lys Asn Lys Ile Leu Lys Phe Arg
            165                 170                 175

Glu Thr Arg Lys Asn Asn Arg Ser Val Ser Trp Lys Thr Tyr Val Ser
        180                 185                 190

Gln Glu Phe Glu Lys Gln Ile Ser Ile Ile Phe Ala Asp Glu Val Thr
    195                 200                 205
```

```
Ala Lys Asn Phe Arg Thr Arg Glu Ser Ser Asp Glu Ser Phe Lys Lys
210                 215                 220

Phe Val Lys Thr Lys Glu Gly Asn Met Lys Asp Tyr Ala Asp Ala Phe
225                 230                 235                 240

Phe Arg Tyr Ile Arg Gly Thr Gln Leu Val Thr Ile Asp Lys Asn Leu
                245                 250                 255

His Leu Lys Ile Ser Ser Leu Lys Gln Asp Ser Val Asp Phe Leu Leu
            260                 265                 270

Lys Asn Thr Asp Arg Asn Ala Leu Asn Leu Ser Leu Met Glu Tyr Glu
        275                 280                 285

Asn Tyr Leu Phe Asp Pro Asp Gln Leu Ile Val Leu Glu Asp Asn Ser
290                 295                 300

Gly Leu Ile Asn Ser Lys Ile Lys Gln Leu Asp Asp Ser Ile Asn Val
305                 310                 315                 320

Glu Ser Leu Lys Ile Asp Asp Ala Lys Asp Leu Leu Asn Asp Leu Glu
                325                 330                 335

Ile Gln Arg Lys Ala Lys Thr Ile Glu Asp Thr Val Asn His Leu Lys
            340                 345                 350

Leu Arg Ser Asp Ile Glu Asp Ile Leu Asp Val Phe Ala Lys Ile Lys
        355                 360                 365

Lys Arg Asp Val Pro Asp Val Pro Leu Phe Leu Glu Trp Asn Ile Trp
370                 375                 380

Arg Ala Phe Ala Ala Leu Asn His Thr Gln Ala Ile Glu Gly Asn Phe
385                 390                 395                 400

Ile Val Asp Leu Asp Gly Met Pro Leu Asn Thr Ala Pro Gly Lys Lys
                405                 410                 415

Pro Asp Ile Glu Ile Asn Tyr Gly Ser Phe Ser Cys Ile Val Glu Val
            420                 425                 430

Thr Met Ser Ser Gly Glu Thr Gln Phe Asn Met Glu Gly Ser Ser Val
        435                 440                 445

Pro Arg His Tyr Gly Asp Leu Val Arg Lys Val Asp His Asp Ala Tyr
450                 455                 460

Cys Ile Phe Ile Ala Pro Lys Val Ala Pro Gly Thr Lys Ala His Phe
465                 470                 475                 480

Phe Asn Leu Asn Arg Leu Ser Thr Lys His Tyr Gly Gly Lys Thr Lys
                485                 490                 495

Ile Ile Pro Met Ser Leu Asp Asp Phe Ile Cys Phe Leu Gln Val Gly
            500                 505                 510

Ile Thr His Asn Phe Gln Asp Ile Asn Lys Leu Lys Asn Trp Leu Asp
        515                 520                 525

Asn Leu Ile Asn Phe Asn Leu Glu Ser Glu Asp Glu Glu Ile Trp Phe
530                 535                 540

Glu Glu Ile Ile Ser Lys Ile Ser Thr Trp Ala Ile
545                 550                 555

<210> SEQ ID NO 13
<211> LENGTH: 323
<212> TYPE: PRT
<213> ORGANISM: Streptomyces spec. Bf-61

<400> SEQUENCE: 13

Met Asn Ser Ser Asp Gly Ile Asp Gly Thr Val Ala Ser Ile Asp Thr
1               5                   10                  15

Ala Arg Ala Leu Leu Lys Arg Phe Gly Phe Asp Ala Gln Arg Tyr Asn
```

```
                20                  25                  30
Val Arg Ser Ala Val Thr Leu Leu Ala Leu Ala Gly Leu Lys Pro Gly
            35                  40                  45

Asp Arg Trp Val Asp Ser Thr Thr Pro Arg Leu Gly Val Gln Lys Ile
        50                  55                  60

Met Asp Trp Ser Gly Glu His Trp Ala Lys Pro Tyr Ala Thr Gly Ser
 65                  70                  75                  80

Arg Glu Asp Phe Arg Lys Lys Thr Leu Arg Gln Trp Val Asp Asn Gly
                85                  90                  95

Phe Ala Val Leu Asn Ala Asp Asn Leu Asn Ile Ala Thr Asn Ser Gln
            100                 105                 110

Leu Asn Glu Tyr Cys Leu Ser Asp Glu Ala Leu Gln Ala Leu Arg Ala
        115                 120                 125

Tyr Gly Thr Glu Gly Phe Glu Glu Ser Leu Val Val Phe Leu Asp Glu
    130                 135                 140

Ala Ser Lys Ala Val Lys Ala Arg Ala Glu Ala Leu Gln Ala Ala Met
145                 150                 155                 160

Ile Ser Val Asp Leu Pro Gly Gly Glu Glu Phe Leu Leu Ser Pro Ala
                165                 170                 175

Gly Gln Asn Pro Leu Leu Lys Lys Met Val Glu Phe Val Pro Arg
            180                 185                 190

Phe Ala Pro Arg Ser Thr Val Leu Tyr Leu Gly Asp Thr Arg Gly Lys
        195                 200                 205

His Ser Leu Phe Glu Arg Glu Ile Phe Glu Glu Val Leu Gly Leu Thr
    210                 215                 220

Phe Asp Pro His Gly Arg Met Pro Asp Leu Ile Leu His Asp Glu Val
225                 230                 235                 240

Arg Gly Trp Leu Phe Leu Met Glu Ala Val Lys Ser Lys Gly Pro Phe
                245                 250                 255

Asp Glu Glu Arg His Arg Ser Leu Gln Glu Leu Phe Val Thr Pro Ser
            260                 265                 270

Ala Gly Leu Ile Phe Val Asn Cys Phe Glu Asn Arg Glu Ser Met Arg
        275                 280                 285

Gln Trp Leu Pro Glu Leu Ala Trp Glu Thr Glu Ala Trp Val Ala Glu
    290                 295                 300

Asp Pro Asp His Leu Ile His Leu Asn Gly Ser Arg Phe Leu Gly Pro
305                 310                 315                 320

Tyr Glu Arg

<210> SEQ ID NO 14
<211> LENGTH: 323
<212> TYPE: PRT
<213> ORGANISM: Streptomyces diastaticus

<400> SEQUENCE: 14

Met Thr Asn Ser Asn Asp Ile Asp Glu Thr Ala Thr Ile Asp Thr
 1               5                  10                  15

Ala Arg Ala Leu Leu Lys Ser Phe Gly Phe Glu Ala Gln Arg His Asn
            20                  25                  30

Val Arg Ser Ala Val Thr Leu Leu Ala Leu Ala Gly Leu Lys Pro Gly
        35                  40                  45

Asp His Trp Ala Asp Ser Thr Thr Pro Arg Leu Gly Val Gln Lys Ile
    50                  55                  60

Met Asp Trp Ser Gly Ala Tyr Trp Ala Lys Pro Tyr Ala Thr Gly Ser
```

```
                65                  70                  75                  80
Arg Glu Asp Phe Arg Lys Lys Thr Leu Arg Gln Trp Val Asp Asn Gly
                    85                  90                  95

Phe Ala Val Leu Asn Pro Asp Asn Leu Asn Ile Ala Thr Asn Ser Gln
            100                 105                 110

Leu Asn Glu Tyr Cys Leu Ser Asp Glu Ala Ala Gln Ala Ile Arg Ser
            115                 120                 125

Tyr Gly Thr Asp Ala Phe Glu Ser Ala Leu Val Asp Phe Leu Ser Lys
        130                 135                 140

Ala Ser Asp Thr Val Arg Ala Arg Ala Glu Ala Leu Arg Ala Ala Met
145                 150                 155                 160

Ile Ser Val Asp Leu Ala Asp Gly Asp Glu Phe Leu Leu Ser Pro Ala
                165                 170                 175

Gly Gln Asn Pro Leu Leu Lys Lys Met Val Glu Glu Phe Met Pro Arg
            180                 185                 190

Phe Ala Pro Gly Ala Lys Val Leu Tyr Ile Gly Asp Trp Arg Gly Lys
        195                 200                 205

His Thr Arg Phe Glu Lys Arg Ile Phe Glu Glu Thr Leu Gly Leu Thr
    210                 215                 220

Phe Asp Pro His Gly Arg Met Pro Asp Leu Val Leu His Asp Lys Val
225                 230                 235                 240

Arg Lys Trp Leu Phe Leu Met Glu Ala Val Lys Ser Lys Gly Pro Phe
                245                 250                 255

Asp Glu Glu Arg His Arg Thr Leu Arg Glu Leu Phe Ala Thr Pro Val
            260                 265                 270

Ala Gly Leu Val Phe Val Asn Cys Phe Glu Asn Arg Glu Ala Met Arg
        275                 280                 285

Gln Trp Leu Pro Glu Leu Ala Trp Glu Thr Glu Ala Trp Val Ala Asp
    290                 295                 300

Asp Pro Asp His Leu Ile His Leu Asn Gly Ser Arg Phe Leu Gly Pro
305                 310                 315                 320

Tyr Glu Arg

<210> SEQ ID NO 15
<211> LENGTH: 602
<212> TYPE: PRT
<213> ORGANISM: Streptococcus sanguis

<400> SEQUENCE: 15

Met Thr Ile Ser Ile Asn Glu Tyr Ser Asp Leu Asn Asn Leu Ala Phe
1               5                   10                  15

Gly Leu Gly Gln Asp Val Ser Gln Asp Leu Lys Glu Leu Val Lys Val
            20                  25                  30

Ala Ser Ile Phe Met Pro Asp Ser Lys Ile His Lys Trp Leu Ile Asp
        35                  40                  45

Thr Arg Leu Glu Glu Val Val Thr Asp Leu Asn Leu Arg Tyr Glu Leu
    50                  55                  60

Lys Ser Val Ile Thr Asn Thr Pro Ile Ser Val Thr Trp Lys Gln Leu
65                  70                  75                  80

Thr Gly Thr Arg Thr Lys Arg Glu Ala Asn Ser Leu Val Gln Ala Val
                85                  90                  95

Phe Pro Gly Gln Cys Ser Arg Leu Ala Ile Val Asp Trp Ala Ala Lys
            100                 105                 110

Asn Tyr Val Ser Val Ala Val Ala Phe Gly Leu Leu Lys Phe His Arg
```

-continued

```
            115                 120                 125
Ala Asp Lys Thr Phe Thr Ile Ser Glu Ile Gly Ile Gln Ala Val Lys
130                 135                 140

Leu Tyr Asp Ser Glu Glu Leu Ala Glu Leu Asp Lys Phe Leu Tyr Glu
145                 150                 155                 160

Arg Leu Leu Glu Tyr Pro Tyr Ala Ala Trp Leu Ile Arg Leu Leu Gly
                    165                 170                 175

Asn Gln Pro Ser Lys Gln Phe Ser Lys Phe Asp Leu Gly Glu His Phe
                180                 185                 190

Gly Phe Ile Asp Glu Leu Gly Phe Glu Thr Ala Pro Ile Glu Ile Phe
            195                 200                 205

Leu Asn Gly Leu Ala Gln Ala Glu Ile Asp Gly Asp Lys Thr Ala Ala
210                 215                 220

Gln Lys Ile Lys Ser Asn Phe Glu Ser Thr Ser Asp Lys Tyr Met Arg
225                 230                 235                 240

Trp Leu Ala Gly Val Leu Val Thr Ala Gly Leu Ala Thr Ser Thr Thr
                    245                 250                 255

Lys Lys Val Thr His Thr Tyr Lys Asn Arg Lys Phe Glu Leu Thr Leu
                260                 265                 270

Gly Thr Val Tyr Gln Ile Thr Ala Lys Gly Leu Thr Ala Leu Lys Glu
            275                 280                 285

Val Asn Gly Lys Ser Arg Tyr Pro Arg Ser Arg Lys Arg Val Met Trp
290                 295                 300

Glu Phe Leu Ala Thr Lys Asp Lys Glu Ala Ile Ala Lys Lys Thr Ser
305                 310                 315                 320

Arg Ser Leu Met Leu Lys His Leu Thr Glu Lys Lys Asn Pro Ile Gln
                    325                 330                 335

Ala Glu Val Ile Ala Thr Leu Ile Asn Thr Asp Tyr Pro Thr Leu Glu
                340                 345                 350

Ile Thr Pro Glu Glu Val Ile Asp Asp Cys Ile Gly Leu Asn Arg Ile
            355                 360                 365

Gly Ile Glu Ile Leu Ile Asp Gly Asp Lys Leu Thr Leu Asn Asp Lys
370                 375                 380

Leu Phe Asp Phe Glu Ile Pro Val Gln Lys Asp Val Val Leu Glu Lys
385                 390                 395                 400

Ser Asp Ile Glu Lys Phe Lys Asn Gln Leu Arg Thr Glu Leu Thr Asn
                    405                 410                 415

Ile Asp His Ser Tyr Leu Lys Gly Ile Asp Ile Ala Ser Lys Lys Lys
                420                 425                 430

Thr Ser Asn Val Glu Asn Thr Glu Phe Glu Ala Ile Ser Thr Lys Ile
            435                 440                 445

Phe Thr Asp Glu Leu Gly Phe Ser Gly Lys His Leu Gly Gly Ser Asn
450                 455                 460

Lys Pro Asp Gly Leu Leu Trp Asp Asp Cys Ala Ile Ile Leu Asp
465                 470                 475                 480

Ser Lys Ala Tyr Ser Glu Gly Phe Pro Leu Thr Ala Ser His Thr Asp
                    485                 490                 495

Ala Met Gly Arg Tyr Leu Arg Gln Phe Thr Glu Arg Lys Glu Glu Ile
                500                 505                 510

Lys Pro Thr Trp Trp Asp Ile Ala Pro Glu His Leu Asp Asn Thr Tyr
            515                 520                 525

Phe Ala Tyr Val Ser Gly Ser Phe Ser Gly Asn Tyr Lys Glu Gln Leu
530                 535                 540
```

```
Gln Lys Phe Arg Gln Asp Thr Asn His Leu Gly Gly Ala Leu Glu Phe
545                 550                 555                 560

Val Lys Leu Leu Leu Leu Ala Asn Asn Tyr Lys Thr Gln Lys Met Ser
                565                 570                 575

Lys Lys Glu Val Lys Lys Ser Ile Leu Asp Tyr Asn Ile Ser Tyr Glu
            580                 585                 590

Glu Tyr Ala Pro Leu Leu Ala Glu Ile Glu
        595                 600
```

<210> SEQ ID NO 16
<211> LENGTH: 593
<212> TYPE: PRT
<213> ORGANISM: Clostridium leptum

<400> SEQUENCE: 16

```
Met Ile His Leu Ile Pro Thr Glu Ala Lys Arg Phe Arg Thr Phe Gly
1               5                   10                  15

Trp Val Gln Asp Pro Ser Asp Phe Arg Ser Leu Cys Asp Val Val Ala
                20                  25                  30

Ile Phe Asp Glu Thr Ser Leu Lys His Gln Glu Leu Ala Gly Gln Val
            35                  40                  45

Ile Pro Ala Leu Val Glu Glu Arg Asp Gly Arg Gln Arg Leu Leu Asp
50                  55                  60

Ala Leu Asn Gln Arg Pro Leu Arg Ile Ser Tyr Thr Asp Leu Val Gly
65                  70                  75                  80

Thr Ser Phe Thr Pro Arg Ser Ala Ala Arg Cys Asn Gly Ile Val Gln
                85                  90                  95

Ala Ala Val Arg Gly Gln Val Arg Pro Phe Ile Gly Asp Trp Pro Ala
            100                 105                 110

Asp Asn Phe Val Arg Trp Ala His Ala Leu Gly Phe Leu Arg Tyr Gly
        115                 120                 125

Tyr Gln Gly Asp Ala Phe Glu Leu Thr Glu Thr Gly Lys Ala Leu Ala
    130                 135                 140

Gln Ala Arg Thr Gln Gly Glu Glu Leu Asn Ser Gln Glu Lys Glu Leu
145                 150                 155                 160

Leu Thr Ser Ala Val Leu Ala Tyr Pro Pro Ala Val Arg Ile Leu Ser
                165                 170                 175

Leu Leu Gly Glu Gly Glu Gly Ala His Leu Thr Lys Phe Glu Leu Gly
            180                 185                 190

Lys Gln Leu Gly Phe Val Gly Glu Asp Gly Phe Thr Ser Leu Pro Gln
        195                 200                 205

Thr Val Leu Val Arg Ser Leu Ala Ser Ser Lys Asp Ala Lys Glu Lys
    210                 215                 220

Asn Lys Met Lys Thr Asp Trp Asp Gly Ser Ser Asp Lys Tyr Ala Arg
225                 230                 235                 240

Met Ile Ala Lys Trp Leu Glu Lys Leu Gly Leu Val Lys Gln Glu Ala
                245                 250                 255

Lys Pro Val Thr Val Thr Leu Ala Gly Arg Lys Tyr Thr Glu Ser Ile
            260                 265                 270

Gly Gln Ser Tyr Val Ile Thr Gly Leu Gly Ile Thr Ala Leu Asn Arg
        275                 280                 285

Thr Leu Gly Lys Ser Arg His Lys Arg Ile Pro Lys Asn Val Ser Phe
    290                 295                 300

Glu Met Met Ala Thr Lys Gly Asp Asp Arg Glu Tyr Leu Arg Thr Arg
```

Arg Thr Cys Val Leu Lys Ala Val Ser Glu Gly Lys Gly Arg Val Ser
305                 310                 315                 320

Tyr Thr Glu Ile Gln Lys Tyr Leu Glu Ala Leu Gly Leu Gln Glu Asp
            325                 330                 335

Glu Ala Thr Ile Arg Asp Val Gln Gly Leu Ile His Ile Gly Leu
        340                 345                 350

Asn Ile Ala Ala Gly Glu Arg Glu Cys Val Trp Lys Asp Ile Asn
    355                 360                 365

Asp Leu Ile Leu Pro Val Pro Lys Lys Leu Ala Lys Ser Ser Gln Ser
370                 375                 380

385                 390                 395                 400

Glu Thr Lys Glu Lys Leu Arg Glu Lys Leu Arg Asn Leu Pro His Glu
            405                 410                 415

Tyr Leu Ser Leu Val Asp Leu Ala Tyr Asp Ser Lys Gln Asn Arg Leu
        420                 425                 430

Phe Glu Met Lys Val Ile Glu Leu Leu Thr Glu Glu Cys Gly Phe Gln
    435                 440                 445

Gly Leu His Leu Gly Gly Ser Arg Arg Pro Asp Gly Val Leu Tyr Thr
450                 455                 460

Ala Gly Leu Thr Asp Asn Tyr Gly Ile Ile Leu Asp Thr Lys Ala Tyr
465                 470                 475                 480

Ser Ser Gly Tyr Ser Leu Pro Ile Ala Gln Ala Asp Glu Met Glu Arg
            485                 490                 495

Tyr Val Arg Glu Asn Gln Thr Arg Asp Glu Leu Val Asn Pro Asn Gln
        500                 505                 510

Trp Trp Glu Asn Phe Glu Asn Gly Leu Gly Thr Phe Tyr Phe Leu Phe
    515                 520                 525

Val Ala Gly His Phe Asn Gly Asn Val Gln Ala Gln Leu Glu Arg Ile
530                 535                 540

Ser Arg Asn Thr Gly Val Leu Gly Ala Ala Ser Ile Ser Gln Leu
545                 550                 555                 560

Leu Leu Leu Ala Asp Ala Ile Arg Gly Gly Arg Met Asp Arg Glu Arg
            565                 570                 575

Leu Arg His Leu Met Phe Gln Asn Glu Glu Phe Leu Leu Glu Gln Glu
        580                 585                 590

Leu

<210> SEQ ID NO 17
<211> LENGTH: 587
<212> TYPE: PRT
<213> ORGANISM: Clostridium spec. 7_2_43 FAA

<400> SEQUENCE: 17

Met Ile Asn Ile Ile Asp Val Asn Asn Lys Thr Ile Arg Thr Phe Gly
1               5                   10                  15

Trp Val Gln Asn Pro Ser Asn Phe Glu Ser Leu Lys Lys Val Val Ala
            20                  25                  30

Ile Phe Asp Asn Thr Ser Lys Thr Tyr Asn Glu Leu Lys Asp Lys Lys
        35                  40                  45

Ile Lys Lys Leu Val Asp Glu Arg Asp Gly Gln Lys Glu Leu Leu Asn
    50                  55                  60

Ala Leu Asn Ala Asn Pro Leu Lys Ile Lys Tyr Cys Asn Leu Val Gly
65                  70                  75                  80

Thr Ser Phe Thr Pro Arg Ser Ser Ala Arg Cys Asn Gly Ile Val Gln

```
            85                  90                  95
Ala Thr Val Lys Gly Gln Arg Lys Glu Phe Ile Asp Asp Trp Ser Ser
            100                 105                 110

Asp Asn Phe Val Arg Trp Ala His Ala Leu Gly Phe Ile Lys Tyr Asn
            115                 120                 125

Tyr Asp Thr Asp Thr Phe Glu Ile Thr Asp Val Gly Arg Lys Tyr Val
            130                 135                 140

Gln Ser Glu Asp Ser Asn Glu Glu Ser Thr Ile Leu Glu Ala
145                 150                 155                 160

Met Leu Ser Tyr Pro Pro Val Ala Arg Val Leu Thr Leu Leu Ser Asn
            165                 170                 175

Gly Glu His Leu Thr Lys Tyr Glu Ile Gly Lys Lys Leu Gly Phe Val
            180                 185                 190

Gly Glu Ala Gly Phe Thr Ser Leu Pro Leu Asn Val Leu Ile Met Thr
            195                 200                 205

Leu Ala Thr Thr Asp Glu Pro Lys Glu Lys Asn Lys Ile Lys Thr Asp
            210                 215                 220

Trp Asp Gly Ser Ser Asp Lys Tyr Ala Arg Met Ile Ser Gly Trp Leu
225                 230                 235                 240

Val Lys Leu Gly Leu Leu Val Gln Arg Pro Lys Leu Val Thr Val Asp
            245                 250                 255

Phe Gly Gly Glu Leu Tyr Ser Glu Thr Ile Gly His Ala Tyr Met Ile
            260                 265                 270

Thr Asp Arg Gly Leu Lys Ala Val Arg Arg Leu Leu Gly Ile Asn Lys
            275                 280                 285

Val Ala Arg Val Ser Lys Asn Val Phe Trp Glu Met Leu Ala Thr Lys
            290                 295                 300

Gly Ile Asp Lys Asn Tyr Ile Arg Thr Arg Ala Tyr Ile Leu Lys
305                 310                 315                 320

Ile Leu Ile Glu Ser Asn Lys Val Leu Thr Leu Glu Asp Ile Lys Gly
            325                 330                 335

Lys Leu Lys Leu Ala Ser Ile Asn Glu Ser Ile Asn Thr Ile Lys Asp
            340                 345                 350

Asp Ile Asn Gly Leu Ile Asn Thr Gly Ile Asn Ile Lys Ser Glu Thr
            355                 360                 365

Thr Gly Tyr Lys Ile Tyr Asp Ser Ile Asn Asp Phe Ile Ile Pro Lys
            370                 375                 380

Thr Gly Asp Thr Glu Gly Ile Lys Ser Asn Ile Ser Leu Leu Lys Asp
385                 390                 395                 400

Glu Leu Arg Gly Gln Ile Ser His Ile Ser His Glu Tyr Leu Ser Leu
            405                 410                 415

Ile Asp Leu Ala Phe Asp Ser Lys Gln Asn Arg Leu Phe Glu Met Lys
            420                 425                 430

Val Leu Glu Leu Leu Val Asn Glu Tyr Gly Phe Lys Gly Arg His Leu
            435                 440                 445

Gly Gly Ser Arg Lys Pro Asp Gly Ile Val Tyr Ser Thr Thr Leu Glu
            450                 455                 460

Asp Asn Phe Gly Ile Ile Val Asp Thr Lys Ala Tyr Ser Glu Gly Tyr
465                 470                 475                 480

Ser Leu Pro Ile Ser Gln Ala Asp Glu Met Glu Arg Tyr Val Arg Glu
            485                 490                 495

Asn Ser Asn Arg Asp Glu Glu Val Asn Pro Asn Lys Trp Trp Glu Asn
            500                 505                 510
```

Phe Ser Glu Glu Val Lys Lys Tyr Tyr Phe Val Phe Ile Ser Gly Ser
            515                 520                 525

Phe Lys Gly Lys Phe Glu Glu Gln Leu Arg Arg Leu Ser Met Thr Thr
            530                 535                 540

Gly Val Asn Gly Ser Ala Val Asn Val Val Asn Leu Leu Leu Gly Ala
545                 550                 555                 560

Glu Lys Ile Arg Ser Gly Glu Met Thr Ile Glu Glu Leu Glu Arg Ala
            565                 570                 575

Met Phe Asn Asn Ser Glu Phe Ile Leu Lys Tyr
            580                 585

<210> SEQ ID NO 18
<211> LENGTH: 589
<212> TYPE: PRT
<213> ORGANISM: Peptoniphilus duerdenii

<400> SEQUENCE: 18

Met Ala Glu Arg Thr Leu Gly Trp Ile Gln Asn Pro Ser Ser Phe Glu
1               5                   10                  15

Asn Leu Lys Asn Val Val Ser Val Phe Asp Lys Asn Ser Asp Ile Tyr
            20                  25                  30

Lys Glu Ile Leu Asn Thr Lys Leu Pro Lys Leu Val Lys Asp Leu Asp
        35                  40                  45

Leu Gln Asn Lys Leu Ile Ser Glu Leu Glu Lys Asp Pro Leu Glu Met
    50                  55                  60

Asp Tyr Val Leu Leu Lys Gly His Gly Ile Lys Ser Gly Gln Lys Arg
65                  70                  75                  80

Ala Asp Ala Glu Cys Ser Gly Ile Val Gln Ala Ile Thr Thr Gln
            85                  90                  95

Gly Gly Arg Ala Tyr Thr Asp Asp Trp Thr Ala Asp Gly Phe Leu Arg
            100                 105                 110

Trp Gly Ile Ser Ile Gly Leu Leu Asp Tyr Asp Thr Glu Lys Asp Thr
        115                 120                 125

Val Ser Ile Thr Lys Leu Gly Glu Lys Phe Val Lys Ser Asn Ser Glu
    130                 135                 140

Asp Ser Asp Lys Glu Ile Leu Ile Ser Ala Phe Leu Ser Tyr Pro Pro
145                 150                 155                 160

Ala Val Arg Ile Leu Thr Leu Leu Glu Asn Gly Asp His Leu Thr Lys
            165                 170                 175

Phe Glu Leu Gly Lys Gln Leu Gly Gly Leu Gly Glu Ala Gly Phe Thr
            180                 185                 190

Ser Ile Pro Gln Asp Leu Tyr Ile Gln Ala Ile Glu Leu Ala Ala Asp
        195                 200                 205

Lys Asp Lys Ala Ser Ile Arg Ser Asn Thr Glu Gly Ser Ala Asp Lys
    210                 215                 220

Tyr Ala Arg Met Ile Ser Gly Trp Leu Ser Lys Val Gly Leu Ile Gln
225                 230                 235                 240

Arg Ile Gly Lys Glu Val Ser Thr Lys Ile Gly Asp Val Glu Tyr Lys
            245                 250                 255

Val Asn Ile Gly His Ser Phe Arg Ile Thr Leu Asn Gly Ile Lys Glu
            260                 265                 270

Leu Lys Arg Ala Met Gly Leu Ser Ser Tyr Pro Lys Thr Asp Lys Ile
        275                 280                 285

Val Tyr Trp Gln Met Leu Ala Thr Lys Gly Lys Asp Arg Asp Tyr Ile

```
            290                 295                 300
Arg Asn Arg Arg Gly Tyr Ile Ile Lys Ala Ile Asn Arg Glu Arg
305                 310                 315                 320

Asn Leu Glu Asp Ile Lys Ala Tyr Leu Leu Glu Asn Asn Ile Asp Glu
                325                 330                 335

Ser Ile Thr Thr Ile Glu Asp Glu Leu Lys Val Ile Glu Ala Met Gly
                340                 345                 350

Leu Ser Phe Lys His Ser Arg Asn Gly Tyr Val Ile Asp Asp Asn Ile
                355                 360                 365

Ile Lys Leu Glu Ile Pro Arg Thr Lys Ile Ser Lys Thr Asn Val Leu
                370                 375                 380

Glu Leu Lys Asp Lys Val Arg Asp Lys Leu Lys Tyr Val Asp His Arg
385                 390                 395                 400

Tyr Leu Ala Leu Ile Asp Leu Ala Tyr Asp Gly Thr Ala Asn Arg Asp
                405                 410                 415

Phe Glu Ile Gln Thr Ile Asp Leu Leu Ile Asn Glu Leu Lys Phe Lys
                420                 425                 430

Gly Val Arg Leu Gly Glu Ser Arg Lys Pro Asp Gly Ile Ile Ser Tyr
                435                 440                 445

Asn Ile Asn Gly Val Ile Ile Asp Asn Lys Ala Tyr Ser Thr Gly Tyr
                450                 455                 460

Asn Leu Pro Ile Asn Gln Ala Asp Glu Met Ile Arg Tyr Ile Glu Glu
465                 470                 475                 480

Asn Gln Thr Arg Asp Glu Lys Ile Asn Ser Asn Lys Trp Trp Glu Ser
                485                 490                 495

Phe Asp Asp Lys Val Lys Asp Phe Asn Tyr Leu Phe Val Ser Ser Phe
                500                 505                 510

Phe Lys Gly Asn Phe Lys Asn Asn Leu Lys His Ile Ala Asn Arg Thr
                515                 520                 525

Gly Val Ser Gly Gly Ala Ile Asn Val Glu Asn Leu Leu Tyr Phe Ala
                530                 535                 540

Glu Glu Leu Lys Ala Gly Arg Leu Ser Tyr Val Asp Ser Phe Lys Met
545                 550                 555                 560

Tyr Asp Asn Asp Glu Ile Tyr Val Gly Asp Phe Ser Asp Tyr Ser Tyr
                565                 570                 575

Val Lys Phe Ala Ala Glu Glu Glu Gly Glu Tyr Leu Thr
                580                 585

<210> SEQ ID NO 19
<211> LENGTH: 279
<212> TYPE: PRT
<213> ORGANISM: Acinetobacter lwoffii

<400> SEQUENCE: 19

Lys Glu Thr Asn Ile Leu Leu Val Glu Gln Leu Glu Glu Thr Leu Asn
1               5                   10                  15

Arg Asn Arg Ile Leu Phe Glu Lys Asn Ser Ser Ile Ala Gln Ala Pro
                20                  25                  30

Ile Gly Glu Ile Lys Asn Tyr Arg Tyr His Leu Glu Glu Leu Leu Phe
            35                  40                  45

Glu Asn Asn Glu Lys Lys Phe Ala Glu Asn Gln Lys Asn Glu Trp Asp
        50                  55                  60

Glu Ile Leu Ala Tyr Met Asp Leu Leu Ile Ser Pro Lys Pro Ile Ser
65                  70                  75                  80
```

```
Ile Glu Ile Ala Asp Lys Glu Ile Ser Ile Pro Ser Gly Glu Arg Pro
                85                  90                  95

Ala Tyr Phe Glu Trp Val Leu Trp Arg Ala Phe Leu Ala Leu Asn His
            100                 105                 110

Leu Ile Ile Glu Pro Gln Gln Cys Arg Arg Phe Lys Val Asp Gln Asp
            115                 120                 125

Phe Lys Pro Ile His Asn Ala Pro Gly Gly Gly Ala Asp Val Ile Phe
130                 135                 140

Glu Tyr Glu Asn Phe Lys Ile Leu Gly Glu Val Thr Leu Thr Ser Asn
145                 150                 155                 160

Ser Arg Gln Glu Ala Ala Glu Gly Glu Pro Val Arg Arg His Ile Ala
                165                 170                 175

Val Glu Thr Val Asn Thr Pro Asp Lys Asp Val Tyr Gly Leu Phe Leu
            180                 185                 190

Ala Leu Thr Ile Asp Thr Asn Thr Ala Glu Thr Phe Arg His Gly Ala
            195                 200                 205

Trp Tyr His Gln Glu Glu Leu Met Asp Val Lys Ile Leu Pro Leu Thr
        210                 215                 220

Leu Glu Ser Phe Lys Lys Tyr Leu Glu Ser Leu Arg Lys Lys Asn Gln
225                 230                 235                 240

Val Glu Thr Gly Ile Phe Asp Leu Lys Lys Met Met Asp Glu Ser Leu
                245                 250                 255

Lys Leu Arg Glu Thr Leu Thr Ala Pro Gln Trp Lys Asn Glu Ile Thr
            260                 265                 270

Asn Lys Phe Ala Arg Pro Ile
            275

<210> SEQ ID NO 20
<211> LENGTH: 201
<212> TYPE: PRT
<213> ORGANISM: Clostridium leptum

<400> SEQUENCE: 20

Lys Leu Ala Lys Ser Ser Gln Ser Glu Thr Lys Glu Lys Leu Arg Glu
1               5                   10                  15

Lys Leu Arg Asn Leu Pro His Glu Tyr Leu Ser Leu Val Asp Leu Ala
                20                  25                  30

Tyr Asp Ser Lys Gln Asn Arg Leu Phe Glu Met Lys Val Ile Glu Leu
            35                  40                  45

Leu Thr Glu Glu Cys Gly Phe Gln Gly Leu His Leu Gly Gly Ser Arg
        50                  55                  60

Arg Pro Asp Gly Val Leu Tyr Thr Ala Gly Leu Thr Asp Asn Tyr Gly
65                  70                  75                  80

Ile Ile Leu Asp Thr Lys Ala Tyr Ser Ser Gly Tyr Ser Leu Pro Ile
                85                  90                  95

Ala Gln Ala Asp Glu Met Glu Arg Tyr Val Arg Glu Asn Gln Thr Arg
            100                 105                 110

Asp Glu Leu Val Asn Pro Asn Gln Trp Trp Glu Asn Phe Glu Asn Gly
            115                 120                 125

Leu Gly Thr Phe Tyr Phe Leu Phe Val Ala Gly His Phe Asn Gly Asn
130                 135                 140

Val Gln Ala Gln Leu Glu Arg Ile Ser Arg Asn Thr Gly Val Leu Gly
145                 150                 155                 160

Ala Ala Ala Ser Ile Ser Gln Leu Leu Leu Ala Asp Ala Ile Arg
                165                 170                 175
```

Gly Gly Arg Met Asp Arg Glu Arg Leu Arg His Leu Met Phe Gln Asn
            180                 185                 190

Glu Glu Phe Leu Leu Glu Gln Glu Leu
            195                 200

<210> SEQ ID NO 21
<211> LENGTH: 250
<212> TYPE: PRT
<213> ORGANISM: Micrococcus lylae

<400> SEQUENCE: 21

Ile Asn Ser Lys Ile Lys Gln Leu Asp Asp Ser Ile Asn Val Glu Ser
1               5                   10                  15

Leu Lys Ile Asp Asp Ala Lys Asp Leu Leu Asn Asp Leu Glu Ile Gln
            20                  25                  30

Arg Lys Ala Lys Thr Ile Glu Asp Thr Val Asn His Leu Lys Leu Arg
        35                  40                  45

Ser Asp Ile Glu Asp Ile Leu Asp Val Phe Ala Lys Ile Lys Lys Arg
    50                  55                  60

Asp Val Pro Asp Val Pro Leu Phe Leu Glu Trp Asn Ile Trp Arg Ala
65                  70                  75                  80

Phe Ala Ala Leu Asn His Thr Gln Ala Ile Glu Gly Asn Phe Ile Val
                85                  90                  95

Asp Leu Asp Gly Met Pro Leu Asn Thr Ala Pro Gly Lys Lys Pro Asp
            100                 105                 110

Ile Glu Ile Asn Tyr Gly Ser Phe Ser Cys Ile Val Glu Val Thr Met
        115                 120                 125

Ser Ser Gly Glu Thr Gln Phe Asn Met Glu Gly Ser Ser Val Pro Arg
    130                 135                 140

His Tyr Gly Asp Leu Val Arg Lys Val Asp His Asp Ala Tyr Cys Ile
145                 150                 155                 160

Phe Ile Ala Pro Lys Val Ala Pro Gly Thr Lys Ala His Phe Phe Asn
                165                 170                 175

Leu Asn Arg Leu Ser Thr Lys His Tyr Gly Gly Lys Thr Lys Ile Ile
            180                 185                 190

Pro Met Ser Leu Asp Asp Phe Ile Cys Phe Leu Gln Val Gly Ile Thr
        195                 200                 205

His Asn Phe Gln Asp Ile Asn Lys Leu Lys Asn Trp Leu Asp Asn Leu
    210                 215                 220

Ile Asn Phe Asn Leu Glu Ser Glu Asp Glu Ile Trp Phe Glu Glu
225                 230                 235                 240

Ile Ile Ser Lys Ile Ser Thr Trp Ala Ile
                245                 250

<210> SEQ ID NO 22
<211> LENGTH: 213
<212> TYPE: PRT
<213> ORGANISM: Peptoniphilus duerdenii

<400> SEQUENCE: 22

Lys Ile Ser Lys Thr Asn Val Leu Glu Leu Lys Asp Lys Val Arg Asp
1               5                   10                  15

Lys Leu Lys Tyr Val Asp His Arg Tyr Leu Ala Leu Ile Asp Leu Ala
            20                  25                  30

Tyr Asp Gly Thr Ala Asn Arg Asp Phe Glu Ile Gln Thr Ile Asp Leu
        35                  40                  45

```
Leu Ile Asn Glu Leu Lys Phe Lys Gly Val Arg Leu Gly Glu Ser Arg
 50                  55                  60

Lys Pro Asp Gly Ile Ile Ser Tyr Asn Ile Asn Gly Val Ile Ile Asp
 65                  70                  75                  80

Asn Lys Ala Tyr Ser Thr Gly Tyr Asn Leu Pro Ile Asn Gln Ala Asp
                 85                  90                  95

Glu Met Ile Arg Tyr Ile Glu Glu Asn Gln Thr Arg Asp Glu Lys Ile
            100                 105                 110

Asn Ser Asn Lys Trp Trp Glu Ser Phe Asp Asp Lys Val Lys Asp Phe
        115                 120                 125

Asn Tyr Leu Phe Val Ser Ser Phe Phe Lys Gly Asn Phe Lys Asn Asn
    130                 135                 140

Leu Lys His Ile Ala Asn Arg Thr Gly Val Ser Gly Gly Ala Ile Asn
145                 150                 155                 160

Val Glu Asn Leu Leu Tyr Phe Ala Glu Glu Leu Lys Ala Gly Arg Leu
                165                 170                 175

Ser Tyr Val Asp Ser Phe Lys Met Tyr Asp Asn Asp Glu Ile Tyr Val
            180                 185                 190

Gly Asp Phe Ser Asp Tyr Ser Tyr Val Lys Phe Ala Ala Glu Glu Glu
        195                 200                 205

Gly Glu Tyr Leu Thr
    210

<210> SEQ ID NO 23
<211> LENGTH: 163
<212> TYPE: PRT
<213> ORGANISM: Streptomyces spec. Bf-61

<400> SEQUENCE: 23

Ile Ser Val Asp Leu Pro Gly Gly Glu Glu Phe Leu Leu Ser Pro Ala
 1               5                  10                  15

Gly Gln Asn Pro Leu Leu Lys Lys Met Val Glu Glu Phe Val Pro Arg
                20                  25                  30

Phe Ala Pro Arg Ser Thr Val Leu Tyr Leu Gly Asp Thr Arg Gly Lys
            35                  40                  45

His Ser Leu Phe Glu Arg Glu Ile Phe Glu Glu Val Leu Gly Leu Thr
         50                 55                  60

Phe Asp Pro His Gly Arg Met Pro Asp Leu Ile Leu His Asp Glu Val
 65                  70                  75                  80

Arg Gly Trp Leu Phe Leu Met Glu Ala Val Lys Ser Lys Gly Pro Phe
                 85                  90                  95

Asp Glu Glu Arg His Arg Ser Leu Gln Glu Leu Phe Val Thr Pro Ser
            100                 105                 110

Ala Gly Leu Ile Phe Val Asn Cys Phe Glu Asn Arg Glu Ser Met Arg
        115                 120                 125

Gln Trp Leu Pro Glu Leu Ala Trp Glu Thr Glu Ala Trp Val Ala Glu
    130                 135                 140

Asp Pro Asp His Leu Ile His Leu Asn Gly Ser Arg Phe Leu Gly Pro
145                 150                 155                 160

Tyr Glu Arg

<210> SEQ ID NO 24
<211> LENGTH: 163
<212> TYPE: PRT
<213> ORGANISM: Streptomyces diastaticus
```

<400> SEQUENCE: 24

```
Ile Ser Val Asp Leu Ala Asp Gly Asp Glu Phe Leu Leu Ser Pro Ala
1               5                   10                  15

Gly Gln Asn Pro Leu Leu Lys Lys Met Val Glu Glu Phe Met Pro Arg
            20                  25                  30

Phe Ala Pro Gly Ala Lys Val Leu Tyr Ile Gly Asp Trp Arg Gly Lys
        35                  40                  45

His Thr Arg Phe Glu Lys Arg Ile Phe Glu Glu Thr Leu Gly Leu Thr
    50                  55                  60

Phe Asp Pro His Gly Arg Met Pro Asp Leu Val Leu His Asp Lys Val
65                  70                  75                  80

Arg Lys Trp Leu Phe Leu Met Glu Ala Val Lys Ser Lys Gly Pro Phe
                85                  90                  95

Asp Glu Glu Arg His Arg Thr Leu Arg Glu Leu Phe Ala Thr Pro Val
            100                 105                 110

Ala Gly Leu Val Phe Val Asn Cys Phe Glu Asn Arg Glu Ala Met Arg
        115                 120                 125

Gln Trp Leu Pro Glu Leu Ala Trp Glu Thr Glu Ala Trp Val Ala Asp
    130                 135                 140

Asp Pro Asp His Leu Ile His Leu Asn Gly Ser Arg Phe Leu Gly Pro
145                 150                 155                 160

Tyr Glu Arg

<210> SEQ ID NO 25
<211> LENGTH: 208
<212> TYPE: PRT
<213> ORGANISM: Streptococcus sanguis

<400> SEQUENCE: 25

Asp Val Val Leu Glu Lys Ser Asp Ile Glu Lys Phe Lys Asn Gln Leu
1               5                   10                  15

Arg Thr Glu Leu Thr Asn Ile Asp His Ser Tyr Leu Lys Gly Ile Asp
            20                  25                  30

Ile Ala Ser Lys Lys Thr Ser Asn Val Glu Asn Thr Glu Phe Glu
        35                  40                  45

Ala Ile Ser Thr Lys Ile Phe Thr Asp Glu Leu Gly Phe Ser Gly Lys
    50                  55                  60

His Leu Gly Gly Ser Asn Lys Pro Asp Gly Leu Leu Trp Asp Asp
65                  70                  75                  80

Cys Ala Ile Ile Leu Asp Ser Lys Ala Tyr Ser Glu Gly Phe Pro Leu
                85                  90                  95

Thr Ala Ser His Thr Asp Ala Met Gly Arg Tyr Leu Arg Gln Phe Thr
            100                 105                 110

Glu Arg Lys Glu Glu Ile Lys Pro Thr Trp Trp Asp Ile Ala Pro Glu
        115                 120                 125

His Leu Asp Asn Thr Tyr Phe Ala Tyr Val Ser Gly Ser Phe Ser Gly
    130                 135                 140

Asn Tyr Lys Glu Gln Leu Gln Lys Phe Arg Gln Asp Thr Asn His Leu
145                 150                 155                 160

Gly Gly Ala Leu Glu Phe Val Lys Leu Leu Leu Ala Asn Asn Tyr
                165                 170                 175

Lys Thr Gln Lys Met Ser Lys Lys Glu Val Lys Ser Ile Leu Asp
            180                 185                 190
```

```
Tyr Asn Ile Ser Tyr Glu Glu Tyr Ala Pro Leu Leu Ala Glu Ile Glu
        195                 200                 205
```

```
<210> SEQ ID NO 26
<211> LENGTH: 196
<212> TYPE: PRT
<213> ORGANISM: Flavobacterium okeanokoites

<400> SEQUENCE: 26

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Glu Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195
```

```
<210> SEQ ID NO 27
<211> LENGTH: 7903
<212> TYPE: DNA
<213> ORGANISM: Artificial sequence
<220> FEATURE:
<223> OTHER INFORMATION: pCAG-ArtTal1-AlwI

<400> SEQUENCE: 27
gacattgatt attgactagt tattaatagt aatcaattac ggggtcatta gttcatagcc    60
catatatgga gttccgcgtt acataactta cggtaaatgg cccgcctggc tgaccgccca   120 acgaccccg cccattgacg tcaataatga cgtatgttcc catagtaacg ccaatagga    180 ctttccattg acgtcaatgg gtggagtatt tacggtaaac tgcccacttg gcagtacatc   240
aagtgtatca tatgccaagt acgcccccta ttgacgtcaa tgacggtaaa tggcccgcct   300
ggcattatgc ccagtacatg accttatggg actttcctac ttggcagtac atctacgtat   360
tagtcatcgc tattaccatg gtcgaggtga gccccacgtt ctgcttcact ctccccatct   420
cccccccctc ccacccccca attttgtatt tatttatttt ttaattattt tgtgcagcga   480
tgggggcggg ggggggggg gggcgcgcgc caggcggggc gggcggggc gaggggcggg    540 gcggggcgag gcggagaggt gcggcggcag ccaatcagag cggcgcgctc cgaaagtttc   600
```

```
cttttatggc gaggcggcgg cggcggcggc cctataaaaa gcgaagcgcg cggcgggcgg    660
gagtcgctgc gcgctgcctt cgccccgtgc cccgctccgc cgccgcctcg cgccgcccgc    720
cccggctctg actgaccgcg ttactcccac aggtgagcgg gcgggacggc ccttctcctc    780
cgggctgtaa ttagcgcttg gtttaatgac ggcttgtttc ttttctgtgg ctgcgtgaaa    840
gccttgaggg gctccgggag ggccctttgt gcggggggga gcggctcggg gggtgcgtgc    900
gtgtgtgtgt gcgtggggag cgccgcgtgc ggctccgcgc tgcccggcgg ctgtgagcgc    960
tgcgggcgcg gcgcggggct tgtgcgctc cgcagtgtgc gcgaggggag cgcggccggg    1020
ggcggtgccc cgcggtgcgg gggggctgc gaggggaaca aaggctgcgt gcggggtgtg    1080
tgcgtggggg ggtgagcagg gggtgtgggc gcgtcggtcg ggctgcaacc ccccctgcac    1140
cccccctcccc gagttgctga gcacggcccg gcttcgggtg cggggctccg tacgggggcgt   1200
ggcgcggggc tcgccgtgcc gggcgggggg tggcggcagg tgggggtgcc gggcggggcg    1260
gggccgcctc gggccgggga gggctcgggg gaggggcgcg gcggccccg gagcgccggc    1320
ggctgtcgag gcgcggcgag ccgcagccat tgccttttat ggtaatcgtg cgagagggcg    1380
cagggacttc ctttgtccca aatctgtgcg gagccgaaat ctgggaggcg ccgccgcacc    1440
ccctctagcg ggcgcggggc gaagcggtgc ggcgccggca ggaaggaaat gggcggggag    1500
ggccttcgtg cgtcgccgcg ccgccgtccc cttctccctc tccagcctcg gggctgtccg    1560
cggggggacg gctgccttcg ggggggacgg ggcagggcgg ggttcggctt ctggcgtgtg    1620
accggcggct ctagagcctc tgctaaccat gttcatgcct tcttcttttt cctacagatc    1680
cttaattaat aatacgactc actatagggg ccgccaccat gggacctaag aaaaagagga    1740
aggtggcggc cgctgactac aaggatgacg acgataaacc aggtggcgga ggtagtggcg    1800
gaggtggggt acccgccagt ccagcagccc aggtggatct gagaaccctc ggctacagcc    1860
agcagcagca ggagaagatc aaaccaaagg tgcggtccac cgtcgctcag caccatgaag    1920
cactggtggg gcacggtttc acacacgccc atattgtggc tctgtctcag catcccgctg    1980
cactcgggac tgtggccgtc aaatatcagg acatgatcgc cgctctgcct gaggcaaccc    2040
acgaagccat tgtgggcgtc ggaaagcagt ggagcggtgc cagagcactc gaagcactcc    2100
tcaccgtcgc cggggaactg cggggtccac cactccagtc cggactggac actggacagc    2160
tgctgaagat cgctaaacgc ggcggagtga cagctgtgga agctgtgcac gcttggagga    2220
atgctctgac aggagcccca ctgaatctta ctccagaaca ggtcgtcgca atcgcaagta    2280
acatcggcgg aaaacaggcc ctcgaaaccg tccagagact cctccccgtg ctgtgccagg    2340
cccacggact gaccccacag caggtggtcg ccatcgctag caacggcgga gggaagcagg    2400
ctctggagac cgtgcagagg ctgctccccg tcctgtgcca ggcacatggg ctcacacctc    2460
agcaggtggt cgcaattgcc tccaatggtg gcggaaaaca ggccctggaa actgtgcaga    2520
gactgctccc cgtgctgtgc aggctcacg gtctcacacc ccagcaggtg gtcgctatcg    2580
catctcatga cggggggcaag caggcactgg agacagtgca gcggctgctc cctgtcctgt    2640
gccaggccca cggactcact cctcagcagg tcgtcgccat tgctagtaac ggcggaggga    2700
aacaggctct ggaaaccgtg cagcgcctgc tccccgtgct gtgccaagcc acggcctga    2760
cccccccagca ggtggtcgca atcgcctcaa acaatggtgg caagcaggcc ctggagactg    2820
tgcagcgact gctcccagtg ctgtgccagg cccatggact cacaccacag caggtcgtcg    2880
ctattgcaag caacaatgga gggaaacagg cactggaaac agtccagagg ctgctccccg    2940
```

```
tgctgtgcca agcgcatgga ctcactcccc agcaggtcgt cgccatcgct tccaataacg   3000
gcggcaagca ggccctggag accgtccaga gactgctccc cgtgctgtgc caagctcacg   3060
gactcacacc tgagcaggtc gtggcaatcg cctctaacat tggagggaaa caggccctgg   3120
aaactgtaca gcggctgctc cccgtgctgt gccaagcaca cggactcact ccacagcagg   3180
tcgtggccat tgcaagtcat gacggaggca agcaggccct ggaaacagtg cagcgcctgc   3240
tccctgtgct gtgccaggct catggtctga ctcctcagca ggtggtggcc atcgcttcca   3300
acaatggagg gaagcaggcc ctggagaccg tacagagact gctccccgtg ctgtgccaag   3360
cgcacggtct gacccctcag caggtcgtcg caatcgccag caatggcggg ggcaagcagg   3420
ctctcgaaac cgtccagcgg ctcctcccag tcctctgtca ggctcacggc ctgacccac    3480 agcaggtcgt cgctattgct tctaatggcg agggcggcc tgctctggag agcattgtgg    3540
ctcagctgtc caggcccgat cctgccctgg ctagatccgc actcactaac gatcatctgg   3600
tcgctctcgc ttgcctcggt ggacggcccg ctctggacgc agtcaaaaag ggtctccccc   3660
atgctcccgc actgatcaag agaaccaaca ggagaattcc tgagggatcc gatcgtttaa   3720
acaaagagac taatatcctc ctcgtcgagc agctggaaga gaccctcaat cgcaatcgca   3780
ttctgtttga aaagaactcc tcaatcgcac aggccccaat tggcgagatc aagaactacc   3840
ggtatcacct ggaggaactg ctcttcgaga acaatgaaaa gaaatttgca gagaaccaga   3900
aaaatgagtg ggacgaaatt ctggcctaca tggatctgct catctcaccc aagcctatca   3960
gcattgagat cgctgacaaa gaaatttcta tcccaagtgg ggagcgaccc gcatatttcg   4020
aatgggtgct gtggagggca tttctggccc tcaaccacct gatcattgag ccccagcagt   4080
gcaggagatt caaggtcgac caggacttca gcctatcca taatgctcca ggcggagggg   4140
cagatgtgat tttcgagtac gaaaacttta agatcctggg cgaggtcacc ctcacaagca   4200
attcccgaca ggaagcagct gagggagaac ccgtgcggcg ccatattgcc gtggagacag   4260
tcaacactcc tgacaaggat gtctatggac tgttcctcgc tctgaccatc gacactaata   4320
ccgccgagac atttcgacac ggggcttggt atcaccagga ggaactgatg gatgtgaaga   4380
ttctccccct gactctcgag tccttcaaga agtatctgga atctctcaga agaaaaaatc   4440
aggtggagac aggaatcttt gacctgaaga aaatgatgga tgaaagcctg aagctccggg   4500
aaaccctgac cgcaccccag tggaaaaatg aaatcacaaa caattcgcc agaccaatct    4560 gaacgcgtaa atgattgcag atccactagt tctagaattc cagctgagcg ccggtcgcta   4620
ccattaccag ttggtctggt gtcaaaaata ataataaccg gcagggggg atctgcatgg    4680 atctttgtga aggaacctta cttctgtggt gtgacataat tggacaaact acctacagag   4740
atttaaagct ctaaggtaaa tataaaattt ttaagtgtat aatgtgttaa actactgatt   4800
ctaattgttt gtgtatttta gattccaacc tatggaactg atgaatggga gcagtggtgg   4860
aatgccagat ccagacatga taagatacat tgatgagttt ggacaaacca caactagaat   4920
gcagtgaaaa aaatgcttta tttgtgaaat tgtgatgct attgctttat tgtaaccat    4980 tataagctgc aataaacaag ttaacaacaa caattgcatt catttatgt ttcaggttca    5040 ggggagggtg tgggaggttt tttaaagcaa gtaaaacctc tacaaatgtg gtatggctga   5100
ttatgatctg cggccgccac tggccgtcgt tttacaacgt cgtgactggg aaaaccctgg   5160
cgttacccaa cttaatcgcc ttgcagcaca tccccctttc gccagctggc gtaatagcga   5220
agaggcccgc accgatcgcc cttcccaaca gttgcgcagc ctgaatggcg aatggaacgc   5280
gccctgtagc ggcgcattaa gcgcggcggg tgtggtggtt acgcgcagcg tgaccgctac   5340
```

```
acttgccagc gccctagcgc ccgctccttt cgctttcttc ccttcctttc tcgccacgtt    5400
cgccggcttt ccccgtcaag ctctaaatcg ggggctccct ttagggttcc gatttagtgc    5460
tttacggcac ctcgacccca aaaaacttga ttagggtgat ggttcacgta gtgggccatc    5520 gcccctgatag acgttttttc gcccttttgac gttggagtcc acgttcttta atagtggact   5580
cttgttccaa actggaacaa cactcaaccc tatctcggtc tattcttttg atttataagg    5640
gattttgccg atttcggcct attggttaaa aaatgagctg atttaacaaa aatttaacgc    5700
gaattttaac aaaatattaa cgcttacaat ttaggtggca cttttcgggg aaatgtgcgc    5760 ggaacccta tttgtttatt tttctaaata cattcaaata tgtatccgct catgagacaa    5820
taaccctgat aaatgcttca ataatattga aaaggaaga gtatgagtat caacatttc     5880 cgtgtcgccc ttattccctt ttttgcggca ttttgccttc ctgttttgc tcacccagaa     5940 acgctggtga agtaaaaga tgctgaagat cagttgggtg cacgagtggg ttacatcgaa    6000
ctggatctca acagcggtaa gatccttgag agttttcgcc ccgaagaacg ttttccaatg   6060
atgagcactt ttaaagttct gctatgtggc gcggtattat cccgtattga cgccgggcaa    6120
gagcaactcg gtcgccgcat acactattct cagaatgact tggttgagta ctcaccagtc    6180
acagaaaagc atcttacgga tggcatgaca gtaagagaat tatgcagtgc tgccataacc    6240
atgagtgata acactgcggc caacttactt ctgacaacga tcggaggacc gaaggagcta    6300
accgcttttt tgcacaacat gggggatcat gtaactcgcc ttgatcgttg ggaaccggag    6360
ctgaatgaag ccataccaaa cgacgagcgt gacaccacga tgcctgtagc aatggcaaca    6420
acgttgcgca aactattaac tggcgaacta cttactctag cttcccggca acaattaata    6480
gactggatgg aggcggataa agttgcagga ccacttctgc gctcggccct tccggctggc    6540
tggtttattg ctgataaatc tggagccggt gagcgtgggt ctcgcggtat cattgcagca    6600
ctggggccag atggtaagcc ctcccgtatc gtagttatct acacgacggg gagtcaggca    6660
actatggatg aacgaaatag acagatcgct gagataggtg cctcactgat taagcattgg    6720
taactgtcag accaagttta ctcatatata ctttagattg atttaaaact tcatttttaa    6780
tttaaaagga tctaggtgaa gatcctttt gataatctca tgaccaaaat cccttaacgt    6840
gagttttcgt tccactgagc gtcagacccc gtagaaaaga tcaaaggatc ttcttgagat    6900 ccttttttc tgcgcgtaat ctgctgcttg caaacaaaaa aaccaccgct accagcggtg    6960
gtttgtttgc cggatcaaga gctaccaact cttttccga aggtaactgg cttcagcaga    7020
gcgcagatac caaatactgt ccttctagtg tagccgtagt taggccacca cttcaagaac    7080
tctgtagcac cgcctacata cctcgctctg ctaatcctgt taccagtggc tgctgccagt    7140
ggcgataagt cgtgtcttac cgggttggac tcaagacgat agttaccgga taaggcgcag    7200
cggtcgggct gaacggggg ttcgtgcaca cagcccagct tggagcgaac gacctacacc     7260
gaactgagat acctacagcg tgagctatga gaaagcgcca cgcttcccga agggagaaag    7320
gcggacaggt atccggtaag cggcagggtc ggaacaggag agcgcacgag ggagcttcca    7380
gggggaaacg cctggtatct ttatagtcct gtcgggtttc gccacctctg acttgagcgt    7440
cgatttttgt gatgctcgtc aggggggcgg agcctatgga aaaacgccag caacgcggcc    7500 ttttttacggt tcctggcctt ttgctggcct tttgctcaca tgttctttcc tgcgttatcc    7560
cctgattctg tggataaccg tattaccgcc tttgagtgag ctgataccgc tcgccgcagc    7620
cgaacgaccg agcgcagcga gtcagtgagc gaggaagcgg aagagcgccc aatacgcaaa    7680
```

| | |
|---|---:|
| ccgcctctcc ccgcgcgttg gccgattcat taatgcagct ggcacgacag gtttcccgac | 7740 |
| tggaaagcgg gcagtgagcg caacgcaatt aatgtgagtt agctcactca ttaggcaccc | 7800 |
| caggctttac actttatgct tccggctcgt atgttgtgtg gaattgtgag cggataacaa | 7860 |
| tttcacacag gaaacagcta tgaccatgag gcgcgccgga ttc | 7903 |

<210> SEQ ID NO 28
<211> LENGTH: 7669
<212> TYPE: DNA
<213> ORGANISM: Artificial sequence
<220> FEATURE:
<223> OTHER INFORMATION: pCAG-ArtTal1-CLEDORF

<400> SEQUENCE: 28

| | |
|---|---:|
| gacattgatt attgactagt tattaatagt aatcaattac ggggtcatta gttcatagcc | 60 |
| catatatgga gttccgcgtt acataactta cggtaaatgg cccgcctggc tgaccgccca | 120 |
| acgaccccg cccattgacg tcaataatga cgtatgttcc catagtaacg ccaataggga | 180 |
| ctttccattg acgtcaatgg gtggagtatt tacggtaaac tgcccacttg gcagtacatc | 240 |
| aagtgtatca tatgccaagt acgccccta ttgacgtcaa tgacggtaaa tggcccgcct | 300 |
| ggcattatgc ccagtacatg accttatggg actttcctac ttggcagtac atctacgtat | 360 |
| tagtcatcgc tattaccatg gtcgaggtga gccccacgtt ctgcttcact ctccccatct | 420 |
| ccccccctc cccaccccca attttgtatt tatttatttt ttaattattt tgtgcagcga | 480 |
| tgggggcggg ggggggggg gggcgcgcgc caggcggggc gggcggggc gaggggcggg | 540 |
| gcggggcgag gcggagaggt gcggcggcag ccaatcagag cggcgcgctc cgaaagtttc | 600 |
| cttttatggc gaggcggcgg cggcggcggc cctataaaaa gcgaagcgcg cggcgggcgg | 660 |
| gagtcgctgc gcgctgcctt cgccccgtgc ccgctccgc cgccgcctcg cgccgcccgc | 720 |
| cccggctctg actgaccgcg ttactcccac aggtgagcgg gcgggacggc ccttctcctc | 780 |
| cgggctgtaa ttagcgcttg gtttaatgac ggcttgtttc ttttctgtgg ctgcgtgaaa | 840 |
| gccttgaggg gctccgggag ggccctttgt gcggggggga gcggctcggg gggtgcgtgc | 900 |
| gtgtgtgtgt gcgtggggag cgccgcgtgc ggctccgcgc tgcccggcgg ctgtgagcgc | 960 |
| tgcgggcgcg gcgcggggct ttgtgcgctc cgcagtgtgc gcgaggggag cgcggccggg | 1020 |
| ggcggtgccc cgcggtgcgg gggggctgc gaggggaaca aaggctgcgt gcggggtgtg | 1080 |
| tgcgtggggg ggtgagcagg gggtgtgggc gcgtcggtcg ggctgcaacc ccccctgcac | 1140 |
| ccccctcccc gagttgctga gcacggcccg gcttcgggtg cggggctccg tacgggcgt | 1200 |
| ggcgcgggc tcgccgtgcc gggcgggggg tggcggcagg tgggggtgcc gggcggggcg | 1260 |
| gggccgcctc gggccgggga gggctcgggg gagggcgcg gcggccccg gagcgccggc | 1320 |
| ggctgtcgag gcgcggcgag ccgcagccat tgccttttat ggtaatcgtg cgagagggcg | 1380 |
| cagggacttc ctttgtccca aatctgtgcg gagccgaaat ctgggaggcg ccgccgcacc | 1440 |
| ccctctagcg ggcgcgggc gaagcggtgc ggcgccggca ggaaggaaat gggcgggag | 1500 |
| ggccttcgtg cgtcgccgcg ccgccgtccc cttctccctc tccagcctcg ggctgtccg | 1560 |
| cggggggacg gctgccttcg gggggacgg ggcaggcgg ggttcggctt ctggcgtgtg | 1620 |
| accggcggct ctagagcctc tgctaaccat gttcatgcct tcttcttttt cctacagatc | 1680 |
| cttaattaat aatacgactc actataggg ccgccaccat gggacctaag aaaaagagga | 1740 |
| aggtggcggc cgctgactac aaggatgacg acgataaacc aggtgcggga ggtagtggcg | 1800 |
| gaggtggggt accgccagt ccagcagccc aggtggatct gagaacctc ggctacagcc | 1860 |

```
agcagcagca ggagaagatc aaaccaaagg tgcggtccac cgtcgctcag caccatgaag     1920
cactggtggg gcacggtttc acacacgccc atattgtggc tctgtctcag catcccgctg     1980
cactcgggac tgtggccgtc aaatatcagg acatgatcgc cgctctgcct gaggcaaccc     2040
acgaagccat tgtgggcgtc ggaaagcagt ggagcggtgc cagagcactc gaagcactcc     2100
tcaccgtcgc cggggaactg cggggtccac cactccagtc cggactggac actggacagc     2160
tgctgaagat cgctaaacgc ggcggagtga cagctgtgga agctgtgcac gcttggagga     2220
atgctctgac aggagcccca ctgaatctta ctccagaaca ggtcgtcgca atcgcaagta     2280
acatcggcgg aaaacaggcc ctcgaaaccg tccagagact cctccccgtg ctgtgccagg     2340
cccacggact gaccccacag caggtggtcg ccatcgctag caacggcgga gggaagcagg     2400
ctctggagac cgtgcagagg ctgctccccg tcctgtgcca ggcacatggg ctcacacctc     2460
agcaggtggt cgcaattgcc tccaatggtg gcggaaaaca ggccctggaa actgtgcaga     2520
gactgctccc cgtgctgtgc caggctcacg gtctcacacc ccagcaggtg gtcgctatcg     2580
catctcatga cgggggcaag caggcactgg agacagtgca gcggctgctc cctgtcctgt     2640
gccaggccca cggactcact cctcagcagg tcgtcgccat tgctagtaac ggcggaggga     2700
aacaggctct ggaaaccgtg cagcgcctgc tccccgtgct gtgccaagcc cacggcctga     2760 cccccccagca ggtggtcgca atcgcctcaa acaatggtgg caagcaggcc ctggagactg     2820
tgcagcgact gctcccagtg ctgtgccagg cccatggact cacaccacag caggtcgtcg     2880
ctattgcaag caacaatgga gggaaacagg cactggaaac agtccagagg ctgctccccg     2940
tgctgtgcca agcgcatgga ctcactcccc agcaggtcgt cgccatcgct tccaataacg     3000
gcggcaagca ggccctggag accgtccaga gactgctccc cgtgctgtgc caagctcacg     3060
gactcacacc tgagcaggtc gtggcaatcg cctctaacat tggagggaaa caggccctgg     3120
aaactgtaca gcggctgctc cccgtgctgt gccaagcaca cggactcact ccacagcagg     3180
tcgtggccat tgcaagtcat gacggaggca agcaggccct ggaaacagtg cagcgcctgc     3240
tccctgtgct gtgccaggct catggtctga ctcctcagca ggtggtggcc atcgcttcca     3300
acaatggagg gaagcaggcc ctggagaccg tacagagact gctccccgtg ctgtgccaag     3360
cgcacggtct gacccctcag caggtcgtcg caatcgccag caatggcggg ggcaagcagg     3420
ctctcgaaac cgtccagcgg ctcctcccag tcctctgtca ggctcacggc ctgacccacac     3480 agcaggtcgt cgctattgct tctaatggcg gagggcggcc tgctctggag agcattgtgg     3540
ctcagctgtc caggcccgat cctgccctgg ctagatccgc actcactaac gatcatctgg     3600
tcgctctcgc ttgcctcggt ggacggcccg ctctggacgc agtcaaaaag ggtctccccc     3660
atgctcccgc actgatcaag agaaccaaca ggagaattcc tgagggatcc gatcgtttaa     3720
acaagctcgc aaagtcaagc cagtccgaaa caaaggaaaa actcagagaa aaactcagaa     3780
acctgcccca tgaatacctg tccctcgtcg acctggccta cgattcaaag cagaaccgcc     3840
tctttgagat gaaagtgatc gaactgctca gaggaatgcg ggttccag ggtctgcacc     3900 tcggcggaag caggagacca gacggcgtcc tgtacaccgc cggactcaca gacaactatg     3960
ggatcattct ggatactaag gcttacagct ccggatattc cctgcccatt gcccaggctg     4020
acgagatgga acgtacgtg cgcgagaatc agactagaga tgaactggtc aaccctaatc     4080
agtggtggga gaactttgaa aatggcctgg gaaccttcta ttttctcttc gtggctgggc     4140
atttcaacgg taatgtccag gcacagctgg agcgaatcag taggaatacc ggcgtgctgg     4200
```

```
gagccgctgc atctatcagt cagctgctcc tgctcgcaga cgccattaga gggggtcgga   4260
tggatagaga gagactgcgg cacctcatgt ttcagaacga agagtttctg ctggaacagg   4320
agctgtgaac gcgtaaatga ttgcagatcc actagttcta gaattccagc tgagcgccgg   4380
tcgctaccat taccagttgg tctggtgtca aaaataataa taaccgggca gggggggatct   4440
gcatggatct ttgtgaagga accttacttc tgtggtgtga cataattgga caaactacct   4500
acagagattt aaagctctaa ggtaaatata aaattttttaa gtgtataatg tgttaaacta   4560
ctgattctaa ttgtttgtgt attttagatt ccaacctatg gaactgatga atgggagcag   4620
tggtggaatg ccagatccag acatgataag atacattgat gagtttggac aaaccacaac   4680
tagaatgcag tgaaaaaaat gctttatttg tgaaatttgt gatgctattg ctttatttgt   4740
aaccattata agctgcaata aacaagttaa caacaacaat tgcattcatt ttatgtttca   4800
ggttcagggg gaggtgtggg aggttttttta aagcaagtaa aacctctaca aatgtggtat   4860
ggctgattat gatctgcggc cgccactggc cgtcgtttta caacgtcgtg actgggaaaa   4920
ccctggcgtt acccaactta atcgccttgc agcacatccc cctttcgcca gctggcgtaa   4980
tagcgaagag gcccgcaccg atcgcccttc ccaacagttg cgcagcctga atggcgaatg   5040
gaacgcgccc tgtagcggcg cattaagcgc ggcgggtgtg gtggttacgc gcagcgtgac   5100
cgctacactt gccagcgccc tagcgcccgc tcctttcgct ttcttccctt cctttctcgc   5160
cacgttcgcc ggctttcccc gtcaagctct aaatcggggg ctccctttag ggttccgatt   5220
tagtgcttta cggcacctcg accccaaaaa acttgattag ggtgatggtt cacgtagtgg   5280
gccatcgccc tgatagacgg ttttttcgccc tttgacgttg gagtccacgt tctttaatag   5340
tggactcttg ttccaaactg gaacaacact caaccctatc tcggtctatt cttttgattt   5400
ataagggatt ttgccgattt cggcctattg gttaaaaaat gagctgattt aacaaaaatt   5460
taacgcgaat tttaacaaaa tattaacgct tacaatttag gtggcacttt tcggggaaat   5520
gtgcgcggaa cccctatttg tttatttttc taaatacatt caaatatgta tccgctcatg   5580
agacaataac cctgataaat gcttcaataa tattgaaaaa ggaagagtat gagtattcaa   5640
catttccgtg tcgcccttat tccctttttt gcggcatttt gccttcctgt ttttgctcac   5700
ccagaaacgc tggtgaaagt aaaagatgct gaagatcagt tgggtgcacg agtgggttac   5760
atcgaactgg atctcaacag cggtaagatc cttgagagtt ttcgccccga agaacgtttt   5820
ccaatgatga gcacttttaa agttctgcta tgtggcgcgg tattatcccg tattgacgcc   5880
gggcaagagc aactcggtcg ccgcatacac tattctcaga atgacttggt tgagtactca   5940
ccagtcacag aaaagcatct tacggatggc atgacagtaa gagaattatg cagtgctgcc   6000
ataaccatga gtgataacac tgcggccaac ttacttctga caacgatcgg aggaccgaag   6060
gagctaaccg cttttttgca caacatgggg gatcatgtaa ctcgccttga tcgttgggaa   6120
ccggagctga atgaagccat accaaacgac gagcgtgaca ccacgatgcc tgtagcaatg   6180
gcaacaacgt tgcgcaaact attaactggc gaactactta ctctagcttc ccggcaacaa   6240
ttaatagact ggatggaggc ggataaagtt gcaggaccac ttctgcgctc ggcccttccg   6300
gctggctggt ttattgctga taaatctgga gccggtgagc gtgggtctcg cggtatcatt   6360
gcagcactgg ggccagatgg taagccctcc cgtatcgtag ttatctacac gacggggagt   6420
caggcaacta tggatgaacg aaatagacag atcgctgaga taggtgcctc actgattaag   6480
cattggtaac tgtcagacca agtttactca tatatacttt agattgattt aaaacttcat   6540
ttttaattta aaaggatcta ggtgaagatc ctttttgata atctcatgac caaaatccct   6600
```

```
taacgtgagt tttcgttcca ctgagcgtca gacccgtag aaaagatcaa aggatcttct    6660
tgagatcctt tttttctgcg cgtaatctgc tgcttgcaaa caaaaaaacc accgctacca    6720
gcggtggttt gtttgccgga tcaagagcta ccaactcttt ttccgaaggt aactggcttc    6780
agcagagcgc agataccaaa tactgtcctt ctagtgtagc cgtagttagg ccaccacttc    6840
aagaactctg tagcaccgcc tacatacctc gctctgctaa tcctgttacc agtggctgct    6900
gccagtggcg ataagtcgtg tcttaccggg ttggactcaa gacgatagtt accggataag    6960
gcgcagcggt cgggctgaac ggggggttcg tgcacacagc ccagcttgga gcgaacgacc    7020
tacaccgaac tgagatacct acagcgtgag ctatgagaaa gcgccacgct tcccgaaggg    7080
agaaaggcgg acaggtatcc ggtaagcggc agggtcggaa caggagagcg cacgagggag    7140
cttccagggg gaaacgcctg gtatctttat agtcctgtcg ggtttcgcca cctctgactt    7200
gagcgtcgat ttttgtgatg ctcgtcaggg gggcggagcc tatggaaaaa cgccagcaac    7260
gcggcctttt tacggttcct ggccttttgc tggccttttg ctcacatgtt ctttcctgcg    7320
ttatcccctg attctgtgga taaccgtatt accgcctttg agtgagctga taccgctcgc    7380
cgcagccgaa cgaccgagcg cagcgagtca gtgagcgagg aagcggaaga gcgcccaata    7440
cgcaaaccgc ctctccccgc gcgttggccg attcattaat gcagctggca cgacaggttt    7500
cccgactgga aagcgggcag tgagcgcaac gcaattaatg tgagttagct cactcattag    7560 gcacccagg ctttacactt tatgcttccg gctcgtatgt tgtgtggaat tgtgagcgga    7620
taacaatttc acacaggaaa cagctatgac catgaggcgc gccggattc          7669

<210> SEQ ID NO 29
<211> LENGTH: 7663
<212> TYPE: DNA
<213> ORGANISM: Artificial sequence
<220> FEATURE:
<223> OTHER INFORMATION: pCAG-ArtTal1-Clo051

<400> SEQUENCE: 29
gacattgatt attgactagt tattaatagt aatcaattac ggggtcatta gttcatagcc      60
catatatgga gttccgcgtt acataactta cggtaaatgg cccgcctggc tgaccgccca     120
acgacccccg cccattgacg tcaataatga cgtatgttcc catagtaacg ccaatagga     180 ctttccattg acgtcaatgg gtggagtatt tacggtaaac tgcccacttg gcagtacatc     240
aagtgtatca tatgccaagt acgccccta ttgacgtcaa tgacggtaaa tggcccgcct     300
ggcattatgc ccagtacatg accttatggg actttcctac ttggcagtac atctacgtat     360
tagtcatcgc tattaccatg gtcgaggtga gccccacgtt ctgcttcact ctccccatct     420
cccccccctc ccacccccca atttgtatt tatttatttt ttaattattt tgtgcagcga     480
tgggggcggg gggggggggg gggcgcgcgc caggcggggc gggcggggc gagggcggg     540 gcggggcgag gcgagaggt gcggcggcag ccaatcagag cggcgcgctc cgaaagtttc     600
cttttatggc gaggcggcgg cggcggcggc cctataaaa gcgaagcgcg cggcgggcgg     660
gagtcgctgc gcgctgcctt cgccccgtgc cccgctccgc cgccgcctcg cgccgcccgc     720
cccggctctg actgaccgcg ttactcccac aggtgagcgg gcgggacggc ccttctcctc     780
cgggctgtaa ttagcgcttg gtttaatgac ggcttgtttc ttttctgtgg ctgcgtgaaa     840
gccttgaggg gctccgggag ggccctttgt gcggggggga gcggctcggg gggtgcgtgc     900
gtgtgtgtgt gcgtggggag cgccgcgtgc ggctccgcgc tgcccggcgg ctgtgagcgc     960
```

```
                                                    -continued tgcgggcgcg gcgcggggct tgtgcgctc cgcagtgtgc gcgagggag cgcggccggg    1020 ggcggtgccc cgcggtgcgg gggggctgc gagggaaca aaggctgcgt gcgggtgtg     1080 tgcgtgggg  ggtgagcagg gggtgtgggc gcgtcggtcg ggctgcaacc ccccctgcac   1140
ccccctcccc gagttgctga gcacggcccg gcttcgggtg cggggctccg tacgggcgt    1200 ggcgcgggc  tcgccgtgcc gggcggggg  tggcggcagg tggggtgcc  gggcggggcg   1260 gggccgcctc gggccggga  gggctcgggg gaggggcgcg gcggccccg  gagcgccggc   1320 ggctgtcgag gcgcggcgag ccgcagccat tgccttttat ggtaatcgtg cgagagggcg   1380
cagggacttc ctttgtccca aatctgtgcg gagccgaaat ctgggaggcg ccgccgcacc   1440
ccctctagcg ggcgcgggc  gaagcggtgc ggcgccggca ggaaggaaat gggcggggag   1500
ggccttcgtg cgtcgccgcg ccgccgtccc cttctccctc tccagcctcg ggctgtccg    1560 cgggggacg  gctgccttcg gggggacgg  ggcagggcgg ggttcggctt ctggcgtgtg   1620
accggcggct ctagagcctc tgctaaccat gttcatgcct tcttctttt  cctacagatc    1680 cttaattaat aatacgactc actatagggg ccgccaccat gggacctaag aaaaagagga   1740
aggtggcggc cgctgactac aaggatgacg acgataaacc aggtggcgga ggtagtggcg   1800
gaggtggggt acccgccagt ccagcagccc aggtggatct gagaaccctc ggctacagcc   1860
agcagcagca ggagaagatc aaaccaaagg tgcggtccac cgtcgctcag caccatgaag   1920
cactggtggg gcacggtttc acacacgccc atattgtggc tctgtctcag catcccgctg   1980
cactcgggac tgtggccgtc aaatatcagg acatgatcgc cgctctgcct gaggcaaccc   2040
acgaagccat tgtgggcgtc ggaaagcagt ggagcggtgc cagagcactc gaagcactcc   2100
tcaccgtcgc cggggaactg cggggtccac cactccagtc cggactggac actggacagc   2160
tgctgaagat cgctaaacgc ggcggagtga cagctgtgga agctgtgcac gcttggagga   2220
atgctctgac aggagcccca ctgaatctta ctccagaaca ggtcgtcgca atcgcaagta   2280
acatcggcgg aaaacaggcc ctcgaaaccg tccagagact cctccccgtg ctgtgccagg   2340
cccacggact gaccccacag caggtggtcg ccatcgctag caacggcgga gggaagcagg   2400
ctctggagac cgtgcagagg ctgctccccg tcctgtgcca ggcacatggg ctcacacctc   2460
agcaggtggt cgcaattgcc tccaatggtg gcggaaaaca ggccctggaa actgtgcaga   2520
gactgctccc cgtgctgtgc caggctcacg gtctcacacc ccagcaggtg gtcgctatcg   2580
catctcatga cggggcaag  caggcactgg agacagtgca gcggctgctc cctgtcctgt   2640
gccaggccca cggactcact cctcagcagg tcgtcgccat tgctagtaac ggcggaggga   2700
aacaggctct ggaaaccgtg cagcgcctgc tccccgtgct gtgccaagcc cacggcctga   2760 cccccagca  ggtggtcgca atcgcctcaa acaatggtgg caagcaggcc ctggagactg   2820
tgcagcgact gctcccagtg ctgtgccagg cccatggact cacaccacag caggtcgtcg   2880
ctattgcaag caacaatgga gggaaacagg cactggaaac agtccagagg ctgctccccg   2940
tgctgtgcca agcgcatgga ctcactcccc agcaggtcgt cgccatcgct tccaataacg   3000
gcggcaagca ggccctggag accgtccaga gactgctccc cgtgctgtgc caagctcacg   3060
gactcacacc tgagcaggtc gtggcaatcg cctctaacat tggagggaaa caggccctgg   3120
aaactgtaca gcggctgctc cccgtgctgt gccaagcaca cggactcact ccacagcagg   3180
tcgtggccat tgcaagtcat gacggaggca agcaggccct ggaaacagtg cagcgcctgc   3240
tccctgtgct gtgccaggct catggtcgta ctcctcagca ggtggtggcc atcgcttcca   3300
acaatggagg gaagcaggcc ctggagaccg tacagagact gctccccgtg ctgtgccaag   3360
```

```
cgcacggtct gaccectcag caggtcgtcg caatcgccag caatggcggg ggcaagcagg   3420
ctctcgaaac cgtccagcgg ctcctcccag tcctctgtca ggctcacggc ctgaccccac   3480
agcaggtcgt cgctattgct tctaatggcg gagggcggcc tgctctggag agcattgtgg   3540
ctcagctgtc caggcccgat cctgccctgg ctagatccgc actcactaac gatcatctgg   3600
tcgctctcgc ttgcctcggt ggacggcccg ctctggacgc agtcaaaaag ggtctccccc   3660
atgctcccgc actgatcaag agaaccaaca ggagaattcc tgagggatcc gatcgtttaa   3720
acgaaggcat caaaagcaac atccctccc tgaaagacga actccggggg cagattagcc    3780
acattagtca cgaataccte tccctcatcg acctggcttt cgatagcaag cagaacaggc   3840
tctttgagat gaaagtgctg gaactgctcg tcaatgagta cgggttcaag ggtcgacacc   3900
tcggcggatc taggaaacca gacggcatcg tgtatagtac cacactggaa gacaactttg   3960
ggatcattgt ggataccaag gcatactctg agggttatag tctgcccatt tcacaggccg   4020
acgagatgga acgtacgtg cgcgagaact caaatagaga tgaggaagtc aaccctaaca    4080
agtggtggga gaacttctct gaggaagtga agaaatacta cttcgtcttt atcagcgggt   4140
ccttcaaggg taaatttgag gaacagctca ggagactgag catgactacc ggcgtgaatg   4200
gcagcgccgt caacgtggtc aatctgctcc tgggcgctga aaagattcgg agcggagaga   4260
tgaccatcga gagctggag agggcaatgt ttaataatag cgagtttatc ctgaaatact    4320
gaacgcgtaa atgattgcag atccactagt tctagaattc cagctgagcg ccggtcgcta   4380
ccattaccag ttggtctggt gtcaaaaata ataataaccg gcagggggg atctgcatgg    4440
atctttgtga aggaacctta cttctgtggt gtgacataat tggacaaact acctacagag   4500
atttaaagct ctaaggtaaa tataaaattt ttaagtgtat aatgtgttaa actactgatt   4560
ctaattgttt gtgtatttta gattccaacc tatggaactg atgaatggga gcagtggtgg   4620
aatgccagat ccagacatga taagatacat tgatgagttt ggacaaacca caactagaat   4680
gcagtgaaaa aaatgcttta tttgtgaaat ttgtgatgct attgctttat ttgtaaccat   4740
tataagctgc aataaacaag ttaacaacaa caattgcatt cattttatgt ttcaggttca   4800
gggggaggtg tgggaggttt tttaaagcaa gtaaaacctc tacaaatgtg gtatggctga   4860
ttatgatctg cggccgccac tggccgtcgt tttacaacgt cgtgactggg aaaaccctgg   4920
cgttacccaa cttaatcgcc ttgcagcaca tccccctttc gccagctggc gtaatagcga   4980
agaggcccgc accgatcgcc cttcccaaca gttgcgcagc ctgaatggcg aatggaacgc   5040
gccctgtagc ggcgcattaa gcgcggcggg tgtggtggtt acgcgcagcg tgaccgctac   5100
acttgccagc gccctagcgc ccgctccttt cgctttcttc ccttcctttc tcgccacgtt   5160
cgccggcttt cccgtcaag ctctaaatcg gggctccct ttagggttcc gatttagtgc     5220
tttacggcac ctcgacccca aaaaacttga ttagggtgat ggttcacgta gtgggccatc   5280
gccctgatag acggtttttc gccctttgac gttggagtcc acgttcttta atagtggact   5340
cttgttccaa actggaacaa cactcaaccc tatctcggtc tattcttttg atttataagg   5400
gattttgccg atttcggcct attggttaaa aatgagctg atttaacaaa aatttaacgc    5460
gaattttaac aaaatattaa cgcttacaat ttaggtggca cttttcgggg aaatgtgcgc   5520
ggaacccct a tttgtttatt tttctaaata cattcaaata tgtatccgct catgagacaa   5580
taaccctgat aaatgcttca ataatattga aaaaggaaga gtatgagtat tcaacatttc   5640
cgtgtcgccc ttattccctt ttttgcggca ttttgccttc ctgttttgc tcacccagaa    5700
```

```
acgctggtga aagtaaaaga tgctgaagat cagttgggtg cacgagtggg ttacatcgaa    5760
ctggatctca acagcggtaa gatccttgag agttttcgcc ccgaagaacg ttttccaatg    5820
atgagcactt ttaaagttct gctatgtggc gcggtattat cccgtattga cgccgggcaa    5880
gagcaactcg gtcgccgcat acactattct cagaatgact tggttgagta ctcaccagtc    5940
acagaaaagc atcttacgga tggcatgaca gtaagagaat tatgcagtgc tgccataacc    6000
atgagtgata acactgcggc caacttactt ctgacaacga tcggaggacc gaaggagcta    6060
accgcttttt tgcacaacat gggggatcat gtaactcgcc ttgatcgttg ggaaccggag    6120
ctgaatgaag ccataccaaa cgacgagcgt gacaccacga tgcctgtagc aatggcaaca    6180
acgttgcgca aactattaac tggcgaacta cttactctag cttcccggca acaattaata    6240
gactggatgg aggcggataa agttgcagga ccacttctgc gctcggccct tccggctggc    6300
tggtttattg ctgataaatc tggagccggt gagcgtgggt ctcgcggtat cattgcagca    6360
ctggggccag atggtaagcc ctcccgtatc gtagttatct acacgacggg gagtcaggca    6420
actatggatg aacgaaatag acagatcgct gagataggtg cctcactgat taagcattgg    6480
taactgtcag accaagttta ctcatatata ctttagattg atttaaaact tcatttttaa    6540
tttaaaagga tctaggtgaa gatcctttt gataatctca tgaccaaaat cccttaacgt    6600
gagttttcgt tccactgagc gtcagacccc gtagaaaaga tcaaaggatc ttcttgagat    6660
cctttttttc tgcgcgtaat ctgctgcttg caaacaaaaa aaccaccgct accagcggtg    6720
gtttgtttgc cggatcaaga ctaccaact cttttccga aggtaactgg cttcagcaga    6780
gcgcagatac caaatactgt ccttctagtg tagccgtagt taggccacca cttcaagaac    6840
tctgtagcac cgcctacata cctcgctctg ctaatcctgt taccagtggc tgctgccagt    6900
ggcgataagt cgtgtcttac cgggttggac tcaagacgat agttaccgga taaggcgcag    6960
cggtcgggct gaacggggg ttcgtgcaca gcccagct tggagcgaac gacctacacc    7020
gaactgagat acctacagcg tgagctatga gaaagcgcca cgcttcccga agggagaaag    7080
gcggacaggt atccggtaag cggcagggtc ggaacaggag agcgcacgag ggagcttcca    7140
gggggaaacg cctggtatct ttatagtcct gtcgggtttc gccacctctg acttgagcgt    7200
cgatttttgt gatgctcgtc agggggggcgg agcctatgga aaaacgccag caacgcggcc    7260
tttttacggt tcctggcctt ttgctggcct tttgctcaca tgttctttcc tgcgttatcc    7320
cctgattctg tggataaccg tattaccgcc tttgagtgag ctgataccgc tcgccgcagc    7380
cgaacgaccg agcgcagcga gtcagtgagc gaggaagcgg aagagcgccc aatacgcaaa    7440
ccgcctctcc ccgcgcgttg gccgattcat taatgcagct ggcacgacag gtttcccgac    7500
tggaaagcgg gcagtgagcg caacgcaatt aatgtgagtt agctcactca ttaggcaccc    7560
caggctttac actttatgct tccggctcgt atgttgtgtg gaattgtgag cggataacaa    7620
tttcacacag gaaacagcta tgaccatgag gcgcgccgga ttc    7663
```

<210> SEQ ID NO 30
<211> LENGTH: 7816
<212> TYPE: DNA
<213> ORGANISM: Artificial sequence
<220> FEATURE:
<223> OTHER INFORMATION: pCAG-ArtTal1-MlyI

<400> SEQUENCE: 30

```
gacattgatt attgactagt tattaatagt aatcaattac ggggtcatta gttcatagcc      60
catatatgga gttccgcgtt acataactta cggtaaatgg cccgcctggc tgaccgccca     120
```

```
acgaccccg  cccattgacg  tcaataatga  cgtatgttcc  catagtaacg  ccaataggga    180 cttccattg   acgtcaatgg  gtggagtatt  tacggtaaac  tgcccacttg  gcagtacatc   240
aagtgtatca  tatgccaagt  acgcccccta  ttgacgtcaa  tgacggtaaa  tggcccgcct   300
ggcattatgc  ccagtacatg  accttatggg  actttcctac  ttggcagtac  atctacgtat   360
tagtcatcgc  tattaccatg  gtcgaggtga  gccccacgtt  ctgcttcact  ctccccatct   420 ccccccctc   cccaccccca  attttgtatt  tatttatttt  ttaattattt  tgtgcagcga   480
tgggggcggg  ggggggggg   gggcgcgcgc  caggcggggc  gggcggggc   gagggcggg    540 gcggggcgag  gcgagaggt   gcggcggcag  ccaatcagag  cggcgcgctc  cgaaagtttc   600
cttttatggc  gaggcggcgg  cggcggcggc  cctataaaaa  gcgaagcgcg  cggcgggcgg   660
gagtcgctgc  gcgctgcctt  cgcccgtgc   cccgctccgc  cgccgcctcg  cgccgcccgc   720
cccggctctg  actgaccgcg  ttactcccac  aggtgagcgg  gcgggacggc  ccttctcctc   780
cgggctgtaa  ttagcgcttg  gtttaatgac  ggcttgtttc  ttttctgtgg  ctgcgtgaaa   840
gccttgaggg  gctccgggag  ggccctttgt  gcggggggga  cggctcggg   gggtgcgtgc   900 gtgtgtgtgt  gcgtggggag  cgccgcgtgc  ggctccgcgc  tgcccggcgg  ctgtgagcgc   960
tgcgggcgcg  gcgcggggct  tgtgcgctc   cgcagtgtgc  gcgaggggag  cgcggccggg  1020
ggcggtgccc  cgcggtgcgg  ggggggctgc  gaggggaaca  aaggctgcgt  gcggggtgtg  1080 tgcgtgggg   ggtgagcagg  gggtgtgggc  gcgtcggtcg  ggctgcaacc  cccctgcac   1140 cccctcccc   gagttgctga  gcacggcccg  gcttcgggtg  cggggctccg  tacggggcgt  1200 ggcgcgggc   tcgccgtgcc  gggcgggg    tggcggcagt  tgggggtgcc  gggcggggcg  1260
gggccgcctc  gggccgggga  gggctcgggg  gagggggcgcg  gcggccccg   gagcgccggc  1320 ggctgtcgag  gcgcggcgag  ccgcagccat  tgccttttat  ggtaatcgtg  cgagagggcg  1380
cagggacttc  ctttgtccca  aatctgtgcg  gagcccgaaat  ctgggaggcg  ccgccgcacc  1440
ccctctagcg  ggcgcggggc  gaagcggtgc  ggcgccggca  ggaaggaaat  gggcgggag   1500 ggccttcgtg  cgtcgccgcg  ccgccgtccc  cttctccctc  tccagcctcg  gggctgtccg  1560
cggggggacg  gctgccttcg  gggggacgg   ggcaggcgg   ggttcggctt  ctggcgtgtg  1620
accggcggct  ctagagcctc  tgctaaccat  gttcatgcct  tcttctttt   cctacagatc  1680 cttaattaat  aatacgactc  actatagggg  ccgccaccat  gggacctaag  aaaaagagga  1740
aggtggcggc  cgctgactac  aaggatgacg  acgataaacc  aggtggcgga  ggtagtggcg  1800
gaggtggggt  acccgccagt  ccagcagccc  aggtggatct  gagaaccctc  ggctacagcc  1860
agcagcagca  ggagaagatc  aaaccaaagg  tgcggtccac  cgtcgctcag  caccatgaag  1920
cactggtggg  gcacggtttc  acacacgccc  atattgtggc  tctgtctcag  catcccgctg  1980
cactcgggac  tgtggccgtc  aaatatcagg  acatgatcgc  cgctctgcct  gaggcaaccc  2040
acgaagccat  tgtgggcgtc  ggaaagcagt  ggagcggtgc  cagagcactc  gaagcactcc  2100
tcaccgtcgc  cggggaactg  cggggtccac  cactccagtc  cggactggac  actggacagc  2160
tgctgaagat  cgctaaacgc  ggcggagtga  cagctgtgga  agctgtgcac  gcttggagga  2220
atgctctgac  aggagcccca  ctgaatctta  ctccagaaca  ggtcgtcgca  atcgcaagta  2280
acatcggcgg  aaaacaggcc  ctcgaaaccg  tccagagact  cctccccgtg  ctgtgccagg  2340
cccacggact  gaccccacag  caggtggtcg  ccatcgctag  caacggcgga  gggaagcagg  2400
ctctggagac  cgtgcagagg  ctgctccccg  tcctgtgcca  ggcacatggg  ctcacacctc  2460
```

-continued

```
agcaggtggt cgcaattgcc tccaatggtg gcggaaaaca ggccctggaa actgtgcaga       2520
gactgctccc cgtgctgtgc caggctcacg gtctcacacc ccagcaggtg gtcgctatcg       2580
catctcatga cgggggcaag caggcactgg agacagtgca gcggctgctc cctgtcctgt       2640
gccaggccca cggactcact cctcagcagg tcgtcgccat tgctagtaac ggcggaggga       2700
aacaggctct ggaaaccgtg cagcgcctgc tccccgtgct gtgccaagcc cacggcctga       2760 cccccccagca ggtggtcgca atcgcctcaa acaatggtgg caagcaggcc ctggagactg      2820
tgcagcgact gctcccagtg ctgtgccagg cccatggact cacaccacag caggtcgtcg       2880
ctattgcaag caacaatgga gggaaacagg cactggaaac agtccagagg ctgctccccg       2940
tgctgtgcca agcgcatgga ctcactcccc agcaggtcgt cgccatcgct tccaataacg       3000
gcggcaagca ggccctggag accgtccaga gactgctccc cgtgctgtgc caagctcacg       3060
gactcacacc tgagcaggtc gtggcaatcg cctctaacat tggagggaaa caggccctgg       3120
aaactgtaca gcggctgctc cccgtgctgt gccaagcaca cggactcact ccacagcagg       3180
tcgtggccat tgcaagtcat gacggaggca agcaggccct ggaaacagtg cagcgcctgc       3240
tccctgtgct gtgccaggct catggtctga ctcctcagca ggtggtggcc atcgcttcca       3300
acaatggagg gaagcaggcc ctggagaccg tacagagact gctccccgtg ctgtgccaag       3360
cgcacggtct gacccctcag caggtcgtcg caatcgccag caatggcggg ggcaagcagg       3420
ctctcgaaac cgtccagcgg ctcctcccag tcctctgtca ggctcacggc ctgaccccac       3480
agcaggtcgt cgctattgct tctaatggcg gagggcggcc tgctctggag agcattgtgg       3540
ctcagctgtc caggcccgat cctgccctgg ctagatccgc actcactaac gatcatctgg       3600
tcgctctcgc ttgcctcggt ggacggcccg ctctggacgc agtcaaaaag ggtctccccc       3660
atgctcccgc actgatcaag agaaccaaca ggagaattcc tgagggatcc gatcgtttaa       3720
acatcaatag caagatcaag cagctggacg atagcatcaa cgtggagtcc ctgaagattg       3780
acgatgccaa agatctgctg aatgacctgg agatccagcg gaaggctaaa accattgaag       3840
atacagtgaa ccacctgaag ctgcgctccg acatcgagga tattctggac gtgttcgcca       3900
aaatcaagaa aagggatgtg cccgacgtgc ctctgttcct ggagtggaat atctggcggg       3960
cctttgccgc tctgaatcat acccaggcta tcgaagggaa ctttattgtg gacctggatg       4020
gcatgccccc tgaatacagct ccaggaaaga aacccgatat cgagattaac tacgaagct        4080 tctcctgcat cgtggaagtg actatgagct ccggggagac ccagtttaac atggaaggct       4140
ctagtgtgcc taggcactac ggagacctgg tgagaaaggt ggaccatgat gcctattgta       4200
tcttcattgc ccctaaggtg gctccaggga ctaaagctca cttctttaac ctgaataggc       4260
tgtctacaaa gcattatggc ggaaagacta agatcattcc aatgagtctg acgatttca       4320 tctgctttct gcaagtgggc attacccaca actttcagga tatcaacaag ctgaaaaatt       4380
ggctggacaa cctgattaac ttcaatctgg agtctgaaga cgaggaaatc tggtttgagg       4440
aaatcatttc taagatcagt acatgggcca tttgaacgcg taaatgattg cagatccact       4500
agttctagaa ttccagctga gcgccggtcg ctaccattac cagttggtct ggtgtcaaaa       4560
ataataataa ccgggcaggg gggatctgca tggatctttg tgaaggaacc ttacttctgt       4620
ggtgtgacat aattggacaa actacctaca gagatttaaa gctctaaggt aaatataaaa       4680
tttttaagtg tataatgtgt taaactactg attctaattg tttgtgtatt ttagattcca       4740
acctatggaa ctgatgaatg ggagcagtgg tggaatgcca gatccagaca tgataagata       4800
cattgatgag tttggacaaa ccacaactag aatgcagtga aaaaaatgct ttatttgtga       4860
```

```
aatttgtgat gctattgctt tatttgtaac cattataagc tgcaataaac aagttaacaa    4920
caacaattgc attcatttta tgtttcaggt tcaggggag gtgtgggagg ttttttaaag    4980
caagtaaaac ctctacaaat gtggtatggc tgattatgat ctgcggccgc cactggccgt    5040
cgttttacaa cgtcgtgact gggaaaaccc tggcgttacc caacttaatc gccttgcagc    5100
acatccccct ttcgccagct ggcgtaatag cgaagaggcc cgcaccgatc gcccttccca    5160
acagttgcgc agcctgaatg gcgaatggaa cgcgccctgt agcggcgcat taagcgcggc    5220
gggtgtggtg gttacgcgca gcgtgaccgc tacacttgcc agcgccctag cgcccgctcc    5280
tttcgctttc ttcccttcct ttctcgccac gttcgccggc tttccccgtc aagctctaaa    5340
tcggggctc cctttagggt tccgatttag tgctttacgg cacctcgacc ccaaaaaact    5400
tgattagggt gatggttcac gtagtgggcc atcgccctga tagacggttt ttcgcccttt    5460
gacgttggag tccacgttct ttaatagtgg actcttgttc caaactggaa caacactcaa    5520
ccctatctcg gtctattctt ttgatttata agggattttg ccgatttcgg cctattggtt    5580
aaaaaatgag ctgatttaac aaaaatttaa cgcgaatttt aacaaaatat taacgcttac    5640
aatttaggtg gcacttttcg gggaaatgtg cgcggaaccc ctatttgttt attttcta    5700
atacattcaa atatgtatcc gctcatgaga caataaccct gataaatgct tcaataatat    5760
tgaaaaagga agagtatgag tattcaacat ttccgtgtcg cccttattcc cttttttgcg    5820
gcatttgcc ttcctgtttt tgctcaccca gaaacgctgg tgaaagtaaa agatgctgaa    5880
gatcagttgg gtgcacgagt gggttacatc gaactggatc tcaacagcgg taagatcctt    5940
gagagttttc gccccgaaga acgttttcca atgatgagca cttttaaagt tctgctatgt    6000
ggcgcggtat tatcccgtat tgacgccggg caagagcaac tcggtcgccg catacactat    6060
tctcagaatg acttggttga gtactcacca gtcacagaaa agcatcttac ggatggcatg    6120
acagtaagag aattatgcag tgctgccata accatgagtg ataacactgc ggccaactta    6180
cttctgacaa cgatcggagg accgaaggag ctaaccgctt ttttgcacaa catgggggat    6240
catgtaactc gccttgatcg ttgggaaccg gagctgaatg aagccatacc aaacgacgag    6300
cgtgacacca cgatgcctgt agcaatggca acaacgttgc gcaaactatt aactggcgaa    6360
ctacttactc tagcttcccg gcaacaatta atagactgga tggaggcgga taaagttgca    6420
ggaccacttc tgcgctcggc ccttccggct ggctggttta ttgctgataa atctggagcc    6480
ggtgagcgtg ggtctcgcgg tatcattgca gcactggggc cagatggtaa gccctcccgt    6540
atcgtagtta tctacacgac ggggagtcag gcaactatgg atgaacgaaa tagacagatc    6600
gctgagatag gtgcctcact gattaagcat tggtaactgt cagaccaagt ttactcatat    6660
atactttaga ttgatttaaa acttcatttt taatttaaaa ggatctaggt gaagatcctt    6720
tttgataatc tcatgaccaa aatcccttaa cgtgagtttt cgttccactg agcgtcagac    6780
cccgtagaaa agatcaaagg atcttcttga gatcctttt ttctgcgcgt aatctgctgc    6840
ttgcaaacaa aaaaaccacc gctaccagcg gtggtttgtt tgccggatca agagctacca    6900
actctttttc cgaaggtaac tggcttcagc agagcgcaga taccaaatac tgtccttcta    6960
gtgtagccgt agttaggcca ccacttcaag aactctgtag caccgcctac atacctcgct    7020
ctgctaatcc tgttaccagt ggctgctgcc agtggcgata agtcgtgtct taccgggttg    7080
gactcaagac gatagttacc ggataaggcg cagcggtcgg gctgaacggg gggttcgtgc    7140
acacagccca gcttggagcg aacgacctac accgaactga gatacctaca gcgtgagcta    7200
```

| | |
|---|---|
| tgagaaagcg ccacgcttcc cgaagggaga aaggcggaca ggtatccggt aagcggcagg | 7260 |
| gtcggaacag gagagcgcac gagggagctt ccaggggggaa acgcctggta tctttatagt | 7320 |
| cctgtcgggt ttcgccacct ctgacttgag cgtcgatttt tgtgatgctc gtcaggggggg | 7380 |
| cggagcctat ggaaaaacgc cagcaacgcg gcctttttac ggttcctggc cttttgctgg | 7440 |
| ccttttgctc acatgttctt tcctgcgtta tcccctgatt ctgtggataa ccgtattacc | 7500 |
| gcctttgagt gagctgatac cgctcgccgc agccgaacga ccgagcgcag cgagtcagtg | 7560 |
| agcgaggaag cggaagagcg cccaatacgc aaaccgcctc tccccgcgcg ttggccgatt | 7620 |
| cattaatgca gctggcacga caggtttccc gactggaaag cgggcagtga gcgcaacgca | 7680 |
| attaatgtga gttagctcac tcattaggca ccccaggctt tacactttat gcttccggct | 7740 |
| cgtatgttgt gtggaattgt gagcggataa caatttcaca caggaaacag ctatgaccat | 7800 |
| gaggcgcgcc ggattc | 7816 |

<210> SEQ ID NO 31
<211> LENGTH: 7705
<212> TYPE: DNA
<213> ORGANISM: Artificial sequence
<220> FEATURE:
<223> OTHER INFORMATION: pCAG-ArtTal1-Pept071

<400> SEQUENCE: 31

| | |
|---|---|
| gacattgatt attgactagt tattaatagt aatcaattac ggggtcatta gttcatagcc | 60 |
| catatatgga gttccgcgtt acataactta cggtaaatgg cccgcctggc tgaccgccca | 120 |
| acgacccccg cccattgacg tcaataatga cgtatgttcc catagtaacg ccaataggga | 180 |
| ctttccattg acgtcaatgg gtggagtatt tacggtaaac tgcccacttg gcagtacatc | 240 |
| aagtgtatca tatgccaagt acgccccta ttgacgtcaa tgacggtaaa tggcccgcct | 300 |
| ggcattatgc ccagtacatg accttatggg actttcctac ttggcagtac atctacgtat | 360 |
| tagtcatcgc tattaccatg gtcgaggtga gccccacgtt ctgcttcact ctccccatct | 420 |
| cccccccctc cccaccccca attttgtatt tatttatttt ttaattattt tgtgcagcga | 480 |
| tgggggcggg gggggggggg gggcgcgcgc caggcggggc ggggcgggc gaggggcggg | 540 |
| gcggggcgag gcggagaggt gcggcggcag ccaatcagag cggcgcgctc gaaagtttc | 600 |
| cttttatggc gaggcggcgg cggcggcggc cctataaaaa gcgaagcgcg cggcgggcgg | 660 |
| gagtcgctgc gcgctgcctt cgccccgtgc ccgctccgc cgccgcctcg cgccgcccgc | 720 |
| cccggctctg actgaccgcg ttactcccac aggtgagcgg gcgggacggc ccttctcctc | 780 |
| cgggctgtaa ttagcgcttg gtttaatgac ggcttgtttc ttttctgtgg ctgcgtgaaa | 840 |
| gccttgaggg gctccgggag ggccctttgt gcggggggga gcggctcggg gggtgcgtgc | 900 |
| gtgtgtgtgt gcgtggggag cgccgcgtgc ggctccgcgc tgcccggcgg ctgtgagcgc | 960 |
| tgcgggcgcg gcgcggggct tgtgcgctc cgcagtgtgc gcgaggggag cgcggccggg | 1020 |
| ggcggtgccc cgcggtgcgg gggggctgc gagggggaaca aaggctgcgt gcggggtgtg | 1080 |
| tgcgtggggg ggtgagcagg gggtgtgggc gcgtcggtcg ggctgcaacc ccccctgcac | 1140 |
| cccctcccc gagttgctga gcacggcccg gcttcgggtg cggggctccg tacgggcgt | 1200 |
| ggcgcggggc tcgccgtgcc gggcgggggg tggcggcagg tgggggtgcc gggcggggcg | 1260 |
| gggccgcctc gggccgggga gggctcgggg gaggggcgcg gcggccccg gagcgccggc | 1320 |
| ggctgtcgag gcgcggcgag ccgcagccat tgcctttat ggtaatcgtg cgagagggcg | 1380 |
| cagggacttc ctttgtccca aatctgtgcg gagccgaaat ctgggaggcg ccgccgcacc | 1440 |

```
ccctctagcg ggcgcggggc gaagcggtgc ggcgccggca ggaaggaaat gggcggggag    1500
ggccttcgtg cgtcgccgcg ccgccgtccc cttctccctc tccagcctcg gggctgtccg    1560
cggggggacg gctgccttcg ggggggacgg ggcagggcgg ggttcggctt ctggcgtgtg    1620
accggcggct ctagagcctc tgctaaccat gttcatgcct tcttcttttt cctacagatc    1680
cttaattaat aatacgactc actataggggg ccgccaccat gggacctaag aaaagagga    1740 aggtggcggc cgctgactac aaggatgacg acgataaacc aggtggcgga ggtagtggcg    1800
gaggtggggt acccgccagt ccagcagccc aggtggatct gagaaccctc ggctacagcc    1860
agcagcagca ggagaagatc aaaccaaagg tgcggtccac cgtcgctcag caccatgaag    1920
cactggtggg gcacggtttc acacacgccc atattgtggc tctgtctcag catcccgctg    1980
cactcgggac tgtggccgtc aaatatcagg acatgatcgc cgctctgcct gaggcaaccc    2040
acgaagccat tgtgggcgtc ggaaagcagt ggagcggtgc cagagcactc gaagcactcc    2100
tcaccgtcgc cggggaactg cggggtccac cactccagtc cggactggac actggacagc    2160
tgctgaagat cgctaaacgc ggcggagtga cagctgtgga agctgtgcac gcttggagga    2220
atgctctgac aggagcccca ctgaatctta ctccagaaca ggtcgtcgca atcgcaagta    2280
acatcggcgg aaaacaggcc ctcgaaaccg tccagagact cctccccgtg ctgtgccagg    2340
cccacggact gaccccacag caggtggtcg ccatcgctag caacggcgga gggaagcagg    2400
ctctggagac cgtgcagagg ctgctccccg tcctgtgcca ggcacatggg ctcacacctc    2460
agcaggtggt cgcaattgcc tccaatggtg gcggaaaaca ggccctggaa actgtgcaga    2520
gactgctccc cgtgctgtgc caggctcacg gtctcacacc ccagcaggtg gtcgctatcg    2580
catctcatga cggggcaag caggcactgg agacagtgca gcggctgctc cctgtcctgt    2640
gccaggccca cggactcact cctcagcagg tcgtcgccat tgctagtaac ggcggaggga    2700
aacaggctct ggaaaccgtg cagcgcctgc tccccgtgct gtgccaagcc cacgccctga    2760 cccccccagca ggtggtcgca atcgcctcaa acaatggtgg caagcaggcc ctggagactg    2820
tgcagcgact gctcccagtg ctgtgccagg cccatggact cacaccacag caggtcgtcg    2880
ctattgcaag caacaatgga gggaaacagg cactggaaac agtccagagg ctgctccccg    2940
tgctgtgcca agcgcatgga ctcactcccc agcaggtcgt cgccatcgct tccaataacg    3000
gcggcaagca ggccctggag accgtccaga gactgctccc cgtgctgtgc aagctcacg    3060 gactcacacc tgagcaggtc gtggcaatcg cctctaacat tggagggaaa caggccctgg    3120
aaactgtaca gcggctgctc cccgtgctgt gccaagcaca cggactcact ccacagcagg    3180
tcgtggccat tgcaagtcat gacggaggca agcaggccct ggaaacagtg cagcgcctgc    3240
tccctgtgct gtgccaggct catggtctga ctcctcagca ggtggtggcc atcgcttcca    3300
acaatggagg gaagcaggcc ctggagaccg tacagagact gctccccgtg ctgtgccaag    3360
cgcacggtct gacccctcag caggtcgtcg caatcgccag caatggcggg ggcaagcagg    3420
ctctcgaaac cgtccagcgg ctcctcccag tcctctgtca ggctcacggc ctgacccac    3480 agcaggtcgt cgctattgct tctaatggcg gagggcggcc tgctctggag agcattgtgg    3540
ctcagctgtc caggcccgat cctgccctgg ctagatccga actcactaac gatcatctgg    3600
tcgctctcgc ttgcctcggt ggacggcccg ctctggacgc agtcaaaaag ggtctccccc    3660
atgctcccgc actgatcaag agaaccaaca ggagaattcc tgagggatcc gatcgtttaa    3720
acaagatcag caaaaccaat gtgctggagc tcaaggacaa agtccgagat aagctgaaat    3780
```

| | |
|---|---|
| acgtggacca caggtatctg gcactcatcg acctcgccta tgatgggacc gctaacaggg | 3840 |
| acttcgaaat ccagacaatt gatctgctca ttaatgagct gaagtttaaa ggggtcaggc | 3900 |
| tcggtgaaag tagaaagccc gacggcatca tttcatacaa catcaatgga gtgatcattg | 3960 |
| ataacaaggc ttactctact ggttataacc tgcctattaa tcaggccgac gagatgatcc | 4020 |
| ggtatattga ggaaaatcag acccgcgatg aaaaaatcaa ctccaataag tggtgggagt | 4080 |
| ctttcgacga taaggtcaaa gacttcaact acctgtttgt gagctccttc tttaagggga | 4140 |
| actttaaaaa caatctgaag catatcgcta acagaacagg tgtcagcggc ggagcaatta | 4200 |
| acgtggagaa tctgctctac ttcgcagagg aactgaaagc cggccggctc tcatatgtgg | 4260 |
| atagctttaa gatgtacgac aacgatgaga tctatgtcgg cgacttctct gattacagtt | 4320 |
| atgtgaagtt tgccgctgag gaagagggag aatacctgac ttgaacgcgt aaatgattgc | 4380 |
| agatccacta gttctagaat tccagctgag cgccggtcgc taccattacc agttggtctg | 4440 |
| gtgtcaaaaa taataataac cgggcagggg ggatctgcat ggatctttgt gaaggaacct | 4500 |
| tacttctgtg gtgtgacata attggacaaa ctacctacag agatttaaag ctctaaggta | 4560 |
| aatataaaat ttttaagtgt ataatgtgtt aaactactga ttctaattgt ttgtgtattt | 4620 |
| tagattccaa cctatggaac tgatgaatgg gagcagtggt ggaatgccag atccagacat | 4680 |
| gataagatac attgatgagt ttggacaaac cacaactaga atgcagtgaa aaaaatgctt | 4740 |
| tatttgtgaa atttgtgatg ctattgcttt atttgtaacc attataagct gcaataaaca | 4800 |
| agttaacaac aacaattgca ttcattttat gtttcaggtt caggggagg tgtgggaggt | 4860 |
| ttttttaaagc aagtaaaacc tctacaaatg tggtatggct gattatgatc tgcggccgcc | 4920 |
| actggccgtc gttttacaac gtcgtgactg ggaaaaccct ggcgttaccc aacttaatcg | 4980 |
| ccttgcagca catccccctt tcgccagctg gcgtaatagc gaagaggccc gcaccgatcg | 5040 |
| cccttcccaa cagttgcgca gcctgaatgg cgaatggaac gcgcctgta gcggcgcatt | 5100 |
| aagcgcggcg ggtgtggtgg ttacgcgcag cgtgaccgct acacttgcca gcgccctagc | 5160 |
| gcccgctcct ttcgctttct tcccttcctt tctcgccacg ttcgccggct ttccccgtca | 5220 |
| agctctaaat cggggggctcc ctttaggggtt ccgatttagt gctttacggc acctcgaccc | 5280 |
| caaaaaactt gattagggtg atggttcacg tagtgggcca tcgccctgat agacggtttt | 5340 |
| tcgccctttg acgttggagt ccacgttctt taatagtgga ctcttgttcc aaactggaac | 5400 |
| aacactcaac cctatctcgg tctattcttt tgatttataa gggattttgc cgatttcggc | 5460 |
| ctattggtta aaaaatgagc tgatttaaca aaaatttaac gcgaatttta acaaaatatt | 5520 |
| aacgcttaca atttaggtgg cacttttcgg ggaaatgtgc gcggaacccc tatttgttta | 5580 |
| tttttctaaa tacattcaaa tatgtatccg ctcatgagac aataaccctg ataaatgctt | 5640 |
| caataatatt gaaaaggaa gagtatgagt attcaacatt tccgtgtcgc ccttattccc | 5700 |
| ttttttgcgg cattttgcct tcctgttttt gctcacccag aaacgctggt gaaagtaaaa | 5760 |
| gatgctgaag atcagttggg tgcacgagtg ggttacatcg aactggatct caacagcggt | 5820 |
| aagatccttg agagttttcg ccccgaagaa cgttttccaa tgatgagcac ttttaaagtt | 5880 |
| ctgctatgtg gcgcggtatt atcccgtatt gacgccgggc aagagcaact cggtcgccgc | 5940 |
| atacactatt ctcagaatga cttggttgag tactcaccag tcacagaaaa gcatcttacg | 6000 |
| gatggcatga cagtaagaga attatgcagt gctgccataa ccatgagtga taacactgcg | 6060 |
| gccaacttac ttctgacaac gatcggagga ccgaaggagc taaccgcttt tttgcacaac | 6120 |
| atggggggatc atgtaactcg ccttgatcgt tgggaaccgg agctgaatga agccatacca | 6180 |

```
aacgacgagc gtgacaccac gatgcctgta gcaatggcaa caacgttgcg caaactatta    6240
actggcgaac tacttactct agcttcccgg caacaattaa tagactggat ggaggcggat    6300
aaagttgcag gaccacttct gcgctcggcc cttccggctg gctggtttat tgctgataaa    6360
tctggagccg gtgagcgtgg gtctcgcggt atcattgcag cactgggcc agatggtaag     6420 ccctcccgta tcgtagttat ctacacgacg gggagtcagg caactatgga tgaacgaaat    6480
agacagatcg ctgagatagg tgcctcactg attaagcatt ggtaactgtc agaccaagtt    6540
tactcatata tactttagat tgatttaaaa cttcattttt aatttaaaag gatctaggtg    6600
aagatccttt ttgataatct catgaccaaa atcccttaac gtgagttttc gttccactga    6660
gcgtcagacc ccgtagaaaa gatcaaagga tcttcttgag atcctttttt tctgcgcgta    6720
atctgctgct tgcaaacaaa aaaccaccg ctaccagcgg tggtttgttt gccggatcaa     6780
gagctaccaa ctcttttcc gaaggtaact ggcttcagca gagcgcagat accaaatact    6840
gtccttctag tgtagccgta gttaggccac cacttcaaga actctgtagc accgcctaca    6900
tacctcgctc tgctaatcct gttaccagtg gctgctgcca gtggcgataa gtcgtgtctt    6960
accgggttgg actcaagacg atagttaccg gataaggcgc agcggtcggg ctgaacgggg    7020
ggttcgtgca cacagcccag cttggagcga acgacctaca ccgaactgag atacctacag    7080
cgtgagctat gagaaagcgc cacgcttccc gaagggagaa aggcggacag gtatccggta    7140
agcggcaggg tcggaacagg agagcgcacg agggagcttc caggggggaaa cgcctggtat    7200 ctttatagtc ctgtcgggtt tcgccacctc tgacttgagc gtcgatttt gtgatgctcg      7260 tcagggggc ggagcctatg gaaaaacgcc agcaacgcgg cctttttacg gttcctggcc       7320
ttttgctggc cttttgctca catgttcttt cctgcgttat cccctgattc tgtggataac    7380
cgtattaccg cctttgagtg agctgatacc gctcgccgca gccgaacgac cgagcgcagc    7440
gagtcagtga gcgaggaagc ggaagagcgc ccaatacgca aaccgcctct ccccgcgcgt    7500
tggccgattc attaatgcag ctggcacgac aggtttcccg actggaaagc gggcagtgag    7560
cgcaacgcaa ttaatgtgag ttagctcact cattaggcac cccaggcttt acactttatg    7620
cttccggctc gtatgttgtg tggaattgtg agcggataac aatttcacac aggaaacagc    7680
tatgaccatg aggcgcgccg gattc                                          7705
```

<210> SEQ ID NO 32
<211> LENGTH: 7555
<212> TYPE: DNA
<213> ORGANISM: Artificial sequence
<220> FEATURE:
<223> OTHER INFORMATION: pCAG-ArtTal1-SbfI

<400> SEQUENCE: 32

```
gacattgatt attgactagt tattaatagt aatcaattac ggggtcatta gttcatagcc      60
catatatgga gttccgcgtt acataactta cggtaaatgg cccgcctggc tgaccgccca     120 acgaccccg cccattgacg tcaataatga cgtatgttcc catagtaacg ccaatagga      180 ctttccattg acgtcaatgg gtggagtatt tacggtaaac tgcccacttg gcagtacatc     240
aagtgtatca tatgccaagt acgccccta ttgacgtcaa tgacggtaaa tggcccgcct      300
ggcattatgc ccagtacatg accttatggg actttcctac ttggcagtac atctacgtat     360
tagtcatcgc tattaccatg gtcgaggtga gccccacgtt ctgcttcact ctccccatct    420
cccccccctc cccacccca attttgtatt tatttatttt ttaattattt tgtgcagcga      480
```

```
tgggggcggg ggggggggggg gggcgcgcgc caggcggggc ggggcggggc gagggggcggg    540
gcggggcgag gcggagaggt gcggcggcag ccaatcagag cggcgcgctc cgaaagtttc    600
cttttatggc gaggcggcgg cggcggcggc cctataaaaa gcgaagcgcg cggcgggcgg    660
gagtcgctgc gcgctgcctt cgccccgtgc cccgctccgc cgccgcctcg cgccgccgc    720
cccggctctg actgaccgcg ttactcccac aggtgagcgg gcgggacggc ccttctcctc    780
cgggctgtaa ttagcgcttg gtttaatgac ggcttgtttc ttttctgtgg ctgcgtgaaa    840
gccttgaggg gctccgggag ggccctttgt gcgggggga gcggctcggg gggtgcgtgc    900
gtgtgtgtgt gcgtggggag cgccgcgtgc ggctccgcgc tgcccggcgg ctgtgagcgc    960
tgcgggcgcg gcgcggggct tgtgcgctc cgcagtgtgc gcgaggggag cgcggccggg   1020
ggcggtgccc cgcggtgcgg ggggggctgc gagggaaca aaggctgcgt gcggggtgtg   1080
tgcgtggggg ggtgagcagg gggtgtgggc gcgtcggtcg ggctgcaacc ccccctgcac   1140
cccctcccc gagttgctga gcacggcccg gcttcgggtg cggggctccg tacggggcgt   1200
ggcgcggggc tcgccgtgcc gggcgggggg tggcggcagg tgggggtgcc gggcggggcg   1260
gggccgcctc gggccgggga gggctcgggg gaggggcgcg gcggccccg gagcgccggc    1320
ggctgtcgag gcgcggcgag ccgcagccat tgccttttat ggtaatcgtg cgagagggcg   1380
cagggacttc ctttgtccca aatctgtgcg gagccgaaat ctgggaggcg ccgccgcacc   1440
ccctctagcg ggcgcgggc gaagcggtgc ggcgccggca ggaaggaaat gggcggggag   1500
ggccttcgtg cgtcgccgcg ccgccgtccc cttctccctc tccagcctcg gggctgtccg   1560
cggggggacg gctgccttcg gggggacgg gcagggcgg ggttcggctt ctggcgtgtg   1620
accggcggct ctagagcctc tgctaaccat gttcatgcct tcttcttttt cctacagatc   1680
cttaattaat aatacgactc actatagggg ccgccaccat gggacctaag aaaaagagga   1740
aggtggcggc cgctgactac aaggatgacg acgataaacc aggtggcgga ggtagtggcg   1800
gaggtggggt acccgccagt ccagcagccc aggtggatct gagaaccctc ggctacagcc   1860
agcagcagca ggagaagatc aaaccaaagg tgcggtccac cgtcgctcag caccatgaag   1920
cactggtggg gcacggtttc acacacgccc atattgtggc tctgtctcag catcccgctg   1980
cactcgggac tgtggccgtc aaatatcagg acatgatcgc cgctctgcct gaggcaaccc   2040
acgaagccat tgtgggcgtc ggaaagcagt ggagcggtgc cagagcactc gaagcactcc   2100
tcaccgtcgc cggggaactg cggggtccac cactccagtc cggactggac actggacagc   2160
tgctgaagat cgctaaacgc ggcggagtga cagctgtgga agctgtgcac gcttggagga   2220
atgctctgac aggagcccca ctgaatctta ctccagaaca ggtcgtcgca atcgcaagta   2280
acatcggcgg aaaacaggcc ctcgaaaccg tccagagact cctccccgtg ctgtgccagg   2340
cccacggact gaccccacag caggtggtcg ccatcgctag caacggcgga gggaagcagg   2400
ctctggagac cgtgcagagg ctgctccccg tcctgtgcca ggcacatggg ctcacacctc   2460
agcaggtggt cgcaattgcc tccaatggtg gcggaaaaca ggccctggaa actgtgcaga   2520
gactgctccc cgtgctgtgc caggctcacg gtctcacacc ccagcaggtg gtcgctatcg   2580
catctcatga cggggggcaag caggcactgg agacagtgca gcggctgctc cctgtcctgt   2640
gccaggccca cggactcact cctcagcagg tcgtcgccat tgctagtaac ggcggaggga   2700
aacaggctct ggaaaccgtg cagcgcctgc tcccgtgct gtgccaagcc cacggcctga   2760
cccccagca ggtggtcgca atcgcctcaa acaatggtgg caagcaggcc ctggagactg   2820
tgcagcgact gctcccagtg ctgtgccagg cccatggact cacaccacag caggtcgtcg   2880
```

```
ctattgcaag caacaatgga gggaaacagg cactggaaac agtccagagg ctgctccccg    2940
tgctgtgcca agcgcatgga ctcactcccc agcaggtcgt cgccatcgct tccaataacg    3000
gcggcaagca ggccctggag accgtccaga gactgctccc cgtgctgtgc caagctcacg    3060
gactcacacc tgagcaggtc gtggcaatcg cctctaacat tggagggaaa caggccctgg    3120
aaactgtaca gcggctgctc cccgtgctgt gccaagcaca cggactcact ccacagcagg    3180
tcgtggccat tgcaagtcat gacgaggca agcaggccct ggaaacagtg cagcgcctgc    3240
tccctgtgct gtgccaggct catggtctga ctcctcagca ggtggtggcc atcgcttcca    3300
acaatggagg gaagcaggcc ctggagaccg tacagagact gctccccgtg ctgtgccaag    3360
cgcacggtct gaccccctcag caggtcgtcg caatcgccag caatggcggg ggcaagcagg    3420
ctctcgaaac cgtccagcgg ctcctcccag tcctctgtca ggctcacggc ctgaccccac    3480
agcaggtcgt cgctattgct tctaatggcg gagggcggcc tgctctggag agcattgtgg    3540
ctcagctgtc caggcccgat cctgccctgg ctagatccgc actcactaac gatcatctgg    3600
tcgctctcgc ttgcctcggt ggacggcccg ctctggacgc agtcaaaaag ggtctccccc    3660
atgctcccgc actgatcaag agaaccaaca ggagaattcc tgagggatcc gatcgtttaa    3720
acatctctgt ggacctgcca ggcggagagg aattcctgct gagtccagcc ggacagaacc    3780
ccctgctgaa gaaaatggtg gaggaattcg tgccccggtt tgctcctcgc agcaccgtgc    3840
tgtacctggg ggacacaagg ggcaagcact ccctgttcga gagagaaatc tttgaggaag    3900
tgctgggcct gaccttcgat cctcacggac ggatgccaga cctgattctg catgatgagg    3960
tgagggggtg gctgttcctg atggaagccg tgaagtctaa aggccccttt gatgaggaaa    4020
ggcatagaag cctgcaggag ctgtttgtga ctccttccgc cggcctgatc ttcgtgaact    4080
gctttgagaa tagggaatct atgagacagt ggctgcccga gctggcttgg gagaccgaag    4140
cctgggtggc tgaagaccct gatcacctga ttcatctgaa tggaagtcgg tttctggggc    4200
catatgagcg ctgaacgcgt aaatgattgc agatccacta gttctagaat tccagctgag    4260
cgccggtcgc taccattacc agttggtctg gtgtcaaaaa taataataac cgggcagggg    4320
ggatctgcat ggatctttgt gaaggaacct tacttctgtg gtgtgacata attggacaaa    4380
ctacctacag agatttaaag ctctaaggta aatataaaat ttttaagtgt ataatgtgtt    4440
aaactactga ttctaattgt ttgtgtattt tagattccaa cctatggaac tgatgaatgg    4500
gagcagtggt ggaatgccag atccagacat gataagatac attgatgagt ttggacaaac    4560
cacaactaga atgcagtgaa aaaatgctt tatttgtgaa atttgtgatg ctattgcttt    4620
atttgtaacc attataagct gcaataaaca agttaacaac acaattgca ttcattttat    4680 gtttcaggtt caggggagg tgtgggaggt ttttaaagc aagtaaaacc tctacaaatg    4740
tggtatggct gattatgatc tgcggccgcc actggccgtc gttttacaac gtcgtgactg    4800
ggaaaaccct ggcgttaccc aacttaatcg ccttgcagca catccccctt tcgccagctg    4860
gcgtaatagc gaagaggccc gcaccgatcg cccttcccaa cagttgcgca gcctgaatgg    4920
cgaatggaac gcgccctgta gcggcgcatt aagcgcggcg ggtgtggtgg ttacgcgcag    4980
cgtgaccgct acacttgcca gcgccctagc gcccgctcct ttcgctttct tcccttcctt    5040
tctcgccacg ttcgccggct ttccccgtca gctctaaat cggggggctcc ctttagggtt    5100 ccgatttagt gctttacggc acctcgaccc caaaaaactt gattagggtg atggttcacg    5160
tagtgggcca tcgccctgat agacggtttt tcgccctttg acgttggagt ccacgttctt    5220
```

```
taatagtgga ctcttgttcc aaactggaac aacactcaac cctatctcgg tctattcttt    5280
tgatttataa gggattttgc cgatttcggc ctattggtta aaaaatgagc tgatttaaca    5340
aaaatttaac gcgaatttta acaaaatatt aacgcttaca atttaggtgg cacttttcgg    5400
ggaaatgtgc gcggaacccc tatttgttta ttttctaaa tacattcaaa tatgtatccg     5460
ctcatgagac aataaccctg ataaatgctt caataatatt gaaaaggaa gagtatgagt     5520 attcaacatt tccgtgtcgc ccttattccc ttttttgcgg catttgcct tcctgttttt     5580 gctcacccag aaacgctggt gaaagtaaaa gatgctgaag atcagttggg tgcacgagtg    5640
ggttacatcg aactggatct caacagcggt aagatccttg agagttttcg ccccgaagaa    5700
cgttttccaa tgatgagcac ttttaaagtt ctgctatgtg gcgcggtatt atcccgtatt    5760
gacgccgggc aagagcaact cggtcgccgc atacactatt ctcagaatga cttggttgag    5820
tactcaccag tcacagaaaa gcatcttacg gatggcatga cagtaagaga attatgcagt    5880
gctgccataa ccatgagtga taacactgcg gccaacttac ttctgacaac gatcggagga    5940
ccgaaggagc taaccgcttt tttgcacaac atggggatg atgtaactcg ccttgatcgt     6000
tgggaaccgg agctgaatga agccatacca aacgacgagc gtgacaccac gatgcctgta    6060
gcaatggcaa caacgttgcg caaactatta actggcgaac tacttactct agcttcccgg    6120
caacaattaa tagactggat ggaggcggat aaagttgcag gaccacttct gcgctcggcc    6180
cttccggctg gctggtttat tgctgataaa tctggagccg gtgagcgtgg gtctcgcggt    6240
atcattgcag cactggggcc agatggtaag ccctcccgta tcgtagttat ctacacgacg    6300
gggagtcagg caactatgga tgaacgaaat agacagatcg ctgagatagg tgcctcactg    6360
attaagcatt ggtaactgtc agaccaagtt tactcatata ctttagat tgatttaaaa     6420 cttcattttt aatttaaaag gatctaggtg aagatccttt tgataatct catgaccaaa    6480 atcccttaac gtgagttttc gttccactga gcgtcagacc ccgtagaaaa gatcaaagga    6540
tcttcttgag atcctttttt tctgcgcgta atctgctgct tgcaaacaaa aaaaccaccg    6600
ctaccagcgg tggtttgttt gccggatcaa gagctaccaa ctctttttcc gaaggtaact    6660
ggcttcagca gagcgcagat accaaatact gtccttctag tgtagccgta gttaggccac    6720
cacttcaaga actctgtagc accgcctaca tacctcgctc tgctaatcct gttaccagtg    6780
gctgctgcca gtggcgataa gtcgtgtctt accgggttgg actcaagacg atagttaccg    6840
gataaggcgc agcggtcggg ctgaacgggg ggttcgtgca cacagcccag cttggagcga    6900
acgacctaca ccgaactgag atacctacag cgtgagctat gagaaagcgc cacgcttccc    6960
gaagggagaa aggcggacag gtatccggta agcggcaggg tcggaacagg agagcgcacg    7020
agggagcttc caggggggaa acgcctggta tctttatagtc ctgtcgggtt tcgccacctc    7080
tgacttgagc gtcgattttt gtgatgctcg tcagggggc ggagcctatg gaaaaacgcc     7140
agcaacgcgg cctttttacg gttcctggcc ttttgctggc cttttgctca catgttcttt    7200
cctgcgttat cccctgattc tgtggataac cgtattaccg cctttgagtg agctgatacc    7260
gctcgccgca gccgaacgac cgagcgcagc gagtcagtga gcgaggaagc ggaagagcgc    7320
ccaatacgca aaccgcctct ccccgcgcgt tggccgattc attaatgcag ctggcacgac    7380
aggtttcccg actggaaagc gggcagtgag cgcaacgcaa ttaatgtgag ttagctcact    7440
cattaggcac cccaggcttt acactttatg cttccggctc gtatgttgtg tggaattgtg    7500
agcggataac aatttcacac aggaaacagc tatgaccatg aggcgcgccg gattc          7555
```

<210> SEQ ID NO 33
<211> LENGTH: 7555
<212> TYPE: DNA
<213> ORGANISM: Artificial sequence
<220> FEATURE:
<223> OTHER INFORMATION: pCAG-ArtTal1-Sda

<400> SEQUENCE: 33

| | | | | | |
|---|---|---|---|---|---|
| gacattgatt | attgactagt | tattaatagt | aatcaattac | ggggtcatta | gttcatagcc | 60 |
| catatatgga | gttccgcgtt | acataactta | cggtaaatgg | cccgcctggc | tgaccgccca | 120 |
| acgacccccg | cccattgacg | tcaataatga | cgtatgttcc | catagtaacg | ccaataggga | 180 |
| ctttccattg | acgtcaatgg | gtggagtatt | tacggtaaac | tgcccacttg | gcagtacatc | 240 |
| aagtgtatca | tatgccaagt | acgccccta | ttgacgtcaa | tgacggtaaa | tggcccgcct | 300 |
| ggcattatgc | ccagtacatg | accttatggg | actttcctac | ttggcagtac | atctacgtat | 360 |
| tagtcatcgc | tattaccatg | gtcgaggtga | gccccacgtt | ctgcttcact | ctccccatct | 420 |
| ccccccctc | ccaccccca | attttgtatt | tatttatttt | ttaattattt | tgtgcagcga | 480 |
| tgggggcggg | ggggggggg | gggcgcgcgc | caggcggggc | gggcggggc | gagggcggg | 540 |
| gcggggcgag | gcggagaggt | gcggcggcag | ccaatcagag | cggcgcgctc | cgaaagtttc | 600 |
| cttttatggc | gaggcggcgg | cggcggcggc | cctataaaaa | gcgaagcgcg | cggcgggcgg | 660 |
| gagtcgctgc | gcgctgcctt | cgccccgtgc | cccgctccgc | cgccgcctcg | cgccgcccgc | 720 |
| cccggctctg | actgaccgcg | ttactcccac | aggtgagcgg | gcgggacggc | ccttctcctc | 780 |
| cgggctgtaa | ttagcgcttg | gtttaatgac | ggcttgtttc | ttttctgtgg | ctgcgtgaaa | 840 |
| gccttgaggg | gctccgggag | ggcccttgt | gcgggggga | gcggctcggg | gggtgcgtgc | 900 |
| gtgtgtgtgt | gcgtggggag | cgccgcgtgc | ggctccgcgc | tgcccggcgg | ctgtgagcgc | 960 |
| tgcgggcgcg | gcgcggggct | tgtgcgctc | cgcagtgtgc | gcgaggggag | cgcggccggg | 1020 |
| ggcggtgccc | cgcggtgcgg | gggggctgc | gagggggaaca | aaggctgcgt | gcggggtgtg | 1080 |
| tgcgtggggg | ggtgagcagg | gggtgtgggc | gcgtcggtcg | ggctgcaacc | ccccctgcac | 1140 |
| ccccctcccc | gagttgctga | gcacggcccg | gcttcgggtg | cggggctccg | tacggggcgt | 1200 |
| ggcgcgggc | tcgccgtgcc | gggcgggggg | tggcggcagg | tggggtgcc | gggcggggcg | 1260 |
| gggccgcctc | gggccgggga | gggctcgggg | gaggggcgcg | gcggccccg | gagcgccggc | 1320 |
| ggctgtcgag | gcgcggcgag | ccgcagccat | tgccttttat | ggtaatcgtg | cgagagggcg | 1380 |
| cagggacttc | ctttgtccca | aatctgtgcg | gagccgaaat | ctgggaggcg | ccgccgcacc | 1440 |
| ccctctagcg | ggcgcggggc | gaagcggtgc | ggcgccggca | ggaaggaaat | gggcgggag | 1500 |
| ggccttcgtg | cgtcgccgcg | ccgccgtccc | cttctccctc | tccagcctcg | ggctgtccg | 1560 |
| cgggggacg | gctgccttcg | gggggacgg | ggcaggggcgg | ggttcggctt | ctggcgtgtg | 1620 |
| accggcggct | ctagagcctc | tgctaaccat | gttcatgcct | tcttcttttt | cctacagatc | 1680 |
| cttaattaat | aatacgactc | actatagggg | ccgccaccat | gggacctaag | aaaagagga | 1740 |
| aggtggcggc | cgctgactac | aaggatgacg | acgataaacc | aggtggcgga | ggtagtggcg | 1800 |
| gaggtggggt | acccgccagt | ccagcagccc | aggtggatct | gagaaccctc | ggctacagcc | 1860 |
| agcagcagca | ggagaagatc | aaaccaaagg | tgcggtccac | cgtcgctcag | caccatgaag | 1920 |
| cactggtggg | gcacggtttc | acacacgccc | atattgtggc | tctgtctcag | catcccgctg | 1980 |
| cactcggac | tgtggccgtc | aaatatcagg | acatgatcgc | cgctctgcct | gaggcaaccc | 2040 |
| acgaagccat | tgtgggcgtc | ggaaagcagt | ggagcggtgc | cagagcactc | gaagcactcc | 2100 |

```
tcaccgtcgc cggggaactg cggggtccac cactccagtc cggactggac actggacagc   2160
tgctgaagat cgctaaacgc ggcggagtga cagctgtgga agctgtgcac gcttggagga   2220
atgctctgac aggagcccca ctgaatctta ctccagaaca ggtcgtcgca atcgcaagta   2280
acatcggcgg aaaacaggcc ctcgaaaccg tccagagact cctccccgtg ctgtgccagg   2340
cccacggact gaccccacag caggtggtcg ccatcgctag caacggcgga gggaagcagg   2400
ctctggagac cgtgcagagg ctgctccccg tcctgtgcca ggcacatggg ctcacacctc   2460
agcaggtggt cgcaattgcc tccaatggtg gcggaaaaca ggccctggaa actgtgcaga   2520
gactgctccc cgtgctgtgc caggctcacg gtctcacacc ccagcaggtg gtcgctatcg   2580
catctcatga cggggggcaag caggcactgg agacagtgca gcggctgctc cctgtcctgt   2640
gccaggccca cggactcact cctcagcagg tcgtcgccat tgctagtaac ggcggaggga   2700
aacaggctct ggaaaccgtg cagcgcctgc tccccgtgct gtgccaagcc cacggcctga   2760 cccccccagca ggtggtcgca atcgcctcaa acaatggtgg caagcaggcc ctggagactg   2820
tgcagcgact gctcccagtg ctgtgccagg cccatggact cacaccacag caggtcgtcg   2880
ctattgcaag caacaatgga gggaaacagg cactggaaac agtccagagg ctgctccccg   2940
tgctgtgcca agcgcatgga ctcactcccc agcaggtcgt cgccatcgct tccaataacg   3000
gcggcaagca ggccctggag accgtccaga gactgctccc cgtgctgtgc aagctcacg   3060 gactcacacc tgagcaggtc gtggcaatcg cctctaacat tggagggaaa caggccctgg   3120
aaactgtaca gcggctgctc cccgtgctgt gccaagcaca cggactcact ccacagcagg   3180
tcgtggccat tgcaagtcat gacgaggca agcaggccct ggaaacagtg cagcgcctgc   3240
tccctgtgct gtgccaggct catggtctga ctcctcagca ggtggtggcc atcgcttcca   3300
acaatggagg gaagcaggcc ctggagaccg tacagagact gctccccgtg ctgtgccaag   3360
cgcacggtct gaccccctcag caggtcgtcg caatcgccag caatggcggg ggcaagcagg   3420
ctctcgaaac cgtccagcgg ctcctcccag tcctctgtca ggctcacggc ctgaccccac   3480
agcaggtcgt cgctattgct tctaatggcg gagggcggcc tgctctggag agcattgtgg   3540
ctcagctgtc caggcccgat cctgccctgg ctagatccgc actcactaac gatcatctgg   3600
tcgctctcgc ttgcctcggt ggacggcccg ctctggacgc agtcaaaaag ggtctccccc   3660
atgctcccgc actgatcaag agaaccaaca ggagaattcc tgaggatcc gatcgtttaa   3720 acattagcgt ggacctcgcc gatggagatg agttcctgct gagccccgct ggacagaatc   3780
ctctgctgaa aaagatggtg gaagaattta tgccacgatt cgcacctgga gctaaggtgc   3840
tgtacatcgg cgactggcga ggaaagcaca cacggttcga gaaacgcatt tttgaggaaa   3900
ccctggggct cacatttgat ccacacggta gaatgcccga cctggtgctc catgataagg   3960
tccggaaatg gctgttcctc atggaggccg tgaagagcaa aggccctttt gacgaggaaa   4020
ggcatagaac tctgcgggaa ctcttcgcta ccccagtcgc aggactggtg ttcgtcaact   4080
gctttgagaa tcgagaagcc atgaggcagt ggctgcccga gctcgcttgg gagaccgaag   4140
catgggtggc cgacgaccct gaccacctga tccacctcaa cgggagcaga ttcctgggac   4200
cctatgaaaa atgaacgcgt aaatgattgc agatccacta gttctagaat tccagctgag   4260
cgccggtcgc taccattacc agttggtctg gtgtcaaaaa taataataac cgggcagggg   4320
ggatctgcat ggatctttgt gaaggaacct tacttctgtg gtgtgacata attggacaaa   4380
ctacctacag agatttaaag ctctaaggta aatataaaat ttttaagtgt ataatgtgtt   4440
aaactactga ttctaattgt ttgtgtattt tagattccaa cctatggaac tgatgaatgg   4500
```

```
gagcagtggt ggaatgccag atccagacat gataagatac attgatgagt tggacaaac    4560
cacaactaga atgcagtgaa aaaaatgctt tatttgtgaa atttgtgatg ctattgcttt    4620
atttgtaacc attataagct gcaataaaca agttaacaac aacaattgca ttcattttat    4680
gtttcaggtt caggggagg tgtgggaggt tttttaaagc aagtaaaacc tctacaaatg     4740
tggtatggct gattatgatc tgcggccgcc actggccgtc gttttacaac gtcgtgactg    4800
ggaaaaccct ggcgttaccc aacttaatcg ccttgcagca catccccctt tcgccagctg    4860
gcgtaatagc gaagaggccc gcaccgatcg cccttcccaa cagttgcgca gcctgaatgg    4920
cgaatggaac gcgccctgta gcggcgcatt aagcgcggcg ggtgtggtgg ttacgcgcag    4980
cgtgaccgct acacttgcca gcgccctagc gcccgctcct ttcgctttct tcccttcctt    5040
tctcgccacg ttcgccggct ttccccgtca agctctaaat cggggctcc ctttagggtt     5100
ccgatttagt gctttacggc acctcgaccc caaaaaactt gattagggtg atggttcacg    5160
tagtgggcca tcgccctgat agacggtttt tcgccctttg acgttggagt ccacgttctt    5220
taatagtgga ctcttgttcc aaactggaac aacactcaac cctatctcgg tctattcttt    5280
tgatttataa gggattttgc cgatttcggc ctattggtta aaaaatgagc tgatttaaca    5340
aaaatttaac gcgaatttta acaaaatatt aacgcttaca atttaggtgg cacttttcgg    5400
ggaaatgtgc gcggaacccc tatttgttta ttttctaaa tacattcaaa tatgtatccg     5460
ctcatgagac aataaccctg ataaatgctt caataatatt gaaaaggaa gagtatgagt     5520
attcaacatt tccgtgtcgc ccttattccc ttttttgcgg cattttgcct tcctgttttt    5580
gctcacccag aaacgctggt gaaagtaaaa gatgctgaag atcagttggg tgcacgagtg    5640
ggttacatcg aactggatct caacagcggt aagatccttg agtttttcg ccccgaagaa     5700
cgttttccaa tgatgagcac ttttaaagtt ctgctatgtg gcgcggtatt atcccgtatt    5760
gacgccgggc aagagcaact cggtcgccgc atacactatt ctcagaatga cttggttgag    5820
tactcaccag tcacagaaaa gcatcttacg gatggcatga cagtaagaga attatgcagt    5880
gctgccataa ccatgagtga taacactgcg gccaacttac ttctgacaac gatcggagga    5940
ccgaaggagc taaccgcttt tttgcacaac atggggatc atgtaactcg ccttgatcgt     6000
tgggaaccgg agctgaatga agccatacca aacgacgagc gtgacaccac gatgcctgta    6060
gcaatggcaa caacgttgcg caaactatta actggcgaac tacttactct agcttcccgg    6120
caacaattaa tagactggat ggaggcggat aaagttgcag gaccacttct gcgctcggcc    6180
cttccggctg gctggtttat tgctgataaa tctggagccg gtgagcgtgg gtctcgcggt    6240
atcattgcag cactggggcc agatggtaag ccctcccgta tcgtagttat ctacacgacg    6300
gggagtcagg caactatgga tgaacgaaat agacagatcg ctgagatagg tgcctcactg    6360
attaagcatt ggtaactgtc agaccaagtt tactcatata ctttagat tgatttaaaa      6420
cttcattttt aatttaaaag gatctaggtg aagatccttt ttgataatct catgaccaaa    6480
atcccttaac gtgagttttc gttccactga gcgtcagacc ccgtagaaaa gatcaaagga    6540
tcttcttgag atcctttttt tctgcgcgta atctgctgct tgcaaacaaa aaaaccaccg    6600
ctaccagcgg tggtttgttt gccggatcaa gagctaccaa ctcttttcc gaaggtaact     6660
ggcttcagca gagcgcagat accaaatact gtccttctag tgtagccgta gttaggccac    6720
cacttcaaga actctgtagc accgcctaca tacctcgctc tgctaatcct gttaccagtg    6780
gctgctgcca gtggcgataa gtcgtgtctt accgggttgg actcaagacg atagttaccg    6840
```

| | |
|---|---|
| gataaggcgc agcggtcggg ctgaacgggg ggttcgtgca cacagcccag cttggagcga | 6900 |
| acgacctaca ccgaactgag atacctacag cgtgagctat gagaaagcgc cacgcttccc | 6960 |
| gaagggagaa aggcggacag gtatccggta agcggcaggg tcggaacagg agagcgcacg | 7020 |
| agggagcttc caggggggaaa cgcctggtat ctttatagtc ctgtcgggtt tcgccacctc | 7080 |
| tgacttgagc gtcgattttt gtgatgctcg tcagggggc ggagcctatg gaaaaacgcc | 7140 |
| agcaacgcgg cctttttacg gttcctggcc ttttgctggc cttttgctca catgttcttt | 7200 |
| cctgcgttat cccctgattc tgtggataac cgtattaccg cctttgagtg agctgatacc | 7260 |
| gctcgccgca gccgaacgac cgagcgcagc gagtcagtga gcgaggaagc ggaagagcgc | 7320 |
| ccaatacgca aaccgcctct ccccgcgcgt tggccgattc attaatgcag ctggcacgac | 7380 |
| aggtttcccg actggaaagc gggcagtgag cgcaacgcaa ttaatgtgag ttagctcact | 7440 |
| cattaggcac cccaggcttt cactttatg cttccggctc gtatgttgtg tggaattgtg | 7500 |
| agcggataac aatttcacac aggaaacagc tatgaccatg aggcgcgccg gattc | 7555 |

<210> SEQ ID NO 34
<211> LENGTH: 7690
<212> TYPE: DNA
<213> ORGANISM: Artificial sequence
<220> FEATURE:
<223> OTHER INFORMATION: pCAG-ArtTal1-StsI

<400> SEQUENCE: 34

| | |
|---|---|
| gacattgatt attgactagt tattaatagt aatcaattac ggggtcatta gttcatagcc | 60 |
| catatatgga gttccgcgtt acataactta cggtaaatgg cccgcctggc tgaccgccca | 120 |
| acgacccccg cccattgacg tcaataatga cgtatgttcc catagtaacg ccaataggga | 180 |
| ctttccattg acgtcaatgg gtggagtatt tacggtaaac tgcccacttg gcagtacatc | 240 |
| aagtgtatca tatgccaagt acgcccccta ttgacgtcaa tgacggtaaa tggcccgcct | 300 |
| ggcattatgc ccagtacatg accttatggg actttcctac ttggcagtac atctacgtat | 360 |
| tagtcatcgc tattaccatg gtcgaggtga gccccacgtt ctgcttcact ctccccatct | 420 |
| cccccccctc cccaccccca attttgtatt tatttatttt ttaattattt tgtgcagcga | 480 |
| tgggggcggg gggggggggg gggcgcgcgc caggcggggc gggggcgggc gagggcggg | 540 |
| gcggggcgag gcggagaggt gcggcggcag ccaatcagag cggcgcgctc cgaaagtttc | 600 |
| cttttatggc gaggcggcgg cggcggcggc cctataaaaa gcgaagcgcg cggcgggcgg | 660 |
| gagtcgctgc gcgctgcctt cgccccgtgc cccgctccgc cgccgcctcg cgccgcccgc | 720 |
| cccggctctg actgaccgcg ttactcccac aggtgagcgg gcgggacggc ccttctcctc | 780 |
| cgggctgtaa ttagcgcttg gtttaatgac ggcttgtttc ttttctgtgg ctgcgtgaaa | 840 |
| gccttgaggg gctccgggag ggccctttgt gcggggggga ggcgctcggg gggtgcgtgc | 900 |
| gtgtgtgtgt gcgtggggag cgccgcgtgc ggctccgcgc tgcccggcgg ctgtgagcgc | 960 |
| tgcgggcgcg gcgcggggct tgtgcgctc cgcagtgtgc gcgaggggag cgcggccggg | 1020 |
| ggcggtgccc cgcggtgcgg gggggctgc gaggggaaca aaggctgcgt gcggggtgtg | 1080 |
| tgcgtggggg ggtgagcagg gggtgtggc gcgtcggtcg gctgcaacc ccccctgcac | 1140 |
| ccccctcccc gagttgctga gcacggcccg gcttcgggtg cggggctccg tacggggcgt | 1200 |
| ggcgcggggc tcgccgtgcc gggcggggg tggcggcagg tggggtgcc gggcggggcg | 1260 |
| gggccgcctc gggccgggga gggctcgggg gaggggcgcg gcggccccg gagcgccggc | 1320 |
| ggctgtcgag gcgcggcgag ccgcagccat tgcctttat ggtaatcgtg cgagagggcg | 1380 |

```
cagggacttc ctttgtccca aatctgtgcg gagccgaaat ctggaggcg ccgccgcacc    1440 ccctctagcg ggcgcggggc gaagcggtgc ggcgccggca ggaaggaaat gggcggggag    1500
ggccttcgtg cgtcgccgcg ccgccgtccc cttctccctc tccagcctcg gggctgtccg    1560
cggggggacg gctgccttcg gggggacgg ggcaggcgg ggttcggctt ctggcgtgtg    1620
accggcggct ctagagcctc tgctaaccat gttcatgcct tcttcttttt cctacagatc    1680
cttaattaat aatacgactc actatagggg ccgccaccat gggacctaag aaaagagga    1740 aggtggcggc cgctgactac aaggatgacg acgataaacc aggtggcgga ggtagtggcg    1800
gaggtggggt acccgccagt ccagcagccc aggtggatct gagaaccctc ggctacagcc    1860
agcagcagca ggagaagatc aaaccaaagg tgcggtccac cgtcgctcag caccatgaag    1920
cactggtggg gcacggtttc acacacgccc atattgtggc tctgtctcag catcccgctg    1980
cactcgggac tgtggccgtc aaatatcagg acatgatcgc cgctctgcct gaggcaaccc    2040
acgaagccat tgtgggcgtc ggaaagcagt ggagcggtgc cagagcactc gaagcactcc    2100
tcaccgtcgc cggggaactg cggggtccac cactccagtc cggactggac actggacagc    2160
tgctgaagat cgctaaacgc ggcggagtga cagctgtgga agctgtgcac gcttggagga    2220
atgctctgac aggagcccca ctgaatctta ctccagaaca ggtcgtcgca atcgcaagta    2280
acatcggcgg aaaacaggcc ctcgaaaccg tccagagact cctccccgtg ctgtgccagg    2340
cccacggact gacccccacag caggtggtcg ccatcgctag caacggcgga gggaagcagg    2400
ctctggagac cgtgcagagg ctgctccccg tcctgtgcca ggcacatggg ctcacacctc    2460
agcaggtggt cgcaattgcc tccaatggtg gcggaaaaca ggccctggaa actgtgcaga    2520
gactgctccc cgtgctgtgc caggctcacg gtctcacacc ccagcaggtg gtcgctatcg    2580
catctcatga cggggcaag caggcactgg agacagtgca gcggctgctc cctgtcctgt    2640
gccaggccca cggactcact cctcagcagg tcgtcgccat tgctagtaac ggcggaggga    2700
aacaggctct ggaaaccgtg cagcgcctgc tccccgtgct gtgccaagcc cacggcctga    2760
ccccccagca ggtggtcgca atcgcctcaa acaatggtgg caagcaggcc ctggagactg    2820
tgcagcgact gctcccagtg ctgtgccagg cccatgggact cacaccacag caggtcgtcg    2880
ctattgcaag caacaatgga gggaaacagg cactggaaac agtccagagg ctgctccccg    2940
tgctgtgcca agcgcatgga ctcactcccc agcaggtcgt cgccatcgct tccaataacg    3000
gcggcaagca ggccctggag accgtccaga gactgctccc cgtgctgtgc aagctcacg    3060 gactcacacc tgagcaggtc gtggcaatcg cctctaacat tggagggaaa caggccctgg    3120
aaactgtaca gcggctgctc cccgtgctgt gccaagcaca cggactcact ccacagcagg    3180
tcgtggccat tgcaagtcat gacggaggca agcaggccct ggaaacagtg cagcgcctgc    3240
tccctgtgct gtgccaggct catggtctga ctcctcagca ggtggtggcc atcgcttcca    3300
acaatggagg gaagcaggcc ctggagaccg tacagagact gctccccgtg ctgtgccaag    3360
cgcacggtct gacccctcag caggtcgtcg caatcgccag caatggcggg ggcaagcagg    3420
ctctcgaaac cgtccagcgg ctcctcccag tcctctgtca ggctcacggc ctgacccac    3480 agcaggtcgt cgctattgct tctaatggcg gagggcggcc tgctctggag agcattgtgg    3540
ctcagctgtc caggcccgat cctgccctgg ctagatccgc actcactaac gatcatctgg    3600
tcgctctcgc ttgcctcggt ggacggcccg ctctggacgc agtcaaaaag ggtctccccc    3660
atgctcccgc actgatcaag agaaccaaca ggagaattcc tgagggatcc gatcgtttaa    3720
```

```
acgatgtggt gctggagaaa agcgacatcg aaaaattcaa gaaccagctg aggaccgagc    3780
tgacaaatat tgatcactcc tacctgaagg gaatcgacat tgcctccaag aaaaagacct    3840
ctaacgtgga gaatacagag tttgaagcta tctctactaa gattttcacc gatgaactgg    3900
gcttcagcgg gaaacatctg gcggaagca ataagccaga tggcctgctg tgggacgatg     3960
actgcgccat cattctggac agtaaggctt acagcgaggg gttcccctg acagcctccc     4020
acactgacgc tatgggcagg tatctgagac agtttactga gcggaaagag gaaatcaagc    4080
ccacctggtg ggatattgcc cctgaacatc tggacaacac ctacttcgct tatgtgagcg    4140
gctcctttc tggaaattat aaagagcagc tgcagaagtt ccgccaggat acaaaccacc     4200
tgggggcgc cctggaattt gtgaagctgc tgctgctggc taacaattac aaaactcaga    4260
agatgtccaa aaaggagtg aaaaagtcta tcctggacta taacattagt tacgaggaat     4320
atgccccct gctggctgag atcgaatgaa cgcgtaaatg attgcagatc cactagttct     4380
agaattccag ctgagcgccg gtcgctacca ttaccagttg gtctggtgtc aaaaataata    4440
ataaccgggc aggggggatc tgcatggatc tttgtgaagg aaccttactt ctgtggtgtg    4500
acataattgg acaaactacc tacagagatt taaagctcta aggtaaatat aaatttttta    4560
agtgtataat gtgttaaact actgattcta attgtttgtg tatttagat tccaacctat     4620
ggaactgatg aatgggagca gtggtggaat gccagatcca gacatgataa gatacattga    4680
tgagttttgga caaccacaa ctagaatgca gtgaaaaaa tgctttattt gtgaaatttg     4740
tgatgctatt gctttatttg taaccattat aagctgcaat aaacaagtta acaacaacaa    4800
ttgcattcat tttatgtttc aggttcaggg ggaggtgtgg gaggtttttt aaagcaagta    4860
aaacctctac aaatgtggta tggctgatta tgatctgcgg ccgccactgg ccgtcgtttt    4920
acaacgtcgt gactgggaaa accctggcgt tacccaactt aatcgccttg cagcacatcc    4980
ccctttcgcc agctggcgta atagcgaaga ggcccgcacc gatcgccctt cccaacagtt    5040
gcgcagcctg aatggcgaat ggaacgcgcc ctgtagcggc gcattaagcg cggcgggtgt    5100
ggtggttacg cgcagcgtga ccgctacact tgccagcgcc ctagcgcccg ctcctttcgc    5160
tttcttccct tccttctcg ccacgttcgc cggcttccc cgtcaagctc taaatcgggg       5220
gctcccttta gggttccgat ttagtgcttt acggcacctc gaccccaaaa aacttgatta    5280
gggtgatggt tcacgtagtg gccatcgcc ctgatagacg ttttcgcc ctttgacgtt       5340
ggagtccacg ttctttaata gtggactctt gttccaaact ggaacaacac tcaaccctat    5400
ctcggtctat tctttttgatt tataagggat tttgccgatt tcggcctatt ggttaaaaaa    5460
tgagctgatt taacaaaaat ttaacgcgaa ttttaacaaa atattaacgc ttacaattta    5520
ggtggcactt ttcggggaaa tgtgcgcgga acccctattt gtttatttt ctaaatacat     5580
tcaaatatgt atccgctcat gagacaataa ccctgataaa tgcttcaata atattgaaaa    5640
aggaagagta tgagtattca acatttccgt gtcgccctta ttcctttttt tgcggcattt    5700
tgccttcctg tttttgctca cccagaaacg ctggtgaaag taaaagatgc tgaagatcag    5760
ttgggtgcac gagtgggtta catcgaactg gatctcaaca gcggtaagat ccttgagagt    5820
tttcgccccg aagaacgttt tccaatgatg agcactttta aagttctgct atgtggcgcg    5880
gtattatccc gtattgacgc cgggcaagag caactcggtc gccgcataca ctattctcag    5940
aatgacttgg ttgagtactc accagtcaca gaaaagcatc ttacggatgg catgacagta    6000
agagaattat gcagtgctgc cataaccatg agtgataaca ctgcggccaa cttacttctg    6060
acaacgatcg gaggaccgaa ggagctaacc gcttttttgc acaacatggg ggatcatgta    6120
```

```
actcgccttg atcgttggga accggagctg aatgaagcca taccaaacga cgagcgtgac    6180
accacgatgc ctgtagcaat ggcaacaacg ttgcgcaaac tattaactgg cgaactactt    6240
actctagctt cccggcaaca attaatagac tggatggagg cggataaagt tgcaggacca    6300
cttctgcgct cggcccttcc ggctggctgg tttattgctg ataaatctgg agccggtgag    6360
cgtgggtctc gcggtatcat tgcagcactg gggccagatg gtaagccctc ccgtatcgta    6420
gttatctaca cgacggggag tcaggcaact atggatgaac gaaatagaca gatcgctgag    6480
ataggtgcct cactgattaa gcattggtaa ctgtcagacc aagtttactc atatatactt    6540
tagattgatt taaaacttca tttttaattt aaaaggatct aggtgaagat cctttttgat    6600
aatctcatga ccaaaatccc ttaacgtgag ttttcgttcc actgagcgtc agaccccgta    6660
gaaaagatca aggatcttc ttgagatcct ttttttctgc gcgtaatctg ctgcttgcaa    6720
acaaaaaaac caccgctacc agcggtggtt tgtttgccgg atcaagagct accaactctt    6780
tttccgaagg taactggctt cagcagagcg cagataccaa atactgtcct tctagtgtag    6840
ccgtagttag gccaccactt caagaactct gtagcaccgc ctacatacct cgctctgcta    6900
atcctgttac cagtggctgc tgccagtggc gataagtcgt gtcttaccgg gttggactca    6960
agacgatagt taccggataa ggcgcagcgg tcgggctgaa cggggggttc gtgcacacag    7020
cccagcttgg agcgaacgac ctacaccgaa ctgagatacc tacagcgtga gctatgagaa    7080
agcgccacgc ttcccgaagg gagaaaggcg gacaggtatc cggtaagcgg cagggtcgga    7140
acaggagagc gcacgaggga gcttccaggg ggaaacgcct ggtatcttta tagtcctgtc    7200
gggtttcgcc acctctgact tgagcgtcga ttttgtgat gctcgtcagg gggcggagc    7260 ctatggaaaa acgccagcaa cgcggccttt ttacggttcc tggccttttg ctggcctttt    7320
gctcacatgt tctttcctgc gttatcccct gattctgtgg ataaccgtat taccgccttt    7380
gagtgagctg ataccgctcg ccgcagccga acgaccgagc gcagcgagtc agtgagcgag    7440
gaagcggaag agcgcccaat acgcaaaccg cctctccccg cgcgttggcc gattcattaa    7500
tgcagctggc acgacaggtt tcccgactgg aaagcgggca gtgagcgcaa cgcaattaat    7560
gtgagttagc tcactcatta ggcaccccag gctttacact ttatgcttcc ggctcgtatg    7620
ttgtgtggaa ttgtgagcgg ataacaattt cacacaggaa acagctatga ccatgaggcg    7680
cgccggattc                                                          7690

<210> SEQ ID NO 35
<211> LENGTH: 7654
<212> TYPE: DNA
<213> ORGANISM: Artificial sequence
<220> FEATURE:
<223> OTHER INFORMATION: pCAG-ArtTal1-FokI

<400> SEQUENCE: 35
gacattgatt attgactagt tattaatagt aatcaattac gggtcatta gttcatagcc      60 catatatgga gttccgcgtt acataactta cggtaaatgg cccgcctggc tgaccgccca    120
acgacccccg cccattgacg tcaataatga cgtatgttcc catagtaacg ccaatagga    180 ctttccattg acgtcaatgg gtggagtatt tacggtaaac tgcccacttg gcagtacatc    240
aagtgtatca tatgccaagt acgccccctta ttgacgtcaa tgacggtaaa tggcccgcct    300
ggcattatgc ccagtacatg acctttatggg actttcctac ttggcagtac atctacgtat    360
tagtcatcgc tattaccatg gtcgaggtga gccccacgtt ctgcttcact ctccccatct    420
```

```
cccccccctc cccaccccca attttgtatt tatttatttt ttaattattt tgtgcagcga    480
tgggggcggg ggggggggggg gggcgcgcgc caggcgggc ggggcgggc gaggggcggg     540
gcggggcgag gcggagaggt gcggcggcag ccaatcagag cggcgcgctc cgaaagtttc    600
cttttatggc gaggcggcgg cggcggcgg cctataaaaa gcgaagcgcg cggcgggcgg    660
gagtcgctgc gcgctgcctt cgccccgtgc cccgctccgc cgccgcctcg cgccgcccgc   720
cccggctctg actgaccgcg ttactcccac aggtgagcgg gcgggacggc ccttctcctc   780
cgggctgtaa ttagcgcttg gtttaatgac ggcttgtttc ttttctgtgg ctgcgtgaaa   840
gccttgaggg gctccgggag ggccctttgt gcggggggga gcggctcggg gggtgcgtgc   900
gtgtgtgtgt gcgtggggag cgccgcgtgc ggctccgcgc tgcccggcgg ctgtgagcgc   960
tgcgggcgcg gcgcgggct ttgtgcgctc cgcagtgtgc gcgaggggag cgcggccggg  1020
ggcggtgccc cgcggtgcgg gggggctgc gaggggaaca aaggctgcgt gcggggtgtg   1080
tgcgtggggg ggtgagcagg gggtgtgggc gcgtcggtcg ggctgcaacc ccccctgcac   1140
cccccctccc gagttgctga gcacggcccg gcttcgggtg cggggctccg tacggggcgt  1200
ggcgcggggc tcgccgtgcc gggcgggggg tggcggcagg tgggggtgcc gggcggggcg  1260
gggccgcctc gggccgggga gggctcgggg gaggggcgcg gcggccccg gagcgccggc   1320
ggctgtcgag gcgcggcgag ccgcagccat tgccttttat ggtaatcgtg cgagagggcg   1380
cagggacttc ctttgtccca aatctgtgcg gagccgaaat ctgggaggcg ccgccgcacc   1440
ccctctagcg ggcgcggggc gaagcggtgc ggcgccggca ggaaggaaat gggcggggag  1500
ggccttcgtg cgtcgccgcg ccgccgtccc cttctccctc tccagcctcg gggctgtccg  1560
cgggggacg gctgccttcg gggggacgg ggcagggcgg ggttcggctt ctggcgtgtg    1620
accgcggct ctagagcctc tgctaaccat gttcatgcct tcttctttt cctacagatc    1680
cttaattaat aatacgactc actataggg ccgccaccat gggacctaag aaaaagagga   1740
aggtggcggc cgctgactac aaggatgacg acgataaacc aggtggcgga ggtagtggcg   1800
gaggtggggt acccgccagt ccagcagccc aggtggatct gagaaccctc ggctacagcc   1860
agcagcagca ggagaagatc aaaccaaagg tgcggtccac cgtcgctcag caccatgaag   1920
cactggtggg gcacggtttc acacacgccc atattgtggc tctgtctcag catcccgctg   1980
cactcgggac tgtggccgtc aaatatcagg acatgatcgc cgctctgcct gaggcaaccc   2040
acgaagccat tgtgggcgtc ggaaagcagt ggagcggtgc cagagcactc gaagcactcc   2100
tcaccgtcgc cggggaactg cggggtccac cactccagtc cggactggac actgacagc    2160
tgctgaagat cgctaaacgc ggcggagtga cagctgtgga agctgtgcac gcttggagga   2220
atgctctgac aggagcccca ctgaatctta ctccagaaca ggtcgtcgca atcgcaagta   2280
acatcggcgg aaaacaggcc ctcgaaaccg tccagagact cctccccgtg ctgtgccagg   2340
cccacggact gaccccacag caggtggtcg ccatcgctag caacggcgga gggaagcagg   2400
ctctggagac cgtgcagagg ctgctccccg tcctgtgcca ggcacatggg ctcacacctc   2460
agcaggtggt cgcaattgcc tccaatggtg gcggaaaaca ggccctggaa actgtgcaga   2520
gactgctccc cgtgctgtgc caggctcacg gtctcacacc ccagcaggtg gtcgctatcg   2580
catctcatga cggggcaag caggcactgg agacagtgca gcggctgctc cctgtcctgt    2640
gccaggccca cggactcact cctcagcagg tcgtcgccat tgctagtaac ggcggaggga   2700
aacaggctct ggaaaccgtg cagcgcctgc tcccgtgct gtgccaagcc cacggcctga    2760
cccccagca ggtggtcgca atcgcctcaa acaatggtgg caagcaggcc ctggagactg    2820
```

```
tgcagcgact gctcccagtg ctgtgccagg cccatggact cacaccacag caggtcgtcg    2880
ctattgcaag caacaatgga gggaaacagg cactggaaac agtccagagg ctgctccccg    2940
tgctgtgcca agcgcatgga ctcactcccc agcaggtcgt cgccatcgct ccaataacg     3000
gcggcaagca ggccctggag accgtccaga gactgctccc cgtgctgtgc caagctcacg    3060
gactcacacc tgagcaggtc gtggcaatcg cctctaacat tggagggaaa caggccctgg    3120
aaactgtaca gcggctgctc cccgtgctgt gccaagcaca cggactcact ccacagcagg    3180
tcgtggccat tgcaagtcat gacggaggca agcaggccct ggaaacagtg cagcgcctgc    3240
tccctgtgct gtgccaggct catggtctga ctcctcagca ggtggtggcc atcgcttcca    3300
acaatggagg gaagcaggcc ctggagaccg tacagagact gctcccgtg  ctgtgccaag    3360
cgcacggtct gacccctcag caggtcgtcg caatcgccag caatggcggg ggcaagcagg    3420
ctctcgaaac cgtccagcgg ctcctcccag tcctctgtca ggctcacggc ctgacccac     3480
agcaggtcgt cgctattgct tctaatggcg agggcggcc  tgtctggag agcattgtgg     3540
ctcagctgtc caggcccgat cctgccctgg ctagatccgc actcactaac gatcatctgg    3600
tcgctctcgc ttgcctcggt ggacggcccg ctctggacgc agtcaaaaag ggtctccccc    3660
atgctcccgc actgatcaag agaaccaaca ggagaattcc tgagggatcc gatcgtttaa    3720
accagctcgt gaaaagcgaa ctcgaagaaa agaaaagtga actgcggcac aaactgaaat    3780
acgtcccaca tgaatacatt gagctgatcg agattgctag gaactccacc caggacagaa    3840
tcctcgagat gaaagtgatg gaattcttta tgaaagtcta cgggtatcgg ggcaagcacc    3900
tgggcggatc tcgcaaacca gatggggcaa tctacactgt gggtagtccc atcgactatg    3960
gcgtgattgt cgataccaag gcctacagtg ggggttataa tctgcccatt ggacaggctg    4020
acgagatgca gcgatacgtg gaggaaaacc agacaagaaa taagcatatc aaccccaatg    4080
agtggtggaa agtgtatcct agctccgtca ctgaattcaa gtttctcttc gtgtcaggcc    4140
actttaaggg aaactacaaa gcacagctga ccaggctcaa tcatattaca aactgcaatg    4200
gcgccgtgct gagcgtcgag gaactgctca tcggcggaga tgatcaag gccggcacac     4260
tcaccctgga ggaggtccgc cgaaaattca ataacgggga aatcaacttc tgaacgcgta    4320
aatgattgca gatccactag ttctagaatt ccagctgagc gccggtcgct accattacca    4380
gttggtctgg tgtcaaaaat aataataacc gggcagggg  gatctgcatg gatctttgtg    4440
aaggaacctt acttctgtgg tgtgacataa ttggacaaac tacctacaga gatttaaagc    4500
tctaaggtaa atataaaatt tttaagtgta taatgtgtta aactactgat tctaattgtt    4560
tgtgtatttt agattccaac ctatggaact gatgaatggg agcagtggtg gaatgccaga    4620
tccagacatg ataagataca ttgatgagtt tggacaaacc acaactagaa tgcagtgaaa    4680
aaaatgcttt atttgtgaaa tttgtgatgc tattgcttta tttgtaacca ttataagctg    4740
caataaacaa gttaacaaca acaattgcat tcattttatg tttcaggttc agggggaggt    4800
gtgggaggtt ttttaaagca agtaaaacct ctacaaatgt ggtatggctg attatgatct    4860
gcggccgcca ctggccgtcg ttttacaacg tcgtgactgg gaaaaccctg gcgttaccca    4920
acttaatcgc cttgcagcac atccccctt  cgccagctgg cgtaatagcg aagaggcccg    4980
caccgatcgc ccttcccaac agttgcgcag cctgaatggc gaatggaacg cgccctgtag    5040
cggcgcatta agcgcggcgg gtgtggtggt tacgcgcagc gtgaccgcta cacttgccag    5100
cgccctagcg cccgctcctt tcgctttctt cccttccttt ctcgccacgt tcgccggctt    5160
```

```
tccccgtcaa gctctaaatc gggggctccc tttagggttc cgatttagtg ctttacggca    5220
cctcgacccc aaaaaacttg attagggtga tggttcacgt agtgggccat cgccctgata    5280
gacggttttt cgcccttttga cgttggagtc cacgttcttt aatagtggac tcttgttcca   5340
aactggaaca acactcaacc ctatctcggt ctattctttt gatttataag gattttgcc    5400
gatttcggcc tattggttaa aaatgagct gatttaacaa aaatttaacg cgaattttaa    5460
caaaatatta acgcttacaa tttaggtggc acttttcggg gaaatgtgcg cggaacccct   5520
atttgtttat ttttctaaat acattcaaat atgtatccgc tcatgagaca ataaccctga   5580
taaatgcttc aataatattg aaaaaggaag agtatgagta ttcaacattt ccgtgtcgcc   5640
cttattccct ttttttgcggc attttgcctt cctgtttttg ctcacccaga aacgctggtg  5700
aaagtaaaag atgctgaaga tcagttgggt gcacgagtgg gttacatcga actggatctc  5760
aacagcggta agatccttga gagttttcgc cccgaagaac gttttccaat gatgagcact   5820
tttaaagttc tgctatgtgg cgcggtatta tcccgtattg acgccgggca agagcaactc   5880
ggtcgccgca tacactattc tcagaatgac ttggttgagt actcaccagt cacagaaaag   5940
catcttacgg atggcatgac agtaagagaa ttatgcagtg ctgccataac catgagtgat   6000
aacactgcgg ccaacttact tctgacaacg atcggaggac cgaaggagct aaccgctttt   6060
ttgcacaaca tgggggatca tgtaactcgc cttgatcgtt gggaaccgga gctgaatgaa   6120
gccataccaa acgacgagcg tgacaccacg atgcctgtag caatggcaac aacgttgcgc   6180
aaactattaa ctggcgaact acttactcta gcttcccggc aacaattaat agactggatg   6240
gaggcggata aagttgcagg accacttctg cgctcggccc ttccggctgg ctggtttatt   6300
gctgataaat ctggagccgg tgagcgtggg tctcgcggta tcattgcagc actggggcca   6360
gatggtaagc cctcccgtat cgtagttatc tacacgacgg ggagtcaggc aactatggat   6420
gaacgaaata gacagatcgc tgagataggt gcctcactga ttaagcattg gtaactgtca   6480
gaccaagttt actcatatat actttagatt gatttaaaac ttcatttta atttaaaagg   6540
atctaggtga agatcctttt tgataatctc atgaccaaaa tcccttaacg tgagttttcg   6600
ttccactgag cgtcagaccc cgtagaaaag atcaaaggat cttcttgaga tccttttttt   6660
ctgcgcgtaa tctgctgctt gcaaacaaaa aaaccaccgc taccagcggt ggtttgtttg   6720
ccggatcaag agctaccaac tctttttccg aaggtaactg gcttcagcag agcgcagata   6780
ccaaatactg tccttctagt gtagccgtag ttaggccacc acttcaagaa ctctgtagca   6840
ccgcctacat acctcgctct gctaatcctg ttaccagtgg ctgctgccag tggcgataag   6900
tcgtgtctta ccgggttgga ctcaagacga tagttaccgg ataaggcgca gcggtcgggc   6960
tgaacggggg gttcgtgcac acagcccagc ttggagcgaa cgacctacac cgaactgaga   7020
tacctacagc gtgagctatg agaaagcgcc acgcttcccg aagggagaaa ggcggacagg   7080
tatccggtaa gcggcagggt cggaacagga gagcgcacga gggagcttcc agggggaaac   7140
gcctggtatc tttatagtcc tgtcgggttt cgccacctct gacttgagcg tcatttttg    7200
tgatgctcgt caggggggcg gagcctatgg aaaaacgcca gcaacgcggc cttttttacgg  7260
ttcctggcct tttgctggcc ttttgctcac atgttcttc ctgcgttatc ccctgattct   7320
gtggataacc gtattaccgc ctttgagtga gctgataccg ctcgccgcag ccgaacgacc   7380
gagcgcagcg agtcagtgag cgaggaagcg gaagagcgcc caatacgcaa accgcctctc   7440
cccgcgcgtt ggccgattca ttaatgcagc tggcacgaca ggtttcccga ctggaaagcg   7500
ggcagtgagc gcaacgcaat taatgtgagt tagctcactc attaggcacc ccaggcttta   7560
```

```
cactttatgc ttccggctcg tatgttgtgt ggaattgtga gcggataaca atttcacaca    7620
ggaaacagct atgaccatga ggcgcgccgg attc                                7654
```

<210> SEQ ID NO 36
<211> LENGTH: 947
<212> TYPE: PRT
<213> ORGANISM: Artificial sequence
<220> FEATURE:
<223> OTHER INFORMATION: ArtTal1-Alw

<400> SEQUENCE: 36

```
Met Gly Pro Lys Lys Arg Lys Val Ala Ala Asp Tyr Lys Asp
1               5                   10                  15

Asp Asp Asp Lys Pro Gly Gly Gly Ser Gly Gly Gly Val Pro
                20                  25                  30

Ala Ser Pro Ala Ala Gln Val Asp Leu Arg Thr Leu Gly Tyr Ser Gln
            35                  40                  45

Gln Gln Gln Glu Lys Ile Lys Pro Lys Val Arg Ser Thr Val Ala Gln
        50                  55                  60

His His Glu Ala Leu Val Gly His Gly Phe Thr His Ala His Ile Val
65                  70                  75                  80

Ala Leu Ser Gln His Pro Ala Ala Leu Gly Thr Val Ala Val Lys Tyr
                85                  90                  95

Gln Asp Met Ile Ala Ala Leu Pro Glu Ala Thr His Glu Ala Ile Val
                100                 105                 110

Gly Val Gly Lys Gln Trp Ser Gly Ala Arg Ala Leu Glu Ala Leu Leu
            115                 120                 125

Thr Val Ala Gly Glu Leu Arg Gly Pro Pro Leu Gln Ser Gly Leu Asp
        130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Glu Gln Val Val Ala Ile Ala Ser Asn Ile Gly Gly Lys
            180                 185                 190

Gln Ala Leu Glu Thr Val Gln Arg Leu Leu Pro Val Leu Cys Gln Ala
        195                 200                 205

His Gly Leu Thr Pro Gln Gln Val Val Ala Ile Ala Ser Asn Gly Gly
    210                 215                 220

Gly Lys Gln Ala Leu Glu Thr Val Gln Arg Leu Leu Pro Val Leu Cys
225                 230                 235                 240

Gln Ala His Gly Leu Thr Pro Gln Gln Val Val Ala Ile Ala Ser Asn
                245                 250                 255

Gly Gly Gly Lys Gln Ala Leu Glu Thr Val Gln Arg Leu Leu Pro Val
            260                 265                 270

Leu Cys Gln Ala His Gly Leu Thr Pro Gln Gln Val Val Ala Ile Ala
        275                 280                 285

Ser His Asp Gly Gly Lys Gln Ala Leu Glu Thr Val Gln Arg Leu Leu
    290                 295                 300

Pro Val Leu Cys Gln Ala His Gly Leu Thr Pro Gln Gln Val Val Ala
305                 310                 315                 320

Ile Ala Ser Asn Gly Gly Gly Lys Gln Ala Leu Glu Thr Val Gln Arg
                325                 330                 335

Leu Leu Pro Val Leu Cys Gln Ala His Gly Leu Thr Pro Gln Gln Val
```

```
              340             345             350
Val Ala Ile Ala Ser Asn Asn Gly Gly Lys Gln Ala Leu Glu Thr Val
            355             360             365
Gln Arg Leu Leu Pro Val Leu Cys Gln Ala His Gly Leu Thr Pro Gln
            370             375             380
Gln Val Val Ala Ile Ala Ser Asn Asn Gly Gly Lys Gln Ala Leu Glu
385             390             395             400
Thr Val Gln Arg Leu Leu Pro Val Leu Cys Gln Ala His Gly Leu Thr
                405             410             415
Pro Gln Gln Val Val Ala Ile Ala Ser Asn Asn Gly Gly Lys Gln Ala
            420             425             430
Leu Glu Thr Val Gln Arg Leu Leu Pro Val Leu Cys Gln Ala His Gly
            435             440             445
Leu Thr Pro Glu Gln Val Val Ala Ile Ala Ser Asn Ile Gly Gly Lys
            450             455             460
Gln Ala Leu Glu Thr Val Gln Arg Leu Leu Pro Val Leu Cys Gln Ala
465             470             475             480
His Gly Leu Thr Pro Gln Gln Val Val Ala Ile Ala Ser His Asp Gly
                485             490             495
Gly Lys Gln Ala Leu Glu Thr Val Gln Arg Leu Leu Pro Val Leu Cys
            500             505             510
Gln Ala His Gly Leu Thr Pro Gln Gln Val Val Ala Ile Ala Ser Asn
            515             520             525
Asn Gly Gly Lys Gln Ala Leu Glu Thr Val Gln Arg Leu Leu Pro Val
            530             535             540
Leu Cys Gln Ala His Gly Leu Thr Pro Gln Gln Val Val Ala Ile Ala
545             550             555             560
Ser Asn Gly Gly Gly Lys Gln Ala Leu Glu Thr Val Gln Arg Leu Leu
                565             570             575
Pro Val Leu Cys Gln Ala His Gly Leu Thr Pro Gln Gln Val Val Ala
            580             585             590
Ile Ala Ser Asn Gly Gly Gly Arg Pro Ala Leu Glu Ser Ile Val Ala
            595             600             605
Gln Leu Ser Arg Pro Asp Pro Ala Leu Ala Arg Ser Ala Leu Thr Asn
            610             615             620
Asp His Leu Val Ala Leu Ala Cys Leu Gly Gly Arg Pro Ala Leu Asp
625             630             635             640
Ala Val Lys Lys Gly Leu Pro His Ala Pro Ala Leu Ile Lys Arg Thr
                645             650             655
Asn Arg Arg Ile Pro Glu Gly Ser Asp Arg Leu Asn Lys Glu Thr Asn
            660             665             670
Ile Leu Leu Val Glu Gln Leu Glu Glu Thr Leu Asn Arg Asn Arg Ile
            675             680             685
Leu Phe Glu Lys Asn Ser Ser Ile Ala Gln Ala Pro Ile Gly Glu Ile
            690             695             700
Lys Asn Tyr Arg Tyr His Leu Glu Glu Leu Leu Phe Glu Asn Asn Glu
705             710             715             720
Lys Lys Phe Ala Glu Asn Gln Lys Asn Glu Trp Asp Glu Ile Leu Ala
                725             730             735
Tyr Met Asp Leu Leu Ile Ser Pro Lys Pro Ile Ser Ile Glu Ile Ala
                740             745             750
Asp Lys Glu Ile Ser Ile Pro Ser Gly Glu Arg Pro Ala Tyr Phe Glu
            755             760             765
```

```
Trp Val Leu Trp Arg Ala Phe Leu Ala Leu Asn His Leu Ile Ile Glu
        770                 775                 780

Pro Gln Gln Cys Arg Arg Phe Lys Val Asp Gln Asp Phe Lys Pro Ile
785                 790                 795                 800

His Asn Ala Pro Gly Gly Gly Ala Asp Val Ile Phe Glu Tyr Glu Asn
            805                 810                 815

Phe Lys Ile Leu Gly Glu Val Thr Leu Thr Ser Asn Ser Arg Gln Glu
            820                 825                 830

Ala Ala Glu Gly Glu Pro Val Arg Arg His Ile Ala Val Glu Thr Val
            835                 840                 845

Asn Thr Pro Asp Lys Asp Val Tyr Gly Leu Phe Leu Ala Leu Thr Ile
        850                 855                 860

Asp Thr Asn Thr Ala Glu Thr Phe Arg His Gly Ala Trp Tyr His Gln
865                 870                 875                 880

Glu Glu Leu Met Asp Val Lys Ile Leu Pro Leu Thr Leu Glu Ser Phe
                885                 890                 895

Lys Lys Tyr Leu Glu Ser Leu Arg Lys Lys Asn Gln Val Glu Thr Gly
            900                 905                 910

Ile Phe Asp Leu Lys Lys Met Met Asp Glu Ser Leu Lys Leu Arg Glu
        915                 920                 925

Thr Leu Thr Ala Pro Gln Trp Lys Asn Glu Ile Thr Asn Lys Phe Ala
        930                 935                 940

Arg Pro Ile
945

<210> SEQ ID NO 37
<211> LENGTH: 869
<212> TYPE: PRT
<213> ORGANISM: Artificial sequence
<220> FEATURE:
<223> OTHER INFORMATION: ArtTal1-CLEDORF

<400> SEQUENCE: 37

Met Gly Pro Lys Lys Arg Lys Val Ala Ala Asp Tyr Lys Asp
1               5                   10                  15

Asp Asp Asp Lys Pro Gly Gly Gly Ser Gly Gly Gly Val Pro
                20                  25                  30

Ala Ser Pro Ala Ala Gln Val Asp Leu Arg Thr Leu Gly Tyr Ser Gln
            35                  40                  45

Gln Gln Gln Glu Lys Ile Lys Pro Lys Val Arg Ser Thr Val Ala Gln
        50                  55                  60

His His Glu Ala Leu Val Gly His Gly Phe Thr His Ala His Ile Val
65                  70                  75                  80

Ala Leu Ser Gln His Pro Ala Ala Leu Gly Thr Val Ala Val Lys Tyr
                85                  90                  95

Gln Asp Met Ile Ala Ala Leu Pro Glu Ala Thr His Glu Ala Ile Val
                100                 105                 110

Gly Val Gly Lys Gln Trp Ser Gly Ala Arg Ala Leu Glu Ala Leu Leu
            115                 120                 125

Thr Val Ala Gly Glu Leu Arg Gly Pro Pro Leu Gln Ser Gly Leu Asp
        130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175
```

```
Leu Thr Pro Glu Gln Val Val Ala Ile Ala Ser Asn Ile Gly Gly Lys
                180                 185                 190

Gln Ala Leu Glu Thr Val Gln Arg Leu Leu Pro Val Leu Cys Gln Ala
            195                 200                 205

His Gly Leu Thr Pro Gln Gln Val Val Ala Ile Ala Ser Asn Gly Gly
        210                 215                 220

Gly Lys Gln Ala Leu Glu Thr Val Gln Arg Leu Leu Pro Val Leu Cys
225                 230                 235                 240

Gln Ala His Gly Leu Thr Pro Gln Gln Val Val Ala Ile Ala Ser Asn
                245                 250                 255

Gly Gly Gly Lys Gln Ala Leu Glu Thr Val Gln Arg Leu Leu Pro Val
            260                 265                 270

Leu Cys Gln Ala His Gly Leu Thr Pro Gln Gln Val Val Ala Ile Ala
        275                 280                 285

Ser His Asp Gly Gly Lys Gln Ala Leu Glu Thr Val Gln Arg Leu Leu
    290                 295                 300

Pro Val Leu Cys Gln Ala His Gly Leu Thr Pro Gln Gln Val Val Ala
305                 310                 315                 320

Ile Ala Ser Asn Gly Gly Lys Gln Ala Leu Glu Thr Val Gln Arg
                325                 330                 335

Leu Leu Pro Val Leu Cys Gln Ala His Gly Leu Thr Pro Gln Gln Val
            340                 345                 350

Val Ala Ile Ala Ser Asn Asn Gly Gly Lys Gln Ala Leu Glu Thr Val
        355                 360                 365

Gln Arg Leu Leu Pro Val Leu Cys Gln Ala His Gly Leu Thr Pro Gln
370                 375                 380

Gln Val Ala Ile Ala Ser Asn Asn Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Gln Gln Val Val Ala Ile Ala Ser Asn Asn Gly Gly Lys Gln Ala
            420                 425                 430

Leu Glu Thr Val Gln Arg Leu Leu Pro Val Leu Cys Gln Ala His Gly
        435                 440                 445

Leu Thr Pro Glu Gln Val Val Ala Ile Ala Ser Asn Ile Gly Gly Lys
    450                 455                 460

Gln Ala Leu Glu Thr Val Gln Arg Leu Leu Pro Val Leu Cys Gln Ala
465                 470                 475                 480

His Gly Leu Thr Pro Gln Gln Val Val Ala Ile Ala Ser His Asp Gly
                485                 490                 495

Gly Lys Gln Ala Leu Glu Thr Val Gln Arg Leu Leu Pro Val Leu Cys
            500                 505                 510

Gln Ala His Gly Leu Thr Pro Gln Gln Val Val Ala Ile Ala Ser Asn
        515                 520                 525

Asn Gly Gly Lys Gln Ala Leu Glu Thr Val Gln Arg Leu Leu Pro Val
    530                 535                 540

Leu Cys Gln Ala His Gly Leu Thr Pro Gln Gln Val Val Ala Ile Ala
545                 550                 555                 560

Ser Asn Gly Gly Gly Lys Gln Ala Leu Glu Thr Val Gln Arg Leu Leu
                565                 570                 575

Pro Val Leu Cys Gln Ala His Gly Leu Thr Pro Gln Gln Val Val Ala
            580                 585                 590
```

```
Ile Ala Ser Asn Gly Gly Arg Pro Ala Leu Glu Ser Ile Val Ala
            595                 600                 605

Gln Leu Ser Arg Pro Asp Pro Ala Leu Ala Arg Ser Ala Leu Thr Asn
610                 615                 620

Asp His Leu Val Ala Leu Ala Cys Leu Gly Gly Arg Pro Ala Leu Asp
625                 630                 635                 640

Ala Val Lys Lys Gly Leu Pro His Ala Pro Ala Leu Ile Lys Arg Thr
                645                 650                 655

Asn Arg Arg Ile Pro Glu Gly Ser Asp Arg Leu Asn Lys Leu Ala Lys
            660                 665                 670

Ser Ser Gln Ser Glu Thr Lys Glu Lys Leu Arg Glu Lys Leu Arg Asn
        675                 680                 685

Leu Pro His Glu Tyr Leu Ser Leu Val Asp Leu Ala Tyr Asp Ser Lys
    690                 695                 700

Gln Asn Arg Leu Phe Glu Met Lys Val Ile Glu Leu Leu Thr Glu Glu
705                 710                 715                 720

Cys Gly Phe Gln Gly Leu His Leu Gly Gly Ser Arg Arg Pro Asp Gly
                725                 730                 735

Val Leu Tyr Thr Ala Gly Leu Thr Asp Asn Tyr Gly Ile Ile Leu Asp
            740                 745                 750

Thr Lys Ala Tyr Ser Ser Gly Tyr Ser Leu Pro Ile Ala Gln Ala Asp
        755                 760                 765

Glu Met Glu Arg Tyr Val Arg Glu Asn Gln Thr Arg Asp Glu Leu Val
    770                 775                 780

Asn Pro Asn Gln Trp Trp Glu Asn Phe Glu Asn Gly Leu Gly Thr Phe
785                 790                 795                 800

Tyr Phe Leu Phe Val Ala Gly His Phe Asn Gly Asn Val Gln Ala Gln
                805                 810                 815

Leu Glu Arg Ile Ser Arg Asn Thr Gly Val Leu Gly Ala Ala Ala Ser
            820                 825                 830

Ile Ser Gln Leu Leu Leu Ala Asp Ala Ile Arg Gly Gly Arg Met
        835                 840                 845

Asp Arg Glu Arg Leu Arg His Leu Met Phe Gln Asn Glu Glu Phe Leu
850                 855                 860

Leu Glu Gln Glu Leu
865

<210> SEQ ID NO 38
<211> LENGTH: 867
<212> TYPE: PRT
<213> ORGANISM: Artificial sequence
<220> FEATURE:
<223> OTHER INFORMATION: ArtTal1-Clo051

<400> SEQUENCE: 38

Met Gly Pro Lys Lys Arg Lys Val Ala Ala Ala Asp Tyr Lys Asp
1               5                   10                  15

Asp Asp Asp Lys Pro Gly Gly Gly Ser Gly Gly Gly Gly Val Pro
                20                  25                  30

Ala Ser Pro Ala Ala Gln Val Asp Leu Arg Thr Leu Gly Tyr Ser Gln
            35                  40                  45

Gln Gln Gln Glu Lys Ile Lys Pro Lys Val Arg Ser Thr Val Ala Gln
        50                  55                  60

His His Glu Ala Leu Val Gly His Gly Phe Thr His Ala His Ile Val
65                  70                  75                  80
```

```
Ala Leu Ser Gln His Pro Ala Ala Leu Gly Thr Val Ala Val Lys Tyr
                85                  90                  95
Gln Asp Met Ile Ala Ala Leu Pro Glu Ala Thr His Glu Ala Ile Val
            100                 105                 110
Gly Val Gly Lys Gln Trp Ser Gly Ala Arg Ala Leu Glu Ala Leu Leu
        115                 120                 125
Thr Val Ala Gly Glu Leu Arg Gly Pro Leu Gln Ser Gly Leu Asp
    130                 135                 140
Thr Gly Gln Leu Leu Lys Ile Ala Lys Arg Gly Gly Val Thr Ala Val
145                 150                 155                 160
Glu Ala Val His Ala Trp Arg Asn Ala Leu Thr Gly Ala Pro Leu Asn
                165                 170                 175
Leu Thr Pro Glu Gln Val Val Ala Ile Ala Ser Asn Ile Gly Gly Lys
            180                 185                 190
Gln Ala Leu Glu Thr Val Gln Arg Leu Leu Pro Val Leu Cys Gln Ala
        195                 200                 205
His Gly Leu Thr Pro Gln Gln Val Val Ala Ile Ala Ser Asn Gly Gly
    210                 215                 220
Gly Lys Gln Ala Leu Glu Thr Val Gln Arg Leu Leu Pro Val Leu Cys
225                 230                 235                 240
Gln Ala His Gly Leu Thr Pro Gln Gln Val Val Ala Ile Ala Ser Asn
                245                 250                 255
Gly Gly Gly Lys Gln Ala Leu Glu Thr Val Gln Arg Leu Leu Pro Val
            260                 265                 270
Leu Cys Gln Ala His Gly Leu Thr Pro Gln Gln Val Val Ala Ile Ala
        275                 280                 285
Ser His Asp Gly Gly Lys Gln Ala Leu Glu Thr Val Gln Arg Leu Leu
    290                 295                 300
Pro Val Leu Cys Gln Ala His Gly Leu Thr Pro Gln Gln Val Val Ala
305                 310                 315                 320
Ile Ala Ser Asn Gly Gly Lys Gln Ala Leu Glu Thr Val Gln Arg
                325                 330                 335
Leu Leu Pro Val Leu Cys Gln Ala His Gly Leu Thr Pro Gln Gln Val
            340                 345                 350
Val Ala Ile Ala Ser Asn Asn Gly Gly Lys Gln Ala Leu Glu Thr Val
        355                 360                 365
Gln Arg Leu Leu Pro Val Leu Cys Gln Ala His Gly Leu Thr Pro Gln
    370                 375                 380
Gln Val Val Ala Ile Ala Ser Asn Asn Gly Gly Lys Gln Ala Leu Glu
385                 390                 395                 400
Thr Val Gln Arg Leu Leu Pro Val Leu Cys Gln Ala His Gly Leu Thr
                405                 410                 415
Pro Gln Gln Val Val Ala Ile Ala Ser Asn Asn Gly Gly Lys Gln Ala
            420                 425                 430
Leu Glu Thr Val Gln Arg Leu Leu Pro Val Leu Cys Gln Ala His Gly
        435                 440                 445
Leu Thr Pro Glu Gln Val Val Ala Ile Ala Ser Asn Ile Gly Gly Lys
    450                 455                 460
Gln Ala Leu Glu Thr Val Gln Arg Leu Leu Pro Val Leu Cys Gln Ala
465                 470                 475                 480
His Gly Leu Thr Pro Gln Gln Val Val Ala Ile Ala Ser His Asp Gly
                485                 490                 495
Gly Lys Gln Ala Leu Glu Thr Val Gln Arg Leu Leu Pro Val Leu Cys
```

```
                500             505             510
Gln Ala His Gly Leu Thr Pro Gln Gln Val Val Ala Ile Ala Ser Asn
            515                 520                 525

Asn Gly Gly Lys Gln Ala Leu Glu Thr Val Gln Arg Leu Leu Pro Val
        530                 535                 540

Leu Cys Gln Ala His Gly Leu Thr Pro Gln Gln Val Val Ala Ile Ala
545                 550                 555                 560

Ser Asn Gly Gly Lys Gln Ala Leu Glu Thr Val Gln Arg Leu Leu
                565                 570                 575

Pro Val Leu Cys Gln Ala His Gly Leu Thr Pro Gln Gln Val Val Ala
            580                 585                 590

Ile Ala Ser Asn Gly Gly Arg Pro Ala Leu Glu Ser Ile Val Ala
        595                 600                 605

Gln Leu Ser Arg Pro Asp Pro Ala Leu Ala Arg Ser Ala Leu Thr Asn
        610                 615                 620

Asp His Leu Val Ala Leu Ala Cys Leu Gly Gly Arg Pro Ala Leu Asp
625                 630                 635                 640

Ala Val Lys Lys Gly Leu Pro His Ala Pro Ala Leu Ile Lys Arg Thr
                645                 650                 655

Asn Arg Arg Ile Pro Glu Gly Ser Asp Arg Leu Asn Glu Gly Ile Lys
            660                 665                 670

Ser Asn Ile Ser Leu Leu Lys Asp Glu Leu Arg Gly Gln Ile Ser His
        675                 680                 685

Ile Ser His Glu Tyr Leu Ser Leu Ile Asp Leu Ala Phe Asp Ser Lys
        690                 695                 700

Gln Asn Arg Leu Phe Glu Met Lys Val Leu Glu Leu Leu Val Asn Glu
705                 710                 715                 720

Tyr Gly Phe Lys Gly Arg His Leu Gly Gly Ser Arg Lys Pro Asp Gly
                725                 730                 735

Ile Val Tyr Ser Thr Thr Leu Glu Asp Asn Phe Gly Ile Ile Val Asp
            740                 745                 750

Thr Lys Ala Tyr Ser Glu Gly Tyr Ser Leu Pro Ile Ser Gln Ala Asp
        755                 760                 765

Glu Met Glu Arg Tyr Val Arg Glu Asn Ser Asn Arg Asp Glu Glu Val
770                 775                 780

Asn Pro Asn Lys Trp Trp Glu Asn Phe Ser Glu Glu Val Lys Lys Tyr
785                 790                 795                 800

Tyr Phe Val Phe Ile Ser Gly Ser Phe Lys Gly Lys Phe Glu Glu Gln
                805                 810                 815

Leu Arg Arg Leu Ser Met Thr Thr Gly Val Asn Gly Ser Ala Val Asn
            820                 825                 830

Val Val Asn Leu Leu Gly Ala Glu Lys Ile Arg Ser Gly Glu Met
        835                 840                 845

Thr Ile Glu Glu Leu Glu Arg Ala Met Phe Asn Asn Ser Glu Phe Ile
850                 855                 860

Leu Lys Tyr
865

<210> SEQ ID NO 39
<211> LENGTH: 918
<212> TYPE: PRT
<213> ORGANISM: Artificial sequence
<220> FEATURE:
<223> OTHER INFORMATION: ArtTal1-Mly
```

```
<400> SEQUENCE: 39

Met Gly Pro Lys Lys Arg Lys Val Ala Ala Asp Tyr Lys Asp
1               5                   10                  15

Asp Asp Asp Lys Pro Gly Gly Gly Ser Gly Gly Gly Gly Val Pro
            20              25                  30

Ala Ser Pro Ala Ala Gln Val Asp Leu Arg Thr Leu Gly Tyr Ser Gln
        35                  40                  45

Gln Gln Gln Glu Lys Ile Lys Pro Lys Val Arg Ser Thr Val Ala Gln
    50                  55                  60

His His Glu Ala Leu Val Gly His Gly Phe Thr His Ala His Ile Val
65                  70                  75                  80

Ala Leu Ser Gln His Pro Ala Ala Leu Gly Thr Val Ala Val Lys Tyr
                85                  90                  95

Gln Asp Met Ile Ala Ala Leu Pro Glu Ala Thr His Glu Ala Ile Val
            100                 105                 110

Gly Val Gly Lys Gln Trp Ser Gly Ala Arg Ala Leu Glu Ala Leu Leu
        115                 120                 125

Thr Val Ala Gly Glu Leu Arg Gly Pro Pro Leu Gln Ser Gly Leu Asp
130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Glu Gln Val Val Ala Ile Ala Ser Asn Ile Gly Gly Lys
            180                 185                 190

Gln Ala Leu Glu Thr Val Gln Arg Leu Leu Pro Val Leu Cys Gln Ala
        195                 200                 205

His Gly Leu Thr Pro Gln Gln Val Val Ala Ile Ala Ser Asn Gly Gly
210                 215                 220

Gly Lys Gln Ala Leu Glu Thr Val Gln Arg Leu Leu Pro Val Leu Cys
225                 230                 235                 240

Gln Ala His Gly Leu Thr Pro Gln Gln Val Val Ala Ile Ala Ser Asn
                245                 250                 255

Gly Gly Gly Lys Gln Ala Leu Glu Thr Val Gln Arg Leu Leu Pro Val
            260                 265                 270

Leu Cys Gln Ala His Gly Leu Thr Pro Gln Gln Val Val Ala Ile Ala
        275                 280                 285

Ser His Asp Gly Gly Lys Gln Ala Leu Glu Thr Val Gln Arg Leu Leu
290                 295                 300

Pro Val Leu Cys Gln Ala His Gly Leu Thr Pro Gln Gln Val Val Ala
305                 310                 315                 320

Ile Ala Ser Asn Gly Gly Lys Gln Ala Leu Glu Thr Val Gln Arg
                325                 330                 335

Leu Leu Pro Val Leu Cys Gln Ala His Gly Leu Thr Pro Gln Gln Val
            340                 345                 350

Val Ala Ile Ala Ser Asn Gly Gly Lys Gln Ala Leu Glu Thr Val
        355                 360                 365

Gln Arg Leu Leu Pro Val Leu Cys Gln Ala His Gly Leu Thr Pro Gln
370                 375                 380

Gln Val Val Ala Ile Ala Ser Asn Gly Gly Lys Gln Ala Leu Glu
385                 390                 395                 400

Thr Val Gln Arg Leu Leu Pro Val Leu Cys Gln Ala His Gly Leu Thr
                405                 410                 415
```

-continued

Pro Gln Gln Val Val Ala Ile Ala Ser Asn Asn Gly Gly Lys Gln Ala
            420                 425                 430

Leu Glu Thr Val Gln Arg Leu Leu Pro Val Leu Cys Gln Ala His Gly
        435                 440                 445

Leu Thr Pro Glu Gln Val Val Ala Ile Ala Ser Asn Ile Gly Gly Lys
    450                 455                 460

Gln Ala Leu Glu Thr Val Gln Arg Leu Leu Pro Val Leu Cys Gln Ala
465                 470                 475                 480

His Gly Leu Thr Pro Gln Gln Val Val Ala Ile Ala Ser His Asp Gly
                485                 490                 495

Gly Lys Gln Ala Leu Glu Thr Val Gln Arg Leu Leu Pro Val Leu Cys
            500                 505                 510

Gln Ala His Gly Leu Thr Pro Gln Gln Val Val Ala Ile Ala Ser Asn
        515                 520                 525

Asn Gly Gly Lys Gln Ala Leu Glu Thr Val Gln Arg Leu Leu Pro Val
    530                 535                 540

Leu Cys Gln Ala His Gly Leu Thr Pro Gln Gln Val Val Ala Ile Ala
545                 550                 555                 560

Ser Asn Gly Gly Lys Gln Ala Leu Glu Thr Val Gln Arg Leu Leu
                565                 570                 575

Pro Val Leu Cys Gln Ala His Gly Leu Thr Pro Gln Gln Val Val Ala
            580                 585                 590

Ile Ala Ser Asn Gly Gly Arg Pro Ala Leu Glu Ser Ile Val Ala
            595                 600                 605

Gln Leu Ser Arg Pro Asp Pro Ala Leu Ala Arg Ser Ala Leu Thr Asn
    610                 615                 620

Asp His Leu Val Ala Leu Ala Cys Leu Gly Gly Arg Pro Ala Leu Asp
625                 630                 635                 640

Ala Val Lys Lys Gly Leu Pro His Ala Pro Ala Leu Ile Lys Arg Thr
                645                 650                 655

Asn Arg Arg Ile Pro Glu Gly Ser Asp Arg Leu Asn Ile Asn Ser Lys
            660                 665                 670

Ile Lys Gln Leu Asp Asp Ser Ile Asn Val Glu Ser Leu Lys Ile Asp
        675                 680                 685

Asp Ala Lys Asp Leu Leu Asn Asp Leu Glu Ile Gln Arg Lys Ala Lys
    690                 695                 700

Thr Ile Glu Asp Thr Val Asn His Leu Lys Leu Arg Ser Asp Ile Glu
705                 710                 715                 720

Asp Ile Leu Asp Val Phe Ala Lys Ile Lys Lys Arg Asp Val Pro Asp
                725                 730                 735

Val Pro Leu Phe Leu Glu Trp Asn Ile Trp Arg Ala Phe Ala Ala Leu
            740                 745                 750

Asn His Thr Gln Ala Ile Glu Gly Asn Phe Ile Val Asp Leu Asp Gly
        755                 760                 765

Met Pro Leu Asn Thr Ala Pro Gly Lys Lys Pro Asp Ile Glu Ile Asn
    770                 775                 780

Tyr Gly Ser Phe Ser Cys Ile Val Glu Val Thr Met Ser Ser Gly Glu
785                 790                 795                 800

Thr Gln Phe Asn Met Glu Gly Ser Ser Val Pro Arg His Tyr Gly Asp
                805                 810                 815

Leu Val Arg Lys Val Asp His Asp Ala Tyr Cys Ile Phe Ile Ala Pro
            820                 825                 830

```
Lys Val Ala Pro Gly Thr Lys Ala His Phe Phe Asn Leu Asn Arg Leu
            835                 840                 845

Ser Thr Lys His Tyr Gly Gly Lys Thr Lys Ile Ile Pro Met Ser Leu
        850                 855                 860

Asp Asp Phe Ile Cys Phe Leu Gln Val Gly Ile Thr His Asn Phe Gln
865                 870                 875                 880

Asp Ile Asn Lys Leu Lys Asn Trp Leu Asp Asn Leu Ile Asn Phe Asn
                885                 890                 895

Leu Glu Ser Glu Asp Glu Ile Trp Phe Glu Glu Ile Ile Ser Lys
            900                 905                 910

Ile Ser Thr Trp Ala Ile
            915
```

<210> SEQ ID NO 40
<211> LENGTH: 881
<212> TYPE: PRT
<213> ORGANISM: Artificial sequence
<220> FEATURE:
<223> OTHER INFORMATION: ArtTal1-Pept071

<400> SEQUENCE: 40

```
Met Gly Pro Lys Lys Arg Lys Val Ala Ala Asp Tyr Lys Asp
1               5                   10                  15

Asp Asp Asp Lys Pro Gly Gly Gly Ser Gly Gly Gly Val Pro
                20                  25                  30

Ala Ser Pro Ala Ala Gln Val Asp Leu Arg Thr Leu Gly Tyr Ser Gln
            35                  40                  45

Gln Gln Gln Glu Lys Ile Lys Pro Lys Val Arg Ser Thr Val Ala Gln
        50                  55                  60

His His Glu Ala Leu Val Gly His Gly Phe Thr His Ala His Ile Val
65                  70                  75                  80

Ala Leu Ser Gln His Pro Ala Ala Leu Gly Thr Val Ala Val Lys Tyr
                85                  90                  95

Gln Asp Met Ile Ala Ala Leu Pro Glu Ala Thr His Glu Ala Ile Val
            100                 105                 110

Gly Val Gly Lys Gln Trp Ser Gly Ala Arg Ala Leu Glu Ala Leu Leu
        115                 120                 125

Thr Val Ala Gly Glu Leu Arg Gly Pro Pro Leu Gln Ser Gly Leu Asp
130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Glu Gln Val Val Ala Ile Ala Ser Asn Ile Gly Gly Lys
            180                 185                 190

Gln Ala Leu Glu Thr Val Gln Arg Leu Leu Pro Val Leu Cys Gln Ala
        195                 200                 205

His Gly Leu Thr Pro Gln Gln Val Val Ala Ile Ala Ser Asn Gly Gly
    210                 215                 220

Gly Lys Gln Ala Leu Glu Thr Val Gln Arg Leu Leu Pro Val Leu Cys
225                 230                 235                 240

Gln Ala His Gly Leu Thr Pro Gln Gln Val Val Ala Ile Ala Ser Asn
                245                 250                 255

Gly Gly Gly Lys Gln Ala Leu Glu Thr Val Gln Arg Leu Leu Pro Val
            260                 265                 270
```

-continued

```
Leu Cys Gln Ala His Gly Leu Thr Pro Gln Gln Val Val Ala Ile Ala
            275                 280                 285

Ser His Asp Gly Gly Lys Gln Ala Leu Glu Thr Val Gln Arg Leu Leu
        290                 295                 300

Pro Val Leu Cys Gln Ala His Gly Leu Thr Pro Gln Gln Val Val Ala
305                 310                 315                 320

Ile Ala Ser Asn Gly Gly Lys Gln Ala Leu Glu Thr Val Gln Arg
                325                 330                 335

Leu Leu Pro Val Leu Cys Gln Ala His Gly Leu Thr Pro Gln Gln Val
            340                 345                 350

Val Ala Ile Ala Ser Asn Asn Gly Gly Lys Gln Ala Leu Glu Thr Val
        355                 360                 365

Gln Arg Leu Leu Pro Val Leu Cys Gln Ala His Gly Leu Thr Pro Gln
370                 375                 380

Gln Val Val Ala Ile Ala Ser Asn Asn Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Gln Gln Val Val Ala Ile Ala Ser Asn Asn Gly Gly Lys Gln Ala
            420                 425                 430

Leu Glu Thr Val Gln Arg Leu Leu Pro Val Leu Cys Gln Ala His Gly
        435                 440                 445

Leu Thr Pro Glu Gln Val Val Ala Ile Ala Ser Asn Ile Gly Gly Lys
    450                 455                 460

Gln Ala Leu Glu Thr Val Gln Arg Leu Leu Pro Val Leu Cys Gln Ala
465                 470                 475                 480

His Gly Leu Thr Pro Gln Gln Val Val Ala Ile Ala Ser His Asp Gly
                485                 490                 495

Gly Lys Gln Ala Leu Glu Thr Val Gln Arg Leu Leu Pro Val Leu Cys
            500                 505                 510

Gln Ala His Gly Leu Thr Pro Gln Gln Val Val Ala Ile Ala Ser Asn
        515                 520                 525

Asn Gly Gly Lys Gln Ala Leu Glu Thr Val Gln Arg Leu Leu Pro Val
    530                 535                 540

Leu Cys Gln Ala His Gly Leu Thr Pro Gln Gln Val Val Ala Ile Ala
545                 550                 555                 560

Ser Asn Gly Gly Gly Lys Gln Ala Leu Glu Thr Val Gln Arg Leu Leu
                565                 570                 575

Pro Val Leu Cys Gln Ala His Gly Leu Thr Pro Gln Gln Val Val Ala
            580                 585                 590

Ile Ala Ser Asn Gly Gly Gly Arg Pro Ala Leu Glu Ser Ile Val Ala
        595                 600                 605

Gln Leu Ser Arg Pro Asp Pro Ala Leu Ala Arg Ser Ala Leu Thr Asn
610                 615                 620

Asp His Leu Val Ala Leu Ala Cys Leu Gly Gly Arg Pro Ala Leu Asp
625                 630                 635                 640

Ala Val Lys Lys Gly Leu Pro His Ala Pro Ala Leu Ile Lys Arg Thr
                645                 650                 655

Asn Arg Arg Ile Pro Glu Gly Ser Asp Arg Leu Asn Lys Ile Ser Lys
            660                 665                 670

Thr Asn Val Leu Glu Leu Lys Asp Lys Val Arg Asp Lys Leu Lys Tyr
        675                 680                 685

Val Asp His Arg Tyr Leu Ala Leu Ile Asp Leu Ala Tyr Asp Gly Thr
```

```
                  690                 695                 700

Ala Asn Arg Asp Phe Glu Ile Gln Thr Ile Asp Leu Leu Ile Asn Glu
705                 710                 715                 720

Leu Lys Phe Lys Gly Val Arg Leu Gly Glu Ser Arg Lys Pro Asp Gly
                725                 730                 735

Ile Ile Ser Tyr Asn Ile Asn Gly Val Ile Ile Asp Asn Lys Ala Tyr
                740                 745                 750

Ser Thr Gly Tyr Asn Leu Pro Ile Asn Gln Ala Asp Glu Met Ile Arg
                755                 760                 765

Tyr Ile Glu Glu Asn Gln Thr Arg Asp Glu Lys Ile Asn Ser Asn Lys
                770                 775                 780

Trp Trp Glu Ser Phe Asp Asp Lys Val Lys Asp Phe Asn Tyr Leu Phe
785                 790                 795                 800

Val Ser Ser Phe Phe Lys Gly Asn Phe Lys Asn Asn Leu Lys His Ile
                805                 810                 815

Ala Asn Arg Thr Gly Val Ser Gly Gly Ala Ile Asn Val Glu Asn Leu
                820                 825                 830

Leu Tyr Phe Ala Glu Glu Leu Lys Ala Gly Arg Leu Ser Tyr Val Asp
                835                 840                 845

Ser Phe Lys Met Tyr Asp Asn Asp Glu Ile Tyr Val Gly Asp Phe Ser
                850                 855                 860

Asp Tyr Ser Tyr Val Lys Phe Ala Ala Glu Glu Gly Glu Tyr Leu
865                 870                 875                 880

Thr

<210> SEQ ID NO 41
<211> LENGTH: 831
<212> TYPE: PRT
<213> ORGANISM: Artificial sequence
<220> FEATURE:
<223> OTHER INFORMATION: ArtTal1-Sbf

<400> SEQUENCE: 41

Met Gly Pro Lys Lys Arg Lys Val Ala Ala Asp Tyr Lys Asp
1               5                   10                  15

Asp Asp Asp Lys Pro Gly Gly Gly Ser Gly Gly Gly Val Pro
                20                  25                  30

Ala Ser Pro Ala Ala Gln Val Asp Leu Arg Thr Leu Gly Tyr Ser Gln
                35                  40                  45

Gln Gln Gln Glu Lys Ile Lys Pro Lys Val Arg Ser Thr Val Ala Gln
                50                  55                  60

His His Glu Ala Leu Val Gly His Gly Phe Thr His Ala His Ile Val
65                  70                  75                  80

Ala Leu Ser Gln His Pro Ala Ala Leu Gly Thr Val Ala Val Lys Tyr
                85                  90                  95

Gln Asp Met Ile Ala Ala Leu Pro Glu Ala Thr His Glu Ala Ile Val
                100                 105                 110

Gly Val Gly Lys Gln Trp Ser Gly Ala Arg Ala Leu Glu Ala Leu Leu
                115                 120                 125

Thr Val Ala Gly Glu Leu Arg Gly Pro Pro Leu Gln Ser Gly Leu Asp
                130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175
```

```
Leu Thr Pro Glu Gln Val Val Ala Ile Ala Ser Asn Ile Gly Gly Lys
            180                 185                 190

Gln Ala Leu Glu Thr Val Gln Arg Leu Leu Pro Val Leu Cys Gln Ala
        195                 200                 205

His Gly Leu Thr Pro Gln Gln Val Val Ala Ile Ala Ser Asn Gly Gly
    210                 215                 220

Gly Lys Gln Ala Leu Glu Thr Val Gln Arg Leu Leu Pro Val Leu Cys
225                 230                 235                 240

Gln Ala His Gly Leu Thr Pro Gln Gln Val Val Ala Ile Ala Ser Asn
                245                 250                 255

Gly Gly Gly Lys Gln Ala Leu Glu Thr Val Gln Arg Leu Leu Pro Val
            260                 265                 270

Leu Cys Gln Ala His Gly Leu Thr Pro Gln Gln Val Val Ala Ile Ala
        275                 280                 285

Ser His Asp Gly Gly Lys Gln Ala Leu Glu Thr Val Gln Arg Leu Leu
    290                 295                 300

Pro Val Leu Cys Gln Ala His Gly Leu Thr Pro Gln Gln Val Val Ala
305                 310                 315                 320

Ile Ala Ser Asn Gly Gly Lys Gln Ala Leu Glu Thr Val Gln Arg
                325                 330                 335

Leu Leu Pro Val Leu Cys Gln Ala His Gly Leu Thr Pro Gln Gln Val
                340                 345                 350

Val Ala Ile Ala Ser Asn Asn Gly Gly Lys Gln Ala Leu Glu Thr Val
            355                 360                 365

Gln Arg Leu Leu Pro Val Leu Cys Gln Ala His Gly Leu Thr Pro Gln
        370                 375                 380

Gln Val Val Ala Ile Ala Ser Asn Asn Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Gln Gln Val Val Ala Ile Ala Ser Asn Asn Gly Gly Lys Gln Ala
                420                 425                 430

Leu Glu Thr Val Gln Arg Leu Leu Pro Val Leu Cys Gln Ala His Gly
            435                 440                 445

Leu Thr Pro Glu Gln Val Val Ala Ile Ala Ser Asn Ile Gly Gly Lys
        450                 455                 460

Gln Ala Leu Glu Thr Val Gln Arg Leu Leu Pro Val Leu Cys Gln Ala
465                 470                 475                 480

His Gly Leu Thr Pro Gln Gln Val Val Ala Ile Ala Ser His Asp Gly
                485                 490                 495

Gly Lys Gln Ala Leu Glu Thr Val Gln Arg Leu Leu Pro Val Leu Cys
            500                 505                 510

Gln Ala His Gly Leu Thr Pro Gln Gln Val Val Ala Ile Ala Ser Asn
        515                 520                 525

Asn Gly Gly Lys Gln Ala Leu Glu Thr Val Gln Arg Leu Leu Pro Val
    530                 535                 540

Leu Cys Gln Ala His Gly Leu Thr Pro Gln Gln Val Val Ala Ile Ala
545                 550                 555                 560

Ser Asn Gly Gly Gly Lys Gln Ala Leu Glu Thr Val Gln Arg Leu Leu
                565                 570                 575

Pro Val Leu Cys Gln Ala His Gly Leu Thr Pro Gln Gln Val Val Ala
            580                 585                 590
```

-continued

```
Ile Ala Ser Asn Gly Gly Arg Pro Ala Leu Glu Ser Ile Val Ala
            595                 600                 605

Gln Leu Ser Arg Pro Asp Pro Ala Leu Ala Arg Ser Ala Leu Thr Asn
610                 615                 620

Asp His Leu Val Ala Leu Ala Cys Leu Gly Gly Arg Pro Ala Leu Asp
625                 630                 635                 640

Ala Val Lys Lys Gly Leu Pro His Ala Pro Ala Leu Ile Lys Arg Thr
                645                 650                 655

Asn Arg Arg Ile Pro Glu Gly Ser Asp Arg Leu Asn Ile Ser Val Asp
            660                 665                 670

Leu Pro Gly Gly Glu Glu Phe Leu Leu Ser Pro Ala Gly Gln Asn Pro
        675                 680                 685

Leu Leu Lys Lys Met Val Glu Glu Phe Val Pro Arg Phe Ala Pro Arg
        690                 695                 700

Ser Thr Val Leu Tyr Leu Gly Asp Thr Arg Gly Lys His Ser Leu Phe
705                 710                 715                 720

Glu Arg Glu Ile Phe Glu Glu Val Leu Gly Leu Thr Phe Asp Pro His
                725                 730                 735

Gly Arg Met Pro Asp Leu Ile Leu His Asp Glu Val Arg Gly Trp Leu
            740                 745                 750

Phe Leu Met Glu Ala Val Lys Ser Lys Gly Pro Phe Asp Glu Glu Arg
        755                 760                 765

His Arg Ser Leu Gln Glu Leu Phe Val Thr Pro Ser Ala Gly Leu Ile
        770                 775                 780

Phe Val Asn Cys Phe Glu Asn Arg Glu Ser Met Arg Gln Trp Leu Pro
785                 790                 795                 800

Glu Leu Ala Trp Glu Thr Glu Ala Trp Val Ala Glu Asp Pro Asp His
                805                 810                 815

Leu Ile His Leu Asn Gly Ser Arg Phe Leu Gly Pro Tyr Glu Arg
            820                 825                 830

<210> SEQ ID NO 42
<211> LENGTH: 831
<212> TYPE: PRT
<213> ORGANISM: Artificial sequence
<220> FEATURE:
<223> OTHER INFORMATION: ArtTal1-SdaI

<400> SEQUENCE: 42

Met Gly Pro Lys Lys Lys Arg Lys Val Ala Ala Asp Tyr Lys Asp
1               5                   10                  15

Asp Asp Asp Lys Pro Gly Gly Gly Ser Gly Gly Gly Gly Val Pro
                20                  25                  30

Ala Ser Pro Ala Ala Gln Val Asp Leu Arg Thr Leu Gly Tyr Ser Gln
            35                  40                  45

Gln Gln Gln Glu Lys Ile Lys Pro Lys Val Arg Ser Thr Val Ala Gln
        50                  55                  60

His His Glu Ala Leu Val Gly His Gly Phe Thr His Ala His Ile Val
65                  70                  75                  80

Ala Leu Ser Gln His Pro Ala Ala Leu Gly Thr Val Ala Val Lys Tyr
                85                  90                  95

Gln Asp Met Ile Ala Ala Leu Pro Glu Ala Thr His Glu Ala Ile Val
            100                 105                 110

Gly Val Gly Lys Gln Trp Ser Gly Ala Arg Ala Leu Glu Ala Leu Leu
        115                 120                 125
```

-continued

```
Thr Val Ala Gly Glu Leu Arg Gly Pro Pro Leu Gln Ser Gly Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Glu Gln Val Val Ala Ile Ala Ser Asn Ile Gly Gly Lys
            180                 185                 190

Gln Ala Leu Glu Thr Val Gln Arg Leu Leu Pro Val Leu Cys Gln Ala
        195                 200                 205

His Gly Leu Thr Pro Gln Gln Val Val Ala Ile Ala Ser Asn Gly Gly
    210                 215                 220

Gly Lys Gln Ala Leu Glu Thr Val Gln Arg Leu Leu Pro Val Leu Cys
225                 230                 235                 240

Gln Ala His Gly Leu Thr Pro Gln Gln Val Val Ala Ile Ala Ser Asn
                245                 250                 255

Gly Gly Gly Lys Gln Ala Leu Glu Thr Val Gln Arg Leu Leu Pro Val
            260                 265                 270

Leu Cys Gln Ala His Gly Leu Thr Pro Gln Gln Val Val Ala Ile Ala
        275                 280                 285

Ser His Asp Gly Gly Lys Gln Ala Leu Glu Thr Val Gln Arg Leu Leu
    290                 295                 300

Pro Val Leu Cys Gln Ala His Gly Leu Thr Pro Gln Gln Val Val Ala
305                 310                 315                 320

Ile Ala Ser Asn Gly Gly Gly Lys Gln Ala Leu Glu Thr Val Gln Arg
                325                 330                 335

Leu Leu Pro Val Leu Cys Gln Ala His Gly Leu Thr Pro Gln Gln Val
            340                 345                 350

Val Ala Ile Ala Ser Asn Asn Gly Gly Lys Gln Ala Leu Glu Thr Val
        355                 360                 365

Gln Arg Leu Leu Pro Val Leu Cys Gln Ala His Gly Leu Thr Pro Gln
    370                 375                 380

Gln Val Val Ala Ile Ala Ser Asn Asn Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Gln Gln Val Val Ala Ile Ala Ser Asn Asn Gly Gly Lys Gln Ala
            420                 425                 430

Leu Glu Thr Val Gln Arg Leu Leu Pro Val Leu Cys Gln Ala His Gly
        435                 440                 445

Leu Thr Pro Glu Gln Val Val Ala Ile Ala Ser Asn Ile Gly Gly Lys
    450                 455                 460

Gln Ala Leu Glu Thr Val Gln Arg Leu Leu Pro Val Leu Cys Gln Ala
465                 470                 475                 480

His Gly Leu Thr Pro Gln Gln Val Val Ala Ile Ala Ser His Asp Gly
                485                 490                 495

Gly Lys Gln Ala Leu Glu Thr Val Gln Arg Leu Leu Pro Val Leu Cys
            500                 505                 510

Gln Ala His Gly Leu Thr Pro Gln Gln Val Val Ala Ile Ala Ser Asn
        515                 520                 525

Asn Gly Gly Lys Gln Ala Leu Glu Thr Val Gln Arg Leu Leu Pro Val
    530                 535                 540

Leu Cys Gln Ala His Gly Leu Thr Pro Gln Gln Val Val Ala Ile Ala
```

```
                      545                 550                 555                 560
Ser Asn Gly Gly Gly Lys Gln Ala Leu Glu Thr Val Gln Arg Leu Leu
                565                 570                 575

Pro Val Leu Cys Gln Ala His Gly Leu Thr Pro Gln Gln Val Val Ala
                580                 585                 590

Ile Ala Ser Asn Gly Gly Arg Pro Ala Leu Glu Ser Ile Val Ala
                595                 600                 605

Gln Leu Ser Arg Pro Asp Pro Ala Leu Ala Arg Ser Ala Leu Thr Asn
                610                 615                 620

Asp His Leu Val Ala Leu Ala Cys Leu Gly Gly Arg Pro Ala Leu Asp
625                 630                 635                 640

Ala Val Lys Lys Gly Leu Pro His Ala Pro Ala Leu Ile Lys Arg Thr
                645                 650                 655

Asn Arg Arg Ile Pro Glu Gly Ser Asp Arg Leu Asn Ile Ser Val Asp
                660                 665                 670

Leu Ala Asp Gly Asp Glu Phe Leu Leu Ser Pro Ala Gly Gln Asn Pro
                675                 680                 685

Leu Leu Lys Lys Met Val Glu Glu Phe Met Pro Arg Phe Ala Pro Gly
                690                 695                 700

Ala Lys Val Leu Tyr Ile Gly Asp Trp Arg Gly Lys His Thr Arg Phe
705                 710                 715                 720

Glu Lys Arg Ile Phe Glu Glu Thr Leu Gly Leu Thr Phe Asp Pro His
                725                 730                 735

Gly Arg Met Pro Asp Leu Val Leu His Asp Lys Val Arg Lys Trp Leu
                740                 745                 750

Phe Leu Met Glu Ala Val Lys Ser Lys Gly Pro Phe Asp Glu Glu Arg
                755                 760                 765

His Arg Thr Leu Arg Glu Leu Phe Ala Thr Pro Val Ala Gly Leu Val
                770                 775                 780

Phe Val Asn Cys Phe Glu Asn Arg Glu Ala Met Arg Gln Trp Leu Pro
785                 790                 795                 800

Glu Leu Ala Trp Glu Thr Glu Ala Trp Val Ala Asp Asp Pro Asp His
                805                 810                 815

Leu Ile His Leu Asn Gly Ser Arg Phe Leu Gly Pro Tyr Glu Arg
                820                 825                 830

<210> SEQ ID NO 43
<211> LENGTH: 876
<212> TYPE: PRT
<213> ORGANISM: Artificial sequence
<220> FEATURE:
<223> OTHER INFORMATION: ArtTal1-StsI

<400> SEQUENCE: 43

Met Gly Pro Lys Lys Lys Arg Lys Val Ala Ala Asp Tyr Lys Asp
1               5                   10                  15

Asp Asp Asp Lys Pro Gly Gly Gly Ser Gly Gly Gly Val Pro
                20                  25                  30

Ala Ser Pro Ala Ala Gln Val Asp Leu Arg Thr Leu Gly Tyr Ser Gln
                35                  40                  45

Gln Gln Gln Glu Lys Ile Lys Pro Lys Val Arg Ser Thr Val Ala Gln
                50                  55                  60

His His Glu Ala Leu Val Gly His Gly Phe Thr His Ala His Ile Val
65                  70                  75                  80

Ala Leu Ser Gln His Pro Ala Ala Leu Gly Thr Val Ala Val Lys Tyr
```

```
                85                  90                  95
Gln Asp Met Ile Ala Ala Leu Pro Glu Ala Thr His Glu Ala Ile Val
            100                 105                 110
Gly Val Gly Lys Gln Trp Ser Gly Ala Arg Ala Leu Glu Ala Leu Leu
            115                 120                 125
Thr Val Ala Gly Glu Leu Arg Gly Pro Leu Gln Ser Gly Leu Asp
            130                 135             140
Thr Gly Gln Leu Leu Lys Ile Ala Lys Arg Gly Gly Val Thr Ala Val
145                 150                 155                 160
Glu Ala Val His Ala Trp Arg Asn Ala Leu Thr Gly Ala Pro Leu Asn
                165                 170                 175
Leu Thr Pro Glu Gln Val Val Ala Ile Ala Ser Asn Ile Gly Gly Lys
            180                 185                 190
Gln Ala Leu Glu Thr Val Gln Arg Leu Leu Pro Val Leu Cys Gln Ala
            195                 200                 205
His Gly Leu Thr Pro Gln Gln Val Val Ala Ile Ala Ser Asn Gly Gly
            210                 215                 220
Gly Lys Gln Ala Leu Glu Thr Val Gln Arg Leu Leu Pro Val Leu Cys
225                 230                 235                 240
Gln Ala His Gly Leu Thr Pro Gln Gln Val Val Ala Ile Ala Ser Asn
                245                 250                 255
Gly Gly Gly Lys Gln Ala Leu Glu Thr Val Gln Arg Leu Leu Pro Val
            260                 265                 270
Leu Cys Gln Ala His Gly Leu Thr Pro Gln Gln Val Val Ala Ile Ala
            275                 280                 285
Ser His Asp Gly Gly Lys Gln Ala Leu Glu Thr Val Gln Arg Leu Leu
            290                 295                 300
Pro Val Leu Cys Gln Ala His Gly Leu Thr Pro Gln Gln Val Val Ala
305                 310                 315                 320
Ile Ala Ser Asn Gly Gly Gly Lys Gln Ala Leu Glu Thr Val Gln Arg
                325                 330                 335
Leu Leu Pro Val Leu Cys Gln Ala His Gly Leu Thr Pro Gln Gln Val
            340                 345                 350
Val Ala Ile Ala Ser Asn Asn Gly Gly Lys Gln Ala Leu Glu Thr Val
            355                 360                 365
Gln Arg Leu Leu Pro Val Leu Cys Gln Ala His Gly Leu Thr Pro Gln
            370                 375                 380
Gln Val Val Ala Ile Ala Ser Asn Asn Gly Gly Lys Gln Ala Leu Glu
385                 390                 395                 400
Thr Val Gln Arg Leu Leu Pro Val Leu Cys Gln Ala His Gly Leu Thr
                405                 410                 415
Pro Gln Gln Val Val Ala Ile Ala Ser Asn Asn Gly Gly Lys Gln Ala
            420                 425                 430
Leu Glu Thr Val Gln Arg Leu Leu Pro Val Leu Cys Gln Ala His Gly
            435                 440                 445
Leu Thr Pro Glu Gln Val Val Ala Ile Ala Ser Asn Ile Gly Gly Lys
            450                 455                 460
Gln Ala Leu Glu Thr Val Gln Arg Leu Leu Pro Val Leu Cys Gln Ala
465                 470                 475                 480
His Gly Leu Thr Pro Gln Gln Val Val Ala Ile Ala Ser His Asp Gly
                485                 490                 495
Gly Lys Gln Ala Leu Glu Thr Val Gln Arg Leu Leu Pro Val Leu Cys
            500                 505                 510
```

Gln Ala His Gly Leu Thr Pro Gln Gln Val Val Ala Ile Ala Ser Asn
                515                 520                 525

Asn Gly Gly Lys Gln Ala Leu Glu Thr Val Gln Arg Leu Leu Pro Val
        530                 535                 540

Leu Cys Gln Ala His Gly Leu Thr Pro Gln Gln Val Val Ala Ile Ala
545                 550                 555                 560

Ser Asn Gly Gly Gly Lys Gln Ala Leu Glu Thr Val Gln Arg Leu Leu
                565                 570                 575

Pro Val Leu Cys Gln Ala His Gly Leu Thr Pro Gln Gln Val Val Ala
            580                 585                 590

Ile Ala Ser Asn Gly Gly Gly Arg Pro Ala Leu Glu Ser Ile Val Ala
            595                 600                 605

Gln Leu Ser Arg Pro Asp Pro Ala Leu Ala Arg Ser Ala Leu Thr Asn
        610                 615                 620

Asp His Leu Val Ala Leu Ala Cys Leu Gly Gly Arg Pro Ala Leu Asp
625                 630                 635                 640

Ala Val Lys Lys Gly Leu Pro His Ala Pro Ala Leu Ile Lys Arg Thr
                645                 650                 655

Asn Arg Arg Ile Pro Glu Gly Ser Asp Arg Leu Asn Asp Val Val Leu
            660                 665                 670

Glu Lys Ser Asp Ile Glu Lys Phe Lys Asn Gln Leu Arg Thr Glu Leu
        675                 680                 685

Thr Asn Ile Asp His Ser Tyr Leu Lys Gly Ile Asp Ile Ala Ser Lys
    690                 695                 700

Lys Lys Thr Ser Asn Val Glu Asn Thr Glu Phe Glu Ala Ile Ser Thr
705                 710                 715                 720

Lys Ile Phe Thr Asp Glu Leu Gly Phe Ser Gly Lys His Leu Gly Gly
                725                 730                 735

Ser Asn Lys Pro Asp Gly Leu Leu Trp Asp Asp Cys Ala Ile Ile
            740                 745                 750

Leu Asp Ser Lys Ala Tyr Ser Glu Gly Phe Pro Leu Thr Ala Ser His
        755                 760                 765

Thr Asp Ala Met Gly Arg Tyr Leu Arg Gln Phe Thr Glu Arg Lys Glu
    770                 775                 780

Glu Ile Lys Pro Thr Trp Trp Asp Ile Ala Pro Glu His Leu Asp Asn
785                 790                 795                 800

Thr Tyr Phe Ala Tyr Val Ser Gly Ser Phe Gly Asn Tyr Lys Glu
                805                 810                 815

Gln Leu Gln Lys Phe Arg Gln Asp Thr Asn His Leu Gly Gly Ala Leu
        820                 825                 830

Glu Phe Val Lys Leu Leu Leu Ala Asn Asn Tyr Lys Thr Gln Lys
    835                 840                 845

Met Ser Lys Lys Glu Val Lys Lys Ser Ile Leu Asp Tyr Asn Ile Ser
850                 855                 860

Tyr Glu Glu Tyr Ala Pro Leu Leu Ala Glu Ile Glu
865                 870                 875

<210> SEQ ID NO 44
<211> LENGTH: 864
<212> TYPE: PRT
<213> ORGANISM: Artificial sequence
<220> FEATURE:
<223> OTHER INFORMATION: ArtTal1-FokI

<400> SEQUENCE: 44

-continued

```
Met Gly Pro Lys Lys Arg Lys Val Ala Ala Asp Tyr Lys Asp
1               5                   10                  15

Asp Asp Asp Lys Pro Gly Gly Gly Ser Gly Gly Gly Val Pro
            20              25              30

Ala Ser Pro Ala Ala Gln Val Asp Leu Arg Thr Leu Gly Tyr Ser Gln
        35              40                  45

Gln Gln Gln Glu Lys Ile Lys Pro Lys Val Arg Ser Thr Val Ala Gln
    50              55                  60

His His Glu Ala Leu Val Gly His Gly Phe Thr His Ala His Ile Val
65              70              75              80

Ala Leu Ser Gln His Pro Ala Ala Leu Gly Thr Val Ala Val Lys Tyr
            85              90                  95

Gln Asp Met Ile Ala Ala Leu Pro Glu Ala Thr His Glu Ala Ile Val
            100             105             110

Gly Val Gly Lys Gln Trp Ser Gly Ala Arg Ala Leu Glu Ala Leu Leu
            115             120             125

Thr Val Ala Gly Glu Leu Arg Gly Pro Pro Leu Gln Ser Gly Leu Asp
        130             135             140

Thr Gly Gln Leu Leu Lys Ile Ala Lys Arg Gly Gly Val Thr Ala Val
145             150             155             160

Glu Ala Val His Ala Trp Arg Asn Ala Leu Thr Gly Ala Pro Leu Asn
                165             170             175

Leu Thr Pro Glu Gln Val Val Ala Ile Ala Ser Asn Ile Gly Gly Lys
            180             185             190

Gln Ala Leu Glu Thr Val Gln Arg Leu Leu Pro Val Leu Cys Gln Ala
        195             200             205

His Gly Leu Thr Pro Gln Gln Val Val Ala Ile Ala Ser Asn Gly Gly
    210             215             220

Gly Lys Gln Ala Leu Glu Thr Val Gln Arg Leu Leu Pro Val Leu Cys
225             230             235             240

Gln Ala His Gly Leu Thr Pro Gln Gln Val Val Ala Ile Ala Ser Asn
            245             250             255

Gly Gly Gly Lys Gln Ala Leu Glu Thr Val Gln Arg Leu Leu Pro Val
            260             265             270

Leu Cys Gln Ala His Gly Leu Thr Pro Gln Gln Val Val Ala Ile Ala
        275             280             285

Ser His Asp Gly Gly Lys Gln Ala Leu Glu Thr Val Gln Arg Leu Leu
    290             295             300

Pro Val Leu Cys Gln Ala His Gly Leu Thr Pro Gln Gln Val Val Ala
305             310             315             320

Ile Ala Ser Asn Gly Gly Lys Gln Ala Leu Glu Thr Val Gln Arg
            325             330             335

Leu Leu Pro Val Leu Cys Gln Ala His Gly Leu Thr Pro Gln Gln Val
            340             345             350

Val Ala Ile Ala Ser Asn Gly Gly Lys Gln Ala Leu Glu Thr Val
        355             360             365

Gln Arg Leu Leu Pro Val Leu Cys Gln Ala His Gly Leu Thr Pro Gln
    370             375             380

Gln Val Val Ala Ile Ala Ser Asn Gly Gly Lys Gln Ala Leu Glu
385             390             395             400

Thr Val Gln Arg Leu Leu Pro Val Leu Cys Gln Ala His Gly Leu Thr
            405             410             415
```

-continued

```
Pro Gln Gln Val Val Ala Ile Ala Ser Asn Asn Gly Gly Lys Gln Ala
                420                 425                 430

Leu Glu Thr Val Gln Arg Leu Leu Pro Val Leu Cys Gln Ala His Gly
            435                 440                 445

Leu Thr Pro Glu Gln Val Val Ala Ile Ala Ser Asn Ile Gly Gly Lys
450                 455                 460

Gln Ala Leu Glu Thr Val Gln Arg Leu Leu Pro Val Leu Cys Gln Ala
465                 470                 475                 480

His Gly Leu Thr Pro Gln Gln Val Val Ala Ile Ala Ser His Asp Gly
                485                 490                 495

Gly Lys Gln Ala Leu Glu Thr Val Gln Arg Leu Leu Pro Val Leu Cys
            500                 505                 510

Gln Ala His Gly Leu Thr Pro Gln Gln Val Val Ala Ile Ala Ser Asn
            515                 520                 525

Asn Gly Gly Lys Gln Ala Leu Glu Thr Val Gln Arg Leu Leu Pro Val
        530                 535                 540

Leu Cys Gln Ala His Gly Leu Thr Pro Gln Gln Val Val Ala Ile Ala
545                 550                 555                 560

Ser Asn Gly Gly Gly Lys Gln Ala Leu Glu Thr Val Gln Arg Leu Leu
                565                 570                 575

Pro Val Leu Cys Gln Ala His Gly Leu Thr Pro Gln Gln Val Val Ala
            580                 585                 590

Ile Ala Ser Asn Gly Gly Gly Arg Pro Ala Leu Glu Ser Ile Val Ala
            595                 600                 605

Gln Leu Ser Arg Pro Asp Pro Ala Leu Ala Arg Ser Ala Leu Thr Asn
        610                 615                 620

Asp His Leu Val Ala Leu Ala Cys Leu Gly Gly Arg Pro Ala Leu Asp
625                 630                 635                 640

Ala Val Lys Lys Gly Leu Pro His Ala Pro Ala Leu Ile Lys Arg Thr
                645                 650                 655

Asn Arg Arg Ile Pro Glu Gly Ser Asp Arg Leu Asn Gln Leu Val Lys
            660                 665                 670

Ser Glu Leu Glu Glu Lys Lys Ser Glu Leu Arg His Lys Leu Lys Tyr
            675                 680                 685

Val Pro His Glu Tyr Ile Glu Leu Ile Glu Ile Ala Arg Asn Ser Thr
        690                 695                 700

Gln Asp Arg Ile Leu Glu Met Lys Val Met Glu Phe Phe Met Lys Val
705                 710                 715                 720

Tyr Gly Tyr Arg Gly Lys His Leu Gly Gly Ser Arg Lys Pro Asp Gly
                725                 730                 735

Ala Ile Tyr Thr Val Gly Ser Pro Ile Asp Tyr Gly Val Ile Val Asp
            740                 745                 750

Thr Lys Ala Tyr Ser Gly Gly Tyr Asn Leu Pro Ile Gly Gln Ala Asp
            755                 760                 765

Glu Met Gln Arg Tyr Val Glu Glu Asn Gln Thr Arg Asn Lys His Ile
        770                 775                 780

Asn Pro Asn Glu Trp Trp Lys Val Tyr Pro Ser Ser Val Thr Glu Phe
785                 790                 795                 800

Lys Phe Leu Phe Val Ser Gly His Phe Lys Gly Asn Tyr Lys Ala Gln
                805                 810                 815

Leu Thr Arg Leu Asn His Ile Thr Asn Cys Asn Gly Ala Val Leu Ser
            820                 825                 830

Val Glu Glu Leu Leu Ile Gly Gly Glu Met Ile Lys Ala Gly Thr Leu
```

```
                835                 840                 845
Thr Leu Glu Glu Val Arg Arg Lys Phe Asn Asn Gly Glu Ile Asn Phe
      850                 855                 860

<210> SEQ ID NO 45
<211> LENGTH: 7374
<212> TYPE: DNA
<213> ORGANISM: Artificial sequence
<220> FEATURE:
<223> OTHER INFORMATION: ArtTal1-Reporter

<400> SEQUENCE: 45
cgttacataa cttacggtaa atggcccgcc tggctgaccg cccaacgacc cccgcccatt     60
gacgtcaata atgacgtatg ttcccatagt aacgccaata gggactttcc attgacgtca    120
atgggtggag tatttacggt aaactgccca cttggcagta catcaagtgt atcatatgcc    180
aagtacgccc cctattgacg tcaatgacgg taaatggccc gcctggcatt atgcccagta    240
catgacctta tgggactttc ctacttggca gtacatctac gtattagtca tcgctattac    300
catggtgatg cggttttggc agtacatcaa tgggcgtgga tagcggtttg actcacgggg    360
atttccaagt ctccacccca ttgacgtcaa tgggagtttg ttttggcacc aaaatcaacg    420
ggactttcca aaatgtcgta acaactccgc cccattgacg caaatgggcg gtaggcgtgt    480
acggtgggag gtctatataa gcagagctcg tttagtgaac cgtcagatcg cctggagacg    540
ccatccacgc tgttttgacc tccatagaag acaccgggac cgatccagcc tccggactct    600
agaggatccg gtactcgacg cactgcagag gacctacttc actaacaacc ggtatggtcg    660
cgagtagctt ggcactggcc gtcgttttac aacgtcgtga ctgggaaaac cctggcgtta    720
cccaacttaa tcgccttgca gcacatcccc ctttcgccag ctggcgtaat agcgaagagg    780
cccgcaccga tcgcccttcc caacagttgc gcagcctgaa tggcgaatgg cgctttgcct    840
ggtttccggc accagaagcg gtgccggaaa gctggctgga gtgcgatctt cctgaggccg    900
atactgtcgt cgtcccctca aactggcaga tgcacggtta cgatgcgccc atctacacca    960
acgtgaccta tcccattacg gtcaatccgc cgtttgttcc cacggagaat ccgacgggtt   1020
gttactcgct cacatttaat gttgatgaaa gctggctata aaaccggtac agttcggcca   1080
ccatggtcgt attctgggac gttttcacac tcttctaacg tcccagaata ctcgagtagc   1140
ttggcactgg ccgtcgtttt acaacgtcgt gactgggaaa accctggcgt tacccaactt   1200
aatcgccttg cagcacatcc cccttcgcc agctggcgta atagcgaaga ggcccgcacc   1260
gatcgccctt cccaacagtt gcgcagcctg aatggcgaat ggcgctttgc ctggtttccg   1320
gcaccagaag cggtgccgga aagctggctg gagtgcgatc ttcctgaggc cgatactgtc   1380
gtcgtcccct caaactggca gatgcacggt tacgatgcgc catctacac caacgtgacc   1440
tatcccatta cggtcaatcc gccgtttgtt cccacggaga atccgacggg ttgttactcg   1500
ctcacattta atgttgatga agctggcta caggaaggcc agacgcgaat tatttttgat   1560
ggcgttaact cggcgtttca tctgtggtgc aacgggcgct gggtcggtta cggccaggac   1620
agtcgtttgc cgtctgaatt tgacctgagc gcattttac gcgccggaga aaaccgcctc   1680
gcggtgatgg tgctgcgctg gagtgacggc agttatctgg aagatcagga tatgtggcgg   1740
atgagcggca ttttccgtga cgtctcgttg ctgcataaac cgactacaca aatcagcgat   1800
ttccatgttg ccactcgctt taatgatgat ttcagccgcg ctgtactgga ggctgaagtt   1860
cagatgtgcg gcgagttgcg tgactaccta cgggtaacag tttctttatg gcagggtgaa   1920
```

```
acgcaggtcg ccagcggcac cgcgcctttc ggcggtgaaa ttatcgatga gcgtggtggt   1980
tatgccgatc gcgtcacact acgtctgaac gtcgaaaacc cgaaactgtg gagcgccgaa   2040
atcccgaatc tctatcgtgc ggtggttgaa ctgcacaccg ccgacggcac gctgattgaa   2100
gcagaagcct gcgatgtcgg tttccgcgag gtgcggattg aaaatggtct gctgctgctg   2160
aacggcaagc cgttgctgat tcgaggcgtt aaccgtcacg agcatcatcc tctgcatggt   2220
caggtcatgg atgagcagac gatggtgcag gatatcctgc tgatgaagca gaacaacttt   2280
aacgccgtgc gctgttcgca ttatccgaac catccgctgt ggtacacgct gtgcgaccgc   2340
tacgccctgt atgtggtgga tgaagccaat attgaaaccc acggcatggt gccaatgaat   2400
cgtctgaccg atgatccgcg ctggctaccg gcgatgagcg aacgcgtaac gcgaatggtg   2460
cagcgcgatc gtaatcaccc gagtgtgatc atctggtcgc tggggaatga atcaggccac   2520
ggcgctaatc acgacgcgct gtatcgctgg atcaaatctg tcgatccttc ccgcccggtg   2580
cagtatgaag gcggcggagc cgacaccacg gccaccgata ttatttgccc gatgtacgcg   2640
cgcgtggatg aagaccagcc cttcccggct gtgccgaaat ggtccatcaa aaaatggctt   2700
tcgctacctg gagagacgcg cccgctgatc ctttgcgaat acgcccacgc gatgggtaac   2760
agtcttggcg gtttcgctaa atactggcag gcgtttcgtc agtatccccg tttacagggc   2820
ggcttcgtct gggactgggt ggatcagtcg ctgattaaat atgatgaaaa cggcaacccg   2880
tggtcggctt acgcggtga ttttggcgat acgccgaacg atcgccagtt ctgtatgaac   2940
ggtctggtct ttgccgaccg cacgccgcat ccagcgctga cggaagcaaa acaccagcag   3000
cagtttttcc agttccgttt atccgggcaa accatcgaag tgaccagcga ataccgtgtc   3060
cgtcatagcg ataacgagct cctgcactgg atggtggcgc tggatggtaa gccgctggca   3120
agcggtgaag tgcctctgga tgtcgctcca caaggtaaac agttgattga actgcctgaa   3180
ctaccgcagc cggagagcgc cgggcaactc tggctcacag tacgcgtagt gcaaccgaac   3240
gcgaccgcat ggtcagaagc cgggcacatc agccgctggc agcagtggcg tctggcggaa   3300
aacctcagtg tgacgctccc cgccgcgtcc cacgccatcc cgcatctgac caccagcgaa   3360
atggattttt gcatcgagct gggtaataag cgttggcaat ttaaccgcca gtcaggcttt   3420
cttttcacaga tgtggattgg cgataaaaaa caactgctga cgccgctgcg cgatcagttc   3480
acccgtgcac cgctggataa cgacattggc gtaagtgaag cgaccgcat tgaccctaac   3540
gcctgggtcg aacgctggaa ggcggcgggc cattaccagg ccgaagcagc gttgttgcag   3600
tgcacggcag atacacttgc tgatgcggtg ctgattacga ccgctcacgc gtggcagcat   3660
caggggaaaa ccttatttat cagccggaaa acctaccgga ttgatggtag tggtcaaatg   3720
gcgattaccg ttgatgttga agtggcgagc gatacaccgc atccggcgcg gattggcctg   3780
aactgccagc tggcgcaggt agcagagcgg gtaaactggc tcggattagg gccgcaagaa   3840
aactatcccg accgccttac tgccgcctgt tttgaccgct gggatctgcc attgtcagac   3900
atgtataccc cgtacgtctt cccgagcgaa aacggtctgc gctgcgggac gcgcgaattg   3960
aattatggcc cacaccagtg gcgcggcgac ttccagttca acatcagccg ctacagtcaa   4020
cagcaactga tggaaaccag ccatcgccat ctgctgcacg cggaagaagg cacatggctg   4080
aatatcgacg gtttccatat ggggattggt ggcgacgact cctggagccc gtcagtatcg   4140
gcggaattac agctgagcgc cggtcgctac cattaccagt tggtctggtg tcaaaaataa   4200
taataaccgg gcaggccatg tctgcccgta tttcgcgtaa ggaaatccat tatgtactat   4260
ttaaaaaaca caaacttttg gatgttcggt ttattctttt tctttactt ttttatcatg   4320
```

```
ggagcctact tcccgttttt cccgatttgg ctacatgaca tcaaccatat cagcaaaagt  4380
gatacgggta ttattttgc cgctatttct ctgttctcgc tattattcca accgctgttt   4440
ggtctgcttt ctgacaaact cggcctcgac tctaggcggc cgcggggatc cagacatgat  4500
aagatacatt gatgagtttg acaaaccac aactagaatg cagtgaaaaa aatgctttat   4560
ttgtgaaatt tgtgatgcta ttgctttatt tgtaaccatt ataagctgca ataaacaagt  4620
taacaacaac aattgcattc attttatgtt tcaggttcag ggggaggtgt gggaggtttt  4680
ttcggatcct ctagagtcga cctgcaggca tgcaagcttg gcgtaatcat ggtcatagct  4740
gtttcctgtg tgaaattgtt atccgctcac aattccacac aacatacgag ccggaagcat  4800
aaagtgtaaa gcctggggtg cctaatgagt gagctaactc acattaattg cgttgcgctc  4860
actgcccgct ttccagtcgg gaaacctgtc gtgccagctg cattaatgaa tcggccaacg  4920
cgcggggaga ggcggtttgc gtattgggcg ctcttccgct tcctcgctca ctgactcgct  4980
gcgctcggtc gttcggctgc ggcgagcggt atcagctcac tcaaaggcgg taatacggtt  5040
atccacagaa tcaggggata acgcaggaaa gaacatgtga gcaaaaggcc agcaaaaggc  5100
caggaaccgt aaaaaggccg cgttgctggc gtttttccat aggctccgcc ccctgacga   5160
gcatcacaaa aatcgacgct caagtcagag gtggcgaaac ccgacaggac tataaagata  5220
ccaggcgttt cccctggaa gctccctcgt gcgctctcct gttccgaccc tgccgcttac   5280
cggatacctg tccgccttc tcccttcggg aagcgtggcg ctttctcata gctcacgctg   5340
taggtatctc agttcggtgt aggtcgttcg ctccaagctg ggctgtgtgc acgaaccccc  5400
cgttcagccc gaccgctgcg ccttatccgg taactatcgt cttgagtcca acccggtaag  5460
acacgactta tcgccactgg cagcagccac tggtaacagg attagcagag cgaggtatgt  5520
aggcggtgct acagagttct tgaagtggtg gcctaactac ggctacacta aaggacagt   5580
atttggtatc tgcgctctgc tgaagccagt taccttcgga aaagagttg gtagctcttg   5640
atccggcaaa caaccaccg ctggtagcgg tggtttttt gtttgcaagc agcagattac    5700
gcgcagaaaa aaaggatctc aagaagatcc tttgatcttt tctacggggt ctgacgctca  5760
gtggaacgaa aactcacgtt aagggatttt ggtcatgaga ttatcaaaaa ggatcttcac  5820
ctagatcctt ttaaattaaa aatgaagttt taaatcaatc taaagtatat atgagtaaac  5880
ttggtctgac agttaccaat gcttaatcag tgaggcacct atctcagcga tctgtctatt  5940
tcgttcatcc atagttgcct gactccccgt cgtgtagata actacgatac gggagggctt  6000
accatctggc cccagtgctg caatgatacc gcgagaccca cgctcaccgg ctccagattt  6060
atcagcaata aaccagccag ccggaagggc cgagcgcaga agtggtcctg caactttatc  6120
cgcctccatc cagtctatta attgttgccg ggaagctaga gtaagtagtt cgccagttaa  6180
tagtttgcgc aacgttgttg ccattgctac aggcatcgtg gtgtcacgct cgtcgtttgg  6240
tatggcttca ttcagctccg gttcccaacg atcaaggcga gttacatgat cccccatgtt  6300
gtgcaaaaaa gcggttagct ccttcggtcc tccgatcgtt gtcagaagta agttggccgc  6360
agtgttatca ctcatggtta tggcagcact gcataattct cttactgtca tgccatccgt  6420
aagatgcttt tctgtgactg gtgagtactc aaccaagtca ttctgagaat agtgtatgcg  6480
gcgaccgagt tgctcttgcc cggcgtcaat acgggataat accgcgccac atagcagaac  6540
tttaaaagtg ctcatcattg gaaaacgttc ttcgggcga aaactctcaa ggatcttacc    6600
gctgttgaga tccagttcga tgtaacccac tcgtgcaccc aactgatctt cagcatcttt  6660
```

| | | |
|---|---|---|
| tactttcacc agcgtttctg ggtgagcaaa acaggaagg caaaatgccg caaaaaggg | 6720 | |
| aataagggcg acacggaaat gttgaatact catactcttc cttttcaat attattgaag | 6780 | |
| catttatcag ggttattgtc tcatgagcgg atacatattt gaatgtattt agaaaaataa | 6840 | |
| acaaatagg gttccgcgca catttccccg aaaagtgcca cctgacgtct aagaaaccat | 6900 | |
| tattatcatg acattaacct ataaaaatag gcgtatcacg aggccctttc gtctcgcgcg | 6960 | |
| tttcggtgat gacggtgaaa acctctgaca catgcagctc ccggagacgg tcacagcttg | 7020 | |
| tctgtaagcg gatgccggga gcagacaagc ccgtcagggc gcgtcagcgg gtgttggcgg | 7080 | |
| gtgtcgggc tggcttaact atgcggcatc agagcagatt gtactgagag tgcaccatat | 7140 | |
| gcggtgtgaa ataccgcaca gatgcgtaag gagaaaatac cgcatcaggc gccattcgcc | 7200 | |
| attcaggctg cgcaactgtt gggaagggcg atcggtgcgg gcctcttcgc tattacgcca | 7260 | |
| gctggcgaaa gggggatgtg ctgcaaggcg attaagttgg gtaacgccag ggttttccca | 7320 | |
| gtcacgacgt tgtaaaacga cggccagtga attcgagctt gcatgcctgc aggt | 7374 | |

<210> SEQ ID NO 46
<211> LENGTH: 7374
<212> TYPE: DNA
<213> ORGANISM: Artificial sequence
<220> FEATURE:
<223> OTHER INFORMATION: TalRab1-Reporter

<400> SEQUENCE: 46

| | | |
|---|---|---|
| cgttacataa cttacggtaa atggcccgcc tggctgaccg cccaacgacc cccgcccatt | 60 | |
| gacgtcaata atgacgtatg ttcccatagt aacgccaata gggactttcc attgacgtca | 120 | |
| atgggtggag tatttacggt aaactgccca cttggcagta catcaagtgt atcatatgcc | 180 | |
| aagtacgccc cctattgacg tcaatgacgg taaatggccc gcctggcatt atgcccagta | 240 | |
| catgacctta tgggactttc ctacttggca gtacatctac gtattagtca tcgctattac | 300 | |
| catggtgatg cggttttggc agtacatcaa tgggcgtgga tagcggtttg actcacgggg | 360 | |
| atttccaagt ctccacccca ttgacgtcaa tgggagtttg ttttggcacc aaaatcaacg | 420 | |
| ggactttcca aaatgtcgta acaactccgc cccattgacg caaatgggcg gtaggcgtgt | 480 | |
| acggtgggag gtctatataa gcagagctcg tttagtgaac cgtcagatcg cctggagacg | 540 | |
| ccatccacgc tgttttgacc tccatagaag acaccgggac cgatccagcc tccgactct | 600 | |
| agaggatccg gtactcgacg acactgcaga gacctacttc actaacaacc ggtatggtcg | 660 | |
| cgagtagctt ggcactggcc gtcgttttac aacgtcgtga ctgggaaaac cctggcgtta | 720 | |
| cccaacttaa tcgccttgca gcacatcccc ctttcgccag ctggcgtaat agcgaagagg | 780 | |
| cccgcaccga tcgcccttcc caacagttgc gcagcctgaa tggcgaatgg cgctttgcct | 840 | |
| ggtttccggc accagaagcg gtgccggaaa gctggctgga gtgcgatctt cctgaggccg | 900 | |
| atactgtcgt cgtcccctca aactggcaga tgcacggtta cgatgcgccc atctacacca | 960 | |
| acgtgaccta tcccattacg gtcaatccgc cgtttgttcc cacggagaat ccgacgggtt | 1020 | |
| gttactcgct cacatttaat gttgatgaaa gctggctata aaccggtac agttcggcca | 1080 | |
| ccatggtcgt gtgcaccaaa acttttcaca ctcttctaag ttttggtgca cacgagtagc | 1140 | |
| ttggcactgg ccgtcgtttt acaacgtcgt gactgggaaa accctggcgt tacccaactt | 1200 | |
| aatcgccttg cagcacatcc cccttttcgcc agctggcgta atagcgaaga ggcccgcacc | 1260 | |
| gatcgccctt cccaacagtt gcgcagcctg aatggcgaat ggcgctttgc ctggtttccg | 1320 | |
| gcaccagaag cggtgccgga aagctggctg gagtgcgatc ttcctgaggc cgatactgtc | 1380 | |

```
gtcgtcccct caaactggca gatgcacggt tacgatgcgc ccatctcacac caacgtgacc    1440
tatcccatta cggtcaatcc gccgtttgtt cccacgagga atccgacggg ttgttactcg    1500
ctcacattta atgttgatga aagctggcta caggaaggcc agacgcgaat tattttttgat   1560
ggcgttaact cggcgtttca tctgtggtgc aacgggcgct gggtcggtta cggccaggac    1620
agtcgtttgc cgtctgaatt tgacctgagc gcattttttac gcgccggaga aaaccgcctc   1680
gcggtgatgg tgctgcgctg gagtgacggc agttatctgg aagatcagga tatgtggcgg    1740
atgagcggca ttttccgtga cgtctcgttg ctgcataaac cgactacaca aatcagcgat    1800
ttccatgttg ccactcgctt taatgatgat ttcagccgcg ctgtactgga ggctgaagtt    1860
cagatgtgcg gcgagttgcg tgactaccta cgggtaacag tttctttatg gcagggtgaa    1920
acgcaggtcg ccagcggcac cgcgcctttc ggcggtgaaa ttatcgatga gcgtggtggt    1980
tatgccgatc gcgtcacact acgtctgaac gtcgaaaacc cgaaactgtg gagcgccgaa    2040
atcccgaatc tctatcgtgc ggtggttgaa ctgcacaccg ccgacggcac gctgattgaa    2100
gcagaagcct gcgatgtcgg ttttccgcgag gtgcggattg aaaatggtct gctgctgctg    2160
aacggcaagc cgttgctgat tcgaggcgtt aaccgtcacg agcatcatcc tctgcatggt    2220
caggtcatgg atgagcagac gatggtgcag gatatcctgc tgatgaagca gaacaacttt    2280
aacgccgtgc gctgttcgca ttatccgaac catccgctgt ggtacacgct gtgcgaccgc    2340
tacggcctgt atgtggtgga tgaagccaat attgaaaccc acggcatggt gccaatgaat    2400
cgtctgaccg atgatccgcg ctggctaccg gcgatgagcg aacgcgtaac gcgaatggtg    2460
cagcgcgatc gtaatcaccc gagtgtgatc atctggtcgc tggggaatga atcaggccac    2520
ggcgctaatc acgacgcgct gtatcgctgg atcaaatctg tcgatccttc ccgcccggtg    2580
cagtatgaag gcggcggagc cgacaccacg gccaccgata ttatttgccc gatgtacgcg    2640
cgcgtggatg aagaccagcc cttcccggct gtgccgaaat ggtccatcaa aaaatggctt    2700
tcgctacctg gagagacgcg cccgctgatc ctttgcgaat acgcccacgc gatgggtaac    2760
agtcttggcg gtttcgctaa atactggcag gcgtttcgtc agtatcccg tttacagggc     2820
ggcttcgtct gggactgggt ggatcagtcg ctgattaaat atgatgaaaa cggcaacccg    2880
tggtcggctt acggcggtga ttttggcgat acgccgaacg atcgccagtt ctgtatgaac    2940
ggtctggtct ttgccgaccg cacgccgcat ccagcgctga cggaagcaaa acaccagcag    3000
cagttttttcc agttccgttt atccgggcaa accatcgaag tgaccagcga ataccttgtc   3060
cgtcatagcg ataacgagct cctgcactgg atggtggcgc tggatggtaa gccgctggca    3120
agcggtgaag tgcctctgga tgtcgctcca caaggtaaac agttgattga actgcctgaa    3180
ctaccgcagc ggagagcgc cgggcaactc tggctcacag tacgcgtagt gcaaccgaac     3240
gcgaccgcat ggtcagaagc cgggcacatc agcgcctggc agcagtggcg tctggcggaa    3300
aacctcagtg tgacgctccc cgccgcgtcc cacgccatcc gcatctgac caccagcgaa     3360
atggatttttt gcatcgagct gggtaataag cgttggcaat taaccgcca gtcaggcttt    3420
ctttcacaga tgtggattgg cgataaaaaa caactgctga cgccgctgcg cgatcagttc    3480
acccgtcacac cgctggataa cgacattggc gtaagtgaag cgaccgcat tgaccctaac     3540
gcctgggtcg aacgctggaa ggcggcgggc cattaccagg ccgaagcagc gttgttgcag    3600
tgcacggcag atacacttgc tgatgcgtg ctgattacga ccgctcacgc gtggcagcat     3660
caggggaaaa ccttatttat cagccggaaa acctaccgga ttgatggtag tggtcaaatg    3720
```

```
gcgattaccg ttgatgttga agtggcgagc gatacaccgc atccggcgcg gattggcctg    3780
aactgccagc tggcgcaggt agcagagcgg gtaaactggc tcggattagg ccgcaagaa    3840 aactatcccg accgccttac tgccgcctgt tttgaccgct gggatctgcc attgtcagac    3900
atgtataccc cgtacgtctt cccgagcgaa aacggtctgc gctgcgggac gcgcgaattg    3960
aattatggcc cacaccagtg gcgcggcgac ttccagttca acatcagccg ctacagtcaa    4020
cagcaactga tggaaaccag ccatcgccat ctgctgcacg cggaagaagg cacatggctg    4080
aatatcgacg gtttccatat ggggattggt ggcgacgact cctggagccc gtcagtatcg    4140
gcggaattac agctgagcgc cggtcgctac cattaccagt tggtctggtg tcaaaaataa    4200
taataaccgg gcaggccatg tctgcccgta tttcgcgtaa ggaaatccat tatgtactat    4260
ttaaaaaaca caaacttttg gatgttcggt ttattctttt tcttttactt ttttatcatg    4320
ggagcctact tcccgttttt cccgatttgg ctacatgaca tcaaccatat cagcaaaagt    4380
gatacgggta ttattttgc cgctatttct ctgttctcgc tattattcca accgctgttt    4440
ggtctgcttt ctgacaaact cggcctcgac tctaggcggc cgcggggatc cagacatgat    4500
aagatacatt gatgagtttg gacaaaccac aactagaatg cagtgaaaaa aatgctttat    4560
ttgtgaaatt tgtgatgcta ttgctttatt tgtaaccatt ataagctgca ataaacaagt    4620
taacaacaac aattgcattc attttatgtt tcaggttcag ggggaggtgt gggaggtttt    4680
ttcggatcct ctagagtcga cctgcaggca tgcaagcttg gcgtaatcat ggtcatagct    4740
gtttcctgtg tgaaattgtt atccgctcac aattccacac aacatacgag ccggaagcat    4800
aaagtgtaaa gcctggggtg cctaatgagt gagctaactc acattaattg cgttgcgctc    4860
actgcccgct ttccagtcgg gaaacctgtc gtgccagctg cattaatgaa tcggccaacg    4920
cgcggggaga ggcggtttgc gtattgggcg ctcttccgct tcctcgctca ctgactcgct    4980
gcgctcggtc gttcggctgc ggcgagcggt atcagctcac tcaaaggcgg taatacggtt    5040
atccacagaa tcaggggata acgcaggaaa gaacatgtga gcaaaaggcc agcaaaaggc    5100
caggaaccgt aaaaaggccg cgttgctggc gtttttccat aggctccgcc cccctgacga    5160
gcatcacaaa aatcgacgct caagtcagag gtggcgaaac ccgacaggac tataaagata    5220
ccaggcgttt ccccctggaa gctccctcgt gcgctctcct gttccgaccc tgccgcttac    5280
cggatacctg tccgcctttc tcccttcggg aagcgtggcg ctttctcata gctcacgctg    5340
taggtatctc agttcggtgt aggtcgttcg ctccaagctg ggctgtgtgc acgaaccccc    5400
cgttcagccc gaccgctgcg ccttatccgg taactatcgt cttgagtcca acccggtaag    5460
acacgactta tcgccactgg cagcagccac tggtaacagg attagcagag cgaggtatgt    5520
aggcggtgct acagagttct tgaagtggtg gcctaactac ggctacacta aggacagt    5580 atttggtatc tgcgctctgc tgaagccagt taccttcgga aaaagagttg gtagctcttg    5640
atccggcaaa caaccaccg ctggtagcgg tggttttttt gtttgcaagc agcagattac    5700
gcgcagaaaa aaaggatctc aagaagatcc tttgatcttt tctacggggt ctgacgctca    5760
gtggaacgaa aactcacgtt aagggatttt ggtcatgaga ttatcaaaaa ggatcttcac    5820
ctagatcctt ttaaattaaa aatgaagttt taaatcaatc taaagtatat atgagtaaac    5880
ttggtctgac agttaccaat gcttaatcag tgaggcacct atctcagcga tctgtctatt    5940
tcgttcatcc atagttgcct gactccccgt cgtgtagata actacgatac gggagggctt    6000
accatctggc cccagtgctg caatgatacc gcgagaccca cgctcaccgg ctccagattt    6060
atcagcaata aaccagccag ccggaagggc cgagcgcaga agtggtcctg caactttatc    6120
```

```
cgcctccatc cagtctatta attgttgccg ggaagctaga gtaagtagtt cgccagttaa    6180
tagtttgcgc aacgttgttg ccattgctac aggcatcgtg gtgtcacgct cgtcgtttgg    6240
tatggcttca ttcagctccg gttcccaacg atcaaggcga gttacatgat cccccatgtt    6300
gtgcaaaaaa gcggttagct ccttcggtcc tccgatcgtt gtcagaagta agttggccgc    6360
agtgttatca ctcatggtta tggcagcact gcataattct cttactgtca tgccatccgt    6420
aagatgcttt tctgtgactg gtgagtactc aaccaagtca ttctgagaat agtgtatgcg    6480
gcgaccgagt tgctcttgcc cggcgtcaat acgggataat accgcgccac atagcagaac    6540
tttaaaagtg ctcatcattg gaaaacgttc ttcgggcga aaactctcaa ggatcttacc    6600
gctgttgaga tccagttcga tgtaacccac tcgtgcaccc aactgatctt cagcatcttt    6660
tactttcacc agcgtttctg ggtgagcaaa aacaggaagg caaaatgccg caaaaaaggg    6720
aataagggcg acacggaaat gttgaatact catactcttc ctttttcaat attattgaag    6780
catttatcag ggttattgtc tcatgagcgg atacatattt gaatgtattt agaaaaataa    6840
acaaataggg gttccgcgca catttccccg aaaagtgcca cctgacgtct aagaaaccat    6900
tattatcatg acattaacct ataaaaatag gcgtatcacg aggccctttc gtctcgcgcg    6960
tttcggtgat gacggtgaaa acctctgaca catgcagctc ccggagacgg tcacagcttg    7020
tctgtaagcg gatgccggga gcagacaagc ccgtcagggc gcgtcagcgg gtgttggcgg    7080
gtgtcggggc tggcttaact atgcggcatc agagcagatt gtactgagag tgcaccatat    7140
gcggtgtgaa ataccgcaca gatgcgtaag gagaaaatac cgcatcaggc gccattcgcc    7200
attcaggctg cgcaactgtt gggaagggcg atcggtgcgg gcctcttcgc tattacgcca    7260
gctggcgaaa gggggatgtg ctgcaaggcg attaagttgg gtaacgccag ggttttccca    7320
gtcacgacgt tgtaaaacga cggccagtga attcgagctt gcatgcctgc aggt          7374
```

<210> SEQ ID NO 47
<211> LENGTH: 7377
<212> TYPE: DNA
<213> ORGANISM: Artificial sequence
<220> FEATURE:
<223> OTHER INFORMATION: TalRab2-Reporter

<400> SEQUENCE: 47

```
cgttacataa cttacggtaa atggcccgcc tggctgaccg cccaacgacc cccgcccatt      60
gacgtcaata atgacgtatg ttcccatagt aacgccaata gggactttcc attgacgtca     120
atgggtggag tatttacggt aaactgccca cttggcagta catcaagtgt atcatatgcc     180
aagtacgccc cctattgacg tcaatgacgg taaatggccc gcctggcatt atgcccagta     240
catgacctta tgggactttc ctacttggca gtacatctac gtattagtca tcgctattac     300
catggtgatg cggttttggc agtacatcaa tgggcgtgga tagcggtttg actcacgggg     360
atttccaagt ctccacccca ttgacgtcaa tgggagtttg ttttggcacc aaaatcaacg     420
ggactttcca aaatgtcgta caactccgc cccattgacg caaatgggcg gtaggcgtgt     480
acggtgggag gtctatataa gcagagctcg tttagtgaac cgtcagatcg cctggagacg     540
ccatccacgc tgttttgacc tccatagaag acaccggga cgatccagcc tccgactct      600 agaggatccg gtactcgacg acactgcaga gacctacttc actaacaacc ggtatggtcg     660
cgagtagctt ggcactggcc gtcgttttac aacgtcgtga ctgggaaaac cctggcgtta     720
cccaacttaa tcgccttgca gcacatcccc ctttcgccag ctggcgtaat agcgaagagg     780
```

```
cccgcaccga tcgcccttcc caacagttgc gcagcctgaa tggcgaatgg cgctttgcct    840
ggtttccggc accagaagcg gtgccggaaa gctggctgga gtgcgatctt cctgaggccg    900
atactgtcgt cgtcccctca aactggcaga tgcacggtta cgatgcgccc atctacacca    960
acgtgaccta tcccattacg gtcaatccgc cgtttgttcc cacggagaat ccgacgggtt   1020
gttactcgct cacatttaat gttgatgaaa gctggctata aaaccggtac agttcggcca   1080
ccatggtcga tggtggcccg gtagttttca cactcttctc actaccgggc caccacgagt   1140
agcttggcac tggccgtcgt tttacaacgt cgtgactggg aaaaccctgg cgttacccaa   1200
cttaatcgcc ttgcagcaca tccccctttc gccagctggc gtaatagcga agaggcccgc   1260
accgatcgcc cttcccaaca gttgcgcagc ctgaatggcg aatggcgctt tgcctggttt   1320
ccggcaccag aagcggtgcc ggaaagctgg ctggagtgcg atcttcctga ggccgatact   1380
gtcgtcgtcc cctcaaactg gcagatgcac ggttacgatg cgcccatcta caccaacgtg   1440
acctatccca ttacggtcaa tccgccgttt gttcccacgg agaatccgac gggttgttac   1500
tcgctcacat ttaatgttga tgaaagctgg ctacaggaag ccagacgcg aattattttt   1560
gatggcgtta actcggcgtt tcatctgtgg tgcaacgggc gctgggtcgg ttacggccag   1620
gacagtcgtt tgccgtctga atttgacctg agcgcatttt tacgcgccgg agaaaaccgc   1680
ctcgcggtga tggtgctgcg ctggagtgac ggcagttatc tggaagatca ggatatgtgg   1740
cggatgagcg gcattttccg tgacgtctcg ttgctgcata aaccgactac acaaatcagc   1800
gatttccatg ttgccactcg ctttaatgat gatttcagcc gcgctgtact ggaggctgaa   1860
gttcagatgt gcggcgagtt gcgtgactac ctacgggtaa cagtttcttt atggcagggt   1920
gaaacgcagg tcgccagcgg caccgcgcct tcggcggtg aaattatcga tgagcgtggt   1980
ggttatgccg atcgcgtcac actacgtctg aacgtcgaaa acccgaaact gtggagcgcc   2040
gaaatcccga atctctatcg tgcggtggtt gaactgcaca ccgccgacgg cacgctgatt   2100
gaagcagaag cctgcgatgt cggttttcgc gaggtgcgga ttgaaaatgg tctgctgctg   2160
ctgaacggca agccgttgct gattcgaggc gttaaccgtc acgagcatca tcctctgcat   2220
ggtcaggtca tggatgagca gacgatggtg caggatatcc tgctgatgaa gcagaacaac   2280
tttaacgccg tgcgctgttc gcattatccg aaccatccgc tgtggtacac gctgtgcgac   2340
cgctacggcc tgtatgtggt ggatgaagcc aatattgaaa cccacggcat ggtgccaatg   2400
aatcgtctga ccgatgatcc gcgctggcta ccggcgatga gcgaacgcgt aacgcgaatg   2460
gtgcagcgcg atcgtaatca cccgagtgtg atcatctggt cgctggggaa tgaatcaggc   2520
cacggcgcta atcacgacgc gctgtatcgc tggatcaaat ctgtcgatcc ttcccgcccg   2580
gtgcagtatg aaggcggcgg agccgacacc acggccaccg atattatttg cccgatgtac   2640
gcgcgcgtgg atgaagacca gcccttcccg gctgtgccga atggtccat caaaaaatgg   2700
ctttcgctac tggagagac gcgcccgctg atcctttgcg aatacgccca cgcgatgggt   2760
aacagtcttg gcggtttcgc taaatactgg caggcgtttc gtcagtatcc ccgtttacag   2820
ggcggcttcg tctgggactg ggtggatcag tcgctgatta aatatgatga aaacggcaac   2880
ccgtggtcgg cttacggcgg tgattttggc gatacgccga cgatcgcca gttctgtatg   2940
aacggtctgg tctttgccga ccgcacgccg catccagcgc tgacggaagc aaaacaccag   3000
cagcagtttt tccagttccg tttatccggg caaaccatcg aagtgaccag cgaataccctg   3060
ttccgtcata gcgataacga gctcctgcac tggatggtgg cgctggatgg taagccgctg   3120
gcaagcggtg aagtgcctct ggatgtcgct ccacaaggta aacagttgat tgaactgcct   3180
```

```
gaactaccgc agccggagag cgccgggcaa ctctggctca cagtacgcgt agtgcaaccg    3240
aacgcgaccg catggtcaga agccgggcac atcagcgcct ggcagcagtg gcgtctggcg    3300
gaaaacctca gtgtgacgct ccccgccgcg tcccacgcca tcccgcatct gaccaccagc    3360
gaaatggatt tttgcatcga gctgggtaat aagcgttggc aatttaaccg ccagtcaggc    3420
tttctttcac agatgtggat tggcgataaa aacaactgc tgacgccgct gcgcgatcag     3480
ttcacccgtg caccgctgga taacgacatt ggcgtaagtg aagcgacccg cattgaccct    3540
aacgcctggg tcgaacgctg gaaggcggcg ggccattacc aggccgaagc agcgttgttg    3600
cagtgcacgg cagatacact tgctgatgcg gtgctgatta cgaccgctca cgcgtggcag    3660
catcagggga aaaccttatt tatcagccgg aaaacctacc ggattgatgg tagtggtcaa    3720
atggcgatta ccgttgatgt tgaagtggcg agcgatacac cgcatccggc gcggattggc    3780
ctgaactgcc agctggcgca ggtagcagag cgggtaaact ggctcggatt agggccgcaa    3840
gaaaactatc ccgaccgcct tactgccgcc tgttttgacc gctgggatct gccattgtca    3900
gacatgtata ccccgtacgt cttcccgagc gaaaacggtc tgcgctgcgg gacgcgcgaa    3960
ttgaattatg gccacaccca gtggcgcggc gacttccagt tcaacatcag ccgctacagt    4020
caacagcaac tgatggaaac cagccatcgc catctgctgc acgcggaaga aggcacatgg    4080
ctgaatatcg acgttttcca tatggggatt ggtggcgacg actcctggag cccgtcagta    4140
tcggcggaat tacagctgag cgccggtcgc taccattacc agttggtctg gtgtcaaaaa    4200
taataataac cgggcaggcc atgtctgccc gtatttcgcg taaggaaatc cattatgtac    4260
tatttaaaaa acacaaactt ttggatgttc ggtttattct ttttcttta ctttttatc      4320 atgggagcct acttcccgtt tttcccgatt tggctacatg acatcaacca tatcagcaaa    4380
agtgatacgg gtattatttt tgccgctatt tctctgttct cgctattatt ccaaccgctg    4440
tttggtctgc tttctgacaa actcggcctc gactctaggc ggccgcgggg atccagacat    4500
gataagatac attgatgagt ttggacaaac cacaactaga atgcagtgaa aaaaatgctt    4560
tatttgtgaa atttgtgatg ctattgcttt atttgtaacc attataagct gcaataaaca    4620
agttaacaac aacaattgca ttcatttat gtttcaggtt caggggagg tgtgggaggt      4680 tttttcggat cctctagagt cgacctgcag gcatgcaagc ttggcgtaat catggtcata    4740
gctgtttcct gtgtgaaatt gttatccgct cacaattcca cacaacatac gagccggaag    4800
cataaagtgt aaagcctggg gtgcctaatg agtgagctaa ctcacattaa ttgcgttgcg    4860
ctcactgccc gctttccagt cgggaaacct gtcgtgccag ctgcattaat gaatcggcca    4920
acgcgcgggg agaggcggtt tgcgtattgg gcgctcttcc gcttcctcgc tcactgactc    4980
gctgcgctcg tcgttcggc tgcggcgagc ggtatcagct cactcaaagg cggtaatacg     5040
gttatccaca gaatcagggg ataacgcagg aaagaacatg tgagcaaaag gccagcaaaa    5100
ggccaggaac cgtaaaaagg ccgcgttgct ggcgtttttc cataggctcc gcccccctga    5160
cgagcatcac aaaaatcgac gctcaagtca gaggtggcga acccgacag gactataaag     5220 ataccaggcg tttccccctg gaagctccct cgtgcgctct cctgttccga ccctgccgct    5280
taccggatac ctgtccgcct ttctcccttc gggaagcgtg gcgctttctc atagctcacg    5340
ctgtaggtat ctcagttcgg tgtaggtcgt tcgctccaag ctgggctgtg tgcacgaacc    5400 cccgttcag cccgaccgct gcgccttatc cggtaactat cgtcttgagt ccaacccggt     5460
aagacacgac ttatcgccac tggcagcagc cactggtaac aggattagca gagcgaggta    5520
```

| | |
|---|---|
| tgtaggcggt gctacagagt tcttgaagtg gtggcctaac tacggctaca ctagaaggac | 5580 |
| agtatttggt atctgcgctc tgctgaagcc agttaccttc ggaaaaagag ttggtagctc | 5640 |
| ttgatccggc aaacaaacca ccgctggtag cggtggtttt tttgtttgca agcagcagat | 5700 |
| tacgcgcaga aaaaaggat ctcaagaaga tcctttgatc ttttctacgg ggtctgacgc | 5760 |
| tcagtggaac gaaaactcac gttaagggat tttggtcatg agattatcaa aaaggatctt | 5820 |
| cacctagatc cttttaaatt aaaaatgaag ttttaaatca atctaaagta tatatgagta | 5880 |
| aacttggtct gacagttacc aatgcttaat cagtgaggca cctatctcag cgatctgtct | 5940 |
| atttcgttca tccatagttg cctgactccc cgtcgtgtag ataactacga tacgggaggg | 6000 |
| cttaccatct ggccccagtg ctgcaatgat accgcgagac ccacgctcac cggctccaga | 6060 |
| tttatcagca ataaaccagc cagccggaag ggccgagcgc agaagtggtc ctgcaacttt | 6120 |
| atccgcctcc atccagtcta ttaattgttg ccgggaagct agagtaagta gttcgccagt | 6180 |
| taatagtttg cgcaacgttg ttgccattgc tacaggcatc gtggtgtcac gctcgtcgtt | 6240 |
| tggtatggct tcattcagct ccggttccca acgatcaagg cgagttacat gatcccccat | 6300 |
| gttgtgcaaa aaagcggtta gctccttcgg tcctccgatc gttgtcagaa gtaagttggc | 6360 |
| cgcagtgtta tcactcatgg ttatggcagc actgcataat tctcttactg tcatgccatc | 6420 |
| cgtaagatgc ttttctgtga ctggtgagta ctcaaccaag tcattctgag aatagtgtat | 6480 |
| gcggcgaccg agttgctctt gcccggcgtc aatacgggat aataccgcgc cacatagcag | 6540 |
| aactttaaaa gtgctcatca ttggaaaacg ttcttcgggg cgaaaactct caaggatctt | 6600 |
| accgctgttg agatccagtt cgatgtaacc cactcgtgca cccaactgat cttcagcatc | 6660 |
| ttttactttc accagcgttt ctgggtgagc aaaaacagga aggcaaaatg ccgcaaaaaa | 6720 |
| gggaataagg gcgacacgga aatgttgaat actcatactc ttccttttc aatattattg | 6780 |
| aagcatttat cagggttatt gtctcatgag cggatacata tttgaatgta tttagaaaaa | 6840 |
| taaacaaata ggggttccgc gcacatttcc ccgaaaagtg ccacctgacg tctaagaaac | 6900 |
| cattattatc atgacattaa cctataaaaa taggcgtatc acgaggccct ttcgtctcgc | 6960 |
| gcgtttcggt gatgacggtg aaaacctctg acacatgcag ctcccggaga cggtcacagc | 7020 |
| ttgtctgtaa gcggatgccg ggagcagaca agcccgtcag ggcgcgtcag cgggtgttgg | 7080 |
| cgggtgtcgg gctggctta actatgcggc atcagagcag attgtactga gagtgcacca | 7140 |
| tatgcggtgt gaaataccgc acagatgcgt aaggagaaaa taccgcatca ggcgccattc | 7200 |
| gccattcagg ctgcgcaact gttgggaagg gcgatcggtg cgggcctctt cgctattacg | 7260 |
| ccagctggcg aaagggggat gtgctgcaag gcgattaagt tgggtaacgc cagggttttc | 7320 |
| ccagtcacga cgttgtaaaa cgacggccag tgaattcgag cttgcatgcc tgcaggt | 7377 |

<210> SEQ ID NO 48
<211> LENGTH: 7383
<212> TYPE: DNA
<213> ORGANISM: Artificial sequence
<220> FEATURE:
<223> OTHER INFORMATION: ArtTal1/TalRab2-Reporter

<400> SEQUENCE: 48

| | |
|---|---|
| cgttacataa cttacggtaa atggcccgcc tggctgaccg cccaacgacc cccgcccatt | 60 |
| gacgtcaata atgacgtatg ttcccatagt aacgccaata gggactttcc attgacgtca | 120 |
| atgggtggag tatttacggt aaactgccca cttggcagta catcaagtgt atcatatgcc | 180 |
| aagtacgccc cctattgacg tcaatgacgg taaatggccc gcctggcatt atgcccagta | 240 |

-continued

```
catgaccttatgggactttcctacttggcagtacatctacgtattagtcatcgctattac      300
catggtgatgcggttttggcagtacatcaatgggcgtggatagcggtttgactcacgggg      360
atttccaagtctccaccccattgacgtcaatgggagtttgttttggcaccaaaatcaacg      420
ggactttccaaaatgtcgtaacaactccgcccccattgacgcaaatgggcggtaggcgtgt     480
acggtgggagtctatataagcagagctcgtttagtgaaccgtcagatcgcctggagacg      540
ccatccacgctgttttgacctccatagaagacaccgggaccgatccagcctccggactct    600
agaggatccggtactcgaggacactgcagagacctacttcactaacaaccggtatggtcg     660
cgagtagcttggcactggccgtcgttttacaacgtcgtgactgggaaaacctggcgtta      720
cccaacttaatcgccttgcagcacatccccctttcgccagctggcgtaatagcgaagagg     780
cccgcaccgatcgcccttcccaacagttgcgcagcctgaatggcgaatggcgctttgcct     840
ggtttccggcaccagaagcggtgccggaaagctggctggagtgcgatcttcctgaggccg      900
atactgtcgtcgtcccctcaaactggcagatgcacggttacgatgcgcccatctacacca     960
acgtgacctatcccattacggtcaatccgccgtttgttcccacggagaatccgacgggtt     1020
gttactcgctcacatttaatgttgatgaaagctggctataaaaccggtacagttcggcca    1080
ccatggtcgtattctgggacgttttttcacactcttctaaactaccgggccaccacgggtc      1140
gcgagtagcttggcactggccgtcgttttacaacgtcgtgactgggaaaacctggcgtt      1200
acccaacttaatcgccttgcagcacatccccctttcgccagctggcgtaatagcgaagag     1260
gcccgcaccgatcgcccttccaacagttgcgcagcctgaatggcgaatggcgctttgcc     1320
tggtttccggcaccagaagcggtgccggaaagctggctggagtgcgatcttcctgaggcc     1380
gatactgtcgtcgtcccctcaaactggcagatgcacggttacgatgcgcccatctacacc    1440
aacgtgacctatcccattacggtcaatccgccgtttgttcccacggagaatccgacgggt    1500
tgttactcgctcacatttaatgttgatgaaagctggctacaggaaggccagacgcgaatt    1560
atttttgatggcgttaactcggcgtttcatctgtggtgcaacgggcgctggtcggttac      1620
ggccaggacagtcgtttgccgtctgaatttgacctgagcgcattttttacgcgccggagaa     1680
aaccgcctcgcggtgatggtgctgcgctggagtgacggcagttatctggaagatcaggat    1740
atgtggcggatgagcggcattttccgtgacgtctcgttgctgcataaaaccgactacacaa    1800
atcagcgattccatgttgccactcgctttaatgatgatttcagccgcgctgtactggag      1860
gctgaagttcagatgtgcggcgagttgcgtgactacctacgggtaacagttctttatgg      1920
cagggtgaaacgcaggtcgccagcggcaccgcgcctttcgcggtgaaatatcgatgag      1980
cgtggtggttatgccgatcgcgtcacactacgtctgaacgtcgaaaacccgaaactgtgg     2040
agcgccgaaatccgaatctctatcgtgcggtggttgaactgcacaccgccgacggcacg      2100
ctgattgaagcagaagcctgcgatgtcggtttccgcgaggtgcggattgaaaatggtctg     2160
ctgctgctgaacggcaagccgttgctgattcgaggcgttaaccgtcacgagcatcatcct     2220
ctgcatggtcaggtcatggatgagcagacgatggtgcaggatatcctgctgatgaagcag    2280
aacaactttaacgccgtgcgctgttcgcattatccgaaccatccgctgtggtacacgctg     2340
tgcgaccgctacgcctgtatgtggtggatgaagccaatattgaaacccacggcatggtg     2400
ccaatgaatcgtctgaccgatgatccgcgctggctaccggcgatgagcgaacgcgtaacg    2460
cgaatggtgcagcgcgatcgtaatcacccgagtgtgatcatctggtcgctggggaatgaa     2520
tcaggccacgcgctaatcagacgcgctgtatcgctggatcaaatctgtcgatccttcc     2580
```

```
cgcccggtgc agtatgaagg cggcggagcc gacaccacgg ccaccgatat tatttgcccg   2640
atgtacgcgc gcgtggatga agaccagccc ttcccggctg tgccgaaatg gtccatcaaa   2700
aaatggcttt cgctacctgg agagacgcgc ccgctgatcc tttgcgaata cgcccacgcg   2760
atgggtaaca gtcttggcgg tttcgctaaa tactggcagg cgtttcgtca gtatcccgt   2820 ttacagggcg gcttcgtctg ggactgggtg gatcagtcgc tgattaaata tgatgaaaac   2880
ggcaacccgt ggtcggctta cggcggtgat tttggcgata cgccaacga tcgccagttc   2940 tgtatgaacg gtctggtctt tgccgaccgc acgccgcatc cagcgctgac ggaagcaaaa   3000
caccagcagc agttttttcca gttccgttta tccgggcaaa ccatcgaagt gaccagcgaa   3060
tacctgttcc gtcatagcga taacgagctc ctgcactgga tggtggcgct ggatggtaag   3120
ccgctggcaa gcgtgaagt gcctctggat gtcgctccac aaggtaaaca gttgattgaa   3180
ctgcctgaac taccgcagcc ggagagcgcc gggcaactct ggctcacagt acgcgtagtg   3240
caaccgaacg cgaccgcatg gtcagaagcc gggcacatca gcgcctggca gcagtggcgt   3300
ctggcggaaa acctcagtgt gacgctcccc gccgcgtccc acgccatccc gcatctgacc   3360
accagcgaaa tggattttttg catcgagctg gtaataagc gttggcaatt taaccgccag   3420
tcaggctttc tttcacagat gtggattggc gataaaaaac aactgctgac gccgctgcgc   3480
gatcagttca cccgtgcacc gctggataac gacattggcg taagtgaagc gacccgcatt   3540
gaccctaacg cctgggtcga acgctggaag gcggcgggcc attaccaggc cgaagcagcg   3600
ttgttgcagt gcacggcaga tacacttgct gatgcggtgc tgattacgac cgctcacgcg   3660
tggcagcatc aggggaaaac cttatttatc agccggaaaa cctaccggat tgatggtagt   3720
ggtcaaatgg cgattaccgt tgatgttgaa gtggcgagcg atacaccgca tccggcgcgg   3780
attggcctga actgccagct ggcgcaggta gcagagcggg taaactggct cggattaggg   3840
ccgcaagaaa actatcccga ccgccttact gccgctgtt ttgaccgctg ggatctgcca   3900
ttgtcagaca tgtataccCC gtacgtcttc ccgagcgaaa acggtctgcg ctgcgggacg   3960
cgcgaattga attatggccc acaccagtgg cgcggcgact ccagttcaa catcagccgc   4020 tacagtcaac agcaactgat ggaaaccagc catcgccatc tgctgcacgc ggaagaaggc   4080
acatggctga atatcgacgg tttccatatg gggattggtg gcgacgactc ctggagcccg   4140
tcagtatcgg cggaattaca gctgagcgcc ggtcgctacc attaccagtt ggtctggtgt   4200
caaaaataat aataaccggg caggccatgt ctgcccgtat ttcgcgtaag gaaatccatt   4260
atgtactatt taaaaacac aaactttttgg atgttcggtt tattctttt cttttacttt   4320 tttatcatgg gagcctactt cccgttttc ccgatttggc tacatgacat caaccatatc   4380
agcaaaagtg atacgggtat tatttttgcc gctatttctc tgttctcgct attattccaa   4440
ccgctgtttg gtctgctttc tgacaaactc ggcctcgact ctaggcggcc gcggggatcc   4500
agacatgata agatacattg atgagtttgg acaaaccaca actagaatgc agtgaaaaaa   4560
atgctttatt tgtgaaattt gtgatgctat tgctttattt gtaaccatta taagctgcaa   4620
taaacaagtt aacaacaaca attgcattca ttttatgttt caggttcagg gggaggtgtg   4680
ggaggttttt tcggatcctc tagagtcgac ctgcaggcat gcaagcttgg cgtaatcatg   4740
gtcatagctg tttcctgtgt gaaattgtta tccgctcaca attccacaca acatacgagc   4800
cggaagcata aagtgtaaag cctggggtgc ctaatgagtg agctaactca cattaattgc   4860
gttgcgctca ctgcccgctt tccagtcggg aaacctgtcg tgccagctgc attaatgaat   4920
cggccaacgc gcggggagag gcggtttgcg tattgggcgc tcttccgctt cctcgctcac   4980
```

```
tgactcgctg cgctcggtcg ttcggctgcg gcgagcggta tcagctcact caaaggcggt    5040
aatacggtta tccacagaat caggggataa cgcaggaaag aacatgtgag caaaaggcca    5100
gcaaaaggcc aggaaccgta aaaaggccgc gttgctggcg ttttTccata ggctccgccc    5160
ccctgacgag catcacaaaa atcgacgctc aagtcagagg tggcgaaacc cgacaggact    5220
ataaagatac caggcgtttc ccCctggaag ctccctcgtg cgctctcctg ttccgaccct    5280
gccgcttacc ggatacctgt ccgcctttct cccttcggga agcgtggcgc tttctcatag    5340
ctcacgctgt aggtatctca gttcggtgta ggtcgttcgc tccaagctgg gctgtgtgca    5400
cgaaccCCCC gttcagcccg accgctgcgc cttatccggt aactatcgtc ttgagtccaa    5460
cccggtaaga cacgacttat cgccactggc agcagccact ggtaacagga ttagcagagc    5520
gaggtatgta ggcggtgcta cagagttctt gaagtggtgg cctaactacg gctacactag    5580
aaggacagta tttggtatct gcgctctgct gaagccagtt accttcggaa aaagagttgg    5640
tagctcttga tccggcaaac aaaccaccgc tggtagcggt ggtttTTTtg tttgcaagca    5700
gcagattacg cgcagaaaaa aaggatctca agaagatcct ttgatctttt ctacggggtc    5760
tgacgctcag tggaacgaaa actcacgtta agggattttg gtcatgagat tatcaaaaag    5820
gatcttcacc tagatccttt taaattaaaa atgaagtttt aaatcaatct aaagtatata    5880
tgagtaaact tggtctgaca gttaccaatg cttaatcagt gaggcaccta tctcagcgat    5940
ctgtctattt cgttcatcca tagttgcctg actccccgtc gtgtagataa ctacgatacg    6000
ggagggctta ccatctggcc ccagtgctgc aatgataccg cgagacccac gctcaccggc    6060
tccagattta tcagcaataa accagccagc cggaagggcc gagcgcagaa gtggtcctgc    6120
aactttatcc gcctccatcc agtctattaa ttgttgccgg gaagctagag taagtagttc    6180
gccagttaat agtttgcgca acgttgttgc cattgctaca ggcatcgtgg tgtcacgctc    6240
gtcgtttggt atggcttcat tcagctccgg ttcccaacga tcaaggcgag ttacatgatc    6300
ccccatgttg tgcaaaaaag cggttagctc cttcggtcct ccgatcgttg tcagaagtaa    6360
gttggccgca gtgttatcac tcatggttat ggcagcactg cataattctc ttactgtcat    6420
gccatccgta agatgctttt ctgtgactgg tgagtactca accaagtcat tctgagaata    6480
gtgtatgcgg cgaccgagtt gctcttgccc ggcgtcaata cgggataata ccgcgccaca    6540
tagcagaact ttaaaagtgc tcatcattgg aaaacgttct cggggcgaa aactctcaag    6600 gatcttaccg ctgttgagat ccagttcgat gtaacccact cgtgcaccca actgatcttc    6660
agcatctttt actttcacca gcgtttctgg gtgagcaaaa acaggaaggc aaaatgccgc    6720
aaaaaaggga ataagggcga cacggaaatg ttgaatactc atactcttcc ttttTcaata    6780
ttattgaagc atttatcagg gttattgtct catgagcgga tacatatttg aatgtattta    6840
gaaaaataaa caaatagggg ttccgcgcac atttccccga aaagtgccac ctgacgtcta    6900
agaaaccatt attatcatga cattaaccta taaaaatagg cgtatcacga ggccctttcg    6960
tctcgcgcgt ttcggtgatg acggtgaaaa cctctgacac atgcagctcc cggagacggt    7020
cacagcttgt ctgtaagcgg atgccggag cagacaagcc cgtcagggcg cgtcagcggg    7080
tgttggcggg tgtcggggct ggcttaacta tgcggcatca gagcagattg tactgagagt    7140
gcaccatatg cggtgtgaaa taccgcacag atgcgtaagg agaaaatacc gcatcaggcg    7200
ccattcgcca ttcaggctgc gcaactgttg gaaggcgcga tcggtgcggg cctcttcgct    7260
attacgccag ctggcgaaag ggggatgtgc tgcaaggcga ttaagttggg taacgccagg    7320
```

```
gttttcccag tcacgacgtt gtaaaacgac ggccagtgaa ttcgagcttg catgcctgca    7380
ggt                                                                  7383

<210> SEQ ID NO 49
<211> LENGTH: 5566
<212> TYPE: DNA
<213> ORGANISM: Artificial sequence
<220> FEATURE:
<223> OTHER INFORMATION: pCMV-hLuc

<400> SEQUENCE: 49
ggtaccgagc tcttacgcgt gctagcccgg gctcgaggag cttggcccat tgcatacgtt     60
gtatccatat cataatatgt acatttatat tggctcatgt ccaacattac cgccatgttg    120
acattgatta ttgactagtt attaatagta atcaattacg ggtcattagt tcatagccc     180 atatatggag ttccgcgtta cataacttac ggtaaatggc ccgcctggct gaccgcccaa    240
cgacccccgc ccattgacgt caataatgac gtatgttccc atagtaacgc caatagggac    300
tttccattga cgtcaatggg tggagtattt acgctaaact gcccacttgg cagtacatca    360
agtgtatcat atgccaagta cgccccctat tgacgtcaat gacggtaaat ggcccgcctg    420
gcattatgcc cagtacatga ccttatggga ctttcctact tggcagtaca tctacgtatt    480
agtcatcgct attaccatgg tgatgcggtt ttggcagtac atcaatgggc gtggatagcg    540
gtttgactca cggggatttc caagtctcca ccccattgac gtcaatggga gtttgttttg    600
gcaccaaaat caacgggact ttccaaaatg tcgtaacaac tccgccccat tgacgcaaat    660
gggcggtagg cgtgtacggt gggaggtcta tataagcaga gctcgtttag tgaaccgtca    720
gatcgcctgg agacgccatc cacgctgttt tgacctccat agaagacacc gggaccgatc    780
cagcctccgc ggccccgaat tagcttggca ttccggtact gttggtaaag ccaccatgga    840
agacgccaaa aacataaaga aaggcccggc gccattctat ccgctggaag atggaaccgc    900
tggagagcaa ctgcataagg ctatgaagag atacgccctg gttcctggaa caattgcttt    960
tacagatgca catatcgagg tggacatcac ttacgctgag tacttcgaaa tgtccgttcg   1020
gttggcagaa gctatgaaac gatatgggct gaatacaaat cacagaatcg tcgtatgcag   1080
tgaaaactct cttcaattct ttatgccggt gttgggcgcg ttatttatcg gagttgcagt   1140
tgcgcccgcg aacgacattt ataatgaacg tgaattgctc aacagtatgg gcatttcgca   1200
gcctaccgtg gtgttcgttt ccaaaaaggg gttgcaaaaa attttgaacg tgcaaaaaaa   1260
gctcccaatc atccaaaaaa ttattatcat ggattctaaa acggattacc agggatttca   1320
gtcgatgtac acgttcgtca catctcatct acctcccggt tttaatgaat acgattttgt   1380
gccagagtcc ttcgatagggg acaagacaat gcactgatc atgaactcct ctggatctac   1440
tggtctgcct aaaggtgtcg ctctgcctca tagaactgcc tgcgtgagat tctcgcatgc   1500
cagagatcct attttggca atcaaatcat tccggatact gcgattttaa gtgttgttcc   1560
attccatcac ggttttggaa tgtttactac actcggatat ttgatatgtg gatttcgagt   1620
cgtcttaatg tatagatttg aagaagagct gtttctgagg agccttcagg attacaagat   1680
tcaaagtgcg ctgctggtgc caaccctatt ctccttcttc gccaaaagca ctctgattga   1740
caaatacgat ttatctaatt tacacgaaat tgcttctggt ggcgctcccc tctctaagga   1800
agtcggggaa gcggttgcca agaggttcca tctgccaggt atcaggcaag atatgggct    1860 cactgagact acatcagcta ttctgattac acccgagggg gatgataaac cgggcgcggt   1920
cggtaaagtt gttccatttt ttgaagcgaa ggttgtggat ctggataccg ggaaaacgct   1980
```

```
gggcgttaat caaagaggcg aactgtgtgt gagaggtcct atgattatgt ccggttatgt    2040
aaacaatccg gaagcgacca acgccttgat tgacaaggat ggatggctac attctggaga    2100
catagcttac tgggacgaag acgaacactt cttcatcgtt gaccgcctga agtctctgat    2160
taagtacaaa ggctatcagg tggctcccgc tgaattggaa tccatcttgc tccaacaccc    2220
caacatcttc gacgcaggtg tcgcaggtct tcccgacgat gacgccggtg aacttcccgc    2280
cgccgttgtt gttttggagc acggaaagac gatgacggaa aaagagatcg tggattacgt    2340
cgccagtcaa gtaacaaccg cgaaaaagtt gcgcggagga gttgtgtttg tggacgaagt    2400
accgaaaggt cttaccggaa aactcgacgc aagaaaaatc agagagatcc tcataaaggc    2460
caagaagggc ggaaagatcg ccgtgtaatt ctagagtcgg ggcggccggc cgcttcgagc    2520
agacatgata agatacattg atgagtttgg acaaaccaca actagaatgc agtgaaaaaa    2580
atgctttatt tgtgaaattt gtgatgctat tgctttattt gtaaccatta agctgcaa    2640 taaacaagtt aacaacaaca attgcattca ttttatgttt caggttcagg ggaggtgtg    2700 ggaggttttt taaagcaagt aaaacctcta caaatgtggt aaaatcgata aggatccgtc    2760
gaccgatgcc cttgagagcc ttcaacccag tcagctcctt ccggtgggcg cggggcatga    2820
ctatcgtcgc cgcacttatg actgtcttct ttatcatgca actcgtagga caggtgccgg    2880
cagcgctctt ccgcttcctc gctcactgac tcgctgcgct cggtcgttcg gctgcggcga    2940
gcggtatcag ctcactcaaa ggcggtaata cggttatcca cagaatcagg ggataacgca    3000
ggaaagaaca tgtgagcaaa aggccagcaa aaggccagga accgtaaaaa ggccgcgttg    3060
ctggcgtttt tccataggct ccgcccccct gacgagcatc acaaaaatcg acgctcaagt    3120
cagaggtggc gaaacccgac aggactataa agataccagg cgtttccccc tggaagctcc    3180
ctcgtgcgct ctcctgttcc gaccctgccg cttaccggat acctgtccgc ctttctccct    3240 tcggaagcg tggcgctttc tcatagctca cgctgtaggt atctcagttc ggtgtaggtc    3300
gttcgctcca agctgggctg tgtgcacgaa ccccccgttc agcccgaccg ctgcgcctta    3360
tccggtaact atcgtcttga gtccaacccg gtaagacacg acttatcgcc actggcagca    3420
gccactggta acaggattag cagagcgagg tatgtaggcg gtgctacaga gttcttgaag    3480
tggtggccta actacggcta cactagaaga acagtatttg gtatctgcgc tctgctgaag    3540
ccagttacct tcggaaaaag agttggtagc tcttgatccg gcaaacaaac caccgctggt    3600
agcggtggtt tttttgtttg caagcagcag attacgcgca gaaaaaaagg atctcaagaa    3660
gatcctttga tcttttctac ggggtctgac gctcagtgga acgaaaactc acgttaaggg    3720
attttggtca tgagattatc aaaaaggatc ttcacctaga tccttttaaa ttaaaaatga    3780
agttttaaat caatctaaag tatatatgag taaacttggt ctgacagtta ccaatgctta    3840
atcagtgagg cacctatctc agcgatctgt ctatttcgtt catccatagt tgcctgactc    3900
cccgtcgtgt agataactac gatacgggag ggcttaccat ctggccccag tgctgcaatg    3960
ataccgcgag acccacgctc accggctcca gatttatcag caataaacca gccagccgga    4020
agggccgagc gcagaagtgg tcctgcaact ttatccgcct ccatccagtc tattaattgt    4080
tgccgggaag ctagagtaag tagttcgcca gttaatagtt tgcgcaacgt tgttgccatt    4140
gctacaggca tcgtggtgtc acgctcgtcg tttggtatgg cttcattcag ctccggttcc    4200
caacgatcaa ggcgagttac atgatccccc atgttgtgca aaaaagcggt tagctccttc    4260
ggtcctccga tcgttgtcag aagtaagttg gccgcagtgt tatcactcat ggttatggca    4320
```

-continued

| | |
|---|---|
| gcactgcata attctcttac tgtcatgcca tccgtaagat gcttttctgt gactggtgag | 4380 |
| tactcaacca agtcattctg agaatagtgt atgcggcgac cgagttgctc ttgcccggcg | 4440 |
| tcaatacggg ataataccgc gccacatagc agaactttaa aagtgctcat cattggaaaa | 4500 |
| cgttcttcgg ggcgaaaact ctcaaggatc ttaccgctgt tgagatccag ttcgatgtaa | 4560 |
| cccactcgtg cacccaactg atcttcagca tcttttactt tcaccagcgt ttctgggtga | 4620 |
| gcaaaaacag gaaggcaaaa tgccgcaaaa aagggaataa gggcgacacg gaaatgttga | 4680 |
| atactcatac tcttcctttt tcaatattat tgaagcattt atcagggtta ttgtctcatg | 4740 |
| agcggataca tatttgaatg tatttagaaa aataaacaaa taggggttcc gcgcacattt | 4800 |
| ccccgaaaag tgccacctga cgcgccctgt agcggcgcat taagcgcggc gggtgtggtg | 4860 |
| gttacgcgca gcgtgaccgc tacacttgcc agcgccctag cgcccgctcc tttcgctttc | 4920 |
| ttcccttcct ttctcgccac gttcgccggc tttccccgtc aagctctaaa tcggggctc | 4980 |
| cctttagggt tccgatttag tgctttacgg cacctcgacc ccaaaaaact tgattagggt | 5040 |
| gatggttcac gtagtgggcc atcgccctga tagacggttt ttcgcccttt gacgttggag | 5100 |
| tccacgttct ttaatagtgg actcttgttc caaactggaa caacactcaa ccctatctcg | 5160 |
| gtctattctt ttgatttata agggattttg ccgatttcgg cctattggtt aaaaaatgag | 5220 |
| ctgatttaac aaaaatttaa cgcgaatttt aacaaaatat taacgcttac aatttgccat | 5280 |
| tcgccattca ggctgcgcaa ctgttgggaa gggcgatcgg tgcgggcctc ttcgctatta | 5340 |
| cgccagccca agctaccatg ataagtaagt aatattaagg tacgggaggt acttggagcg | 5400 |
| gccgcaataa aatatcttta ttttcattac atctgtgtgt tggttttttg tgtgaatcga | 5460 |
| tagtactaac atacgctctc catcaaaaca aaacgaaaca aaacaaacta gcaaaatagg | 5520 |
| ctgtccccag tgcaagtgca ggtgccagaa catttctcta tcgata | 5566 |

<210> SEQ ID NO 50
<211> LENGTH: 2961
<212> TYPE: DNA
<213> ORGANISM: Artificial sequence
<220> FEATURE:
<223> OTHER INFORMATION: pBS

<400> SEQUENCE: 50

| | |
|---|---|
| gtaaaacgac ggccagtgag cgcgcgtaat acgactcact atagggcgaa ttggagctcc | 60 |
| accgcggtgg cggccgctct agaactagtg gatccccccgg gctgcaggaa ttcgatatca | 120 |
| agcttatcga taccgtcgac ctcgaggggg ggcccggtac ccagcttttg ttccctttag | 180 |
| tgagggttaa ttgcgcgctt ggcgtaatca tggtcatagc tgtttcctgt gtgaaattgt | 240 |
| tatccgctca caattccaca acacatacga gccggaagca taaagtgtaa agcctggggt | 300 |
| gcctaatgag tgagctaact cacattaatt gcgttgcgct cactgcccgc tttccagtcg | 360 |
| ggaaacctgt cgtgccagct gcattaatga atcggccaac gcgcggggag aggcggtttg | 420 |
| cgtattgggc gctcttccgc ttcctcgctc actgactcgc tgcgctcggt cgttcggctg | 480 |
| cggcgagcgg tatcagctca ctcaaaggcg gtaatacggt tatccacaga atcaggggat | 540 |
| aacgcaggaa agaacatgtg agcaaaaggc cagcaaaagg ccaggaaccg taaaaaggcc | 600 |
| gcgttgctgg cgtttttcca taggctccgc cccccctgacg agcatcacaa aaatcgacgc | 660 |
| tcaagtcaga ggtggcgaaa cccgacagga ctataaagat accaggcgtt tcccctggga | 720 |
| agctccctcg tgcgctctcc tgttccgacc ctgccgctta ccggatacct gtccgccttt | 780 |
| ctcccttcgg gaagcgtggc gctttctcat agctcacgct gtaggtatct cagttcggtg | 840 |

```
taggtcgttc gctccaagct gggctgtgtg cacgaacccc ccgttcagcc cgaccgctgc    900
gccttatccg gtaactatcg tcttgagtcc aacccggtaa gacacgactt atcgccactg    960
gcagcagcca ctggtaacag gattagcaga gcgaggtatg taggcggtgc tacagagttc   1020
ttgaagtggt ggcctaacta cggctacact agaaggacag tatttggtat ctgcgctctg   1080
ctgaagccag ttaccttcgg aaaaagagtt ggtagctctt gatccggcaa acaaaccacc   1140
gctggtagcg gtggtttttt tgtttgcaag cagcagatta cgcgcagaaa aaaggatct    1200
caagaagatc ctttgatctt ttctacgggg tctgacgctc agtggaacga aaactcacgt   1260
taagggattt tggtcatgag attatcaaaa aggatcttca cctagatcct tttaaattaa   1320
aaatgaagtt ttaaatcaat ctaaagtata tatgagtaaa cttggtctga cagttaccaa   1380
tgcttaatca gtgaggcacc tatctcagcg atctgtctat ttcgttcatc catagttgcc   1440
tgactccccg tcgtgtagat aactacgata cgggagggct taccatctgg ccccagtgct   1500
gcaatgatac cgcgagaccc acgctcaccg gctccagatt tatcagcaat aaaccagcca   1560
gccggaaggg ccgagcgcag aagtggtcct gcaactttat ccgcctccat ccagtctatt   1620
aattgttgcc gggaagctag agtaagtagt tcgccagtta atagtttgcg caacgttgtt   1680
gccattgcta caggcatcgt ggtgtcacgc tcgtcgtttg gtatggcttc attcagctcc   1740
ggttcccaac gatcaaggcg agttacatga tcccccatgt tgtgcaaaaa agcggttagc   1800
tccttcggtc ctccgatcgt tgtcagaagt aagttggccg cagtgttatc actcatggtt   1860
atggcagcac tgcataattc tcttactgtc atgccatccg taagatgctt ttctgtgact   1920
ggtgagtact caaccaagtc attctgagaa tagtgtatgc ggcgaccgag ttgctcttgc   1980
ccggcgtcaa tacgggataa taccgcgcca catagcagaa ctttaaaagt gctcatcatt   2040
ggaaaacgtt cttcggggcg aaaactctca aggatcttac cgctgttgag atccagttcg   2100
atgtaaccca ctcgtgcacc caactgatct tcagcatctt ttactttcac cagcgtttct   2160
gggtgagcaa aaacaggaag gcaaaatgcc gcaaaaaagg aataagggc gacacggaaa    2220
tgttgaatac tcatactctt cctttttcaa tattattgaa gcatttatca gggttattgt   2280
ctcatgagcg gatacatatt tgaatgtatt tagaaaaata acaaataggg gttccgcgc    2340
acatttcccc gaaaagtgcc acctaaattg taagcgttaa tattttgtta aaattcgcgt   2400
taaattttg ttaaatcagc tcattttttta accaataggc cgaaatcggc aaaatccctt    2460
ataaatcaaa agaatagacc gagatagggt tgagtgttgt tccagtttgg aacaagagtc   2520
cactattaaa gaacgtggac tccaacgtca aagggcgaaa aaccgtctat cagggcgatg   2580
gcccactacg tgaaccatca ccctaatcaa gttttttggg gtcgaggtgc cgtaaagcac   2640
taaatcggaa ccctaaaggg agcccccgat ttagagcttg acggggaaag ccggcgaacg   2700
tggcgagaaa ggaagggaag aaagcgaaag gagcgggcgc tagggcgctg gcaagtgtag   2760
cggtcacgct gcgcgtaacc accacacccg ccgcgcttaa tgcgccgcta cagggcgcgt   2820
cccattcgcc attcaggctg cgcaactgtt gggaagggcg atcggtgcgg gcctcttcgc   2880
tattacgcca gctggcgaaa gggggatgtg ctgcaaggcg attaagttgg gtaacgccag   2940
ggttttccca gtcacgacgt t                                             2961
```

<210> SEQ ID NO 51
<211> LENGTH: 7164
<212> TYPE: DNA
<213> ORGANISM: Artificial sequence
<220> FEATURE:

<223> OTHER INFORMATION: pCMVbeta

<400> SEQUENCE: 51

```
gaattcgagc ttgcatgcct gcaggtcgtt acataactta cggtaaatgg cccgcctggc      60
tgaccgccca acgaccccccg cccattgacg tcaataatga cgtatgttcc catagtaacg     120
ccaataggga ctttccattg acgtcaatgg gtggagtatt tacggtaaac tgcccacttg     180
gcagtacatc aagtgtatca tatgccaagt acgccccccta ttgacgtcaa tgacggtaaa    240
tggcccgcct ggcattatgc ccagtacatg accttatggg actttcctac ttggcagtac    300
atctacgtat tagtcatcgc tattaccatg gtgatgcggt tttggcagta catcaatggg    360
cgtggatagc ggtttgactc acggggattt ccaagtctcc accccattga cgtcaatggg    420
agtttgtttt ggcaccaaaa tcaacgggac tttccaaaat gtcgtaacaa ctccgcccca    480
ttgacgcaaa tgggcggtag gcgtgtacgg tgggaggtct atataagcag agctcgttta    540
gtgaaccgtc agatcgcctg gagacgccat ccacgctgtt ttgacctcca tagaagacac    600
cgggaccgat ccagcctccg gactctagag gatccggtac tcgaggaact gaaaaaccag    660
aaagttaact ggtaagttta gtcttttttgt cttttatttc aggtcccgga tccggtggtg    720
gtgcaaatca agaactgct cctcagtgga tgttgccttt acttctaggc ctgtacggaa      780
gtgttacttc tgctctaaaa gctgcggaat tgtacccgcg gccgcaattc ccggggatcg    840
aaagagcctc taaagcaaa aagaagtca ccatgtcgtt tactttgacc aacaagaacg       900
tgattttcgt tgccggtctg ggaggcattg gtctggacac cagcaaggag ctgctcaagc    960
gcgatcccgt cgttttacaa cgtcgtgact gggaaaaccc tggcgttacc caacttaatc    1020
gccttgcagc acatccccct ttcgccagct ggcgtaatag cgaagaggcc cgcaccgatc    1080
gcccttccca acagttgcgc agcctgaatg gcgaatggcg ctttgcctgg tttccggcac    1140
cagaagcggt gccggaaagc tggctggagt gcgatcttcc tgaggccgat actgtcgtcg    1200
tccccctcaaa ctggcagatg cacgttacg atgcgcccat ctacaccaac gtaacctatc    1260
ccattacggt caatccgccg tttgttccca cggagaatcc gacgggttgt tactcgctca    1320
catttaatgt tgatgaaagc tggctacagg aaggccagac gcgaattatt tttgatggcg    1380
ttaactcggc gtttcatctg tggtgcaacg ggcgctgggt cggttacggc caggacagtc    1440
gtttgccgtc tgaatttgac ctgagcgcat ttttacgcgc cggagaaaac cgcctcgcgg    1500
tgatggtgct gcgttggagt gacggcagtt atctggaaga tcaggatatg tggcggatga    1560
gcggcatttt ccgtgacgtc tcgttgctgc ataaaccgac tacacaaatc agcgatttcc    1620
atgttgccac tcgctttaat gatgatttca gccgcgctgt actggaggct gaagttcaga    1680
tgtgcggcga gttgcgtgac tacctacggg taacagtttc tttatggcag ggtgaaacgc    1740
aggtcgccag cggcaccgcg cctttcggcg gtgaaattat cgatgagcgt ggtggttatg    1800
ccgatcgcgt cacactacgt ctgaacgtca aaaacccgaa actgtggagc gccgaaatcc    1860
cgaatctcta tcgtgcggtg gttgaactgc acaccgccga cggcacgctg attgaagcag    1920
aagcctgcga tgtcggtttc cgcgaggtgc ggattgaaaa tggtctgctg ctgctgaacg    1980
gcaagccgtt gctgattcga ggcgttaacc gtcacgagca tcatcctctg catggtcagg    2040
tcatggatga gcagacgatg gtgcaggata tcctgctgat gaagcagaac aactttaacg    2100
ccgtgcgctg ttcgcattat ccgaaccatc cgctgtggta cacgctgtgc gaccgctacg    2160
gcctgtatgt ggtggatgaa gccaatattg aaacccacgg catggtgcca atgaatcgtc    2220
tgaccgatga tccgcgctgg ctaccggcga tgagcgaacg cgtaacgcga atggtgcagc    2280
```

```
gcgatcgtaa tcacccgagt gtgatcatct ggtcgctggg gaatgaatca ggccacggcg    2340
ctaatcacga cgcgctgtat cgctggatca aatctgtcga tccttcccgc ccggtgcagt    2400
atgaaggcgg cggagccgac accacggcca ccgatattat ttgcccgatg tacgcgcgcg    2460
tggatgaaga ccagcccttc ccggctgtgc cgaaatggtc catcaaaaaa tggctttcgc    2520
tacctggaga gacgcgcccg ctgatccttt gcgaatacgc ccacgcgatg gtaacagtc     2580 ttggcggttt cgctaaatac tggcaggcgt ttcgtcagta tccccgttta cagggcggct    2640
tcgtctggga ctgggtggat cagtcgctga ttaaatatga tgaaaacggc aacccgtggt    2700
cggcttacgg cggtgatttt ggcgatacgc cgaacgatcg ccagttctgt atgaacggtc    2760
tggtctttgc cgaccgcacg ccgcatccag cgctgacgga agcaaaacac cagcagcagt    2820
ttttccagtt ccgtttatcc gggcaaacca tcgaagtgac cagcgaatac ctgttccgtc    2880
atagcgataa cgagctcctg cactggatgg tggcgctgga tggtaagccg ctggcaagcg    2940
gtgaagtgcc tctggatgtc gctccacaag gtaaacagtt gattgaactg cctgaactac    3000
cgcagccgga gagcgccggg caactctggc tcacagtacg cgtagtgcaa ccgaacgcga    3060
ccgcatggtc agaagccggg cacatcagcg cctggcagca gtggcgtctg gcggaaaacc    3120
tcagtgtgac gctccccgcc gcgtcccacg ccatcccgca tctgaccacc agcgaaatgg    3180
atttttgcat cgagctgggt aataagcgtt ggcaatttaa ccgccagtca ggctttcttt    3240
cacagatgtg gattggcgat aaaaaacaac tgctgacgcc gctgcgcgat cagttcaccc    3300
gtgcaccgct ggataacgac attggcgtaa gtgaagcgac ccgcattgac cctaacgcct    3360
gggtcgaacg ctgaaggcg gcgggccatt accaggccga agcagcgttg ttgcagtgca    3420
cggcagatac acttgctgat gcggtgctga ttacgaccgc tcacgcgtgg cagcatcagg    3480
ggaaaacctt atttatcagc cggaaaacct accggattga tggtagtggt caaatggcga    3540
ttaccgttga tgttgaagtg gcgagcgata caccgcatcc ggcgcggatt ggcctgaact    3600
gccagctggc gcaggtagca gagcgggtaa actggctcgg attagggccg caagaaaact    3660
atcccgaccg ccttactgcc gcctgttttg accgctggga tctgccattg tcagacatgt    3720
ataccccgta cgtcttcccg agcgaaaacg gtctgcgctg cgggacgcgc gaattgaatt    3780
atggcccaca ccagtggcgc ggcgacttcc agttcaacat cagccgctac agtcaacagc    3840
aactgatgga aaccagccat cgccatctgc tgcacgcgga agaaggcaca tggctgaata    3900
tcgacggttt ccatatgggg attggtggcg acgactcctg gagcccgtca gtatcggcgg    3960
aattacagct gagcgccggt cgctaccatt accagttggt ctggtgtcaa aaataataat    4020
aaccgggcag gccatgtctg cccgtatttc gcgtaaggaa atccattatg tactatttaa    4080
aaaacacaaa cttttggatg ttcggtttat tcttttcctt ttactttttt atcatgggag    4140
cctacttccc gttttcccg atttggctac atgacatcaa ccatatcagc aaaagtgata    4200
cgggtattat ttttgccgct atttctctgt tctcgctatt attccaaccg ctgtttggtc    4260
tgctttctga caaactcggc ctcgactcta ggcggccgcg gggatccaga catgataaga    4320
tacattgatg agtttggaca aaccacaact agaatgcagt gaaaaaaatg ctttatttgt    4380
gaaatttgtg atgctattgc tttatttgta accattataa gctgcaataa acaagttaac    4440
aacaacaatt gcattcattt tatgtttcag gttcaggggg aggtgtggga ggttttttcg    4500
gatcctctag agtcgacctg caggcatgca agcttggcgt aatcatggtc atagctgttt    4560
cctgtgtgaa attgttatcc gctcacaatt ccacacaaca tacgagccgg aagcataaag    4620
```

```
tgtaaagcct ggggtgccta atgagtgagc taactcacat taattgcgtt gcgctcactg    4680
cccgctttcc agtcgggaaa cctgtcgtgc cagctgcatt aatgaatcgg ccaacgcgcg    4740
gggagaggcg gtttgcgtat tgggcgctct tccgcttcct cgctcactga ctcgctgcgc    4800
tcggtcgttc ggctgcggcg agcggtatca gctcactcaa aggcggtaat acggttatcc    4860
acagaatcag gggataacgc aggaaagaac atgtgagcaa aaggccagca aaaggccagg    4920
aaccgtaaaa aggccgcgtt gctggcgttt ttccataggc tccgcccccc tgacgagcat    4980
cacaaaaatc gacgctcaag tcagaggtgg cgaaacccga caggactata agataccag    5040
gcgtttcccc ctggaagctc cctcgtgcgc tctcctgttc cgaccctgcc gcttaccgga    5100
tacctgtccg cctttctccc ttcgggaagc gtggcgcttt ctcatagctc acgctgtagg    5160
tatctcagtt cggtgtaggt cgttcgctcc aagctgggct gtgtgcacga accccccgtt    5220
cagcccgacc gctgcgcctt atccggtaac tatcgtcttg agtccaaccc ggtaagacac    5280
gacttatcgc cactggcagc agccactggt aacaggatta gcagagcgag gtatgtaggc    5340
ggtgctacag agttcttgaa gtggtggcct aactacggct acactagaag gacagtattt    5400
ggtatctgcg ctctgctgaa gccagttacc ttcggaaaaa gagttggtag ctcttgatcc    5460
ggcaaacaaa ccaccgctgg tagcggtggt ttttttgttt gcaagcagca gattacgcgc    5520
agaaaaaaag gatctcaaga agatcctttg atcttttcta cggggtctga cgctcagtgg    5580
aacgaaaact cacgttaagg gattttggtc atgagattat caaaaaggat cttcacctag    5640
atccttttaa attaaaaatg aagttttaaa tcaatctaaa gtatatatga gtaaacttgg    5700
tctgacagtt accaatgctt aatcagtgag gcacctatct cagcgatctg tctatttcgt    5760
tcatccatag ttgcctgact ccccgtcgtg tagataacta cgatacggga gggcttacca    5820
tctggcccca gtgctgcaat gataccgcga gacccacgct caccggctcc agatttatca    5880
gcaataaacc agccagccgg aagggccgag cgcagaagtg gtcctgcaac tttatccgcc    5940
tccatccagt ctattaattg ttgccgggaa gctagagtaa gtagttcgcc agttaatagt    6000
ttgcgcaacg ttgttgccat tgctacaggc atcgtggtgt cacgctcgtc gtttggtatg    6060
gcttcattca gctccggttc ccaacgatca aggcgagtta catgatcccc catgttgtgc    6120
aaaaaagcgg ttagctcctt cggtcctccg atcgttgtca gaagtaagtt ggccgcagtg    6180
ttatcactca tggttatggc agcactgcat aattctctta ctgtcatgcc atccgtaaga    6240
tgcttttctg tgactggtga gtactcaacc aagtcattct gagaatagtg tatgcggcga    6300
ccgagttgct cttgcccggc gtcaatacgg gataataccg cgccacatag cagaacttta    6360
aaagtgctca tcattggaaa acgttcttcg ggcgaaaac tctcaaggat cttaccgctg    6420
ttgagatcca gttcgatgta acccactcgt gcacccaact gatcttcagc atcttttact    6480
ttcaccagcg tttctgggtg agcaaaaaca ggaaggcaaa atgccgcaaa aaagggaata    6540
agggcgacac ggaaatgttg aatactcata ctcttccttt ttcaatatta ttgaagcatt    6600
tatcagggtt attgtctcat gagcggatac atatttgaat gtatttagaa aaataaacaa    6660
ataggggttc cgcgcacatt tccccgaaaa gtgccacctg acgtctaaga aaccattatt    6720
atcatgacat taacctataa aaataggcgt atcacgaggc cctttcgtct cgcgcgtttc    6780
ggtgatgacg gtgaaaacct ctgacacatg cagctcccgg agacggtcac agcttgtctg    6840
taagcggatg ccgggagcag acaagcccgt cagggcgcgt cagcgggtgt tggcgggtgt    6900
cggggctggc ttaactatgc ggcatcagag cagattgtac tgagagtgca ccatatgcgg    6960
tgtgaaatac cgcacagatg cgtaaggaga aaataccgca tcaggcgcca ttcgccattc    7020
```

```
aggctgcgca actgttggga agggcgatcg gtgcgggcct cttcgctatt acgccagctg    7080
gcgaaagggg gatgtgctgc aaggcgatta agttgggtaa cgccagggtt ttcccagtca    7140
cgacgttgta aaacgacggc cagt                                           7164
```

<210> SEQ ID NO 52
<211> LENGTH: 7867
<212> TYPE: DNA
<213> ORGANISM: Artificial sequence
<220> FEATURE:
<223> OTHER INFORMATION: pCAG-TalRab2-Clo051

<400> SEQUENCE: 52

```
ggcgcgccgg attcgacatt gattattgac tagttattaa tagtaatcaa ttacggggtc      60
attagttcat agcccatata tggagttccg cgttacataa cttacggtaa atggcccgcc     120
tggctgaccg cccaacgacc cccgcccatt gacgtcaata atgacgtatg ttcccatagt     180
aacgccaata gggactttcc attgacgtca atgggtggag tatttacggt aaactgccca     240
cttggcagta catcaagtgt atcatatgcc aagtacgccc cctattgacg tcaatgacgg     300
taaatggccc gcctggcatt atgcccagta catgacctta tgggactttc ctacttggca     360
gtacatctac gtattagtca tcgctattac catggtcgag gtgagcccca cgttctgctt     420
cactctcccc atctccccc  cctccccacc cccaattttg tatttattta ttttttaatt     480
attttgtgca gcgatggggg cggggggggg gggggggcgc gcgccaggcg gggcggggcg     540
gggcgagggg cggggcgggg cgaggcggag aggtgcggcg gcagccaatc agagcggcgc     600
gctccgaaag tttccttttt atggcgaggcg gcggcggcg  cggccctata aaaagcgaag     660
cgcgcggcgg gcgggagtcg ctgcgcgctg ccttcgcccc gtgccccgct ccgccgccgc     720
ctcgcgccgc ccgccccggc tctgactgac cgcgttactc ccacaggtga gcgggcggga     780
cggcccttct cctccgggct gtaattagcg cttggtttaa tgacggcttg tttcttttct     840
gtggctgcgt gaaagccttg agggcgctccg ggagggccct ttgtgcgggg gggagcggct     900
cggggggtgc gtgcgtgtgt gtgtgcgtgg ggagcgccgc gtgcggctcc gcgctgcccg     960
gcggctgtga gcgctgcggg cgcggcgcgg ggctttgtgc gctccgcagt gtgcgcgagg    1020
ggagcgcggc cggggcggt  gccccgcggt gcgggggggg ctgcgagggg aacaaaggct    1080
gcgtgcgggg tgtgtgcgtg ggggggtgag caggggggtgt gggcgcgtcg gtcgggctgc    1140
aaccccccct gcaccccccct ccccgagttg ctgagcacgg cccggcttcg ggtgcggggc    1200
tccgtacggg gcgtggcgcg gggctcgccg tgccggggcgg ggggtggcgg caggtggggg    1260
tgccgggcgg ggcggggccg cctcgggccg gggagggctc ggggagggg  cgcggcggcc    1320 cccggagcgc cggcggctgt cgaggcgcgg cgagccgcag ccattgcctt ttatggtaat    1380
cgtgcgagag ggcgcaggga cttcctttgt cccaaatctg tgcggagccg aaatctggga    1440
ggcgccgccg caccccctct agcgggcgcg ggcgaagcg  gtgcggcgcc ggcaggaagg    1500
aaatgggcgg gagggccctt cgtgcgtcgc cgcgccgccg tccccttctc cctctccagc    1560
ctcggggctg tccgcggggg gacggctgcc ttcgggggg  acgggcagg gcggggttcg    1620 gcttctggcg tgtgaccggc ggctctagag cctctgctaa ccatgttcat gccttcttct    1680
ttttcctaca gatccttaat taataatacg actcactata ggggccgcca ccatgggacc    1740
taagaaaaag aggaaggtgg cggccgctga ctacaaggat gacgacgata aaccaggtgg    1800
cggaggtagt ggcggaggtg gggtacccgc cagtccagca gcccaggtgg atctgagaac    1860
```

```
cctcggctac agccagcagc agcaggagaa gatcaaacca aaggtgcggt ccaccgtcgc   1920
tcagcaccat gaagcactgg tggggcacgg tttcacacac gcccatattg tggctctgtc   1980
tcagcatccc gctgcactcg ggactgtggc cgtcaaatat caggacatga tcgccgctct   2040
gcctgaggca acccacgaag ccattgtggg cgtcggaaag cagtggagcg gtgccagagc   2100
actcgaagca ctcctcaccg tcgccgggga actgcggggt ccaccactcc agtccggact   2160
ggacactgga cagctgctga agatcgctaa acgcggcgga gtgacagctg tggaagctgt   2220
gcacgcttgg aggaatgctc tgacaggagc cccactgaat ctgacacccc agcaggtggt   2280
ggccattgct agcaacaatg ggggcaagca ggctctggag acagtgcagc gcctgctgcc   2340
tgtgctgtgc caggctcacg gactgactcc acagcaggtg gtggccatcg cttccaacaa   2400
tggagggaaa caggctctgg aaacagtgca gaggctgctg cccgtgctgt gccaggctca   2460
tggactgaca cctcagcagg tcgtcgccat tgcttctaac ggcggaggga agcaggctct   2520
ggagactgtg cagagactgc tgccagtgct gtgccaggcc catggactga cccctcagca   2580
ggtcgtggct atcgctagta acaatggcgg aaaacaggct ctggaaactg tgcagcggct   2640
gctccccgtg ctgtgccagg cccacggcct cactccacag caggtcgtcg ctatcgcctc   2700
taataacggg gcaagcagg ctctggagac agtacagcg ctgttacccg tgctgtgcca   2760
ggcacacggc ctcacacctc agcaggtcgt ggcaatcgct tcccatgacg agggaaaca   2820
ggctctggaa acggtccaga ggctgctccc cgtgctgtgc caagctcacg gcctcacccc   2880
tcagcaggtg gtcgctattg cttctcatga tggcggaaag caggctctgg agaccgtgca   2940
gagactgctc cctgtgctgt gccaagccca cggcctgact ccacagcagg tcgtggccat   3000
cgctagtcat gacggggca aacaggctct ggaaacagta cagcggctgt acccgtgct   3060
gtgccaagcc catggcctca cacctcagca agtcgtcgct atcgctagca acaatggagg   3120
gaagcaggct ctggagacgg tgcagcgcct gctcccagtg ctgtgccaag ctcatggcct   3180
caccccctcag caagtcgtcg caattgcttc caataacggc ggaaaacagg ctctggaaac   3240
cgtccagagg ctgctgcccg tgctgtgcca agcacatggc ttaactccac agcaagtggt   3300
ggccattgct tctaatgggg gcggaaagca ggccctggag acagtccaga gactgttgcc   3360
cgtgctgtgc caagcgcatg gactgacacc tgaacaggtc gtcgctatcg ctagtaatat   3420
tgggggcaaa caggccctgg aaacagtgca gcggctgctt cccgtgctgt gccaggcgca   3480
tggactcaca ccccagcagg tcgtcgcaat cgcctctaat aacggaggga agcaggccct   3540
ggaaaccgtg cagagactgt acctgtgct gtgccaggca catggtctga caccacagca   3600
ggtggtcgca attgctagca atggcggagg gaagcaggcc ctggagactg tccagagact   3660
gctacccgtg ctgtgccaag cgcacggcct gaccccacag caggtcgtcg ctattgcttc   3720
taatggcgga gggcggcctg ctctggagag cattgtggct cagctgtcca ggcccgatcc   3780
tgccctggct agatccgcac tcactaacga tcatctggtc gctctcgctt gcctcggtgg   3840
acggcccgct ctgacgcag tcaaaaaggg tctcccccat gctcccgcac tgatcaagag   3900
aaccaacagg agaattcctg agggatccga tcgtttaaac gaaggcatca aaagcaacat   3960
ctccctcctg aaagacgaac tccgggggca gattagccac attagtcacg aatacctctc   4020
cctcatcgac ctggctttcg atagcaagca gaacaggctc tttgagatga agtgctgga   4080
actgctcgtc aatgagtacg ggttcaaggg tcgacacctc ggcggatcta ggaaaccaga   4140
cggcatcgtg tatagtacca cactggaaga caactttggg atcattgtgg ataccaaggc   4200
atactctgag ggttatagtc tgcccatttc acaggccgac gagatggaac ggtacgtgcg   4260
```

```
cgagaactca aatagagatg aggaagtcaa ccctaacaag tggtgggaga acttctctga    4320
ggaagtgaag aaatactact tcgtctttat cagcgggtcc ttcaagggta aatttgagga    4380
acagctcagg agactgagca tgactaccgg cgtgaatggc agcgccgtca acgtggtcaa    4440
tctgctcctg ggcgctgaaa agattcggag cggagagatg accatcgaag agctggagag    4500
ggcaatgttt aataatagcg agtttatcct gaaatactga acgcgtaaat gattgcagat    4560
ccactagttc tagaattcca gctgagcgcc ggtcgctacc attaccagtt ggtctggtgt    4620
caaaaataat aataaccggg caggggggat ctgcatggat cttttgtgaag gaaccttact   4680
tctgtggtgt gacataattg acaaactac ctacagagat ttaaagctct aaggtaaata    4740
taaaatttt aagtgtataa tgtgttaaac tactgattct aattgtttgt gtattttaga    4800
ttccaaccta tggaactgat gaatgggagc agtggtggaa tgccagatcc agacatgata    4860
agatacattg atgagtttgg acaaaccaca actagaatgc agtgaaaaaa atgctttatt    4920
tgtgaaattt gtgatgctat tgctttattt gtaaccatta taagctgcaa taaacaagtt    4980
aacaacaaca attgcattca ttttatgttt caggttcagg gggaggtgtg ggaggttttt    5040
taaagcaagt aaaacctcta caaatgtggt atggctgatt atgatctgcg ccgccactg    5100
gccgtcgttt tacaacgtcg tgactgggaa accctggcg ttacccaact taatcgcctt    5160
gcagcacatc ccccttttcgc cagctggcgt aatagcgaag aggcccgcac cgatcgccct    5220
tcccaacagt tgcgcagcct gaatggcgaa tggaacgcgc cctgtagcgg cgcattaagc    5280
gcggcgggtg tggtggttac gcgcagcgtg accgctacac ttgccagcgc cctagcgccc    5340
gctcctttcg ctttcttccc ttcctttctc gccacgttcg ccggctttcc ccgtcaagct    5400
ctaaatcggg ggctcccttt agggttccga tttagtgctt tacggcacct cgaccccaaa    5460
aaacttgatt agggtgatgg ttcacgtagt gggccatcgc cctgatagac ggtttttcgc    5520
cctttgacgt tggagtccac gttctttaat agtggactct tgttccaaac tggaacaaca    5580
ctcaaccta tctcggtcta ttctttgat ttataaggga ttttgccgat ttcggcctat    5640
tggttaaaaa atgagctgat ttaacaaaaa tttaacgcga attttaacaa aatattaacg    5700
cttacaattt aggtggcact tttcggggaa atgtgcgcgg aaccctatt tgtttatttt    5760
tctaaataca ttcaaatatg tatccgctca tgagacaata accctgataa atgcttcaat    5820
aatattgaaa aaggaagagt atgagtattc aacatttccg tgtcgccctt attccctttt    5880
ttgcggcatt ttgccttcct gttttgctc acccagaaac gctggtgaaa gtaaaagatg    5940
ctgaagatca gttgggtgca cgagtgggtt acatcgaact ggatctcaac agcggtaaga    6000
tccttgagag ttttcgcccc gaagaacgtt ttccaatgat gagcactttt aaagttctgc    6060
tatgtggcgc ggtattatcc cgtattgacg ccgggcaaga gcaactcggt cgccgcatac    6120
actattctca gaatgacttg gttgagtact caccagtcac agaaaagcat cttacggatg    6180
gcatgacagt aagagaatta tgcagtgctg ccataaccat gagtgataac actgcggcca    6240
acttacttct gacaacgatc ggaggaccga aggagctaac cgcttttttg cacaacatgg    6300
gggatcatgt aactcgcctt gatcgttggg aaccggagct gaatgaagcc ataccaaacg    6360
acgagcgtga caccacgatg cctgtagcaa tggcaacaac gttgcgcaaa ctattaactg    6420
gcgaactact tactctagct tcccggcaac aattaataga ctggatggag gcggataaag    6480
ttgcaggacc acttctgcgc tcggcccttc cggctggctg gtttattgct gataaatctg    6540
gagccggtga gcgtgggtct cgcggtatca ttgcagcact ggggccagat ggtaagccct    6600
```

-continued

```
cccgtatcgt agttatctac acgacgggga gtcaggcaac tatggatgaa cgaaatagac     6660
agatcgctga gataggtgcc tcactgatta agcattggta actgtcagac caagtttact     6720
catatatact ttagattgat ttaaaacttc atttttaatt taaaaggatc taggtgaaga     6780
tcctttttga taatctcatg accaaaatcc cttaacgtga gttttcgttc cactgagcgt     6840
cagaccccgt agaaaagatc aaaggatctt cttgagatcc ttttttttctg cgcgtaatct     6900
gctgcttgca acaaaaaaa ccaccgctac cagcggtggt ttgtttgccg gatcaagagc     6960
taccaactct tttttccgaag gtaactggct tcagcagagc gcagatacca atactgtcc      7020
ttctagtgta gccgtagtta ggccaccact tcaagaactc tgtagcaccg cctacatacc     7080
tcgctctgct aatcctgtta ccagtggctg ctgccagtgg cgataagtcg tgtcttaccg     7140
ggttggactc aagacgatag ttaccggata aggcgcagcg gtcgggctga acggggggtt     7200
cgtgcacaca gcccagcttg gagcgaacga cctacaccga actgagatac ctacagcgtg     7260
agctatgaga aagcgccacg cttcccgaag ggagaaaggc ggacaggtat ccggtaagcg     7320
gcagggtcgg aacaggagag cgcacgaggg agcttccagg gggaaacgcc tggtatcttt     7380
atagtcctgt cgggtttcgc cacctctgac ttgagcgtcg atttttgtga tgctcgtcag     7440
gggggcggag cctatggaaa aacgccagca acgcggcctt tttacggttc ctggccttt      7500
gctggccttt tgctcacatg ttctttcctg cgttatcccc tgattctgtg gataaccgta     7560
ttaccgcctt tgagtgagct gataccgctc gccgcagccg aacgaccgag cgcagcgagt     7620
cagtgagcga ggaagcggaa gagcgcccaa tacgcaaacc gcctctcccc gcgcgttggc     7680
cgattcatta atgcagctgg cacgacaggt ttcccgactg gaaagcgggc agtgagcgca     7740
acgcaattaa tgtgagttag ctcactcatt aggcacccca ggctttacac tttatgcttc     7800
cggctcgtat gttgtgtgga attgtgagcg gataacaatt tcacacagga aacagctatg     7860
accatga                                                             7867
```

<210> SEQ ID NO 53
<211> LENGTH: 935
<212> TYPE: PRT
<213> ORGANISM: Artificial sequence
<220> FEATURE:
<223> OTHER INFORMATION: TalRab2-Clo051

<400> SEQUENCE: 53

```
Met Gly Pro Lys Lys Arg Lys Val Ala Ala Asp Tyr Lys Asp
1               5                   10                  15

Asp Asp Asp Lys Pro Gly Gly Gly Ser Gly Gly Gly Val Pro
                20                  25                  30

Ala Ser Pro Ala Ala Gln Val Asp Leu Arg Thr Leu Gly Tyr Ser Gln
            35                  40                  45

Gln Gln Gln Glu Lys Ile Lys Pro Lys Val Arg Ser Thr Val Ala Gln
        50                  55                  60

His His Glu Ala Leu Val Gly His Gly Phe Thr His Ala His Ile Val
65                  70                  75                  80

Ala Leu Ser Gln His Pro Ala Ala Leu Gly Thr Val Ala Val Lys Tyr
                85                  90                  95

Gln Asp Met Ile Ala Ala Leu Pro Glu Ala Thr His Glu Ala Ile Val
            100                 105                 110

Gly Val Gly Lys Gln Trp Ser Gly Ala Arg Ala Leu Glu Ala Leu Leu
        115                 120                 125

Thr Val Ala Gly Glu Leu Arg Gly Pro Pro Leu Gln Ser Gly Leu Asp
```

-continued

```
            130                 135                 140
Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Gln Gln Val Val Ala Ile Ala Ser Asn Asn Gly Gly Lys
                180                 185                 190

Gln Ala Leu Glu Thr Val Gln Arg Leu Leu Pro Val Leu Cys Gln Ala
                195                 200                 205

His Gly Leu Thr Pro Gln Gln Val Val Ala Ile Ala Ser Asn Asn Gly
210                 215                 220

Gly Lys Gln Ala Leu Glu Thr Val Gln Arg Leu Leu Pro Val Leu Cys
225                 230                 235                 240

Gln Ala His Gly Leu Thr Pro Gln Gln Val Val Ala Ile Ala Ser Asn
                245                 250                 255

Gly Gly Lys Gln Ala Leu Glu Thr Val Gln Arg Leu Leu Pro Val
                260                 265                 270

Leu Cys Gln Ala His Gly Leu Thr Pro Gln Gln Val Val Ala Ile Ala
                275                 280                 285

Ser Asn Asn Gly Gly Lys Gln Ala Leu Glu Thr Val Gln Arg Leu Leu
                290                 295                 300

Pro Val Leu Cys Gln Ala His Gly Leu Thr Pro Gln Gln Val Val Ala
305                 310                 315                 320

Ile Ala Ser Asn Asn Gly Gly Lys Gln Ala Leu Glu Thr Val Gln Arg
                325                 330                 335

Leu Leu Pro Val Leu Cys Gln Ala His Gly Leu Thr Pro Gln Gln Val
                340                 345                 350

Val Ala Ile Ala Ser His Asp Gly Gly Lys Gln Ala Leu Glu Thr Val
                355                 360                 365

Gln Arg Leu Leu Pro Val Leu Cys Gln Ala His Gly Leu Thr Pro Gln
                370                 375                 380

Gln Val Val Ala Ile Ala Ser His Asp Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Gln Gln Val Val Ala Ile Ala Ser His Asp Gly Gly Lys Gln Ala
                420                 425                 430

Leu Glu Thr Val Gln Arg Leu Leu Pro Val Leu Cys Gln Ala His Gly
                435                 440                 445

Leu Thr Pro Gln Gln Val Val Ala Ile Ala Ser Asn Asn Gly Gly Lys
                450                 455                 460

Gln Ala Leu Glu Thr Val Gln Arg Leu Leu Pro Val Leu Cys Gln Ala
465                 470                 475                 480

His Gly Leu Thr Pro Gln Gln Val Val Ala Ile Ala Ser Asn Asn Gly
                485                 490                 495

Gly Lys Gln Ala Leu Glu Thr Val Gln Arg Leu Leu Pro Val Leu Cys
                500                 505                 510

Gln Ala His Gly Leu Thr Pro Gln Gln Val Val Ala Ile Ala Ser Asn
                515                 520                 525

Gly Gly Gly Lys Gln Ala Leu Glu Thr Val Gln Arg Leu Leu Pro Val
                530                 535                 540

Leu Cys Gln Ala His Gly Leu Thr Pro Glu Gln Val Val Ala Ile Ala
545                 550                 555                 560
```

Ser Asn Ile Gly Gly Lys Gln Ala Leu Glu Thr Val Gln Arg Leu Leu
             565                 570                 575

Pro Val Leu Cys Gln Ala His Gly Leu Thr Pro Gln Gln Val Val Ala
         580                 585                 590

Ile Ala Ser Asn Asn Gly Gly Lys Gln Ala Leu Glu Thr Val Gln Arg
         595                 600                 605

Leu Leu Pro Val Leu Cys Gln Ala His Gly Leu Thr Pro Gln Gln Val
     610                 615                 620

Val Ala Ile Ala Ser Asn Gly Gly Lys Gln Ala Leu Glu Thr Val
625                 630                 635                 640

Gln Arg Leu Leu Pro Val Leu Cys Gln Ala His Gly Leu Thr Pro Gln
                 645                 650                 655

Gln Val Val Ala Ile Ala Ser Asn Gly Gly Arg Pro Ala Leu Glu
             660                 665                 670

Ser Ile Val Ala Gln Leu Ser Arg Pro Asp Pro Ala Leu Ala Arg Ser
             675                 680                 685

Ala Leu Thr Asn Asp His Leu Val Ala Leu Ala Cys Leu Gly Gly Arg
         690                 695                 700

Pro Ala Leu Asp Ala Val Lys Lys Gly Leu Pro His Ala Pro Ala Leu
705                 710                 715                 720

Ile Lys Arg Thr Asn Arg Arg Ile Pro Glu Gly Ser Asp Arg Leu Asn
                 725                 730                 735

Glu Gly Ile Lys Ser Asn Ile Ser Leu Leu Lys Asp Glu Leu Arg Gly
             740                 745                 750

Gln Ile Ser His Ile Ser His Glu Tyr Leu Ser Leu Ile Asp Leu Ala
         755                 760                 765

Phe Asp Ser Lys Gln Asn Arg Leu Phe Glu Met Lys Val Leu Glu Leu
     770                 775                 780

Leu Val Asn Glu Tyr Gly Phe Lys Gly Arg His Leu Gly Gly Ser Arg
785                 790                 795                 800

Lys Pro Asp Gly Ile Val Tyr Ser Thr Thr Leu Glu Asp Asn Phe Gly
                 805                 810                 815

Ile Ile Val Asp Thr Lys Ala Tyr Ser Glu Gly Tyr Ser Leu Pro Ile
             820                 825                 830

Ser Gln Ala Asp Glu Met Glu Arg Tyr Val Arg Glu Asn Ser Asn Arg
         835                 840                 845

Asp Glu Glu Val Asn Pro Asn Lys Trp Trp Glu Asn Phe Ser Glu Glu
     850                 855                 860

Val Lys Lys Tyr Tyr Phe Val Phe Ile Ser Gly Ser Phe Lys Gly Lys
865                 870                 875                 880

Phe Glu Glu Gln Leu Arg Arg Leu Ser Met Thr Thr Gly Val Asn Gly
                 885                 890                 895

Ser Ala Val Asn Val Val Asn Leu Leu Leu Gly Ala Glu Lys Ile Arg
             900                 905                 910

Ser Gly Glu Met Thr Ile Glu Glu Leu Glu Arg Ala Met Phe Asn Asn
         915                 920                 925

Ser Glu Phe Ile Leu Lys Tyr
     930                 935

<210> SEQ ID NO 54
<211> LENGTH: 7867
<212> TYPE: DNA
<213> ORGANISM: Artificial sequence
<220> FEATURE:

<223> OTHER INFORMATION: pCAG-RabChtTal1-Clo051

<400> SEQUENCE: 54

```
ggcgcgccgg attcgacatt gattattgac tagttattaa tagtaatcaa ttacggggtc      60
attagttcat agcccatata tggagttccg cgttacataa cttacggtaa atggcccgcc     120
tggctgaccg cccaacgacc cccgcccatt gacgtcaata atgacgtatg ttcccatagt     180
aacgccaata gggactttcc attgacgtca atgggtggag tatttacggt aaactgccca     240
cttggcagta catcaagtgt atcatatgcc aagtacgccc cctattgacg tcaatgacgg     300
taaatggccc gcctggcatt atgcccagta catgacctta tgggactttc ctacttggca     360
gtacatctac gtattagtca tcgctattac catggtcgag gtgagcccca cgttctgctt     420
cactctcccc atctcccccc cctccccacc cccaattttg tatttattta ttttttaatt     480
attttgtgca gcgatggggg cggggggggg ggggggcgc gcgccaggcg gggcggggcg      540
gggcgagggg cggggcgggg cgaggcgag aggtgcggcg gcagccaatc agagcggcgc      600
gctccgaaag tttcctttta tggcgaggcg gcggcggcgg cggccctata aaaagcgaag     660
cgcgcggcgg gcgggagtcg ctgcgcgctg ccttcgcccc gtgccccgct ccgccgccgc     720
ctcgcgccgc ccgcccggc tctgactgac gcgttactc ccacaggtga gcgggcggga      780
cggccctcct cctccgggct gtaattagcg cttggtttaa tgacggcttg tttcttttct     840
gtggctgcgt gaaagccttg aggggctccg ggagggccct ttgtgcgggg gggagcggct     900
cgggggtgc gtgcgtgtgt gtgtgcgtgg ggagcgccgc gtgcggctcc gcgctgcccg     960
gcggctgtga gcgctgcggg cgcggcgcgg ggctttgtgc gctccgcagt gtgcgcgagg    1020
ggagcgcggc cggggcggt gccccgcggt gcgggggggg ctgcgagggg aacaaaggct    1080
gcgtgcgggg tgtgtgcgtg gggggtgag caggggtgt gggcgcgtcg gtcgggctgc     1140
aaccccccct gcacccccct ccccgagttg ctgagcacgg cccggcttcg ggtgcgggc     1200
tccgtacggg gcgtggcgcg gggctcgccc tgccggcgg ggggtggcgg caggtggggg    1260
tgccgggcgg ggcggggccg cctcgggccg gggagggctc ggggagggg cgcggcggcc     1320
cccgagcgc cggcggctgt cgaggcgcgg cgagccgcag ccattgcctt ttatggtaat    1380
cgtgcgagag ggcgcaggga cttcctttgt cccaaatctg tgcggagccg aaatctggga    1440
ggcgccgccg caccccctct agcgggcgcg ggcgaagcg gtgcggcgcc ggcaggaagg    1500
aaatgggcgg ggagggcctt cgtgcgtcgc cgcgccgccg tccccttctc cctctccagc    1560
ctcggggctg tccgcggggg gacggctgcc ttcgggggg acgggcagg gcggggttcg     1620
gcttctggcg tgtgaccggc ggctctagag cctctgctaa ccatgttcat gccttcttct    1680
ttttcctaca gatccttaat taataatacg actcactata ggggccgcca ccatgggacc    1740
taagaaaaag aggaaggtgg cggccgctga ctacaaggat gacgacgata aaccaggtgg    1800
cggaggtagt ggcggaggtg gggtaccgc cagtccagca gcccaggtgg atctgagaac    1860
cctcggctac agccagcagc agcaggagaa gatcaaacca aaggtgcggt ccaccgtcgc    1920
tcagcaccat gaagcactgg tggggcacgg tttcacacac gcccatattg tggctctgtc    1980
tcagcatccc gctgcactcg ggactgtggc cgtcaaatat caggacatga tcgccgctct    2040
gcctgaggca acccacgaag ccattgtggg cgtcggaaag cagtggagcg gtgccagagc    2100
actcgaagca ctcctcaccg tcgccgggga actgcggggt ccaccactcc agtccggact    2160
ggacactgga cagctgctga agatcgctaa acgcggcgga gtgacagctg tggaagctgt    2220
gcacgcttgg aggaatgctc tgacaggagc cccactgaat cttacacccg aacaggtggt    2280
```

```
ggccatcgct agtaacattg ggggcaaaca ggctctggaa acagtacagc ggctgttacc    2340
tgtgctgtgc caggctcatg gcctcacacc tcagcaggtc gtcgcaatcg cctccaatgg    2400
cggagggaag caggccctgg aaacggtgca gagactgtta ccagtgctgt gccaggccca    2460
tggcctaaca ccccagcagg tggtggccat cgccagccac gacggcggca agcaggccct    2520
ggaaaccgtg cagaggctgc tgcctgtgct gtgccaggct catggcctga cacctgagca    2580
ggtcgtcgcc atcgccagca acatcggcgg caagcaggcc ctggaaaccg tgcagaggct    2640
gctgccagtg ctgtgccagg cccatggctt aacacccgaa caggtggtgg ccatcgcttc    2700
taatattggg ggcaagcagg ccctggaaac agtccagaga ctgttgcctg tgctgtgcca    2760
ggctcatggc ttgacacctc agcaggtcgt cgctatcgcc tctaataagg ggggcaagca    2820
ggctctggag acagtacagc gcctgttacc agtgctgtgc caggcccacg gctcacacc    2880 ccagcaggtg gtggcaatcg cttcccatga cggagggaaa caggctctgg aaacggtcca    2940
gaggctgctc cctgtgctgt gccaggctca cggtctaaca ccccagcagg tggtggccat    3000
tgctagcaac aatgggggca agcaggctct ggagacagtg cagcgcctgc tgcctgtgct    3060
gtgccaggct catggcctca cacctcagca ggtcgtcgcc atcgccagcc acgacggcgg    3120
caagcaggcc ctggaaaccg tgcagaggct gctgccagtg ctgtgccagg cccatggcct    3180
aacaccccag caggtggtgg caatcgcctc aatggcgga gggaagcagg ccctggaaac    3240
ggtgcagaga ctgttacctg tgctgtgcca ggctcatggc ctgacacctg agcaggtcgt    3300
cgctatcgct agcaatatcg gagggaagca ggctctggaa actgtccagc gcctgctccc    3360
agtgctgtgc caggcccatg gcttaacacc ccagcaggtg gtggcaattg ctagcaatgg    3420
cggagggaag caggccctgg agactgtcca gagactgcta cctgtgctgt gccaggctca    3480
tggcttgaca cctcagcagg tcgtcgctat cgcctctaat aagggggca agcaggctct    3540 ggagacagta cagcgcctgt taccagtgct gtgccaggcc cacgggctca cccccagca    3600 ggtggtggcc atcgccagca acggcggcgg caagcaggcc ctggaaaccg tgcagaggct    3660
gctgcctgtg ctgtgccagg ctcacggcct gaccccacag caggtcgtcg ctattgcttc    3720
taatggcgga gggcggcctg ctctggagag cattgtggct cagctgtcca ggcccgatcc    3780
tgccctggct agatccgcac tcactaacga tcatctggtc gctctcgctt gcctcgtgg    3840 acggcccgct ctggacgcag tcaaaaaggg tctcccccat gctcccgcac tgatcaagag    3900
aaccaacagg agaattcctg agggatccga tcgtttaaac gaaggcatca aaagcaacat    3960
ctccctcctg aaagacgaac tccggggca gattagccac attagtcacg aatacctctc    4020
cctcatcgac ctggctttcg atagcaagca gaacaggctc tttgagatga agtgctgga    4080 actgctcgtc aatgagtacg ggttcaaggg tcgacacctc gcggatcta ggaaaccaga    4140 cggcatcgtg tatagtacca cactggaaga caactttggg atcattgtgg ataccaaggc    4200
atactctgag ggttatagtc tgcccatttc acaggccgac gagatggaac ggtacgtgcg    4260
cgagaactca aatagagatg aggaagtcaa ccctaacaag tggtgggaga acttctctga    4320
ggaagtgaag aaatactact tcgtctttat cagcgggtcc ttcaagggta aatttgagga    4380
acagctcagg agactgagca tgactaccgg cgtgaatggc agcgccgtca acgtggtcaa    4440
tctgctcctg ggcgctgaaa agattcggag cggagagatg accatcgaag agctggagag    4500
ggcaatgttt aataatagcg agtttatcct gaaaatactga acgcgtaaat gattgcagat    4560
ccactagttc tagaattcca gctgagcgcc ggtcgctacc attaccagtt ggtctggtgt    4620
```

```
caaaaataat aataaccggg caggggggat ctgcatggat ctttgtgaag gaaccttact   4680
tctgtggtgt gacataattg gacaaactac ctacagagat ttaaagctct aaggtaaata   4740 taaaatttt  aagtgtataa tgtgttaaac tactgattct aattgtttgt gtattttaga   4800
ttccaaccta tggaactgat gaatgggagc agtggtggaa tgccagatcc agacatgata   4860
agatacattg atgagtttgg acaaaccaca actagaatgc agtgaaaaaa atgctttatt   4920
tgtgaaattt gtgatgctat tgctttattt gtaaccatta taagctgcaa taaacaagtt   4980
aacaacaaca attgcattca ttttatgttt caggttcagg gggaggtgtg ggaggttttt   5040
taaagcaagt aaaacctcta caaatgtggt atggctgatt atgatctgcg gccgccactg   5100
gccgtcgttt tacaacgtcg tgactgggaa aaccctggcg ttacccaact taatcgcctt   5160
gcagcacatc ccccttttcgc cagctggcgt aatagcgaag aggcccgcac cgatcgccct   5220
tcccaacagt tgcgcagcct gaatggcgaa tggaacgcgc cctgtagcgg cgcattaagc   5280
gcggcgggtg tggtggttac gcgcagcgtg accgctacac ttgccagcgc cctagcgccc   5340
gctcctttcg ctttcttccc ttcctttctc gccacgttcg ccggctttcc ccgtcaagct   5400
ctaaatcggg ggctcccttt agggttccga tttagtgctt tacggcacct cgaccccaaa   5460
aaacttgatt agggtgatgg ttcacgtagt gggccatcgc cctgatagac ggtttttcgc   5520
cctttgacgt tggagtccac gttctttaat agtggactct tgttccaaac tggaacaaca   5580 ctcaaccctat ctcggtcta ttcttttgat ttataaggga ttttgccgat ttcggcctat   5640
tggttaaaaa atgagctgat ttaacaaaaa tttaacgcga attttaacaa aatattaacg   5700
cttacaattt aggtggcact tttcggggaa atgtgcgcgg aacccctatt tgtttatttt   5760
tctaaataca ttcaaatatg tatccgctca tgagacaata accctgataa atgcttcaat   5820
aatattgaaa aaggaagagt atgagtattc aacatttccg tgtcgccctt attccctttt   5880
ttgcggcatt ttgccttcct gttttttgctc acccagaaac gctggtgaaa gtaaaagatg   5940
ctgaagatca gttgggtgca cgagtgggtt acatcgaact ggatctcaac agcggtaaga   6000
tccttgagag ttttcgcccc gaagaacgtt ttccaatgat gagcactttt aaagttctgc   6060
tatgtggcgc ggtattatcc cgtattgacg ccgggcaaga gcaactcggt cgccgcatac   6120
actattctca gaatgacttg gttgagtact caccagtcac agaaaagcat cttacggatg   6180
gcatgacagt aagagaatta tgcagtgctg ccataaccat gagtgataac actgcggcca   6240
acttacttct gacaacgatc ggaggaccga aggagctaac cgcttttttg cacaacatgg   6300
gggatcatgt aactcgcctt gatcgttggg aaccggagct gaatgaagcc ataccaaacg   6360
acgagcgtga caccacgatg cctgtagcaa tggcaacaac gttgcgcaaa ctattaactg   6420
gcgaactact tactctagct tcccggcaac aattaataga ctggatggag gcggataaag   6480
ttgcaggacc acttctgcgc tcggcccttc cggctggctg gtttattgct gataaatctg   6540
gagccggtga gcgtgggtct cgcggtatca ttgcagcact ggggccagat ggtaagccct   6600
cccgtatcgt agttatctac acgacgggga gtcaggcaac tatggatgaa cgaaatagac   6660
agatcgctga gataggtgcc tcactgatta agcattggta actgtcagac caagtttact   6720
catatatact ttagattgat ttaaaacttc attttaatt taaaaggatc taggtgaaga   6780
tcctttttga taatctcatg accaaaatcc cttaacgtga gttttcgttc cactgagcgt   6840 cagacccccgt agaaaagatc aaaggatctt cttgagatcc ttttttctg cgcgtaatct   6900 gctgcttgca aacaaaaaaa ccaccgctac cagcggtggt ttgttgccg gatcaagagc   6960 taccaactct ttttccgaag gtaactggct tcagcagagc gcagatacca atactgtcc    7020
```

```
ttctagtgta gccgtagtta ggccaccact tcaagaactc tgtagcaccg cctacatacc    7080
tcgctctgct aatcctgtta ccagtggctg ctgccagtgg cgataagtcg tgtcttaccg    7140
ggttggactc aagacgatag ttaccggata aggcgcagcg gtcgggctga acggggggtt    7200
cgtgcacaca gcccagcttg gagcgaacga cctacaccga actgagatac ctacagcgtg    7260
agctatgaga aagcgccacg cttcccgaag ggagaaaggc ggacaggtat ccggtaagcg    7320
gcagggtcgg aacaggagag cgcacgaggg agcttccagg gggaaacgcc tggtatcttt    7380
atagtcctgt cgggtttcgc cacctctgac ttgagcgtcg attttttgtga tgctcgtcag    7440 gggggcggag cctatggaaa aacgccagca acgcggcctt tttacggttc ctggccttt    7500 gctggccttt tgctcacatg ttctttcctg cgttatcccc tgattctgtg ataaccgta    7560 ttaccgcctt tgagtgagct gataccgctc gccgcagccg aacgaccgag cgcagcgagt    7620
cagtgagcga ggaagcggaa gagcgcccaa tacgcaaacc gcctctcccc gcgcgttggc    7680
cgattcatta atgcagctgg cacgacaggt ttcccgactg gaaagcgggc agtgagcgca    7740
acgcaattaa tgtgagttag ctcactcatt aggcacccca ggctttacac tttatgcttc    7800
cggctcgtat gttgtgtgga attgtgagcg gataacaatt tcacacagga aacagctatg    7860
accatga                                                              7867
```

<210> SEQ ID NO 55
<211> LENGTH: 935
<212> TYPE: PRT
<213> ORGANISM: Artificial sequence
<220> FEATURE:
<223> OTHER INFORMATION: RabChtTal1-Clo051

<400> SEQUENCE: 55

```
Met Gly Pro Lys Lys Arg Lys Val Ala Ala Ala Asp Tyr Lys Asp
 1               5                  10                  15

Asp Asp Asp Lys Pro Gly Gly Gly Ser Gly Gly Gly Val Pro
                20                  25                  30

Ala Ser Pro Ala Ala Gln Val Asp Leu Arg Thr Leu Gly Tyr Ser Gln
                35                  40                  45

Gln Gln Gln Glu Lys Ile Lys Pro Lys Val Arg Ser Thr Val Ala Gln
            50                  55                  60

His His Glu Ala Leu Val Gly His Gly Phe Thr His Ala His Ile Val
65                  70                  75                  80

Ala Leu Ser Gln His Pro Ala Ala Leu Gly Thr Val Ala Val Lys Tyr
                85                  90                  95

Gln Asp Met Ile Ala Ala Leu Pro Glu Ala Thr His Glu Ala Ile Val
                100                 105                 110

Gly Val Gly Lys Gln Trp Ser Gly Ala Arg Ala Leu Glu Ala Leu Leu
            115                 120                 125

Thr Val Ala Gly Glu Leu Arg Gly Pro Pro Leu Gln Ser Gly Leu Asp
        130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Glu Gln Val Val Ala Ile Ala Ser Asn Ile Gly Gly Lys
                180                 185                 190

Gln Ala Leu Glu Thr Val Gln Arg Leu Leu Pro Val Leu Cys Gln Ala
            195                 200                 205
```

-continued

His Gly Leu Thr Pro Gln Gln Val Ala Ile Ala Ser Asn Gly Gly
    210                 215                 220

Gly Lys Gln Ala Leu Glu Thr Val Gln Arg Leu Leu Pro Val Leu Cys
225                 230                 235                 240

Gln Ala His Gly Leu Thr Pro Gln Gln Val Ala Ile Ala Ser His
                245                 250                 255

Asp Gly Gly Lys Gln Ala Leu Glu Thr Val Gln Arg Leu Leu Pro Val
                260                 265                 270

Leu Cys Gln Ala His Gly Leu Thr Pro Glu Gln Val Val Ala Ile Ala
        275                 280                 285

Ser Asn Ile Gly Gly Lys Gln Ala Leu Glu Thr Val Gln Arg Leu Leu
290                 295                 300

Pro Val Leu Cys Gln Ala His Gly Leu Thr Pro Glu Gln Val Val Ala
305                 310                 315                 320

Ile Ala Ser Asn Ile Gly Gly Lys Gln Ala Leu Glu Thr Val Gln Arg
                325                 330                 335

Leu Leu Pro Val Leu Cys Gln Ala His Gly Leu Thr Pro Gln Gln Val
                340                 345                 350

Val Ala Ile Ala Ser Asn Lys Gly Gly Lys Gln Ala Leu Glu Thr Val
        355                 360                 365

Gln Arg Leu Leu Pro Val Leu Cys Gln Ala His Gly Leu Thr Pro Gln
370                 375                 380

Gln Val Val Ala Ile Ala Ser His Asp Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Gln Gln Val Val Ala Ile Ala Ser Asn Asn Gly Gly Lys Gln Ala
                420                 425                 430

Leu Glu Thr Val Gln Arg Leu Leu Pro Val Leu Cys Gln Ala His Gly
                435                 440                 445

Leu Thr Pro Gln Gln Val Val Ala Ile Ala Ser His Asp Gly Gly Lys
        450                 455                 460

Gln Ala Leu Glu Thr Val Gln Arg Leu Leu Pro Val Leu Cys Gln Ala
465                 470                 475                 480

His Gly Leu Thr Pro Gln Gln Val Val Ala Ile Ala Ser Asn Gly Gly
                485                 490                 495

Gly Lys Gln Ala Leu Glu Thr Val Gln Arg Leu Leu Pro Val Leu Cys
                500                 505                 510

Gln Ala His Gly Leu Thr Pro Glu Gln Val Val Ala Ile Ala Ser Asn
        515                 520                 525

Ile Gly Gly Lys Gln Ala Leu Glu Thr Val Gln Arg Leu Leu Pro Val
        530                 535                 540

Leu Cys Gln Ala His Gly Leu Thr Pro Gln Gln Val Val Ala Ile Ala
545                 550                 555                 560

Ser Asn Gly Gly Gly Lys Gln Ala Leu Glu Thr Val Gln Arg Leu Leu
                565                 570                 575

Pro Val Leu Cys Gln Ala His Gly Leu Thr Pro Gln Gln Val Val Ala
                580                 585                 590

Ile Ala Ser Asn Lys Gly Gly Lys Gln Ala Leu Glu Thr Val Gln Arg
            595                 600                 605

Leu Leu Pro Val Leu Cys Gln Ala His Gly Leu Thr Pro Gln Gln Val
        610                 615                 620

```
Val Ala Ile Ala Ser Asn Gly Gly Lys Gln Ala Leu Glu Thr Val
625                 630                 635                 640

Gln Arg Leu Leu Pro Val Leu Cys Gln Ala His Gly Leu Thr Pro Gln
    645                 650                 655

Gln Val Val Ala Ile Ala Ser Asn Gly Gly Arg Pro Ala Leu Glu
        660                 665                 670

Ser Ile Val Ala Gln Leu Ser Arg Pro Asp Pro Ala Leu Ala Arg Ser
    675                 680                 685

Ala Leu Thr Asn Asp His Leu Val Ala Leu Ala Cys Leu Gly Gly Arg
    690                 695                 700

Pro Ala Leu Asp Ala Val Lys Lys Gly Leu Pro His Ala Pro Ala Leu
705                 710                 715                 720

Ile Lys Arg Thr Asn Arg Arg Ile Pro Glu Gly Ser Asp Arg Leu Asn
            725                 730                 735

Glu Gly Ile Lys Ser Asn Ile Ser Leu Leu Lys Asp Glu Leu Arg Gly
                740                 745                 750

Gln Ile Ser His Ile Ser His Glu Tyr Leu Ser Leu Ile Asp Leu Ala
            755                 760                 765

Phe Asp Ser Lys Gln Asn Arg Leu Phe Glu Met Lys Val Leu Glu Leu
770                 775                 780

Leu Val Asn Glu Tyr Gly Phe Lys Gly Arg His Leu Gly Gly Ser Arg
785                 790                 795                 800

Lys Pro Asp Gly Ile Val Tyr Ser Thr Thr Leu Glu Asp Asn Phe Gly
            805                 810                 815

Ile Ile Val Asp Thr Lys Ala Tyr Ser Glu Gly Tyr Ser Leu Pro Ile
        820                 825                 830

Ser Gln Ala Asp Glu Met Glu Arg Tyr Val Arg Glu Asn Ser Asn Arg
    835                 840                 845

Asp Glu Glu Val Asn Pro Asn Lys Trp Trp Glu Asn Phe Ser Glu Glu
    850                 855                 860

Val Lys Lys Tyr Tyr Phe Val Phe Ile Ser Gly Ser Phe Lys Gly Lys
865                 870                 875                 880

Phe Glu Glu Gln Leu Arg Arg Leu Ser Met Thr Thr Gly Val Asn Gly
            885                 890                 895

Ser Ala Val Asn Val Val Asn Leu Leu Leu Gly Ala Glu Lys Ile Arg
                900                 905                 910

Ser Gly Glu Met Thr Ile Glu Leu Glu Arg Ala Met Phe Asn Asn
            915                 920                 925

Ser Glu Phe Ile Leu Lys Tyr
930                 935

<210> SEQ ID NO 56
<211> LENGTH: 7867
<212> TYPE: DNA
<213> ORGANISM: Artificial sequence
<220> FEATURE:
<223> OTHER INFORMATION: pCAG-RabChtTal2-Clo051

<400> SEQUENCE: 56
ggcgcgccgg attcgacatt gattattgac tagttattaa tagtaatcaa ttacggggtc     60
attagttcat agcccatata tggagttccg cgttacataa cttacggtaa atggcccgcc    120
tggctgaccg cccaacgacc cccgcccatt gacgtcaata atgacgtatg ttcccatagt    180
aacgccaata gggactttcc attgacgtca atgggtggag tatttacggt aaactgccca    240
cttggcagta catcaagtgt atcatatgcc aagtacgccc cctattgacg tcaatgacgg    300
```

```
taaatggccc gcctggcatt atgcccagta catgacccta tgggactttc ctacttggca    360
gtacatctac gtattagtca tcgctattac catggtcgag gtgagcccca cgttctgctt    420
cactctcccc atctccccc cctccccacc cccaattttg tatttattta ttttttaatt    480
attttgtgca gcgatggggg cggggggggg ggggggcgc gcgccaggcg gggcggggcg    540
gggcgagggg cggggcgggg cgaggcggag aggtgcggcg gcagccaatc agagcggcgc    600
gctccgaaag tttccttta tggcgaggcg gcggcggcgg cggccctata aaaagcgaag    660
cgcgcggcgg gcgggagtcg ctgcgcgctg ccttcgcccc gtgccccgct ccgccgccgc    720
ctcgcgccgc ccgccccggc tctgactgac cgcgttactc ccacaggtga gcgggcggga    780
cggcccttct cctccgggct gtaattagcg cttggtttaa tgacggcttg tttcttttct    840
gtggctgcgt gaaagccttg aggggctccg ggagggccct ttgtgcgggg gggagcggct    900
cgggggggtgc gtgcgtgtgt gtgtgcgtgg ggagcgccgc gtgcggctcc gcgctgcccg    960
gcggctgtga gcgctgcggg cgcggcgcgg ggctttgtgc gctccgcagt gtgcgcgagg   1020
ggagcgcggc cggggcggt gccccgcggt gcgggggggg ctgcgagggg aacaaaggct   1080
gcgtgcgggg tgtgtgcgtg ggggggtgag caggggggtgt gggcgcgtcg gtcgggctgc   1140
aaccccccct gcacccccct ccccgagttg ctgagcacgg cccggcttcg ggtgcgggc   1200
tccgtacggg gcgtggcgcg gggctcgccg tgccggcgg ggggtggcgg caggtggggg   1260
tgccgggcgg ggcggggccg cctcgggccg gggagggctc ggggagggg cgcggcggcc   1320
cccgagcgc cggcggctgt cgaggcgcgg cgagccgcag ccattgcctt ttatggtaat   1380
cgtgcgagag ggcgcaggga cttcctttgt cccaaatctg tgcggagccg aaatctggga   1440
ggcgccgccg cacccctct agcgggcgcg gggcgaagcg gtgcggcgcc ggcaggaagg   1500
aaatgggcgg ggagggcctt cgtgcgtcgc cgcgccgccg tccccttctc cctctccagc   1560
ctcggggctg tccgcggggg gacgctgcc ttcgggggg acgggcagg gcggggttcg   1620
gcttctggcg tgtgaccggc ggctctagag cctctgctaa ccatgttcat gccttcttct   1680
ttttcctaca gatccttaat taataatacg actcactata ggggccgcca ccatgggacc   1740
taagaaaaag aggaaggtgg cggccgctga ctacaaggat gacgacgata aaccaggtgg   1800
cggaggtagt ggcggaggtg gggtacccgc cagtccagca gcccaggtgg atctgagaac   1860
cctcggctac agccagcagc agcaggagaa gatcaaacca aaggtgcggt ccaccgtcgc   1920
tcagcaccat gaagcactgg tggggcacgg tttcacacac gcccatattg tggctctgtc   1980
tcagcatccc gctgcactcg ggactgtggc cgtcaaatat caggacatga tcgccgctct   2040
gcctgaggca acccacgaag ccattgtggg cgtcggaaag cagtggagcg gtgccagagc   2100
actcgaagca ctcctcaccg tcgccgggga actgcgggt ccaccactcc agtccggact   2160
ggacactgga cagctgctga agatcgctaa acgcggcgga gtgacagctg tggaagctgt   2220
gcacgcttgg aggaatgctc tgacaggagc cccactgaat cttacacccc agcaggtggt   2280
ggccattgct agcaacaatg ggcaagca ggctctggag acagtgcagc gcctgctgcc   2340
tgtgctgtgc caggctcatg gcctcacacc tcagcaggtc gtcgccattg cttctaacaa   2400
tggagggaag caggctctgg agactgtgca gagactgctg ccagtgctgt gccaggccca   2460
tggcctaaca ccccagcagg tggtggccat cgccagccac gacggcggca agcaggccct   2520
ggaaaccgtg cagaggctgc tgcctgtgct gtgccaggct catggcctga cacctcagca   2580
ggtcgtcgcc atcgccagcc acgacggcgg caagcaggcc ctggaaaccg tgcagaggct   2640
```

```
gctgccagtg ctgtgccagg cccatggctt aacaccccag caggtggtgg ccatcgctag    2700
tcatgacggg ggcaaacagg ctctggaaac agtacagcgg ctgttacctg tgctgtgcca    2760
ggctcatggc ttgacacctc agcaggtcgt cgctatcgcc tctaataagg ggggcaagca    2820
ggctctggag acagtacagc gcctgttacc agtgctgtgc caggcccacg ggctcacacc    2880
ccagcaggtg gtggcaattg cttccaataa gggcggaaaa caggctctgg aaaccgtcca    2940
gaggctgctg cctgtgctgt gccaggctca cggtctaaca ccccagcagg tggtggccat    3000
cgcttccaac ggagggggca acaggctct ggaaacagtg cagaggctgc tgcctgtgct    3060
gtgccaggct catggcctca cacctgagca ggtcgtcgcc atcgccagca acatcggcgg    3120
caagcaggcc ctggaaaccg tgcagaggct gctgccagtg ctgtgccagg cccatggcct    3180
aacaccccag caggtggtgg caattgcttc aataagggc ggaaaacagg ctctggaaac    3240
cgtccagagg ctgctgcctg tgctgtgcca ggctcatggc ctgacacctc agcaggtcgt    3300
cgcaatcgcc tccaatggcg gagggaagca ggccctggaa acggtgcaga gactgttacc    3360
agtgctgtgc caggcccatg gcttaacacc ccagcaggtg gtggcaatcg cctctaataa    3420
gggagggaag caggccctgg aaaccgtgca gagactgtta cctgtgctgt gccaggctca    3480
tggcttgaca cctcagcagg tcgtcgctat cgctagtcat gatggcggaa acaggctct    3540 ggaaactgtg cagcggctgc tcccagtgct gtgccaggcc cacgggctca caccccagca    3600
ggtggtggcc atcgccagca acaagggcgg caagcaggcc ctggaaaccg tgcagaggct    3660
gctgcctgtg ctgtgccagg ctcacggcct gaccccacag caggtcgtcg ctattgcttc    3720
taatggcgga gggcggcctg ctctggagag cattgtggct cagctgtcca ggcccgatcc    3780
tgccctggct agatccgcac tcactaacga tcatctggtc gctctcgctt gcctcggtgg    3840 acggccgct ctgacgcag tcaaaaaggg tctcccccat gctcccgcac tgatcaagag    3900
aaccaacagg agaattcctg agggatccga tcgtttaaac gaaggcatca aaagcaacat    3960
ctccctcctg aaagacgaac tccggggca gattagccac attagtcacg aatacctctc    4020
cctcatcgac ctggctttcg atagcaagca gaacaggctc tttgagatga agtgctgga    4080 actgctcgtc aatgagtacg ggttcaaggg tcgacacctc ggcggatcta ggaaccaga    4140 cggcatcgtg tatagtacca cactggaaga caactttggg atcattgtgg ataccaaggc    4200
atactctgag ggttatagtc tgcccatttc acaggccgac gagatggaac ggtacgtgcg    4260
cgagaactca aatagagatg aggaagtcaa ccctaacaag tggtgggaga acttctctga    4320
ggaagtgaag aaatactact tcgtctttat cagcgggtcc ttcaagggta atttgaggaa    4380
acagctcagg agactgagca tgactaccgg cgtgaatggc agcgccgtca acgtggtcaa    4440
tctgctcctg ggcgctgaaa agattcgag cggagagatg accatcgaag agctggagag    4500
ggcaatgttt aataatagcg agtttatcct gaaatactga acgcgtaaat gattgcagat    4560
ccactagttc tagaattcca gctgagcgcc ggtcgctacc attaccagtt ggtctggtgt    4620
caaaaataat aataaccggg cagggggat ctgcatggat ctttgtgaag gaaccttact    4680
tctgtggtgt gacataattg gacaaactac ctacagagat ttaaagctct aaggtaaata    4740 taaaatttt aagtgtataa tgtgttaaac tactgattct aattgtttgt gtatttaga    4800 ttccaaccta tggaactgat gaatgggagc agtggtggaa tgccagatcc agacatgata    4860
agatacattg atgagtttgg acaaaccaca actagaatgc agtgaaaaaa atgctttatt    4920
tgtgaaattt gtgatgctat tgctttattt gtaaccatta taagctgcaa taaacaagtt    4980
aacaacaaca attgcattca ttttatgttt caggttcagg gggaggtgtg ggaggttttt    5040
```

```
taaagcaagt aaaacctcta caaatgtggt atggctgatt atgatctgcg gccgccactg   5100
gccgtcgttt tacaacgtcg tgactgggaa accctggcg ttacccaact taatcgcctt    5160
gcagcacatc ccccttcgc cagctggcgt aatagcgaag aggcccgcac cgatcgccct    5220
tcccaacagt tgcgcagcct gaatggcgaa tggaacgcgc cctgtagcgg cgcattaagc   5280
gcggcgggtg tggtggttac gcgcagcgtg accgctacac ttgccagcgc cctagcgccc   5340
gctcctttcg ctttcttccc ttcctttctc gccacgttcg ccggctttcc ccgtcaagct   5400
ctaaatcggg ggctcccttt agggttccga tttagtgctt tacggcacct cgaccccaaa   5460
aaacttgatt agggtgatgg ttcacgtagt gggccatcgc cctgatagac ggttttcgc    5520
cctttgacgt tggagtccac gttctttaat agtggactct tgttccaaac tggaacaaca   5580
ctcaaccta tctcggtcta ttcttttgat ttataaggga ttttgccgat tcggcctat     5640
tggttaaaaa atgagctgat ttaacaaaaa tttaacgcga ttttaacaa aatattaacg    5700
cttacaattt aggtggcact tttcggggaa atgtgcgcgg aaccctatt tgtttattt    5760
tctaaataca ttcaaatatg tatccgctca tgagacaata accctgataa atgcttcaat   5820
aatattgaaa aaggaagagt atgagtattc aacatttccg tgtcgccctt attccctttt   5880
ttgcggcatt ttgccttcct gttttgctc acccagaaac gctggtgaaa gtaaaagatg    5940
ctgaagatca gttgggtgca cgagtgggtt acatcgaact ggatctcaac agcggtaaga   6000
tccttgagag ttttcgcccc gaagaacgtt ttccaatgat gagcactttt aaagttctgc   6060
tatgtggcgc ggtattatcc cgtattgacg ccgggcaaga gcaactcggt cgccgcatac   6120
actattctca gaatgacttg gttgagtact caccagtcac agaaaagcat cttacggatg   6180
gcatgacagt aagagaatta tgcagtgctg ccataaccat gagtgataac actgcggcca   6240
acttacttct gacaacgatc ggaggaccga aggagctaac cgctttttg cacaacatgg    6300
gggatcatgt aactcgcctt gatcgttggg aaccggagct gaatgaagcc ataccaaacg   6360
acgagcgtga caccacgatg cctgtagcaa tggcaacaac gttgcgcaaa ctattaactg   6420
gcgaactact tactctagct tcccggcaac aattaataga ctggatggag gcggataaag   6480
ttgcaggacc acttctgcgc tcggcccttc cggctggctg gtttattgct gataaatctg   6540
gagccggtga gcgtgggtct cgcggtatca ttgcagcact ggggccagat ggtaagccct   6600
cccgtatcgt agttatctac acgacgggga gtcaggcaac tatggatgaa cgaaatagac   6660
agatcgctga gataggtgcc tcactgatta agcattggta actgtcagac caagtttact   6720
catatatact ttagattgat ttaaaacttc atttttaatt taaaaggatc taggtgaaga   6780
tccttttga taatctcatg accaaaatcc cttaacgtga gttttcgttc cactgagcgt    6840
cagacccc agaaaagatc aaaggatctt cttgagatcc ttttttctg cgcgtaatct      6900
gctgcttgca acaaaaaaa ccaccgctac cagcggtggt ttgtttgccg atcaagagc     6960
taccaactct ttttccgaag gtaactggct tcagcagagc gcagatacca aatactgtcc   7020
ttctagtgta gccgtagtta ggccaccact tcaagaactc tgtagcaccg cctacatacc   7080
tcgctctgct aatcctgtta ccagtggctg ctgccagtgg cgataagtcg tgtcttaccg   7140
ggttggactc aagacgatag ttaccggata aggcgcagcg tcgggctga acgggggtt     7200
cgtgcacaca gcccagcttg gagcgaacga cctacaccga actgagatac ctacagcgtg   7260
agctatgaga aagcgccacg cttcccgaag ggagaaaggc ggacaggtat ccggtaagcg   7320
gcagggtcgg aacaggagag cgcacgaggg agcttccagg gggaaacgcc tggtatcttt   7380
```

-continued

```
atagtcctgt cgggtttcgc cacctctgac ttgagcgtcg attttttgtga tgctcgtcag    7440 gggggcggag cctatggaaa aacgccagca acgcggcctt tttacggttc ctggccttttt   7500 gctggccttt tgctcacatg ttctttcctg cgttatcccc tgattctgtg gataaccgta    7560
ttaccgcctt tgagtgagct gataccgctc gccgcagccg aacgaccgag cgcagcgagt    7620
cagtgagcga ggaagcggaa gagcgcccaa tacgcaaacc gcctctcccc gcgcgttggc    7680
cgattcatta atgcagctgg cacgacaggt ttcccgactg gaaagcgggc agtgagcgca    7740
acgcaattaa tgtgagttag ctcactcatt aggcaccccca ggctttacac tttatgcttc    7800
cggctcgtat gttgtgtgga attgtgagcg gataacaatt tcacacagga aacagctatg    7860
accatga                                                              7867
```

<210> SEQ ID NO 57
<211> LENGTH: 935
<212> TYPE: PRT
<213> ORGANISM: Artificial sequence
<220> FEATURE:
<223> OTHER INFORMATION: RabChtTal2-Clo051

<400> SEQUENCE: 57

```
Met Gly Pro Lys Lys Arg Lys Val Ala Ala Asp Tyr Lys Asp
1               5                   10                  15

Asp Asp Asp Lys Pro Gly Gly Gly Ser Gly Gly Gly Val Pro
            20                  25                  30

Ala Ser Pro Ala Ala Gln Val Asp Leu Arg Thr Leu Gly Tyr Ser Gln
        35                  40                  45

Gln Gln Gln Glu Lys Ile Lys Pro Lys Val Arg Ser Thr Val Ala Gln
    50                  55                  60

His His Glu Ala Leu Val Gly His Gly Phe Thr His Ala His Ile Val
65                  70                  75                  80

Ala Leu Ser Gln His Pro Ala Ala Leu Gly Thr Val Ala Val Lys Tyr
                85                  90                  95

Gln Asp Met Ile Ala Ala Leu Pro Glu Ala Thr His Glu Ala Ile Val
            100                 105                 110

Gly Val Gly Lys Gln Trp Ser Gly Ala Arg Ala Leu Glu Ala Leu Leu
        115                 120                 125

Thr Val Ala Gly Glu Leu Arg Gly Pro Pro Leu Gln Ser Gly Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Gln Gln Val Val Ala Ile Ala Ser Asn Asn Gly Gly Lys
            180                 185                 190

Gln Ala Leu Glu Thr Val Gln Arg Leu Leu Pro Val Leu Cys Gln Ala
        195                 200                 205

His Gly Leu Thr Pro Gln Gln Val Val Ala Ile Ala Ser Asn Asn Gly
    210                 215                 220

Gly Lys Gln Ala Leu Glu Thr Val Gln Arg Leu Leu Pro Val Leu Cys
225                 230                 235                 240

Gln Ala His Gly Leu Thr Pro Gln Gln Val Val Ala Ile Ala Ser His
                245                 250                 255

Asp Gly Gly Lys Gln Ala Leu Glu Thr Val Gln Arg Leu Leu Pro Val
            260                 265                 270
```

-continued

```
Leu Cys Gln Ala His Gly Leu Thr Pro Gln Gln Val Val Ala Ile Ala
            275                 280                 285

Ser His Asp Gly Gly Lys Gln Ala Leu Glu Thr Val Gln Arg Leu Leu
            290                 295                 300

Pro Val Leu Cys Gln Ala His Gly Leu Thr Pro Gln Gln Val Val Ala
305                 310                 315                 320

Ile Ala Ser His Asp Gly Gly Lys Gln Ala Leu Glu Thr Val Gln Arg
                325                 330                 335

Leu Leu Pro Val Leu Cys Gln Ala His Gly Leu Thr Pro Gln Gln Val
            340                 345                 350

Val Ala Ile Ala Ser Asn Lys Gly Gly Lys Gln Ala Leu Glu Thr Val
            355                 360                 365

Gln Arg Leu Leu Pro Val Leu Cys Gln Ala His Gly Leu Thr Pro Gln
        370                 375                 380

Gln Val Val Ala Ile Ala Ser Asn Lys Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Gln Gln Val Val Ala Ile Ala Ser Asn Gly Gly Gly Lys Gln Ala
            420                 425                 430

Leu Glu Thr Val Gln Arg Leu Leu Pro Val Leu Cys Gln Ala His Gly
            435                 440                 445

Leu Thr Pro Glu Gln Val Val Ala Ile Ala Ser Asn Ile Gly Gly Lys
            450                 455                 460

Gln Ala Leu Glu Thr Val Gln Arg Leu Leu Pro Val Leu Cys Gln Ala
465                 470                 475                 480

His Gly Leu Thr Pro Gln Gln Val Val Ala Ile Ala Ser Asn Lys Gly
                485                 490                 495

Gly Lys Gln Ala Leu Glu Thr Val Gln Arg Leu Leu Pro Val Leu Cys
            500                 505                 510

Gln Ala His Gly Leu Thr Pro Gln Gln Val Val Ala Ile Ala Ser Asn
            515                 520                 525

Gly Gly Gly Lys Gln Ala Leu Glu Thr Val Gln Arg Leu Leu Pro Val
        530                 535                 540

Leu Cys Gln Ala His Gly Leu Thr Pro Gln Gln Val Val Ala Ile Ala
545                 550                 555                 560

Ser Asn Lys Gly Gly Lys Gln Ala Leu Glu Thr Val Gln Arg Leu Leu
                565                 570                 575

Pro Val Leu Cys Gln Ala His Gly Leu Thr Pro Gln Gln Val Val Ala
            580                 585                 590

Ile Ala Ser His Asp Gly Gly Lys Gln Ala Leu Glu Thr Val Gln Arg
            595                 600                 605

Leu Leu Pro Val Leu Cys Gln Ala His Gly Leu Thr Pro Gln Gln Val
        610                 615                 620

Val Ala Ile Ala Ser Asn Lys Gly Gly Lys Gln Ala Leu Glu Thr Val
625                 630                 635                 640

Gln Arg Leu Leu Pro Val Leu Cys Gln Ala His Gly Leu Thr Pro Gln
                645                 650                 655

Gln Val Val Ala Ile Ala Ser Asn Gly Gly Gly Arg Pro Ala Leu Glu
            660                 665                 670

Ser Ile Val Ala Gln Leu Ser Arg Pro Asp Pro Ala Leu Ala Arg Ser
            675                 680                 685

Ala Leu Thr Asn Asp His Leu Val Ala Leu Ala Cys Leu Gly Gly Arg
```

```
                690             695             700
Pro Ala Leu Asp Ala Val Lys Lys Gly Leu Pro His Ala Pro Ala Leu
705                 710                 715                 720

Ile Lys Arg Thr Asn Arg Ile Pro Glu Gly Ser Asp Arg Leu Asn
                725                 730                 735

Glu Gly Ile Lys Ser Asn Ile Ser Leu Leu Lys Asp Glu Leu Arg Gly
            740                 745                 750

Gln Ile Ser His Ile Ser His Glu Tyr Leu Ser Leu Ile Asp Leu Ala
        755                 760                 765

Phe Asp Ser Lys Gln Asn Arg Leu Phe Glu Met Lys Val Leu Glu Leu
770                 775                 780

Leu Val Asn Glu Tyr Gly Phe Lys Gly Arg His Leu Gly Gly Ser Arg
785                 790                 795                 800

Lys Pro Asp Gly Ile Val Tyr Ser Thr Thr Leu Glu Asp Asn Phe Gly
                805                 810                 815

Ile Ile Val Asp Thr Lys Ala Tyr Ser Glu Gly Tyr Ser Leu Pro Ile
            820                 825                 830

Ser Gln Ala Asp Glu Met Glu Arg Tyr Val Arg Glu Asn Ser Asn Arg
        835                 840                 845

Asp Glu Glu Val Asn Pro Asn Lys Trp Trp Glu Asn Phe Ser Glu Glu
850                 855                 860

Val Lys Lys Tyr Tyr Phe Val Phe Ile Ser Gly Ser Phe Lys Gly Lys
865                 870                 875                 880

Phe Glu Glu Gln Leu Arg Arg Leu Ser Met Thr Thr Gly Val Asn Gly
                885                 890                 895

Ser Ala Val Asn Val Val Asn Leu Leu Leu Gly Ala Glu Lys Ile Arg
            900                 905                 910

Ser Gly Glu Met Thr Ile Glu Glu Leu Glu Arg Ala Met Phe Asn Asn
        915                 920                 925

Ser Glu Phe Ile Leu Lys Tyr
930                 935

<210> SEQ ID NO 58
<211> LENGTH: 6607
<212> TYPE: DNA
<213> ORGANISM: Artificial sequence
<220> FEATURE:
<223> OTHER INFORMATION: pRab38-chtTAL

<400> SEQUENCE: 58
caccgcatta ccctgggcgt tgaaaccgaa gaagacctgg atttgaaata ggcgttttct      60
ttacatttct aaagtgggac tcctcacttg taaaggaaaa ataatgata cttttaagac     120 ttccaggatg actaaatggt gtgtatgaga agatttataa acatctgccg ctacttacaa     180
tgataagacc acttgtgtgt tgttcagctt ggagaattta ggataggagt ggaggctgaa     240
agaaaagtaa gcccttagca tttcctctca ggtggcctct actttaggtc attaacagtt     300
gaataggcgc taagagatag cattaccact ttatagaagc ccaggcaaaa ggagattaaa     360
gggtttgcct aaattctttc aactctaagg gccagagaag acctaagtct actgctttgc     420
tgtttctcaa ggtctcccca actttacaac actgtgtggg tggcaacagg gcttaatagc     480
ctcagaagac ctgggtattt ttcgacactc agttctctcc ccggcagaac gtggaaaaca     540
aaatccacat aagtttgtgt catggacggg aggcgagaga aaaatctctg tgaaaggagt     600
aaagcactgt gcaaatacca gcttgacagg cagtagcact ggggtcccgg gtcctttagc     660
```

```
ttccagtccc aggagttgct cttgtctcct cccactctgg agtccgcaga gtaggaagga    720
ggattaaacc cggggagga gttccgcacc agctccctat cctgcgccag cacgcctagc    780
ctaagcgccc acatagagct ccggtctccg tcggtgccca gccccggctg tgcttcccag    840
agcaagctcc aggctccgca agacccgcgg gcctccagga tgcagacacc tcacaaggag    900
cacctgtaca agctgctggt gatcggcgac ctggtagtgg gcaagaccag cattattaaa    960
cggtacgtgc atcaaaattt ctcctctcat tatcgagcca ccattggtgt ggacttcgcg   1020
ctgaaggtgc tccactggga cccagagacg gtggtgcgct gcagctctg ggacattgct   1080
ggtgagcgat cagagcagcg cgcaacgggt gagggtggag tgagccagtg aggagttcgg   1140
gggtgaaggt tcggggagtg gaaaatgact tttcagtcgg ttccagtccc gggacccttg   1200
agtgcaatca gcaggagat ccggatcgcc tgggcgctcc actcttggaa agtttggctt   1260
aatggcttgg aaacctgatt tcaaagaaat ggaagtgttt tcttttcttt ctttcctttt   1320
tttttttttt ttttttcttt tgctgttgt ttctgttgga gtcgtcccca ctctacctgt   1380
aacttctaga taacttcgct ggctctcact ggctgtgaga aagcgaacca ctttctcctg   1440
ggattcttgg gtgcagagaa ggctgtcgcc tggactcaca aggagattgt agtcgcattc   1500
ttgtttcatt ctagtccttt tctggacaca ggtagccgcg acttggccca gagtatctca   1560
cgtggctttc atccttcgtg tttagagggg aagcccctag gaaatttaag aaggagcagg   1620
attatcttag gaatttagtt tctttcaaat ctcactacta tcatctcctt gcttattggc   1680
ctcttcagtc agaaaaattt gagatgctaa atttgtatac atctagaacg aactatctct   1740
tctcactcca ctcccctctt ccccatctct cttccgtctc cctccatcct tggctatctc   1800
ttcttcactt tccatttcaa acaggagact gtgtatgttt tttaggaaaa cattaaaaaa   1860
aaaaccacaa aaacaaaaac aaaacggaga cagggtcccg tcatgtaact ctgctaacct   1920
atatcaagct gaccttgacc tcatagagac ccacttgcct ctgcctccct agaggcaagg   1980
gtcggggtta tggtgatgtt aatgtcgttt gctttaagat tccttgattt gatcttggtg   2040
tatttttttga gaaatctaaa gtatgaaatc agagtttgac taacagcttc taccagctcc   2100
tagccacaat aaagactgag gcaggctata gttagtgctc aatactgggt cctacctggc   2160
tgcttgtaac ctgggcatgc ctagcattct agatgctaac tcaccaaagc agtagcattt   2220
taagctgcaa atggctaggc agcgacagct caagaatctt cttgctttgg agttttaaac   2280
tccaatgaga ttttccatga tccctttcaa ataaccctac ttaatctctc ttcatagccc   2340
acagtaccaa gaagcctttg ataagctctg gattgaaaag aagcagttct ttttcaaaag   2400
atgtgctcat ttgaactagt gcatttccct ggaaacactt tgccaggact tgagatgggc   2460
actaagaagg aaaattcctc aaaggacatg tacagtcttg agatgcattc gcttctgtag   2520
ccatgagctt gctggtcttg agataaggtt agttggtgta gctaggttca tggtttggag   2580
tctttggcag ttctagagaa gcatgagcta ttagagactt ggagattgca tcaagtagag   2640
ccttttgagc ttttcactgt gtacctgggc cctctgtcgc tgcacgtttt agtgtctgaa   2700
atgtctttca gctgtagcag ttttctcggg accccagttt aaaatagctt actgtttaaa   2760
agatgtagct gtagctagca ttattgaact agcataatta tagtctaaat agcattatgt   2820
cttcagcctt gttatatgtt ggtgagtttt agtttcctct tctaaacggg aagaacagaa   2880
agatgtaatg attctgagct tccagagtga gacacctcta gagagaaata ccttcttctg   2940
aagactaccg tgtgattaca gataaattct gatatctttg tttagctttt gatatctata   3000
aacagggagt gtatttatc tctccaaatg agagaagaat aaacaataat gcaaggtaaa   3060
```

```
ggcaatagtg ctacactcta ggagttacca ctctttgtac atttatttat aaatactaag   3120
caagaggaac atgccataca tacactgact aagtcctaac aagtggcagt tcttatatca   3180
cacatttatc ttgccctcaa atgccagtcc agcatcagtt tagtctcatg catttggcag   3240
cataaggcag tttgagttcc acacttgctc tcagaagcaa tttaactccc acacttggga   3300
atcctttcct aagccacagt ttcagaccaa agttttggtg aaggctataa tcacagaagt   3360
ctgcacaagt agggagtctg aaggatctga gctccattca gcagtcagag cggcatccaa   3420
ccccaaggta atgctcagct cactttgata acttcaagct caaaggccct gaactgctga   3480
gttggaggtt gaaagatgtt tgggtaaaag caaggtaatt ggcggatagg atggttgtaa   3540
cgtaattgtt tcaagttgta ttagagacct ctgggttcta aggggatatg aaatccaacc   3600
tccactctcc actgagattc aagttaggtt aagtatgcct ttgagtaccc tcaagtcaca   3660
gcatgccact ctccttttct taactctaat atgtatctat aaagaacggg tagtagtcaa   3720
ctgagtcgac ggtatcgata agcttgatcc agcttttgtt cccttagtg agggttaatt    3780 gcgcgcttgg cgtaatcatg gtcatagctg tttcctgtgt gaaattgtta tccgctcaca   3840
attccacaca acatacgagc cggaagcata aagtgtaaag cctggggtgc ctaatgagtg   3900
agctaactca cattaattgc gttgcgctca ctgcccgctt tccagtcggg aaacctgtcg   3960
tgccagctgc attaatgaat cggccaacgc gcggggagag cggtttgcg tattgggcgc    4020 tcttccgctt cctcgctcac tgactcgctg cgctcggtcg ttcggctgcg gcgagcggta   4080
tcagctcact caaaggcggt aatacggtta tccacagaat caggggataa cgcaggaaag   4140
aacatgtgag caaaaggcca gcaaaaggcc aggaaccgta aaaaggccgc gttgctggcg   4200 ttttccata ggctccgccc ccctgacgag catcacaaaa atcgacgctc aagtcagagg    4260
tggcgaaacc cgacaggact ataaagatac caggcgtttc cccctggaag ctccctcgtg   4320
cgctctcctg ttccgaccct gccgcttacc ggatacctgt ccgcctttct cccttcggga   4380
agcgtggcgc tttctcatag ctcacgctgt aggtatctca gttcggtgta ggtcgttcgc   4440
tccaagctgg gctgtgtgca cgaaccccc gttcagcccg accgctgcgc cttatccggt    4500
aactatcgtc ttgagtccaa cccggtaaga cacgacttat cgccactggc agcagccact   4560
ggtaacagga ttagcagagc gaggtatgta ggcggtgcta cagagttctt gaagtggtgg   4620
cctaactacg gctacactag aaggacagta tttggtatct gcgctctgct gaagccagtt   4680
accttcggaa aaagagttgg tagctcttga tccggcaaac aaaccaccgc tggtagcggt   4740
ggtttttttg tttgcaagca gcagattacg cgcagaaaaa aaggatctca agaagatcct   4800
ttgatctttt ctacggggtc tgacgctcag tggaacgaaa actcacgtta agggattttg   4860
gtcatgagat tatcaaaaag gatcttcacc tagatccttt taaattaaaa atgaagtttt   4920
aaatcaatct aaagtatata tgagtaaact tggtctgaca gttaccaatg cttaatcagt   4980
gaggcaccta tctcagcgat ctgtctattt cgttcatcca tagttgcctg actccccgtc   5040
gtgtagataa ctacgatacg ggagggctta ccatctggcc ccagtgctgc aatgataccg   5100
cgagacccac gctcaccggc tccagattta tcagcaataa accagccagc cggaagggcc   5160
gagcgcagaa gtggtcctgc aactttatcc gcctccatcc agtctattaa ttgttgccgg   5220
gaagctagag taagtagttc gccagttaat agtttgcgca acgttgttgc cattgctaca   5280
ggcatcgtgg tgtcacgctc gtcgtttggt atggcttcat tcagctccgg ttcccaacga   5340
tcaaggcgag ttacatgatc cccatgttg tgcaaaaaag cggttagctc cttcggtcct    5400
```

```
ccgatcgttg tcagaagtaa gttggccgca gtgttatcac tcatggttat ggcagcactg     5460
cataattctc ttactgtcat gccatccgta agatgctttt ctgtgactgg tgagtactca     5520
accaagtcat tctgagaata gtgtatgcgg cgaccgagtt gctcttgccc ggcgtcaata     5580
cgggataata ccgcgccaca tagcagaact ttaaaagtgc tcatcattgg aaaacgttct     5640
tcggggcgaa aactctcaag gatcttaccg ctgttgagat ccagttcgat gtaacccact     5700
cgtgcaccca actgatcttc agcatctttt actttcacca gcgtttctgg gtgagcaaaa     5760
acaggaaggc aaaatgccgc aaaaaaggga taagggcga cacggaaatg ttgaatactc      5820
atactcttcc ttttcaata ttattgaagc atttatcagg gttattgtct catgagcgga      5880
tacatatttg aatgtattta gaaaaataaa caaatagggg ttccgcgcac atttccccga     5940
aaagtgccac ctaaattgta agcgttaata ttttgttaaa attcgcgtta aattttgtt      6000
aaatcagctc atttttttaac caataggccg aaatcggcaa aatcccttat aaatcaaaag    6060
aatagaccga gatagggttg agtgttgttc cagtttggaa caagagtcca ctattaaaga    6120
acgtggactc caacgtcaaa gggcgaaaaa ccgtctatca gggcgatggc ccactacgtg    6180
aaccatcacc ctaatcaagt ttttggggt cgaggtgccg taaagcacta atcggaacc     6240
ctaaagggag ccccgattt agagcttgac ggggaaagcc ggcgaacgtg gcgagaaagg    6300
aaggaagaa agcgaaagga gcgggcgcta gggcgctggc aagtgtagcg gtcacgctgc    6360
gcgtaaccac cacaccccgcc gcgcttaatg cgccgctaca gggcgcgtcc cattcgccat    6420
tcaggctgcg caactgttgg aagggcgat cggtgcgggc ctcttcgcta ttacgccagc    6480
tggcgaaagg gggatgtgct gcaaggcgat taagttgggt aacgccaggg ttttcccagt    6540
cacgacgttg taaaacgacg gccagtgagc gcgcgtaata cgactcacta tagggcgaat    6600
tggagct                                                              6607

<210> SEQ ID NO 59
<211> LENGTH: 202
<212> TYPE: DNA
<213> ORGANISM: Mus musculus

<400> SEQUENCE: 59
atgcagacac ctcacaagga gcacctgtac aagctgctgg tgatcggcga cctgggtgtg      60
ggcaagacca gcattatcaa gcgctatgtg caccaaaact tctcctcgca ctaccgggcc     120
accattggtg tggacttcgc gctgaaggtg ctccactggg acccagagac ggtggtgcgc     180
ttgcagctct gggacattgc tg                                              202

<210> SEQ ID NO 60
<211> LENGTH: 8218
<212> TYPE: DNA
<213> ORGANISM: Artificial sequence
<220> FEATURE:
<223> OTHER INFORMATION: pRab38-chtTAL-neo

<400> SEQUENCE: 60
caccgcatta ccctgggcgt tgaaaccgaa gaagacctgg atttgaaata ggcgttttct       60
ttacatttct aaagtgggac tcctcacttg taaaaggaaa aataatgata cttttaagac      120
ttccaggatg actaaatggt gtgtatgaga agatttataa acatctgccg ctacttacaa     180
tgataagacc acttgtgtgt tgttcagctt ggagaattta ggataggagt ggaggctgaa     240
agaaaagtaa gcccttagca tttcctctca ggtggcctct actttaggtc attaacagtt     300
gaataggcgc taagagatag cattaccact ttatagaagc ccaggcaaaa ggagattaaa     360
```

```
gggtttgcct aaattctttc aactctaagg gccagagaag acctaagtct actgctttgc      420
tgtttctcaa ggtctcccca actttacaac actgtgtggg tggcaacagg gcttaatagc      480
ctcagaagac ctgggtattt ttcgacactc agttctctcc ccggcagaac gtggaaaaca      540
aaatccacat aagtttgtgt catggacggg aggcgagaga aaaatctctg tgaaaggagt      600
aaagcactgt gcaaatacca gcttgacagg cagtagcact ggggtcccgg gtcctttagc      660
ttccagtccc aggagttgct cttgtctcct cccactctgg agtccgcaga gtaggaagga      720
ggattaaacc cggggagga gttccgcacc agctccctat cctgcgccag cacgcctagc       780
ctaagcgccc acatagagct ccggtctccg tcggtgccca gccccggctg tgcttcccag      840
agcaagctcc aggctccgca agacccgcgg gcctccagga tgcagacacc tcacaaggag      900
cacctgtaca agctgctggt gatcggcgac ctggtagtgg gcaagaccag cattattaaa      960
cggtacgtgc atcaaaatac cgggtagggg aggcgctttt cccaaggcag tctggagcat     1020
gcgctttagc agcccccgctg gcacttggc gctacacaag tggcctctgg cctcgcacac     1080
attccacatc caccggtagg cgccaaccgg ctccgttctt tggtggcccc ttcgcgccac     1140
cttctactcc tcccctagtc aggaagttcc ccccgcccc gcagctcgcg tcgtgcagga      1200
cgtgacaaat ggaagtagca cgtctcacta gtctcgtgca gatggacagc accgctgagc     1260
aatggaagcg ggtaggcctt tggggcagcg gccaatagca gctttgctcc ttcgctttct     1320
gggctcagag gctgggaagg ggtgggtccg ggggcgggct caggggcggg ctcaggggcg     1380
gggcgggcgc ccgaaggtcc tccggaggcc cggcattctg cacgcttcaa aagcgcacgt     1440
ctgccgcgct gttctcctct tcctcatctc cgggcctttc gacctgcagc caatatggga     1500
tcggccattg aacaagatgg attgcacgca ggttctccgg ccgcttgggt ggagaggcta     1560
ttcggctatg actgggcaca acagacaatc ggctgctctg atgccgccgt gttccggctg     1620
tcagcgcagg ggcgcccggt tctttttgtc aagaccgacc tgtccggtgc cctgaatgaa     1680
ctgcaggacg aggcagcgcg gctatcgtgg ctggccacga cgggcgttcc ttgcgcagct     1740
gtgctcgacg ttgtcactga agcgggaagg gactggctgc tattgggcga agtgccgggg     1800
caggatctcc tgtcatctca ccttgctcct gccgagaaag tatccatcat ggctgatgca     1860
atgcggcggc tgcatacgct tgatccggct acctgcccat tcgaccacca agcgaaacat     1920
cgcatcgagc gagcacgtac tcggatggaa gccggtcttg tcgatcagga tgatctggac     1980
gaagagcatc aggggctcgc gccagccgaa ctgttcgcca ggctcaaggc gcgcatgccc     2040
gacggcgatg atctcgtcgt gacccatggc gatgcctgct tgccgaatat catggtggaa     2100
aatggccgct ttctggatt catcgactgt ggccggctgg gtgtggcgga ccgctatcag      2160
gacatagcgt tggctacccg tgatattgct gaagagcttg gcggcgaatg ggctgaccgc     2220
ttcctcgtgc tttacggtat cgccgctccc gattcgcagc gcatcgcctt ctatcgcctt     2280
cttgacgagt tcttctgagg ggatcaattc tctagagctc gctgatcagc ctcgactgtg     2340
ccttctagtt gccagccatc tgttgtttgc ccctcccccg tgccttcctt gaccctggaa     2400
ggtgccactc ccactgtcct ttcctaataa aatgaggaaa ttgcatcgca ttgtctgagt     2460
aggtgtcatt ctattctggg gggtggggtg ggcaggaca gcaaggggga ggattgggaa      2520
gacaatagca ggcatgctgg ggatgcggtg gctctatgg cttctgaggc ggaaagaacc      2580
agctggggtt tctcctctca ttatcgagcc accattggtg tggacttcgc gctgaaggtg     2640
ctccactggg acccagagac ggtggtgcgc ttgcagctct gggacattgc tggtgagcga     2700
```

```
tcagagcagc gcgcaacggg tgagggtgga gtgagccagt gaggagttcg ggggtgaagg    2760
ttcggggagt ggaaaatgac ttttcagtcg gttccagtcc cgggacccct gagtgcaatc    2820
aagcaggaga tccggatcgc ctgggcgctc cactcttgga aagtttggct taatggcttg    2880
gaaacctgat ttcaaagaaa tggaagtgtt ttcttttctt tctttccttt tttttttttt    2940
ttttttttct tttgctgttg tttctgttgg agtcgtcccc actctacctg taacttctag    3000
ataacttcgc tggctctcac tggctgtgag aaagcgaacc actttctcct gggattcttg    3060
ggtgcagaga aggctgtcgc ctggactcac aaggagattg tagtcgcatt cttgtttcat    3120
tctagtcctt ttctggacac aggtagccgc gacttggccc agagtatctc acgtggcttt    3180
catccttcgt gtttagaggg gaagccccta ggaaatttaa gaaggagcag gattatctta    3240
ggaatttagt ttcttttcaaa tctcactact atcatctcct tgcttattgg cctcttcagt    3300
cagaaaaatt tgagatgcta aatttgtata catctagaac gaactatctc ttctcactcc    3360
actcccctct tccccatctc tcttccgtct ccctccatcc ttggctatct cttcttcact    3420
ttccatttca acaggagac tgtgtatgtt ttttaggaaa acattaaaaa aaaaaccaca    3480
aaaacaaaaa caaaacggag acagggtccc gtcatgtaac tctgctaacc tatatcaagc    3540
tgaccttgac ctcatagaga cccacttgcc tctgcctccc tagaggcaag ggtcggggtt    3600
atggtgatgt taatgtcgtt tgctttaaga ttccttgatt tgatcttggt gtattttttg    3660
agaaatctaa agtatgaaat cagagtttga ctaacagctt ctaccagctc ctagccacaa    3720
taaagactga ggcaggctat agttagtgct caatactggg tcctacctgg ctgcttgtaa    3780
cctgggcatg cctagcattc tagatgctaa ctcaccaaag cagtagcatt ttaagctgca    3840
aatggctagg cagcgacagc tcaagaatct tcttgctttg gagttttaaa ctccaatgag    3900
attttccatg atccctttca ataacccta cttaatctct cttcatagcc cacagtacca    3960
agaagccttt gataagctct ggattgaaaa gaagcagttc ttttcaaaa gatgtgctca    4020
tttgaactag tgcatttccc tggaaacact ttgccaggac ttgagatggg cactaagaag    4080
gaaaattcct caaaggacat gtacagtctt gagatgcatt cgcttctgta gccatgagct    4140
tgctggtctt gagataaggt tagttggtgt agctaggttc atggtttgga gtctttggca    4200
gttctagaga agcatgagct attagagact tggagattgc atcaagtaga gccttttgag    4260
cttttcactg tgtacctggg ccctctgtcg ctgcacgttt tagtgtctga aatgtctttc    4320
agctgtagca gttttctcgg gaccccagtt taaaatagct tactgtttaa aagatgtagc    4380
tgtagctagc attattgaac tagcataatt atagtctaaa tagcattatg tcttcagcct    4440
tgttatatgt tggtgagttt tagtttcctc ttctaaacgg gaagaacaga aagatgtaat    4500
gattctgagc ttcagagtg agacacctct agagagaaat accttcttct gaagactacc    4560
gtgtgattac agataaattc tgatatcttt gtttagcttt tgatatctat aaacagggag    4620
tgtattttat ctctccaaat gagagaagaa taaacaataa tgcaaggtaa aggcaatagt    4680
gctacactct aggagttacc actctttgta catttattta taaatactaa gcaagaggaa    4740
catgccatac atacactgac taagtcctaa caagtggcag ttcttatatc acacatttat    4800
cttgccctca aatgccagtc cagcatcagt ttagtctcat gcatttggca gcataaggca    4860
gtttgagttc cacacttgct ctcagaagca atttaactcc cacacttggg aatcctttcc    4920
taagccacag tttcagacca aagttttggt gaaggctata atcacagaag tctgcacaag    4980
tagggagtct gaaggatctg agctccattc agcagtcaga gcggcatcca accccaaggt    5040
aatgctcagc tcactttgat aacttcaagc tcaaaggccc tgaactgctg agttggaggt    5100
```

```
tgaaagatgt ttgggtaaaa gcaaggtaat tggcggatag gatggttgta acgtaattgt    5160
ttcaagttgt attagagacc tctgggttct aagggggatat gaaatccaac ctccactctc    5220
cactgagatt caagttaggt taagtatgcc tttgagtacc ctcaagtcac agcatgccac    5280 tctcctttc ttaactctaa tatgtatcta taaagaacgg gtagtagtca actgagtcga    5340
cggtatcgat aagcttgatc cagcttttgt tcccttagt gagggttaat tgcgcgcttg    5400
gcgtaatcat ggtcatagct gtttcctgtg tgaaattgtt atccgctcac aattccacac    5460
aacatacgag ccggaagcat aaagtgtaaa gcctggggtg cctaatgagt gagctaactc    5520
acattaattg cgttgcgctc actgcccgct ttccagtcgg gaaacctgtc gtgccagctg    5580
cattaatgaa tcggccaacg cgcggggaga ggcggtttgc gtattgggcg ctcttccgct    5640
tcctcgctca ctgactcgct gcgctcggtc gttcggctgc ggcgagcggt atcagctcac    5700
tcaaaggcgg taatacggtt atccacagaa tcaggggata acgcaggaaa gaacatgtga    5760
gcaaaaggcc agcaaaaggc caggaaccgt aaaaaggccg cgttgctggc gtttttccat    5820
aggctccgcc ccctgacga gcatcacaaa aatcgacgct caagtcagag gtggcgaaac    5880
ccgacaggac tataaagata ccaggcgttt ccccctggaa gctccctcgt gcgctctcct    5940
gttccgaccc tgccgcttac cggatacctg tccgcctttc tcccttcggg aagcgtggcg    6000
ctttctcata gctcacgctg taggtatctc agttcggtgt aggtcgttcg ctccaagctg    6060
ggctgtgtgc acgaaccccc cgttcagccc gaccgctgcg ccttatccgg taactatcgt    6120
cttgagtcca acccggtaag acacgactta tcgccactgg cagcagccac tggtaacagg    6180
attagcagag cgaggtatgt aggcggtgct acagagttct tgaagtggtg gcctaactac    6240
ggctacacta aaggacagt atttggtatc tgcgctctgc tgaagccagt taccttcgga    6300
aaaagagttg gtagctcttg atccggcaaa caaaccaccg ctggtagcgg tggtttttt    6360 gtttgcaagc agcagattac gcgcagaaaa aaaggatctc aagaagatcc tttgatcttt    6420
tctacggggt ctgacgctca gtggaacgaa aactcacgtt aagggatttt ggtcatgaga    6480
ttatcaaaaa ggatcttcac ctagatcctt ttaaattaaa aatgaagttt taaatcaatc    6540
taaagtatat atgagtaaac ttggtctgac agttaccaat gcttaatcag tgaggcacct    6600
atctcagcga tctgtctatt tcgttcatcc atagttgcct gactccccgt cgtgtagata    6660
actacgatac gggagggctt accatctggc cccagtgctg caatgatacc gcgagaccca    6720
cgctcaccgg ctccagattt atcagcaata aaccagccag ccggaagggc cgagcgcaga    6780
agtggtcctg caactttatc cgcctccatc cagtctatta attgttgccg ggaagctaga    6840
gtaagtagtt cgccagttaa tagtttgcgc aacgttgttg ccattgctac aggcatcgtg    6900
gtgtcacgct cgtcgtttgg tatggcttca ttcagctccg gttcccaacg atcaaggcga    6960
gttacatgat cccccatgtt gtgcaaaaaa gcggttagct ccttcggtcc tccgatcgtt    7020
gtcagaagta agttggccgc agtgttatca ctcatggtta tggcagcact gcataattct    7080
cttactgtca tgccatccgt aagatgcttt tctgtgactg gtgagtactc aaccaagtca    7140
ttctgagaat agtgtatgcg gcgaccgagt tgctcttgcc cggcgtcaat acgggataat    7200
accgcgccac atagcagaac tttaaaagtg ctcatcattg gaaaacgttc ttcggggcga    7260
aaactctcaa ggatcttacc gctgttgaga tccagttcga tgtaacccac tcgtgcaccc    7320
aactgatctt cagcatcttt tactttcacc agcgtttctg ggtgagcaaa aacaggaagg    7380
caaaatgccg caaaaaaggg aataagggcg acacggaaat gttgaatact catactcttc    7440
```

| | |
|---|---|
| ctttttcaat attattgaag catttatcag ggttattgtc tcatgagcgg atacatattt | 7500 |
| gaatgtattt agaaaaataa acaaataggg gttccgcgca catttccccg aaaagtgcca | 7560 |
| cctaaattgt aagcgttaat atttgttaa aattcgcgtt aaattttgt taaatcagct | 7620 |
| cattttttaa ccaataggcc gaaatcggca aaatcccta taaatcaaaa gaatagaccg | 7680 |
| agatagggtt gagtgttgtt ccagtttgga acaagagtcc actattaaag aacgtggact | 7740 |
| ccaacgtcaa agggcgaaaa accgtctatc agggcgatgg cccactacgt gaaccatcac | 7800 |
| cctaatcaag ttttttgggg tcgaggtgcc gtaaagcact aaatcggaac cctaaaggga | 7860 |
| gccccccgatt tagagcttga cggggaaagc cggcgaacgt ggcgagaaag gaagggaaga | 7920 |
| aagcgaaagg agcgggcgct agggcgctgg caagtgtagc ggtcacgctg cgcgtaacca | 7980 |
| ccacacccgc cgcgcttaat gcgccgctac agggcgcgtc ccattcgcca ttcaggctgc | 8040 |
| gcaactgttg ggaagggcga tcggtgcggg cctcttcgct attacgccag ctggcgaaag | 8100 |
| ggggatgtgc tgcaaggcga ttaagttggg taacgccagg gttttcccag tcacgacgtt | 8160 |
| gtaaaacgac ggccagtgag cgcgcgtaat acgactcact ataggggcgaa ttggagct | 8218 |

<210> SEQ ID NO 61
<211> LENGTH: 9989
<212> TYPE: DNA
<213> ORGANISM: Artificial sequence
<220> FEATURE:
<223> OTHER INFORMATION: pCMV-Rab-Reporter (hygro)

<400> SEQUENCE: 61

| | |
|---|---|
| gaattcgagc ttgcatgcct gcaggtcgtt acataactta cggtaaatgg cccgcctggc | 60 |
| tgaccgccca acgacccccg cccattgacg tcaataatga cgtatgttcc catagtaacg | 120 |
| ccaataggga ctttccattg acgtcaatgg gtggagtatt tacggtaaac tgcccacttg | 180 |
| gcagtacatc aagtgtatca tatgccaagt acgccccta ttgacgtcaa tgacggtaaa | 240 |
| tggcccgcct ggcattatgc ccagtacatg accttatggg actttcctac ttggcagtac | 300 |
| atctacgtat tagtcatcgc tattaccatg gtgatgcggt tttggcagta catcaatggg | 360 |
| cgtggatagc ggtttgactc acggggattt ccaagtctcc accccattga cgtcaatggg | 420 |
| agtttgtttt ggcaccaaaa tcaacgggac tttccaaaat gtcgtaacaa ctccgcccca | 480 |
| ttgacgcaaa tgggcggtag gcgtgtacgg tgggaggtct atataagcag agctcgttta | 540 |
| gtgaaccgtc agatcgcctg gagacgccat ccacgctgtt ttgacctcca tagaagacac | 600 |
| cgggaccgat ccagcctccg gactctagag gatccggtac tcgaggacac tgcagagacc | 660 |
| tacttcacta caaccggta tggtcgccag tagcttggca ctggccgtcg ttttacaacg | 720 |
| tcgtgactgg gaaaaccctg gcgttaccca acttaatcgc cttgcagcac atccccctt | 780 |
| cgccagctgg cgtaatagcg aagaggcccg caccgatcgc ccttcccaac agttgcgcag | 840 |
| cctgaatggc gaatgcgct ttgcctggtt tccggcacca gaagcggtgc cggaaagctg | 900 |
| gctggagtgc gatcttcctg aggccgatac tgtcgtcgtc ccctcaaact ggcagatgca | 960 |
| cggttacgat gcgcccatct acaccaacgt gacctatccc attacggtca atccgccgtt | 1020 |
| tgttcccacg gagaatccga cgggttgtta ctcgctcaca tttaatgttg atgaaagctg | 1080 |
| gctataaaac cggtacagtt cggccaccat ggtcgtatca agcgctatgt gcaccaaaac | 1140 |
| ttctcctcgc actaccgggc caccattggt cgagtagctt ggcactggcc gtcgttttac | 1200 |
| aacgtcgtga ctgggaaaac cctggcgtta cccaacttaa tcgccttgca gcacatcccc | 1260 |
| ctttcgccag ctggcgtaat agcgaagagg cccgcaccga tcgcccttcc caacagttgc | 1320 |

```
gcagcctgaa tggcgaatgg cgctttgcct ggtttccggc accagaagcg gtgccggaaa   1380
gctggctgga gtgcgatctt cctgaggccg atactgtcgt cgtccctca aactggcaga   1440
tgcacggtta cgatgcgccc atctacacca acgtgaccta tcccattacg gtcaatccgc   1500
cgtttgttcc cacggagaat ccgacggggtt gttactcgct cacatttaat gttgatgaaa   1560
gctggctaca ggaaggccag acgcgaatta tttttgatgg cgttaactcg gcgtttcatc   1620
tgtggtgcaa cgggcgctgg gtcggttacg gccaggacag tcgtttgccg tctgaatttg   1680
acctgagcgc attttttacgc gccggagaaa accgcctcgc ggtgatggtg ctgcgctgga   1740
gtgacggcag ttatctggaa gatcaggata tgtggcggat gagcggcatt ttccgtgacg   1800
tctcgttgct gcataaaccg actacacaaa tcagcgattt ccatgttgcc actcgcttta   1860
atgatgattt cagccgcgct gtactggagg ctgaagttca gatgtgcggc gagttgcgtg   1920
actacctacg ggtaacagtt tctttatggc agggtgaaac gcaggtcgcc agcggcaccg   1980
cgcctttcgg cggtgaaatt atcgatgagc gtggtggtta tgccgatcgc gtcacactac   2040
gtctgaacgt cgaaaacccg aaactgtgga cgccgaaat cccgaatctc tatcgtgcgg   2100
tggttgaact gcacaccgcc gacggcacgc tgattgaagc agaagcctgc gatgtcggtt   2160
tccgcgaggt gcggattgaa aatggtctgc tgctgctgaa cggcaagccg ttgctgattc   2220
gaggcgttaa ccgtcacgag catcatcctc tgcatggtca ggtcatggat gagcagacga   2280
tggtgcagga tatcctgctg atgaagcaga acaactttaa cgccgtgcgc tgttcgcatt   2340
atccgaacca tccgctgtgg tacacgctgt gcgaccgcta cggcctgtat gtggtggatg   2400
aagccaatat tgaaacccac ggcatggtgc caatgaatcg tctgaccgat gatccgcgct   2460
ggctaccggc gatgagcgaa cgcgtaacgc gaatggtgca cgcgatcgt aatcacccga   2520
gtgtgatcat ctggtcgctg gggaatgaat caggccacgg cgctaatcac gacgcgctgt   2580
atcgctggat caaatctgtc gatccttccc gcccggtgca gtatgaaggc ggcggagccg   2640
acaccacggc caccgatatt atttgcccga tgtacgcgcg cgtggatgaa gaccagccct   2700
tcccggctgt gccgaaatgg tccatcaaaa aatggctttc gctacctgga gagacgcgcc   2760
cgctgatcct ttgcgaatac gcccacgcga tgggtaacag tcttggcggt ttcgctaaat   2820
actggcaggc gtttcgtcag tatccccgtt tacagggcgg cttcgtctgg gactgggtgg   2880
atcagtcgct gattaaatat gatgaaaacg gcaacccgtg gtcggcttac ggcggtgatt   2940
ttggcgatac gccgaacgat cgccagttct gtatgaacgg tctggtcttt gccgaccgca   3000
cgccgcatcc agcgctgacg gaagcaaaac accagcagca gttttttccag ttccgttttat   3060
ccgggcaaac catcgaagtg accagcgaat acctgttccg tcatagcgat aacgagctcc   3120
tgcactggat ggtggcgctg gatggtaagc gctggcaag cggtgaagtg cctctggatg   3180
tcgctccaca aggtaaacag ttgattgaac tgcctgaact accgcagccg gagagcgccg   3240
ggcaactctg gctcacagta cgcgtagtgc aaccgaacgc gaccgcatgg tcagaagccg   3300
gcacatcag cgcctggcag cagtggcgtc tggcggaaaa cctcagtgtg acgctccccg   3360
ccgcgtccca cgccatcccg catctgacca ccagcgaaat ggattttgc atcgagctgg   3420
gtaataagcg ttggcaattt aaccgccagt caggctttct ttcacagatg tggattggcg   3480
ataaaaaaca actgctgacg ccgctgcgcg atcagttcac ccgtgcaccg ctggataacg   3540
acattggcgt aagtgaagcg acccgcattg accctaacgc ctgggtcgaa cgctggaagg   3600
cggcgggcca ttaccaggcc gaagcagcgt tgttgcagtg cacggcagat acacttgctg   3660
```

```
atgcggtgct gattacgacc gctcacgcgt ggcagcatca ggggaaaacc ttatttatca   3720
gccggaaaac ctaccggatt gatggtagtg gtcaaatggc gattaccgtt gatgttgaag   3780
tggcgagcga tacaccgcat ccggcgcgga ttggcctgaa ctgccagctg gcgcaggtag   3840
cagagcgggt aaactggctc ggattagggc cgcaagaaaa ctatcccgac cgccttactg   3900
ccgcctgttt tgaccgctgg gatctgccat tgtcagacat gtataccccg tacgtcttcc   3960
cgagcgaaaa cggtctgcgc tgcgggacgc gcgaattgaa ttatgggcca caccagtggc   4020
gcggcgactt ccagttcaac atcagccgct acagtcaaca gcaactgatg gaaaccagcc   4080
atcgccatct gctgcacgcg gaagaaggca catggctgaa tatcgacggt ttccatatgg   4140
ggattggtgg cgacgactcc tggagcccgt cagtatcggc ggaattccag ctgagcgccg   4200
gtcgctacca ttaccagttg gtctggtgtc aggggatccc ccgggctgca gccaatatgg   4260
gatcggccat tgaacaagat ggattgcacg caggttctcc ggccgcttgg gtggagaggc   4320
tattcggcta tgactgggca caacagacaa tcggctgctc tgatgccgcc gtgttccggc   4380
tgtcagcgca ggggcgcccg gttcttttg tcaagaccga cctgtccggt gccctgaatg   4440
aactgcagga cgaggcagcg cggctatcgt ggctggccac gacgggcgtt ccttgcgcag   4500
ctgtgctcga cgttgtcact gaagcgggaa gggactggct gctattgggc gaagtgccgg   4560
ggcaggatct cctgtcatct caccttgctc ctgccgagaa agtatccatc atggctgatg   4620
caatgcggcg gctgcatacg cttgatccgg ctacctgccc attcgaccac caagcgaaac   4680
atcgcatcga gcgagcacgt actcggatgg aagccggtct tgtcgatcag gatgatctgg   4740
acgaagagca tcaggggctc gcgccagccg aactgttcgc caggctcaag gcgcgcatgc   4800
ccgacggcga ggatctcgtc gtgacccatg gcgatgcctg cttgccgaat atcatggtgg   4860
aaaatggccg cttttctgga ttcatcgact gtggccggct gggtgtggcg gaccgctatc   4920
aggacatagc gttggctacc cgtgatattg ctgaagagct tggcggcgaa tgggctgacc   4980
gcttcctcgt gctttacggt atcgccgctc ccgattcgca gcgcatcgcc ttctatcgcc   5040
ttcttgacga gttcttctga ggggatcaat tctctagagc tcgctgatca gcctcgactg   5100
tgccttctag ttgccagcca tctgttgttt gcccctcccc cgtgccttcc ttgaccctgg   5160
aaggtgccac tcccactgtc ctttcctaat aaaatgagga aattgcatcg cattgtctga   5220
gtaggtgtca ttctattctg ggggtgggg tggggcagga cagcaagggg gaggattggg   5280
aagacaatag caggcatgct ggggatgcgg tgggctctat ggcttctgag acggaaagaa   5340
ccagctgggg ctcgatcctc tagagtcgac gtttgatctg atatcatcga tgaattctac   5400
cgggtagggg aggcgctttt cccaaggcag tctggagcat gcgctttagc agccccgctg   5460
ggcacttggc gctacacaag tggcctctgg cctcgcacac attccacatc caccggtagg   5520
cgccaaccgg ctccgttctt tggtggcccc ttcgcgccac cttctactcc tcccctagtc   5580
aggaagttcc cccccgcccc gcagctcgcg tcgtgcagga cgtgacaaat ggaagtagca   5640
cgtctcacta gtctcgtgca gatggacagc accgctgagc aatggaagcg ggtaggcctt   5700
tggggcagcg gccaatagca gctttgctcc ttcgctttct gggctcagag gctgggaagg   5760
ggtgggtccg ggggcgggct caggggcggg ctcaggggcg gggcgggcgc ccgaaggtcc   5820
tccggaggcc cggcattctg cacgcttcaa aagcgcacgt ctgccgcgct gttctcctct   5880
tcctcatctc cgggcctttc gacccgatcca gccgccacca tgaaaaagcc tgaactcacc   5940
gcgacgtctg tcgagaagtt tctgatcgaa aagttcgaca cgtctccga cctgatgcag   6000
ctctcggagg gcgaagaatc tcgtgctttc agcttcgatg taggagggcg tggatatgtc   6060
```

```
ctgcgggtaa atagctgcgc cgatggtttc tacaaagatc gttatgttta tcggcacttt    6120
gcatcggccg cgctcccgat tccggaagtg cttgacattg gggaattcag cgagagcctg    6180
acctattgca tctcccgccg tgcacagggt gtcacgttgc aagacctgcc tgaaaccgaa    6240
ctgcccgctg ttctgcagcc ggtcgcgsag gccatggatg cgatcgctgc ggccgatctt    6300
agccagacga gcgggttcgg cccattcgga ccgcaaggaa tcggtcaata cactacatgg    6360
cgtgatttca tatgcgcgat tgctgatccc catgtgtatc actggcaaac tgtgatggac    6420
gacaccgtca gtgcgtccgt cgcgcaggct ctcgatgagc tgatgctttg gccgaggac     6480 tgccccgaag tccggcacct cgtgcacgcg gatttcggct ccaacaatgt cctgacggac    6540
aatggccgca taacagcggt cattgactgg agcgaggcga tgttcgggga ttcccaatac    6600
gaggtcgcca acatcttctt ctggaggccg tggttggctt gtatggagca gcagacgcgc    6660
tacttcgagc ggaggcatcc ggagcttgca ggatcgccgc ggctccgggc gtatatgctc    6720
cgcattggtc ttgaccaact ctatcagagc ttggttgacg gcaatttcga tgatgcagct    6780
tgggcgcagg gtcgatgcga cgcaatcgtc cgatccggag ccgggactgt cgggcgtaca    6840
caaatcgccc gcagaagcgc ggccgtctgg accgatggct gtgtagaagt actcgccgat    6900
agtggaaacc gacgcccag cactcgtccg agggcaaagg aatagtcgag aaattgatga    6960
tctattaaac aataaagatg tccactaaaa tggaagtttt tcctgtcata ctttgttaag    7020
aagggtgaga acagagtacc tacattttga atggaaggat tggagctacg ggggtggggg    7080
tggggtggga ttagataaat gcctgctctt tactgaaggc tctttactat tgctttatga    7140
taatgtttca tagttggata tcataattta acaagcaaa accaaattaa gggccagctc     7200
attcctccca ctcatgatct atagatcaaa catgcatgaa gttcctattc gaagttcct    7260 attctctaga aagtatagga acttcataaa acctgcaggc atgcaagcga tcgcggccgg    7320
ccaaggcccg cggggccact agttctagag cggccagctt ggcgtaatca tggtcatagc    7380
tgtttcctgt gtgaaattgt tatccgctca caattccaca caacatacga gccggaagca    7440
taaagtgtaa agcctggggt gcctaatgag tgagctaact cacattaatt gcgttgcgct    7500
cactgcccgc tttccagtcg ggaaacctgt cgtgccagct gcattaatga atcggccaac    7560
gcgcggggag aggcggtttg cgtattgggc gctcttccgc ttcctcgctc actgactcgc    7620
tgcgctcggt cgttcggctg cggcgagcgg tatcagctca ctcaaaggcg gtaatacggt    7680
tatccacaga atcaggggat aacgcaggaa agaacatgtg agcaaaaggc cagcaaaagg    7740
ccaggaaccg taaaaaggcc gcgttgctgg cgttttccca taggctccgc cccctgacg    7800 agcatcacaa aaatcgacgc tcaagtcaga ggtggcgaaa cccgacagga ctataaagat    7860
accaggcgtt tccccctgga agctccctcg tgcgctctcc tgttccgacc ctgccgctta    7920
ccggatacct gtccgccttt ctcccttcgg gaagcgtggc gctttctcat agctcacgct    7980
gtaggtatct cagttcggtg taggtcgttc gctccaagct gggctgtgtg cacgaacccc    8040
ccgttcagcc cgaccgctgc gccttatccg gtaactatcg tcttgagtcc aacccggtaa    8100
gacacgactt atcgccactg gcagcagcca ctggtaacag gattagcaga gcgaggtatg    8160
taggcggtgc tacagagttc ttgaagtggt ggcctaacta cggctacact agaaggacag    8220
tatttggtat ctgcgctctg ctgaagccag ttaccttcgg aaaaagagtt ggtagctctt    8280
gatccggcaa acaaaccacc gctggtagcg gtggtttttt tgtttgcaag cagcagatta    8340
cgcgcagaaa aaaaggatct caagaagatc ctttgatctt ttctacgggg tctgacgctc    8400
```

```
agtggaacga aaactcacgt taagggattt tggtcatgag attatcaaaa aggatcttca      8460
cctagatcct tttaaattaa aaatgaagtt ttaaatcaat ctaaagtata tatgagtaaa      8520
cttggtctga cagttaccaa tgcttaatca gtgaggcacc tatctcagcg atctgtctat      8580
ttcgttcatc catagttgcc tgactccccg tcgtgtagat aactacgata cgggagggct      8640
taccatctgg ccccagtgct gcaatgatac cgcgagaccc acgctcaccg gctccagatt      8700
tatcagcaat aaaccagcca gccggaaggg ccgagcgcag aagtggtcct gcaactttat      8760
ccgcctccat ccagtctatt aattgttgcc gggaagctag agtaagtagt tcgccagtta      8820
atagtttgcg caacgttgtt gccattgcta caggcatcgt ggtgtcacgc tcgtcgtttg      8880
gtatggcttc attcagctcc ggttcccaac gatcaaggcg agttacatga tcccccatgt      8940
tgtgcaaaaa agcggttagc tccttcggtc ctccgatcgt tgtcagaagt aagttggccg      9000
cagtgttatc actcatggtt atggcagcac tgcataattc tcttactgtc atgccatccg      9060
taagatgctt ttctgtgact ggtgagtact caaccaagtc attctgagaa tagtgtatgc      9120
ggcgaccgag ttgctcttgc ccggcgtcaa tacgggataa taccgcgcca catagcagaa      9180
ctttaaaagt gctcatcatt ggaaaacgtt cttcggggcg aaaactctca aggatcttac      9240
cgctgttgag atccagttcg atgtaaccca ctcgtgcacc caactgatct tcagcatctt      9300
ttactttcac cagcgtttct gggtgagcaa aaacaggaag gcaaaatgcc gcaaaaaagg      9360
gaataagggc gacacggaaa tgttgaatac tcatactctt cctttttcaa tattattgaa      9420
gcatttatca gggttattgt ctcatgagcg gatacatatt tgaatgtatt tagaaaaata      9480
aacaaatagg ggttccgcgc acatttcccc gaaaagtgcc acctgacgtc taagaaacca      9540
ttattatcat gacattaacc tataaaaata ggcgtatcac gaggccctttt cgtctcgcgc      9600 gtttcggtga tgacggtgaa aacctctgac acatgcagct cccggagacg gtcacagctt      9660
gtctgtaagc ggatgccggg agcagacaag cccgtcaggg cgcgtcagcg ggtgttggcg      9720
ggtgtcgggc tggcttaac tatgcggcat cagagcagat tgtactgaga gtgcaccata      9780
tgcggtgtga ataccgcac agatgcgtaa ggagaaaata ccgcatcagg cgccattcgc      9840
cattcaggct gcgcaactgt tgggaagggc gatcggtgcg ggcctcttcg ctattacgcc      9900
agctggcgaa agggggatgt gctgcaaggc gattaagttg ggtaacgcca gggttttccc      9960
agtcacgacg ttgtaaaacg acggccagt                                        9989
```

<210> SEQ ID NO 62
<211> LENGTH: 12
<212> TYPE: DNA
<213> ORGANISM: Artificial Sequence
<220> FEATURE:
<223> OTHER INFORMATION: DNA target sequence

<400> SEQUENCE: 62

```
attctgggac gt                                                            12
```

<210> SEQ ID NO 63
<211> LENGTH: 14
<212> TYPE: DNA
<213> ORGANISM: Mus musculus

<400> SEQUENCE: 63

```
ggtggcccgg tagt                                                          14
```

<210> SEQ ID NO 64
<211> LENGTH: 34

```
<212> TYPE: PRT
<213> ORGANISM: Xanthomonas campestris

<400> SEQUENCE: 64

Leu Thr Pro Glu Gln Val Val Ala Ile Ala Ser Asn Ile Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 65
<211> LENGTH: 34
<212> TYPE: PRT
<213> ORGANISM: Xanthomonas campestris

<400> SEQUENCE: 65

Leu Thr Pro Gln Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 66
<211> LENGTH: 34
<212> TYPE: PRT
<213> ORGANISM: Xanthomonas campestris

<400> SEQUENCE: 66

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly

<210> SEQ ID NO 67
<211> LENGTH: 34
<212> TYPE: PRT
<213> ORGANISM: Xanthomonas campestris

<400> SEQUENCE: 67

Leu Thr Pro Gln Gln Val Val Ala Ile Ala Ser Asn Asn Gly Gly Lys
1               5                   10                  15

Gln Ala Leu Glu Thr Val Gln Ala Leu Leu Pro Val Leu Cys Gln Ala
            20                  25                  30

His Gly
```

PROTEIN HAVING NUCLEASE ACTIVITY, FUSION PROTEINS AND USES THEREOF

The text file entitled "Vossius_03USnew_ST25.txt," created on Jun. 27, 2016, having 404,886 bytes of data, is hereby incorporated by reference in its entirety in this application.

The present invention relates to a nucleic acid molecule encoding (I) a polypeptide having the activity of an endonuclease, which is (a) a nucleic acid molecule encoding a polypeptide comprising or consisting of the amino acid sequence of SEQ ID NO: 1; (b) a nucleic acid molecule comprising or consisting of the nucleotide sequence of SEQ ID NO: 2; (c) a nucleic acid molecule encoding an endonuclease, the amino acid sequence of which is at least 70% identical to the amino acid sequence of SEQ ID NO: 1; (d) a nucleic acid molecule comprising or consisting of a nucleotide sequence which is at least 50% identical to the nucleotide sequence of SEQ ID NO: 2; (e) a nucleic acid molecule which is degenerate with respect to the nucleic acid molecule of (d); or (f) a nucleic acid molecule corresponding to the nucleic acid molecule of any one of (a) to (e) wherein T is replaced by U; (II) a fragment of the polypeptide of (I) having the activity of an endonuclease. Also, the present invention relates to a vector comprising the nucleic acid molecule and a protein encoded by said nucleic acid molecule. Further, the invention relates to a method of modifying the genome of a eukaryotic cell and a method of producing a non-human vertebrate or mammal.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

Nucleases remain to be one of the most important tools of molecular biologists since their discovery in the late 1960s. Nucleases are enzymes capable of cleaving the phosphodiester bonds between the nucleotide subunits of nucleic acids. Enzymes catalyzing DNA and RNA cleavage are integral parts of major DNA metabolic processes such as DNA replication, DNA recombination, DNA repair, site-specific recombination and RNA splicing. In addition, nuclease activities are essential in RNA processing, maturation, RNA interference and are components of microbial defense mechanisms.

RNA and DNA present only two types of phosphodiester bonds for cleavage, 5'- or 3'- of a scissile phosphate and the fundamental chemistry is bimolecular nucleophilic substitution. Nonetheless, structures and catalytic mechanisms of RNA and DNA nucleases are greatly varied and complex. Nucleases may be endo- or exonucleases, DNA or RNA specific, topoisomerases, recombinases, ribozymes, or RNA splicing enzymes. Their reaction can be divided into the three stages of nucleophilic attack, the formation of a negatively charged penta-covalent intermediate and the breakage of the scissile bond. Nucleases utilize a variety of nucleophiles to cleave a scissile phosphate bond. The most common nucleophiles are water molecules deprotonated by a general base for direct hydrolysis. For DNA cleavage, the side chains of Ser, Tyr and His serve as nucleophiles to form a covalent DNA phosphoryl-protein intermediate, which is subsequently resolved either by phosphoryl transfer reaction back to DNA during recombination and topoisomerization or by hydrolysis in two-step cleavage reactions. To enable the controlled degradation or processing of cellular DNA or RNA, nuclease activities are strictly regulated by stringent substrate specificity, confined localization, or by potent inhibitors.

For convenience nucleases can be classified according to their catalytic mechanism into three major classes based on their metal-ion dependence (Yang, W. (2011). Q. Rev. Biophys. 44(1): 1-93). These classes of two-metal-ion-dependent, one-metal-ion-dependent and metal-independent nucleases are further divided into families or superfamilies according to sequence and structure conservation and functional diversity.

Restriction Endonucleases

Various families of restriction endonucleases are found among all three catalytic classes. The type I, III and IV restriction enzymes are multisubunit and complex molecular machines that combine multiple activities including restriction, methylation and DNA translocation, require additional cofactors (AdoMet, ATP or GTP), bind more than one target site, and cleave outside the recognition sequence, often at a random distance. Type II restriction endonucleases are enzymes that recognize short DNA sequences (usually 4-8-bp long) and cleave the target in both strands at, or in close proximity to the recognition site. Orthodox type II restriction enzymes are homodimeric, cleave within palindromic sequences, require $Mg^{2+}$ ions and can act on single copies of their targets. Because of their remarkably high specificity in recognizing and cleaving their target sequences, they are of high interest as the most frequently used tools for recombinant DNA technology (Pingoud, A., M. Fuxreiter, et al. (2005). Cell Mol Life Sci 62(6): 685-707; Orlowski, J. and J. M. Bujnicki (2008). Nucleic Acids Res 36(11): 3552-69).

In nature, type II REases (restriction endonucleases) are found in prokaryotic organisms, where they form restriction-modification systems with DNA methyltransferases of the same or very similar substrate specificity. DNA methyltransferases use S-adenosylmethionine (AdoMet) as a methyl group donor to modify specific bases in the target sequence, thereby rendering it resistant to cleavage by the restriction enzyme. While the Restriction-Modification system's own DNA is protected against self-degradation by the nuclease, any foreign DNA (e.g. from phages) that invades the host cell and lacks methylation, can be efficiently destroyed. In order to distinguish the components of restriction-modification systems the names of methylases and nucleases are preceded with 'M'. and 'R.' prefixes (e.g. M.FokI and R.FokI).

Many commonly used type-II restriction endonucleases share the conserved motif PD-(D/E)XK. Said motif is generally found in proteins that interact with nucleic acid molecules such as DNA and is not limited to the presence in nucleases. The three catalytic residues are located close to each other on an uneven β-hairpin. The first D is located at the beginning of the first and shorter strand, and the E and K, separated by a hydrophobic residue x, are located in the middle of the second and longer strand. The first D is most conserved and coordinates both metal ions, whereas the second E can be replaced by Q, D, N, H or S, and the third K can be replaced E, Q, D, S, N or T. By varying dimeric interfaces and thus the relative positions of the two catalytic centers, dimeric endonucleases can cleave DNA to generate blunt ends or staggered ends with various 5'- or 3'-overhangs. The catalytic module invariably approaches DNA from the minor groove side, and the sequence-specific binding is conducted by a separate module/subdomain in the major groove. The first two carboxylates of the DEK motif coordinate the metal ions. The third, which usually is hydrogen bonded with both the nucleophilic water and the DNA-binding module in the major groove, couples DNA sequence recognition with the cleavage reaction. Members of this superfamily have a very diverse primary sequence and thus different structures surrounding the catalytic core. Database searches with restriction enzyme sequences typically reveal either no significant similarity to any protein, or very high similarity (>90% identity) to a few isoschizomers, and no similarity to other proteins. This strongly biased distribution of similarities and dissimilarities made comparative sequence analysis of all restricition enzymes difficult and raised a question whether the diversity of amino acid sequences of restriction endonucleases indicates polyphyletic evolution (convergence) or extreme divergence from a common ancestor.

While ~70% of restriction endonucleases belong to the PD-(D/E)XK superfamily, other superfamily members can be monomeric or tetrameric and be involved in other processes such as DNA repair and homologous recombination. In addition to endonucleases, members in this superfamily can also be 5'- or 3'-exonucleases. The most comprehensive source of information on restriction enzymes is the REBASE database (rebase.neb.com) that lists several thousand functionally characterized enzymes and several thousand putative enzymes, inferred from sequence comparisons or genomic analyses. Therefore, a large disproportion exists between the number of known or predicted sequences and the small number of ~50 experimentally characterized proteins with known three-dimensional structures. Presently, a large fraction of putative enzymes remains without any predictions or experimental data.

Type II REases are further subdivided into several types according to their recognition site symmetry, structural organization or cofactor requirement. Most of the restriction enzymes used for recombinant DNA work belong to type IIP (P—palindromic). Type IIA enzymes recognize asymmetric sequences, like Bpu10I, a dimer of non-identical subunits, each of which is responsible for cleavage of one strand of the DNA. Type IIB enzymes cleave DNA at both sides of the recognition sequence, an example being BpII that cleaves the topstrand 8 nucleotides before and 13 nucleotides after the recognition sequence, while the bottom strand is cleaved 13 nucleotides before and 8 nucleotides after the recognition sequence. Type IIC enzymes have both cleavage and modification domains within one polypeptide. Type IIE enzymes need to interact with two copies of their recognition sequence for efficient cleavage, one copy being the target for cleavage, the other serving as an allosteric effector. Type IIE enzymes like NaeI recognize palindromic nucleotide sequences in a manner similar to the type IIP enzymes and cleave DNA within the boundaries of their recognition sites; however, they possess a separate DNA binding domain to perform allosteric function. Type IIF enzymes are typically homotetrameric restriction endonucleases that also interact with two copies of their recognition site, but cleave both of them in a concerted manner. Type IIG enzymes, essentially a subgroup of Type IIC enzymes, have both cleavage and modification domains within one polypeptide. They are in general stimulated by AdoMet, but otherwise behave as typical Type II enzymes. Type IIH enzymes behave like type II enzymes, but their genetic organization resembles Type I Restriction-Modification systems. Type IIM enzymes recognize a specific methylated sequence and cleave the DNA at a fixed site. The best known representative is DpnI which cleaves Gm6ATC, Gm6ATm4C and Gm6ATm5C, yet not GATC, GATm4C, GATm5C or hemimethylated sites. Many other restriction enzymes are more or less tolerant to methylation, but for Type IIM enzymes the methyl group is an essential recognition element. Orthodox Type IIP enzymes like EcoRI recognize symmetric nucleotide sequences and cleave within their recognition sites. They share both a common structural core comprising the five stranded mixed β-sheet flanked by α-helices. The DNA binding sites of Type IIP enzymes, however, are highly diverse and usually form a patch on the protein surface composed of amino acid residues located on the different structural elements (α-helices, β-strands, loops). Orthodox Type IIP enzymes interact with DNA as homodimers, and each subunit contributes to the recognition of half of the palindromic sequence. Type IIS enzymes cleave at least one strand of the target DNA outside of the recognition sequence. The best-known type IIS enzyme is FokI, which like many other type IIS enzymes interacts with two recognition sites before cleaving DNA. Type IIS enzymes are active as homodimers and are composed of two domains, one responsible for target recognition and the other for catalysis (also serving as the dimerization domain). This is apparent from the crystal structure and biochemical studies of FokI (Bitinaite, J., D. A. Wah, et al. (1998). Proc Natl Acad Sci USA 95(18): 10570-5; Wah, D. A., J. Bitinaite, et al. (1998). Proc Natl Acad Sci USA 95(18): 10564-9). Crystal structure analysis of FokI reveals that it is composed of a specific DNA binding module fused to the cleavage domain that possesses a conserved endonuclease catalytic core but cuts DNA in a nonspecific manner. Modular architecture is also characteristic for the type IIS enzyme BfiI, which is composed of two DNA binding domains fused to the dimeric catalytic core similar to the nonspecific nuclease belonging to the phospholipase D family. The presence of a separate nuclease domain has been also reported from the crystal structure of the Type IIP enzyme SdaI (Tamulaitiene, G., A. Jakubauskas, et al. (2006). Structure 14(9): 1389-400)

Modified Restriction Enzymes and Chimaeric Nucleases as Tools for Genome Editing Nucleases that cleave nucleic acid molecules at specific sites rather than randomly are of increasing importance in emerging technologies such as, e.g., in genetic engineering and gene targeting. Gene targeting is a process in which a DNA molecule introduced into a cell replaces the corresponding chromosomal segment by homologous recombination, and thus presents a precise way to manipulate the genome (Capecchi, M. R. (2005). Nat Rev Genet 6(6): 507-12). In the past, the application of gene targeting to mammalian cells has been limited by its low efficiency. Experiments in model systems have demonstrated that the frequency of homologous recombination of a gene targeting vector is strongly increased if a double-strand break is induced within its chromosomal target sequence. Using the yeast homing endonuclease I-SceI, that cuts DNA at an 18 base pair-long recognition site, it was initially shown that homologous recombination and gene targeting are stimulated over 1000-fold in mammalian cells when a recognition site is inserted into a target gene and I-SceI is expressed in these cells (Rouet, P., Smih, F., Jasin, M.; Mol Cell Biol 1994; 14: 8096-8106; Rouet, P., Smih, F. Jasin, M; Proc Natl Acad Sci USA 1994; 91: 6064-6068). In the absence of a gene targeting vector for homology directed repair, the cells frequently close the double-strand break by non-homologous end-joining (NHEJ). Since this mechanism is error-prone it frequently leads to the deletion or insertion of multiple nucleotides at the cleavage site. If the cleavage site is located within the coding region of a gene it is thereby possible to identify and select mutants that exhibit reading frameshift mutations from a mutagenised population and that represent non-functional knockout alleles of the targeted gene.

Therefore, sequence specific nucleases represent an important tool for biotechnology to modify the genome of model organisms or cell lines. In order to construct nucleases that specifically recognise new target sequences within genes, two approaches have been pursued that rely on the modification of natural homing endonucleases or on the fusion of a natural or engineered DNA binding domain to a nuclease domain. Such modified restriction enzymes or chimaeric nucleases can target large DNA sites (up to 36 bp) and can be engineered to bind to desired DNA sequences.

Homing endonucleases, such as I-SceI of yeast, are natural genetic elements that catalyze their own duplication into recipient alleles by creating site-specific DSBs that initiate their own genetic transfer by homologous recombination. A key feature of these enzymes is that they create double-strand breaks at recognition sites that are 14- to 40-bp long. The major limitation to the use of homing endonucleases in gene targeting is that each enzyme recognises exclusively its natural target sequence. By protein engineering it has been attempted to modify homing endonucleases in order to recognize new target sites. In this work, modifications could be made that alter the natural target site within some nucleotides, but it is yet not possible to design enzymes specific for entirely new target regions.

Due to the difficulty of manipulating the sequence recognition of homing enonucleases, zinc-finger nucleases (ZFN) are presently the most commonly used artificial nucleases for genetic engineering (Urnov, F. D., E. J. Rebar, et al. Nat Rev Genet 11(9): 636-46). Zinc-finger nucleases were developed by fusing the nonsequence-specific cleavage domain of the FokI type IIS restriction endonuclease (Fn domain) to a new DNA binding domain. The advantage of zinc-finger nucleases is that the zinc-finger DNA binding domain can be modified to recognize novel target sequences, including those in endogenous genes. The protein modules known as zinc-fingers are found in the DNA-binding domain of the most abundant family of transcription factors in most eukaryotic genomes. Each finger is composed of 30 amino-acids, coordinates one Zn2+-ion using two cysteines and two histidine residues, and contacts primarily three basepairs of DNA. Two critical features of the structure are that each finger binds its 3-bp target site independently and that each nucleotide seemed to be contacted by a single amino acid side chain projecting from one end of the α-helix into the major groove of the DNA. Individual fingers have been designed to recognize many of the 64 different target triplets, but the greatest success has been in designing zinc fingers to recognize 5'-GNN-3' triplets. Although zinc-finger recognition codes have been proposed, no code currently exists that consistently results in zinc-fingers with high affinity binding. Improving the specificity of zinc-finger binding, such as by increasing the number of fingers or by constructing multifinger proteins using two-finger units, remains an active area of research.

Using zinc-finger nucleases in the absence of a gene targeting vector for homology directed repair, knockout alleles were generated in mammalian cell lines and knockout zebra fish and rats were obtained upon the expression of ZFN mRNA in one cell embryos (Santiago Y, Chan E, Liu P Q, Orlando S, Zhang L, Urnov F D, Holmes M C, Guschin D, Waite A, Miller J C, Rebar E J, Gregory P D, Klug A, Collingwood T N.; Proc Natl Acad Sci USA 2008; 105:5809-5814; Doyon Y, McCammon J M, Miller J C, Faraji F, Ngo C, Katibah G E, Amora R, Hocking T D, Zhang L, Rebar E J, Gregory P D, Urnov F D, Amacher S L.; Nat Biotechnol 2008; 26:702-708; Geurts A M, Cost G J, Freyvert Y, Zeitler B, Miller J C, Choi V M, Jenkins S S, Wood A, Cui X, Meng X, Vincent A, Lam S, Michalkiewicz M, Schilling R, Foeckler J, Kalloway S, Weiler H, Menoret S, Anegon I, Davis G D, Zhang L, Rebar E J, Gregory P D, Urnov F D, Jacob H J, Buelow R.; Science 2009; 325:433). Furthermore, zinc-finger nucleases were used in the presence of exogeneous gene targeting vectors that contain homology regions to the target gene for homology driven repair of the double strand break through gene conversion. This methodology has been applied to gene engineering in mammalian cell lines and gene correction in primary human cells (Urnov F D, Miller J C, Lee Y L, Beausejour C M, Rock J M, Augustus S, Jamieson A C, Porteus M H, Gregory P D, Holmes M C.; Nature 2005; 435:646-651; Porteus M H, Baltimore D. 2003. Science 300: 763; Hockemeyer D, Soldner F, Beard C, Gao Q, Mitalipova M, DeKelver R C, Katibah G E, Amora R, Boydston E A, Zeitler B, Meng X, Miller J C, Zhang L, Rebar E J, Gregory P D, Urnov F D, Jaenisch R.; Nat Biotechnol 2009; 27:851-857).

Although the use of zinc-finger nucleases results in a higher frequency of homologous recombination, considerable efforts and time are required to design zinc-finger proteins that bind a new DNA target sequence at high efficiency and that act as sequence specific nuclease. In addition, it has been long ignored that the nature of the nuclease domain of zinc-finger and other chimaeric nucleases may represent an equally important success factor for the overall activity of the fusion protein. The reason for this neglection is based on the fact that up to date only a single nuclease domain has been found that retains nuclease activity within a separate protein folding domain and that can be combined with DNA binding domains, in order to generate a sequence specific nuclease fusion proteins. This nuclease domain is derived from the type IIS FokI restriction enzyme that has been characterised in detail and is known to act as an obligate dimer (Bitinaite, J., D. A. Wah, et al. (1998). Proc Natl Acad Sci USA 95(18): 10570-5; Wah, D. A., J. Bitinaite, et al. (1998). Proc Natl Acad Sci USA 95(18): 10564-9). In most other restriction enzymes DNA recognition and cleavage are combined into a single protein domain and can not be separated. An exception is the SdaI enzyme that has been structurally characterised to posses a separate nuclease domain (Tamulaitiene, G., A. Jakubauskas, et al. (2006). Structure 14(9): 1389-400). In addition, it has not been possible to isolate mutants that loose DNA recognition but retain DNA cleavage activity.

Therefore, due to the lack other comparable functional nuclease domains, it was for a long time essentially unknown whether the enzymatic properties of the FokI Fn domain may constitute a limiting factor for the nuclease activity of Fn domain fusion proteins. For example, the intrinsic structure of the Fn domain may restrict its enzymatic processivity or the small dimerisation interface of two Fn domains may lead to a suboptimal interaction and a low cleavage rate of the DNA substrate.

By site-directed mutagenesis the FokI Fn domain has been engineered into the KK and EL variants that preferentially act as heterodimers (Miller, J. C., M. C. Holmes, et al. (2007). Nat Biotechnol 25(7): 778-85). The use of these variants provides the improved target sequence specificity of zinc-finger nucleases and reduces toxicity in mammalian cells since less genomic off-target sequences are recognised and processed. However, the overall nuclease activity of the KK and EL variants is at most comparable to that of the Fn wildtype domain.

Only very recently it has been found that the wildtype FokI Fn domain indeed exhibits only a suboptimal enzymatic nuclease activity that limits the use of zinc-finger nucleases for genome engineering. In a study of directed protein evolution the Fn domain has been randomly mutagenised and subjected to an E. coli based nuclease assay able to select mutants that exhibit increased enzymatic activity (Guo, J., T. Gaj, et al. (2010), J Mol Biol 400(1): 96-107). By this procedure it has been possible to isolate mutants that exhibit >10-fold higher nuclease activity as compared to the wildtype Fn domain. Upon coupling of these mutants to zinc-finger domains such fusion proteins showed a three to sixfold improved substrate processing in mammalian cells. However, it remains unknown at present whether the activity of the Fn domain can be further enhanced or whether the intrinsic protein architecture of the Fn domain may restrict any further improvements.

Besides zinc-finger DNA-binding domains fused to nuclease domains, very recently also TAL effector protein DNA-binding domains have been identified. As compared to zinc-finger motifs, TAL repeat elements within TAL effector proteins provide a new type of DNA binding domain that may be combined with a nuclease domain into sequence specific nucleases. A key feature of the TAL peptide elements is provided by their modulatory nature. Thereby, new sequence specific DNA-binding proteins can be generated through the combination of just four basic TAL elements that are each specific for the A, C, G or T nucleotide. Currently, only the nuclease domain of FokI is successfully used in fusion with TAL effector protein DNA-binding domains (Miller et al. (2010). Nat. Biotechnol. 29, 143-148).

In summary, there is an ongoing need for nucleases that can be used in various experimental settings including their fusion to other proteins and modification of the nuclease domain.

The technical problem underlying the present invention was to identify alternative and/or improved means and methods for cleaving nucleic acid molecules.

The solution to this technical problem is achieved by providing the embodiments characterized in the claims.

Accordingly, the present invention relates in a first embodiment to a nucleic acid molecule encoding (I) a polypeptide having the activity of an endonuclease, which is (a) a nucleic acid molecule encoding a polypeptide comprising or consisting of the amino acid sequence of SEQ ID NO: 1; (b) a nucleic acid molecule comprising or consisting of the nucleotide sequence of SEQ ID NO: 2; (c) a nucleic acid molecule encoding an endonuclease, the amino acid sequence of which is at least 70% identical to the amino acid sequence of SEQ ID NO: 1; (d) a nucleic acid molecule comprising or consisting of a nucleotide sequence which is at least 50% identical to the nucleotide sequence of SEQ ID NO: 2; (e) a nucleic acid molecule which is degenerate with respect to the nucleic acid molecule of (d); or (f) a nucleic acid molecule corresponding to the nucleic acid molecule of any one of (a) to (e) wherein T is replaced by U; (II) a fragment of the polypeptide of (I) having the activity of an endonuclease.

In accordance with the present invention the term "nucleic acid molecule" defines a linear molecular chain consisting of at least (for each) 2, 5, 10, 25, 50, 75, 100, 250, 500, such as at least 750, 1000, or at least 2500 or more nucleotides. The group of molecules designated herein as "nucleic acid molecules" also comprises complete genes. The term "nucleic acid molecule" is interchangeably used herein with the term "polynucleotide".

The term "nucleic acid molecule" in accordance with the present invention includes DNA, such as cDNA or double or single stranded genomic DNA and RNA. In this regard, "DNA" (deoxyribonucleic acid) means any chain or sequence of the chemical building blocks adenine (A), guanine (G), cytosine (C) and thymine (T), called nucleotide bases, that are linked together on a deoxyribose sugar backbone. DNA can have one strand of nucleotide bases, or two complimentary strands which may form a double helix structure. "RNA" (ribonucleic acid) means any chain or sequence of the chemical building blocks adenine (A), guanine (G), cytosine (C) and uracil (U), called nucleotide bases that are linked together on a ribose sugar backbone. RNA typically has one strand of nucleotide bases. Included are also single- and double-stranded hybrid molecules, i.e., DNA-RNA. The nucleic acid molecule may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Polynucleotides may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The polynucleotides may be derivatized by formation of a methyl or ethyl phosphotriester or an alkyl phosphoramidate linkage. Further included are nucleic acid mimicking molecules known in the art such as synthetic or semi-synthetic derivatives of DNA or RNA and mixed polymers. Such nucleic acid mimicking molecules or nucleic acid derivatives according to the invention include phosphorothioate nucleic acid, phosphoramidate nucleic acid, 2'-O-methoxyethyl ribonucleic acid, morpholino nucleic acid, hexitol nucleic acid (HNA), peptide nucleic acid (PNA) and locked nucleic acid (LNA) (see Braasch and Corey, Chem Biol 2001, 8: 1). LNA is an RNA derivative in which the ribose ring is constrained by a methylene linkage between the 2'-oxygen and the 4'-carbon. Also included are nucleic acids containing modified bases, for example thiouracil, thio-guanine and fluoro-uracil. A nucleic acid molecule typically carries genetic information, including the information used by cellular machinery to make proteins and/or polypeptides. The nucleic acid molecule of the invention may additionally comprise promoters, enhancers, response elements, signal sequences, polyadenylation sequences, introns, 5'- and 3'-non-coding regions, and the like.

The term "polypeptide" as used herein interchangeably with the term "protein" describes linear molecular chains of amino acids, including single chain proteins, containing more than 30 amino acids, whereas the term "peptide" describes linear molecular chains of amino acids, including single chain proteins, containing less than and up to 30 amino acids. Polypeptides may further form oligomers consisting of at least two identical or different molecules. The corresponding higher order structures of such multimers are, correspondingly, termed homo- or heterodimers, homo- or heterotrimers etc. The polypeptides of the invention may form heteromultimers or homomultimers, such as heterodimers or homodimers. Furthermore, peptidomimetics of such proteins/polypeptides where amino acid(s) and/or peptide bond(s) have been replaced by functional analogues are also encompassed by the invention. Such functional analogues include all known amino acids other than the 20 gene-encoded amino acids, such as selenocysteine. The terms "polypeptide" and "protein" also refer to naturally modified polypeptides and proteins where the modification is effected e.g. by glycosylation, acetylation, phosphorylation, ubiquitinylation and similar modifications which are well known in the art.

The term "a polypeptide having the activity of an endonuclease" as used herein means a polypeptide which is capable of cleaving the phosphodiester bonds between nucleotides subunits of nucleic acids within a polynucleotide chain.

According to the invention, the endonuclease enzymatic activity is considered as stable when, in the respective conditions, the enzyme is capable of lasting long enough to obtain the desired effect, namely the cleavage of its substrate. In this regard it is noted that endonuclease activity can be assayed as described in the examples of the specification or by methods well known in the art. For example, a nucleic acid molecule can be exposed to a protein whose endonuclease activity is to be assessed under conditions that are suitable for endonuclease enzymatic activity. After incubation, the composition comprising the nucleic acid molecule (with or without said protein to be assessed) may be subjected to an assay for assessing the length of a nucleic acid molecule such as, e.g., gel-electrophoresis, to determine whether the nucleic acid molecule has been cleaved.

In accordance with the present invention, the term "percent (%) sequence identity" describes the number of matches ("hits") of identical nucleotides/amino acids of two or more aligned nucleic acid or amino acid sequences as compared to the number of nucleotides or amino acid residues making up the overall length of the template nucleic acid or amino acid sequences. In other terms, using an alignment, for two or more sequences or subsequences the percentage of amino acid residues or nucleotides that are the same (e.g. 95% identity) may be determined, when the (sub)sequences are compared and aligned for maximum correspondence over a window of comparison, or over a designated region as measured using a sequence comparison algorithm as known in the art, or when manually aligned and visually inspected. This definition also applies to the complement of any sequence to be aligned. Amino acid sequence analysis and alignment in connection with the present invention was carried out using the NCBI BLAST algorithm (Stephen F. Altschul, Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402) and the CLC main workbench software (version 5.7.1; CLC bio, Aarhus, Denmark) which are preferably employed in accordance with this invention. Preferably, the published standard parameters are used (Altschul et al. loc cit.). The skilled person is aware of additional suitable programs to align nucleic acid sequences. A preferred program for nucleic acid sequence alignment in accordance with the invention is the CLC main workbench software using the standard alignment parameters of the software program (version 5.7.1; CLC bio, Aarhus, Denmark).

As defined in the embodiments herein above, certain amino acid sequence identities are envisaged by the invention. Also envisaged are—with increasing preference—amino acid sequence identities of at least 75%, at least 80%, at least 85%, at least 90%, at least 95%, at least 97.5%, at least 98%, at least 98.5%, at least 99%, at least 99.5%, at least 99.8%, and 100% identity to the respective amino acid sequence in accordance with the invention.

As defined in the embodiments herein above, certain nucleotide sequence identities are envisaged by the invention. Also envisaged are—with increasing preference—nucleotide sequence identities of at least 55%, at least 60%, at least 65%, at least 70%, at least 75%, at least 80%, at least 85%, at least 90%, at least 95%, at least 97.5%, at least 98%, at least 98.5%, at least 99%, at least 99.5%, at least 99.8%, and 100% identity to the respective nucleic acid sequence in accordance with the invention.

It will be readily appreciated by the skilled person that more than one nucleic acid molecule may encode the same polypeptide due to the degeneracy of the genetic code. Degeneracy results because a triplet code designates 20 amino acids and a stop codon. Because four bases exist which are utilized to encode genetic information, triplet codons are required to produce at least 21 different codes. The possible $4^3$ possibilities for bases in triplets give 64 possible codons, meaning that some degeneracy must exist. As a result, some amino acids are encoded by more than one triplet, i.e. by up to six. The degeneracy mostly arises from alterations in the third position in a triplet. This means that nucleic acid molecules having different sequences, but still encoding the same polypeptide are envisaged and can be employed in accordance with the method of present invention.

Fragments according to the present invention are polypeptides having the activity of an endonuclease as defined herein above and comprise at least 90 amino acids. In this regard, it is preferred—with increasing preference—that the fragments according the present invention are polypeptides of at least 100, at least 125, at least 150, at least 200 amino acids, at least 300 amino acids, at least 400 amino acids. Fragments of the polypeptide of the invention, which substantially retain endonuclease activity, include N-terminal truncations, C-terminal truncations, amino acid substitutions, internal deletions and addition of amino acids (either internally or at either terminus of the protein). For example, conservative amino acid substitutions are known in the art and may be introduced into the endonuclease of the invention without substantially affecting endonuclease activity, i.e. reducing said activity.

As is evident from the examples, the inventor was able to identify and isolate a novel nuclease, in particular the endonuclease domain, derived from a *Clostridium* strain as detailed below. Specifically, the inventor could establish the utility of the gene product of a putative bacterial gene without known functional connotation as a sequence unspecific nuclease. The novel nuclease can be employed in various experimental settings just as any other nuclease. For example, it may be used to randomly cleave nucleic acid molecules or, e.g., in fusion with DNA-binding domains, for site-specific cleavage of nucleic acid molecules. Importantly, and as outlined below and specifically in the examples, the novel endonuclease can be used in combination with TAL effector protein DNA-binding domains as part of a fusion protein for sequence-specific nucleic acid cleavage. In this respect, the novel nuclease shows its superiority over state of the art endonucleases other than FokI which could so far not be shown to be active in corresponding fusion proteins. Briefly, the inventors tested the gene product of said uncharacterised, hypothetical microbial gene which they designated as "Clo051" (SEQ ID NO: 17) and which is derived from the genome of *Clostridium* spec. 7_2_43FAA (NCBI Reference Sequence: ZP_05132802.1; publication/database release date: Jun. 9, 2010), more specifically its putative nuclease domain (see FIGS. 5 and 6), for its endonuclease activity in combination with the DNA-binding domain of a TAL effector protein. Also various known endonuclease proteins were tested in combination with TAL effector protein DNA binding domains as well as two more hypothetical microbial genes. Surprisingly, only the nuclease domain from Clo051 could be shown to be active, whereas the other fusion proteins did not show activity (see Example 1 for details). The comparative experiments emphasized the significance of the finding of the present invention in that a novel nuclease has been identified that also exhibits activity when fused to the DNA-binding domains of TAL effector proteins. TAL effector proteins are expressed by plant pathogens of the genus *Xanthomonas* and reprogram host cells by mimicking eukaryotic transcription factors. TAL effector proteins are characterized by a central domain of tandem repeats of 32 to 34 amino acid that constitute a DNA-binding domain. The number and order of repeats in a TAL effector protein determines its specific DNA binding activity. (Boch, J., et al. 2009 Science 326: 1509-12). The amino acid sequences of the repeats are conserved, except for two adjacent highly variable residues (at positions 12 and 13) that determine specificity towards the DNA base A, G, C or T. Binding to DNA is mediated by contacting a nucleotide of the DNA double helix with the variable residues at position 12 and 13 within the Tal effector motif resulting into a one-to-one correspondence between sequential repeats in the Tal effector proteins and sequential nucleotides in the target DNA. Binding to longer DNA sequences is achieved by linking several of these Tal effector motifs in tandem to form a "DNA-binding domain of a Tal effector protein". The use of such DNA-binding domains of Tal effector proteins for the creation of Tal effector motif—nuclease fusion proteins that recognize and cleave a specific target sequence depends on the reliable creation of DNA-binding domains of Tal effector proteins that can specifically recognize said particular target. The advantage of the TAL repeat elements, as compared to e.g. zinc-finger elements, is provided by their truly modular nature. Thereby, new sequence specific DNA binding proteins can be generated through the combination of the four basic TAL elements that are specific for the A, C, G or T nucleotide.

It is important to note that in the present invention the Clo051 nuclease domain fused to DNA-binding domains of TAL effector proteins has been tested and found to be active in mammalian, specifically human cultured cells. Therefore, the utility of Clo051 nuclease domain fusion proteins for DNA and gene manipulation, specifically but without limitation in mammalian cells has been directly proven in the biological system that provides important applications for this technology. This finding is of particular importance since studies on protein function that are performed in lower eucaryotic organisms, like e.g. yeast, do not allow a definite conclusion on the utility of the protein under study in mammalian cells. For example, a specific protein may function optimal at 30° Celsius, the growth temperature of yeast, but becomes unstable or inactive at 37° Celsius as the typical body temperature of mammals. In addition, the intracellular milieu of e.g. yeast cells, like ion and protein concentration, protein diversity and protein degradation mechanisms, are distinguished from the intracellular milieu of mammalian cells.

While the examples only describe the use of the nuclease domain of Clo051 (SEQ ID NO: 1), e.g. in combination with DNA-binding domains, the skilled person will appreciate that one may also employ the entire sequence of Clo051 as set forth in SEQ ID NO: 17 or shorter fragments thereof having endonuclease activity and comprising the amino acid sequence of SEQ ID NO: 1. The amino acid sequence of SEQ ID NO: 1 starts at E389 and ends at Y587 of the amino acid of SEQ ID NO: 17 as also exemplified in FIG. 5.

In a preferred embodiment of the nucleic acid molecule of the invention, in (I)(c) in said amino acid sequence having at least 70% sequence identity to SEQ ID NO: 1 the amino acid residues P66, D67, D84 and/or K86 of SEQ ID NO: 1 are not modified.

The nuclease domain of Clo051, like many type-II restriction endonucleases and e.g. the DNA repair protein MutH, share the conserved sequence motif PD-(D/E)XK within the core of their catalytic domain. The core serves as a scaffold for a weakly conserved active site, typically comprising two or three acidic residues (Asp or Glu) and one Lys residue, which together form the hallmark bipartite catalytic motif [(P)D. Xn. (D/E)XK] (where X is any amino acid). This motif has led to naming this superfamily of proteins as 'PD-(D/E)XK'. Work on restriction enzymes and DNA repair proteins has shown that the three catalytic residues are located close to each other on an uneven β-hairpin. The first D is located at the beginning of the first and shorter strand, and the E and K, separated by a hydrophobic residue x, are located in the middle of the second and longer strand. The catalytic module invariably approaches DNA from the minor groove side, and the sequence-specific binding is conducted by a separate module/subdomain in the major groove. The first two carboxylates of the DEK motif coordinate the metal ions. The first D is most conserved and coordinates both metal ions, whereas the second E can be replaced by Q, D, N, H or S, and the third K can be replaced E, Q, D, S, N or T. The Lysine residue in the conserved DEK motif coordinates the nucleophilic water in conjunction with the phosphate 3' to the scissile bond; the same Lysine is also hydrogen bonded with a carbonyl oxygen in the DNA binding module. This Lysine, which is conserved in many restriction endonucleases and is replaced by Glu or Gln in BamHI and BgIII, has been proposed as a sensor for DNA binding and a hub that couples base recognition and DNA cleavage (Lee et al. (2005). Molecular Cell 20, 155-166; Orlowski, J. and J. M. Bujnicki (2008). Nucleic Acids Res 36(11): 3552-69).

The primary sequence of the Clo051 nuclease domain between the positions E389 and Y587 of the sequence of SEQ ID NO: 17, i.e. the sequence of SEQ ID NO: 1, exhibits a unique distribution of the positively charged arginine (R) and lysine (K) residues and of negatively charged glutamate (E) and aspartate (D) residues (FIG. 13). These residues constitute a three-dimensional landscape of charges within the Clo051 domain that determines the unique tertiary structure of this nuclease, as shown in the structural model in FIG. 6. Certain replacements of polar versus non-polar residues or of non-polar residues against polar residues, e.g. at the positions S35 and/or R58 of SEQ ID NO:1 (or S423 and R446 of SEQ ID NO: 17), alter the three-dimensional structure of the protein chain and may result into an increase of the nuclease activity. Such amino acid replacements may be made by trial and error or may follow specific hypotheses on the structural and functional impact on the Clo051 nuclease domain. Alternatively, a large number of randomly mutagenised variants of the Clo051 nuclease domain coding region can be assembled in a library by mutagenic, error prone PCR. This library of mutant molecules can be tested for the presence of hyperactive nuclease variants by a phenotypic screening assay in *E. coli*, yeast or mammalian cells that is coupled to a functional nuclease readout, e.g. as described for the improvement of the FLP recombinase (Buchholz et al., Nat. Biotechnol. 16, 657-62, 1998). Such a functional screen for improved nuclease variants can result into the replacement of single or multiple residues that lead to increased nuclease activity as compared to the Clo051 wildtype form.

Also envisaged are embodiments where more than the amino acid residues P66, D67, D84 and/or K86 of SEQ ID NO: 1 are not modified such as, e.g., amino acid stretches as, e.g. from at least P66 to at least K86, at least R64 to at least Y88, at least G62 to at least E90, as well as L60 to at least Y92 of SEQ ID NO: 1.

In a preferred embodiment of the invention, the nucleic acid molecule further encodes a DNA-binding domain.

In this embodiment the nucleic acid molecule of the invention encodes a fusion protein having the activity of an endonuclease and comprises a DNA-binding domain and a cleavage domain comprising or consisting of the novel endonuclease domain. The term "fusion protein" is well-known in the art and has the same meaning herein. Namely, it refers to a protein generated by joining two or more target nucleic acid sequences, e.g. genes, which originally code for separate proteins to create a fusion construct. Translation of said fusion construct results in a single protein with the functional properties derived from said separate proteins. The two proteins giving rise to the fusion protein may be connected by a linker, such as, e.g., a peptide linker. In other words, the DNA-binding domain and the cleavage domain of the nucleases may be directly fused to one another or may be fused via a linker.

The term "linker" as used in accordance with the present invention relates to a sequel of amino acids (i.e. peptide linkers) as well as to non-peptide linkers.

Peptide linkers as envisaged by the present invention are peptide or polypeptide linkers of at least 1 amino acid in length. Preferably, the linkers are 1 to 100 amino acids in length. More preferably, the linkers are 5 to 50 amino acids in length and even more preferably, the linkers are 10 to 20 amino acids in length. It is well known to the skilled person that the nature, i.e. the length and/or amino acid sequence of the linker may modify or enhance the stability and/or solubility of the molecule. Thus, the length and sequence of a linker depends on the composition of the respective portions of the fusion protein.

The skilled person is aware of methods to test the suitability of different linkers. For example, the properties of the molecule can easily be tested by testing the nuclease activity as well as the DNA-binding specificity of the respective portions of the fusion protein to be used in the method of the invention.

It will be appreciated by the skilled person that when the fusion protein is provided as a nucleic acid molecule encoding the fusion protein in expressible form, the linker is a peptide linker also encoded by said nucleic acid molecule.

The term "non-peptide linker", as used in accordance with the present invention, refers to linkage groups having two or more reactive groups but excluding peptide linkers as defined above. For example, the non-peptide linker may be a polymer having reactive groups at both ends, which individually bind to reactive groups of the individual portions of the fusion protein, for example, an amino terminus, a lysine residue, a histidine residue or a cysteine residue. The reactive groups of the polymer include an aldehyde group, a propionic aldehyde group, a butyl aldehyde group, a maleimide group, a ketone group, a vinyl sulfone group, a thiol group, a hydrazide group, a carbonyldimidazole (CDI) group, a nitrophenyl carbonate (NPC) group, a trysylate group, an isocyanate group, and succinimide derivatives. Examples of succinimide derivatives include succinimidyl propionate (SPA), succinimidyl butanoic acid (SBA), succinimidyl carboxymethylate (SCM), succinimidyl succinamide (SSA), succinimidyl succinate (SS), succinimidyl carbonate, and N-hydroxy succinimide (NHS). The reactive groups at both ends of the non-peptide polymer may be the same or different. For example, the non-peptide polymer may have a maleimide group at one end and an aldehyde group at another end. Preferably, the linker is a peptide linker. More preferably, the peptide linker consists of seven glycine residues.

Also the fusion protein may be flanked N- or C-terminally by additional sequences unrelated to said proteins in the fusion protein. In accordance with the present invention, a fusion protein of the invention comprises a DNA-binding domain. The term "DNA-binding domain" has the same meaning as known in the art and relates to a sequence motif/conformation within a protein that binds to DNA motifs. Protein domains that can specifically bind to a nucleic acid sequence include, e.g., zinc finger repeats, the helix-turn-helix (HTH) motif of homeodomains, and the ribbon-helix-helix (RHH) motif. Specific binding refers to the sequence specific binding and is specific, when a DNA-binding domain statistically only binds to a particular sequence and does not or essentially not bind to an unrelated sequence. The skilled person is well-aware of sequences encoding DNA-binding domains (Rohs et al. (2010). Annu. Rev. Biochem. 79, 233-269; Maeder et al. (2009). Nat. Protocols 10, 1471-1501).

In a more preferred embodiment of the nucleic acid molecule of the invention, the DNA-binding domain is a TAL effector motif of a TAL effector protein.

This embodiment relates to a nucleic acid molecule also encoding a TAL nuclease. The term "TAL nuclease" as used herein, is well known in the art and refers to a fusion protein comprising a DNA-binding domain, wherein the DNA-binding domain comprises or consists of Tal effector motifs of a TAL effector protein and the non-specific cleavage domain of a restriction nuclease. The fusion protein of the invention that is also employed in the method of the invention below retains or essentially retains the enzymatic activity of the endonuclease of the invention. In accordance with the present invention, said endonuclease activity (also referred to as function) is essentially retained if at least 60% of the biological activity of the endonuclease activity are retained. Preferably, at least 75% or at least 80% of the endonuclease activity are retained. More preferred is that at least 90% such as at least 95%, even more preferred at least 98% such as at least 99% of the biological activity of the endonuclease are retained. Most preferred is that the biological activity is fully, i.e. to 100%, retained. Also in accordance with the invention, fusion proteins having an increased biological activity compared to the endonuclease when not fused to a DNA-binding domain, i.e. more than 100% activity, are envisaged. Methods of assessing biological activity of (restriction) endonucleases are well known to the person skilled in the art and include, without being limiting, the incubation of an endonuclease with recombinant DNA and the analysis of the reaction products by gel electrophoresis (Bloch K D.; Curr Protoc Mol Biol 2001; Chapter 3:Unit 3.2).

The term "Tal effector protein", as used herein, refers to proteins belonging to the TAL (transcription activator-like) family of proteins. These proteins are expressed by bacterial plant pathogens of the genus *Xanthomonas*. Members of the large TAL effector family are key virulence factors of *Xanthomonas* and reprogram host cells by mimicking eukaryotic transcription factors. The pathogenicity of many bacteria depends on the injection of effector proteins via type III secretion into eukaryotic cells in order to manipulate cellular processes. TAL effector proteins from plant pathogenic *Xanthomonas* are important virulence factors that act as transcriptional activators in the plant cell nucleus. PthXo1, a TAL effector protein of a *Xanthomonas* rice pathogen, activates expression of the rice gene Os8N3, allowing *Xanthomonas* to colonize rice plants. TAL effector proteins are characterized by a central domain of tandem repeats, i.e. a DNA-binding domain as well as nuclear localization signals (NLSs) and an acidic transcriptional activation domain. Members of this effector family are highly conserved and differ mainly in the amino acid sequence of their repeats and in the number of repeats. The number and order of repeats in a TAL effector protein determine its specific activity. These repeats are referred to herein as "TAL effector motifs". One exemplary member of this effector family, AvrBs3 from *Xanthomonas campestris* pv. vesicatoria, contains 17.5 repeats and induces expression of UPA (up-regulated by AvrBs3) genes, including the Bs3 resistance gene in pepper plants (Kay, et al. 2005 Mol Plant Microbe Interact 18(8): 838-48; Kay, S. and U.

Bonas 2009 Curr Opin Microbiol 12(1): 37-43). The repeats of AvrBs3 are essential for DNA binding of AvrBs3 and represent a distinct type of DNA binding domain. The mechanism of sequence specific DNA recognition has been elucidated by recent studies on the AvrBs3, Hax2, Hax3 and Hax4 proteins that revealed the TAL effectors' DNA recognition code (Boch, J., et al. 2009 Science 326: 1509-12).

Tal effector motifs or repeats are 32 to 34 amino acid protein sequence motifs. The amino acid sequences of the repeats are conserved, except for two adjacent highly variable residues (at positions 12 and 13) that determine specificity towards the DNA base A, G, C or T. In other words, binding to DNA is mediated by contacting a nucleotide of the DNA double helix with the variable residues at position 12 and 13 within the Tal effector motif of a particular Tal effector protein (Boch, J., et al. 2009 Science 326: 1509-12). Therefore, a one-to-one correspondence between sequential amino acid repeats in the Tal effector proteins and sequential nucleotides in the target DNA was found. Each Tal effector motif primarily recognizes a single nucleotide within the DNA substrate. For example, the combination of histidine at position 12 and aspartic acid at position 13 specifically binds cytosine; the combination of asparagine at both position 12 and position 13 specifically binds guanosine; the combination of asparagine at position 12 and isoleucine at position 13 specifically binds adenosine and the combination of asparagine at position 12 and glycine at position 13 specifically binds thymidine. Binding to longer DNA sequences is achieved by linking several of these Tal effector motifs in tandem to form a "DNA-binding domain of a Tal effector protein". Thus, a DNA-binding domain of a Tal effector protein relates to DNA-binding domains found in naturally occurring Tal effector proteins as well as to DNA-binding domains designed to bind to a specific target nucleotide sequence as described in the examples below. The use of such DNA-binding domains of Tal effector proteins for the generation of Tal effector motif—nuclease fusion proteins that recognize and cleave a specific target sequence depends on the reliable generation of DNA-binding domains of Tal effector proteins that can specifically recognize said particular target. Methods for the generation of DNA-binding domains of Tal effector proteins are well-known in the art (Zhang et al. (2011). Nat Biotechol. 29, 149-153; Cermak et al. (2011). Nucleic Acis Res. April 14, PubMed identifier 21493687).

Preferably, the DNA-binding domain is derived from the Tal effector motifs found in naturally occurring Tal effector proteins, such as for example Tal effector proteins selected from the group consisting of AvrBs3, Hax2, Hax3 or Hax4 (Bonas et al. 1989. Mol Gen Genet 218(1): 127-36; Kay et al. 2005 Mol Plant Microbe Interact 18(8): 838-48).

Envisaged in accordance with the present invention are fusion proteins that are provided as a DNA-binding domain of a Tal effector protein coupled with a single nuclease domain. These monomeric proteins can be combined to act as a functional dimer in order to develop nuclease activity through the cooperation of two nuclease domains, each being part of one fusion protein.

Preferably, the TAL nuclease in accordance with the present invention comprises more than one, i.e. several Tal effector motifs, such as at least 12 Tal effector motifs, such as for example at least 14 or at least 16 Tal effector motifs. More preferably, the TAL nuclease comprises at least 18 Tal effector motifs. In other words, the DNA-binding domain of a Tal effector protein within said fusion protein is comprised of at least 18 Tal effector motifs. In the case of fusion proteins consisting of dimers as described above this means that each fusion protein monomer comprises at least nine Tal effector motifs. Methods for testing the DNA-binding specificity of a fusion protein in accordance with the present invention are known to the skilled person and include, without being limiting, transcriptional reporter gene assays and electrophoretic mobility shift assays (EMSA).

Preferably, the binding site of the fusion protein is up to 500 nucleotides, such as up to 250 nucleotides, up to 100 nucleotides, up to 50 nucleotides, up to 25 nucleotides, up to 10 nucleotides such as up to 5 nucleotides upstream (i.e. 5') or downstream (i.e. 3') of the nucleotide(s) that is/are modified in accordance with the method of the present invention as detailed below.

In another embodiment, the invention relates to a vector encoding the nucleic acid molecule of the invention.

The term "vector" in accordance with the invention preferably means a plasmid, cosmid, virus, bacteriophage or another vector used e.g. conventionally in genetic engineering which carries the nucleic acid molecule of the invention either encoding the peptide or the fusion protein of the invention. Accordingly, the nucleic acid molecule of the invention may be inserted into several commercially available vectors. Non-limiting examples include prokaryotic plasmid vectors, such as of the pUC-series, pBluescript (Stratagene), the pET-series of expression vectors (Novagen) or pCRTOPO (Invitrogen) and vectors compatible with an expression in mammalian cells like pREP (Invitrogen), pcDNA3 (Invitrogen), pCEP4 (Invitrogen), pMC1 neo (Stratagene), pXT1 (Stratagene), pSG5 (Stratagene), EBO-pSV2neo, pBPV-1, pdBPVMMTneo, pRSVgpt, pRSVneo, pSV2-dhfr, plZD35, pLXIN, pSIR (Clontech), pIRES-EGFP (Clontech), pEAK-10 (Edge Biosystems) pTriEx-Hygro (Novagen) and pCINeo (Promega). Examples for plasmid vectors suitable for *Pichia pastoris* comprise e.g. the plasmids pAO815, pPIC9K and pPIC3.5K (all Intvitrogen).

The nucleic acid molecule of the present invention referred to above may also be inserted into vectors such that a (further) translational fusion with another nucleic acid molecule is generated. To this aim, overlap extension PCR can be applied (e.g. Wurch, T., Lestienne, F., and Pauwels, P. J., A modified overlap extension PCR method to create chimeric genes in the absence of restriction enzymes, Biotechn. Techn. 12, 9 Sep. 1998, 653-657). The products arising therefrom are termed fusion proteins and will be described further below. The other nucleic acid molecules may encode a protein which may e.g. increase the solubility and/or facilitate the purification of the protein encoded by the nucleic acid molecule of the invention. Non-limiting examples include pET32, pET41, pET43. The vectors may also contain an additional expressible nucleic acid coding for one or more chaperones to facilitate correct protein folding. Suitable bacterial expression hosts comprise e.g. strains derived from BL21 (such as BL21(DE3), BL21(DE3)PlysS, BL21(DE3)RIL, BL21(DE3)PRARE) or Rosetta®.

Particularly preferred plasmids which can be used to introduce the nucleic acid encoding the polypeptide of the invention having the activity of an endonuclease into the host cell are: pUC18/19 (Roche Biochemicals), pBluescript II (Alting-Mees, et al. (1992). Meth. Enzymol., 216, 483-495), pKK-177-3H (Roche Biochemicals), pBTac2 (Roche Biochemicals), pKK223-3 (Amersham Pharmacia Biotech), pKK-233-3 (Stratagene) and pET (Novagen).

For vector modification techniques, see Sambrook and Russel, 2001. Generally, vectors can contain one or more origins of replication (ori) and inheritance systems for cloning or expression, one or more markers for selection in the host, e.g., antibiotic resistance, and one or more expression cassettes. Suitable origins of replication include, for example, the Col E1, the SV40 viral and the M13 origins of replication.

The coding sequences inserted in the vector can e.g. be synthesized by standard methods, or isolated from natural sources. Ligation of the coding sequences to transcriptional regulatory elements and/or to other amino acid encoding sequences can be carried out using established methods. Transcriptional regulatory elements (parts of an expression cassette) ensuring expression in prokaryotes or eukaryotic cells are well known to those skilled in the art. These elements comprise regulatory sequences ensuring the initiation of the transcription (e.g., translation initiation codon, transcriptional termination sequences, promoters, enhancers, and/or insulators), internal ribosomal entry sites (IRES) and optionally poly-A signals ensuring termination of transcription and stabilization of the transcript. Additional regulatory elements may include transcriptional as well as translational enhancers, and/or naturally-associated or heterologous promoter regions. The regulatory elements may heterologous regulatory elements. Preferably, the nucleic acid molecule of the invention is operably linked to such expression control sequences allowing expression in prokaryotes or eukaryotic cells. The vector may further comprise nucleotide sequences encoding secretion signals as further regulatory elements. Such sequences are well known to the person skilled in the art. Furthermore, depending on the expression system used, leader sequences capable of directing the expressed polypeptide to a cellular compartment may be added to the coding sequence of the nucleic acid molecule of the invention. Such leader sequences are well known in the art. Specifically designed vectors allow the shuttling of DNA between different hosts, such as bacteria-fungal cells or bacteria-animal cells.

The co-transfection with a selectable marker such as kanamycin or ampicillin resistance genes for culturing in *E. coli* and other bacteria allows the identification and isolation of the transfected cells. Selectable markers for mammalian cell culture are the dhfr, gpt, neomycin, hygromycin resistance genes. The transfected nucleic acid can also be amplified to express large amounts of the encoded polypeptide. The DHFR (dihydrofolate reductase) marker is useful to develop cell lines that carry several hundred or even several thousand copies of the gene of interest. Another useful selection marker is the enzyme glutamine synthase (GS) (Fisher et al., Infect Immun. 1991 October; 59(10):3562-5; Bebbington et al., Biotechnology (N Y). 1992 February; 10(2):169-75).

Using such markers, the cells are grown in selective medium and the cells with the highest resistance are selected.

In another embodiment the invention relates to a host cell comprising, e.g., as a result of transformation, transduction, microinjection or transfection, the nucleic acid molecule or the vector of the invention.

A variety of host-expression systems may be conceived to express the endonuclease coding sequence in a host cell using a suitable vector.

The "host cell" in accordance with the invention may be produced by introducing the nucleic acid molecule or vector(s) of the invention into the host cell which upon its/their presence preferably mediates the expression of the nucleic acid molecule of the invention encoding the endonuclease of the invention. The host from which the host cell is derived may be any prokaryote or eukaryotic cell.

A suitable eukaryotic host cell may be a vertebrate cell, an amphibian cell, a fish cell, an insect cell, a fungal/yeast cell, a nematode cell or a plant cell. The insect cell may be a *Spodoptera frugiperda* cell, a *Drosophila* S2 cell or a *Spodoptera* Sf9 cell, the fungal/yeast cell may a *Saccharomyces cerevisiae* cell, *Pichia pastoris* cell or an *Aspergillus* cell. It is preferred that the vertebrate cell is a mammalian cell such as a human cell, CHO, COS, 293 or Bowes melanoma cell. The plant cell is preferably selected independently from a cell of *Anacardium, Anona, Arachis, Artocarpus, Asparagus, Atropa, Avena, Brassica, Carica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoseyamus, Lactuca, Linum, Lolium, Lupinus, Lycopersicon, Malus, Manihot, Majorana, Medicago, Nicotiana, Olea, Oryza, Panieum, Pannesetum, Passiflora, Persea, Phaseolus, Pistachia, Pisum, Pyrus, Prunus, Psidium, Raphanus, Ricinus, Secale, Senecio, Sinapis, Solanum, Sorghum, Theobromus, Trigonella, Triticum, Vicia, Vitis, Vigna* and *Zea*. The cell may be a part of a cell line. The cell from plant may, e.g., be derived from root, leave, bark, needle, bole or caulis.

Suitable prokaryotes (bacteria) useful as hosts for the invention are those generally used for cloning and/or expression like *E. coli* (e.g., *E coli* strains BL21, HB101, DH5a, XL1 Blue, Y1090 and JM101), *Salmonella typhimurium, Serratia marcescens, Burkholderia glumae, Pseudomonas putida, Pseudomonas fluorescens, Pseudomonas stutzeri, Streptomyces lividans, Lactococcus lactis, Mycobacterium smegmatis, Streptomyces* or *Bacillus subtilis*. Appropriate culture mediums and conditions for the above described host cells are known in the art.

Preferred examples for host cell to be genetically engineered with the nucleic acid molecule or the vector(s) of the invention is a cell of yeast, *E. coli* and/or a species of the genus *Bacillus* (e.g., *B. subtilis*). The most preferred host cell is *Bacillus* spec.

In a further embodiment the invention relates to a method of producing a protein or fusion having the activity of an endonuclease as defined herein above comprising the steps: (a) culturing the host cell of the invention and (b) isolating the produced protein or fusion protein having the activity of said endonuclease.

Suitable conditions for culturing a prokaryotic or eukaryotic host are well known to the person skilled in the art. Suitable conditions for culturing *E. coli* DH18BΔkat E (Invitrogen), *Pichia pastoris* or *Aspergillus niger* are, for example provided in the examples of the invention. In general, suitable conditions for culturing bacteria are growing them under aeration in Luria Bertani (LB) medium. To increase the yield and the solubility of the expression product, the medium can be buffered or supplemented with suitable additives known to enhance or facilitate both. *E. coli* can be cultured from 4 to about 37° C., the exact temperature or sequence of temperatures depends on the molecule to be overexpressed. In general, *Aspergillus* sp. may be grown on Sabouraud dextrose agar, or potato dextrose agar at about to 10° C. to about 40° C., and preferably at about 25° C. Suitable conditions for yeast cultures are known, for example from Guthrie and Fink, "Guide to Yeast Genetics and Molecular Cell Biology" (2002); Academic Pr Inc. The skilled person is also aware of all these conditions and may further adapt these conditions to the needs of a particular host species and the requirements of the polypeptide expressed. In case an inducible promoter controls the nucleic acid of the invention in the vector present in the host cell, expression of the polypeptide can be induced by addition of an appropriate inducing agent. Suitable expression protocols and strategies are known to the skilled person.

Depending on the cell type and its specific requirements, mammalian cell culture can e.g. be carried out in RPMI or DMEM medium containing 10% (v/v) FCS, 2 mM L-glutamine and 100 U/ml penicillin/streptomycin. The cells can be kept at 37° C. in a 5% CO2, water saturated atmosphere.

Suitable expression protocols for eukaryotic cells are well known to the skilled person and can be retrieved e.g. from in Sambrook, 2001.

Methods of isolation of the polypeptide produced are well-known in the art and comprise without limitation method steps such as ion exchange chromatography, gel filtration chromatography (size exclusion chromatography), affinity chromatography, high pressure liquid chromatography (HPLC), reversed phase HPLC, disc gel electrophoresis or immunoprecipitation, see, for example, in Sambrook, 2001.

The step of protein isolation is preferably a step of protein purification. Protein purification in accordance with the invention specifies a process or a series of processes intended to further isolate the polypeptide of the invention from a complex mixture preferably to homogeneity. Purification steps, for example, exploit differences in protein size, physico-chemical properties and binding affinity. For example, proteins may be purified according to their isoelectric points by running them through a pH graded gel or an ion exchange column. Further, proteins may be separated according to their size or molecular weight via size exclusion chromatography or by SDS-PAGE (sodium dodecyl sulfate-polyacrylamide gel electrophoresis) analysis. In the art, proteins are often purified by using 2D-PAGE and are then further analysed by peptide mass fingerprinting to establish the protein identity. This is very useful for scientific purposes and the detection limits for protein are very low and nanogram amounts of protein are sufficient for their analysis. Proteins may also be separated by polarity/hydrophobicity via high performance liquid chromatography or reversed-phase chromatography. Thus, methods for protein purification are well known to the skilled person.

Furthermore, the invention relates in one embodiment to a protein or fusion protein having the activity of an endonuclease encoded by the nucleic acid molecule or vector of the invention.

The definitions for proteins or fusion proteins having the activity of an endonuclease encoded by the nucleic acid molecule or vector of the invention already given in the above embodiments pertaining to the nucleic acid molecule or vector of the invention apply explicitly also to this embodiment.

As a consequence of its endonuclease activity, another embodiment of the invention relates to the use of the protein or fusion protein of the invention to cleave a nucleic acid molecule, e.g. in one of the methods of the invention described below.

Furthermore, the present invention also relates to a kit comprising the nucleic acid molecule, the protein and/or the fusion protein of the invention. The various components of the kit may be packaged in one or more containers such as one or more vials. The vials may, in addition to the components, comprise preservatives or buffers for storage. In addition, the kit may contain instructions for use.

In another embodiment, the invention relates to a method of modifying a target sequence in the genome of a eukaryotic cell, the method comprising the step: (a) introducing into said cell the nucleic acid molecule, the vector or the protein or fusion protein of the invention.

The term "modifying" as used in accordance with the present invention refers to random and site-specific genomic manipulations resulting in changes in the nucleotide sequence of the genome of the eukaryotic host. When the fusion protein of the invention is introduced, site-specific modification of said "target sequence" in the genome is achieved via the DNA-binding domain. When only the protein of the invention is introduced, the "target sequence" is no specific sequence, because the novel endonuclease is not site-specific. Thus, the protein of the invention may be used to introduce random mutations into a genome, i.e. the "target sequence" occurs multiple times with in the genome and does not depend on a specific sequence motif. The genetic material comprising these changes in its nucleotide sequence is also referred to herein as the "modified target sequence" when modification is site-specific as, e.g. in the case of using the fusion protein of the invention. The term "modifying" includes, but is not limited to, substitution, insertion and deletion of one or more nucleotides within the target sequence. In the process of homologous recombination, the end product may reflect a deletion of sequences. As is understood by the skilled person, a homologous recombination, on the other hand, always also includes the incorporation of genetic material from the donor DNA sequence, which in this embodiment, however, leads to an overall deletion. It is understood by the skilled person that by simply introducing double-strand breaks into the genome of a cell modifications can be introduced that are the result of homologous recombination (in the presence and absence of exogenous donor sequences) or an endogenous DNA-repair mechanism such as, e.g., the non-homologous end joining (NHEJ) DNA repair that is prone to introducing small deletions at the site of the double-strand break in the course of ligating the broken ends.

The term "substitution", as used herein, refers to the replacement of nucleotides with other nucleotides. The term includes for example the replacement of single nucleotides resulting in point mutations. Said point mutations can lead to an amino acid exchange in the resulting protein product but may also not be reflected on the amino acid level. Also encompassed by the term "substitution" are mutations resulting in the replacement of multiple nucleotides, such as for example parts of genes, such as parts of exons or introns as well as replacement of entire genes.

The term "insertion" in accordance with the present invention refers to the incorporation of one or more nucleotides into a nucleic acid molecule. Insertion of parts of genes, such as parts of exons or introns as well as insertion of entire genes is also encompassed by the term "insertion". When the number of inserted nucleotides is not dividable by three, the insertion can result in a frameshift mutation within a coding sequence of a gene. Such frameshift mutations will alter the amino acids encoded by a gene following the mutation. In some cases, such a mutation will cause the active translation of the gene to encounter a premature stop codon, resulting in an end to translation and the production of a truncated protein. When the number of inserted nucleotides is instead dividable by three, the resulting insertion is an "in-frame insertion". In this case, the reading frame remains intact after the insertion and translation will most likely run to completion if the inserted nucleotides do not code for a stop codon. However, because of the inserted nucleotides, the resulting protein will contain, depending on the size of the insertion, one or multiple new amino acids that may effect the function of the protein.

The term "deletion" as used in accordance with the present invention refers to the loss of nucleotides or part of genes, such as exons or introns as well as entire genes. As defined with regard to the term "insertion", the deletion of a number of nucleotides that is not evenly dividable by three will lead to a frameshift mutation, causing all of the codons occurring after the deletion to be read incorrectly during translation, potentially producing a severely altered and most likely non-functional protein. If a deletion does not result in a frameshift mutation, i.e. because the number of nucleotides deleted is dividable by three, the resulting protein is nonetheless altered as the it will lack, depending on the size of the deletion, several amino acids that may affect or effect the function of the protein.

The above defined modifications are not restricted to coding regions in the genome, but can also occur in non-coding regions of the target genome, for example in regulatory regions such as promoter or enhancer elements or in introns.

Examples of modifications of the target genome include, without being limiting, the introduction of mutations into a wild type gene in order to analyse its effect on gene function; the replacement of an entire gene with a mutated gene or, alternatively, if the target sequence comprises mutation(s), the alteration of these mutations to identify which mutation is causative of a particular effect; the removal of entire genes or proteins or the removal of regulatory elements from genes or proteins as well as the introduction of fusion-partners, such as for example purification tags such as the his-tag or the tap-tag etc. In the latter case, the term "addition" may also be used instead of "insertion" so as to describe the preferable addition of a tag to a terminus of a polypeptide rather than within the sequence of a polypeptide The term "eukaryotic cell" as used herein, refers to any cell of a unicellular or multi-cellular eukaryotic organism, including cells from animals like vertebrates and from fungi and plants. Preferably, but without limitation, the cell is a mammalian cell. The term "mammalian cell" as used herein, is well known in the art and refers to any cell belonging to an animal that is grouped into the class of mammalia. The term "cell" as used in connection with the present invention can refer to a single and/or isolated cell or to a cell that is part of a multicellular entity such as a tissue, an organism or a cell culture another. In other words the method can be performed in vivo, ex vivo or in vitro. Depending on the particular goal to be achieved through modifying the genome of a mammalian cell, cells of different mammalian subclasses such as prototheria or theria may be used. For example, within the subclass of theria, preferably cells of animals of the infraclass eutheria, more preferably of the order primates, artiodactyla, perissodactyla, rodentia and lagomorpha are used in the method of the invention as detailed below. Furthermore, within a species one may choose a cell to be used in the method of the invention based on the tissue type and/or capacity to differentiate equally depending on the goal to be achieved by modifying the genome. Three basic categories of cells make up the mammalian body: germ cells, somatic cells and stem cells. A germ cell is a cell that gives rise to gametes and thus is continuous through the generations. Stem cells can divide and differentiate into diverse specialized cell types as well as self renew to produce more stem cells. In mammals there are two main types of stem cells: embryonic stem cells and adult stem cells. Somatic cells include all cells that are not a gametes, gametocytes or undifferentiated stem cells. The cells of a mammal can also be grouped by their ability to differentiate. A totipotent (also known as omnipotent) cell is a cell that is able to differentiate into all cell types of an adult organism including placental tissue such as a zygote (fertilized oocyte) and subsequent blastomeres, whereas pluripotent cells, such as embryonic stem cells, cannot contribute to extraembryonic tissue such as the placenta, but have the potential to differentiate into any of the three germ layers endoderm, mesoderm and ectoderm. Multipotent progenitor cells have the potential to give rise to cells from multiple, but limited number of cell lineages. Further, there are oligopotent cells that can develop into only a few cell types and unipotent cells (also sometimes termed a precursor cell) that can develop into only one cell type. There are four basic types of tissues: muscle tissue, nervous tissue, connective tissue and epithelial tissue that a cell to be used in the method of the invention can be derived from, such as for example hematopoietic stem cells or neuronal stem cells. To the extent human cells are envisaged for use in the method of the invention, it is preferred that such human cell is not obtained from a human embryo, in particular not via methods entailing destruction of a human embryo. On the other hand, human embryonic stem cells are at the skilled person's disposal such as taken from existent embryonic stem cell lines commercially available. Accordingly, the present invention may be worked with human embryonic stem cells without any need to use or destroy a human embryo. Alternatively, or instead of human embryonic stem cells, pluripotent cells that resemble embryonic stem cells such induced pluripotent stem (iPS) cells may be used, the generation of which is state of the art (Hargus G et al., Proc Natl Acad Sci USA 107:15921-15926; Jaenisch R. and Young R., 2008, Cell 132:567-582; Saha K, and Jaenisch R., 2009, Cell Stem Cell 5:584-595).

The term "nucleic acid molecules encoding said protein or fusion protein in expressible form" refers to a nucleic acid molecule which, upon expression in a cell or a cell-free system, results in a functional protein or fusion protein of the invention. Preferably, but without limitation, said nucleic acid is mRNA. Alternatively, DNA having appropriate transcription signals to enable expression or cDNA may be used.

Introduction of the protein, fusion protein or of the nucleic acid molecule encoding said protein, fusion protein in expressible form into a cell can be achieved by methods known in the art and depends on the nature of said proteins or nucleic acid molecules. For example, and in the case of introducing nucleic acid molecules, said introducing can be achieved by chemical based methods (calcium phosphate, liposomes, DEAE-dextrane, polyethylenimine, nucleofection), non chemical methods (electroporation, sonoporation, optical transfection, gene electrotransfer, hydrodynamic delivery), particle-based methods (gene gun, magnetofection, impalefection) and viral methods. Preferably, the nucleic acid molecules are to be introduced into the nucleus by methods such as, e.g., microinjection or nucleofection. Methods for carrying out microinjection are well known in the art and are described for example in Nagy et al. (Nagy A, Gertsenstein M, Vintersten K, Behringer R., 2003. Manipulating the Mouse Embryo. Cold Spring Harbour, N.Y.: Cold Spring Harbour Laboratory Press) as well as in the examples herein below. It is understood by the skilled person that depending on the method of introduction it may be advantageous to adapt DNA molecules. For example, a linear DNA molecule may be more efficient in homologous recombination events when using electroporation as method to introduce said DNA molecule into a, e.g., mammalian cell, whereas a circular DNA molecule may be more advantageous when injecting cells.

All the definitions and preferred embodiments defined above with regard to the nucleic acid molecule, protein or fusion protein of the invention also apply mutatis mutandis in the context of the method of the invention.

In accordance with the present invention, the term "target sequence in the genome" refers to the genomic location that is to be modified by the method of the invention. The "target sequence in the genome" comprises but is not restricted to the nucleotide(s) subject to the particular modification. Furthermore, and preferably with regard to the fusion protein of the invention the term "target sequence in the genome" also comprises regions for binding of homologous sequences of a second nucleic acid molecule. In other words, the term "target sequence in the genome" also comprises the sequence flanking/surrounding the relevant nucleotide(s) to be modified. In some instances, the term "target sequence" may also refer to the entire gene to be modified.

Specific binding has been defined herein above and ensures that double-strand breaks are only introduced within said target sequence.

In a more preferred embodiment of the method of the invention, the modification of said target sequence is by homologous recombination with a donor nucleic acid sequence, further comprising the step: (b) introducing a nucleic acid molecule into said cell, wherein said nucleic acid molecule comprises said donor nucleic acid sequence, wherein said donor DNA sequence is flanked upstream by a first flanking element and downstream by a second flanking element, wherein said first and second flanking element are different and wherein each of said first and second flanking element are homologous to a continuous DNA sequence on either side of the double-strand break introduced in (a) of the method of the invention within said target sequence in the genome of said eukaryotic cell.

The term "homologous recombination", is used according to the definitions provided in the art. Thus, it refers to a mechanism of genetic recombination in which two DNA strands comprising similar nucleotide sequences exchange genetic material. Cells use homologous recombination during meiosis, where it serves to rearrange DNA to create an entirely unique set of haploid chromosomes, but also for the repair of damaged DNA, in particular for the repair of double strand breaks. The mechanism of homologous recombination is well known to the skilled person and has been described, for example by Paques and Haber Paques F, Haber J E.; Microbiol Mol Biol Rev 1999; 63:349-404). In the method of the present invention, homologous recombination of the donor sequence is enabled by the presence of said first and said second flanking element being placed upstream (5') and downstream (3'), respectively, of said donor DNA sequence each of which being homologous to a continuous DNA sequence within said target sequence.

In accordance with the present invention, the term "donor DNA sequence" refers to a DNA sequence that serves as a template in the process of homologous recombination and that carries the modification that is to be introduced into the target sequence. By using this donor DNA sequence as a template, the genetic information, including the modifications, is copied into the target sequence within the genome of the cell by way of homologous recombination. In non-limiting examples, the donor nucleic acid sequence can be essentially identical to the part of the target sequence to be replaced, with the exception of one nucleotide which differs and results in the introduction of a point mutation upon homologous recombination or it can consist of an additional gene previously not present in the target sequence. Conceivably, the nature, i.e. its length, base composition, similarity with the target sequence, of the donor DNA sequence depends on how the target sequence is to be modified as well as the particular goal to be achieved by the modification of the target sequence. It is understood by those skilled in the art that said donor DNA sequence is flanked by sequences that are homologous to sequences within the target sequence to enable homologous recombination to take place leading to the incorporation of the donor DNA sequence into the genome of said cell. In addition to being homologous to a continuous DNA sequence within the genomic DNA, the first and the second flanking element are different to allow targeted homologous recombination to take place.

The term "homologous to a continuous DNA sequence on either side of the double-strand break introduced in (a) of the method of the invention within said target sequence", in accordance with the present invention, refers to regions having sufficient sequence identity to ensure specific binding to the target sequences that lie upstream and downstream of the location of the double-strand break. The term "homologous" as used herein can be interchanged with the term "identical" as outlined herein elsewhere with regard to varying levels of sequence identity. Methods to evaluate the identity level between two nucleic acid sequences are well known in the art and have been described herein above. These methods involving programs, in addition to providing a pairwise sequence alignment, also report the sequence identity level (usually in percent identity) and the probability for the occurrence of the alignment by chance (P-value) and can further be used to predict the occurrence of specific binding.

Preferably, said first and second flanking element being "homologous to a continuous DNA sequence within said target sequence" (also referred to as "homology arms" in the art) have a sequence identity with the corresponding part of the target sequence of at least 95%, more preferred at least 97%, more preferred at least 98%, more preferred at least 99%, even more preferred at least 99.9% and most preferred 100%. The above defined sequence identities are defined only with respect to those parts of the target sequence which serve as binding sites for the homology arms, i.e. said first and said second flanking element. Thus, the overall sequence identity between the entire target sequence and the homologous regions of the nucleic acid molecule of step (b) of the method of modifying a target sequence of the present invention can differ from the above defined sequence identities, due to the presence of the part of the target sequence which is to be replaced by the donor DNA sequence.

The flanking elements homologous to the target sequence comprised in the DNA molecule have a length of at least 170 bp each. Preferably, the elements each have a length of at least 250 nucleotides, at least 300 nucleotides, at least 400 nucleotides, at least 500 nucleotides, such as at least 600 nucleotides, at least 750 bp nucleotides, more preferably at least 1000 nucleotides, such as at least 1500 nucleotides, even more preferably at least 2000 nucleotides and most preferably at least 2500 nucleotides. The maximum length of the elements homologous to the target sequence comprised in the nucleic acid molecule depends on the type of cloning vector used and can be up to a length 20.000 nucleotides each in *E. coli* high copy plasmids using the col El replication origin (e.g. pBluescript) or up to a length of 300.000 nucleotides each in plasmids using the F-factor origin (e.g. in BAC vectors such as for example pTARBAC1).

The DNA molecules comprising the donor DNA sequence and the flanking elements are—necessarily if the site-specific nuclease (fusion protein) binding site is contained undisrupted within one of the flanking elements and preferably if the site-specific nuclease (fusion protein) binding site is disrupted by the donor sequence, i.e. one part on each of the flanking elements—modified so that the fusion protein not introduce a double-strand break into the sequence of the donor DNA as part of a DNA molecule. When the fusion protein is a TAL or zinc-finger nuclease, this can be achieved, e.g., by modifying either the binding or cleavage motif (see Example 2, FIG. 12).

It will be appreciated by one of skill in the art that said DNA molecule to be introduced into the cell in item (b) of the method of the invention may comprise all a nucleic acid molecule (sequence) encoding said fusion protein in expressible form and the nucleic acid molecule comprising the donor nucleic acid sequence and the flanking elements homologous to the target sequence. Alternatively, the nucleic acid molecule of item (b) may be a distinct nucleic acid molecule, to be introduced in addition to the nucleic acid molecules encoding said fusion protein in expressible form of item (a).

Also envisaged in a preferred embodiment of the method of the invention is that said cell is analysed for successful modification of said target sequence in the genome.

Methods for analysing for the presence or absence of a modification are well known in the art and include, without being limiting, assays based on physical separation of nucleic acid molecules, sequencing assays as well as cleavage and digestion assays and DNA analysis by the polymerase chain reaction (PCR).

Examples for assays based on physical separation of nucleic acid molecules include without limitation MALDI-TOF, denaturating gradient gel electrophoresis and other such methods known in the art, see for example Petersen et al., Hum. Mutat. 20 (2002) 253-259; Hsia et al., Theor. Appl. Genet. 111 (2005) 218-225; Tost and Gut, Clin. Biochem. 35 (2005) 335-350; Palais et al., Anal. Biochem. 346 (2005) 167-175.

Examples for sequencing assays comprise without limitation approaches of sequence analysis by direct sequencing, fluorescent SSCP in an automated DNA sequencer and pyrosequencing. These procedures are common in the art, see e.g. Adams et al. (Ed.), "Automated DNA Sequencing and Analysis", Academic Press, 1994; Alphey, "DNA Sequencing: From Experimental Methods to Bioinformatics", Springer Verlag Publishing, 1997; Ramon et al., J. Transl. Med. 1 (2003) 9; Meng et al., J. Clin. Endocrinol. Metab. 90 (2005) 3419-3422.

Examples for cleavage and digestion assays include without limitation restriction digestion assays such as restriction fragments length polymorphism assays (RFLP assays), RNase protection assays, assays based on chemical cleavage methods and enzyme mismatch cleavage assays, see e.g. Youil et al., Proc. Natl. Acad. Sci. U.S.A. 92 (1995) 87-91; Todd et al., J. Oral Maxil. Surg. 59 (2001) 660-667; Amar et al., J. Clin. Microbiol. 40 (2002) 446-452.

Alternatively, instead of analysing the cells for the presence or absence of the desired modification, in particular in the case of sequence-specific modification, successfully modified cells may be selected by incorporation of appropriate selection markers. Selection markers include positive and negative selection markers, which are well known in the art and routinely employed by the skilled person. Non-limiting examples of selection markers include dhfr, gpt, neomycin, hygromycin, dihydrofolate reductase, G418 or glutamine synthase (GS) (Murphy et al., Biochem J. 1991, 227:277; Bebbington et al., Bio/Technology 1992, 10:169). Using these markers, the cells are grown in selective medium and the cells with the highest resistance are selected. Also envisaged are combined positive-negative selection markers, which may be incorporated into the target genome by homologous recombination or random integration. After positive selection, the first cassette comprising the positive selection marker flanked by recombinase recognition sites is exchanged by recombinase mediated cassette exchange against a second, marker-less cassette. Clones containing the desired exchange cassette are then obtained by negative selection.

In a preferred embodiment of the method of the invention, the cell is selected from the group consisting of a mammalian or vertebrate cell, a plant cell or a fungal cell.

In another preferred embodiment of the method of the invention, the cell is an oocyte.

As used herein the term "oocyte" refers to the female germ cell involved in reproduction, i.e. the ovum or egg cell. In accordance with the present invention, the term "oocyte" comprises both oocytes before fertilisation as well as fertilised oocytes, which are also called zygotes. Thus, the oocyte before fertilisation comprises only maternal chromosomes, whereas an oocyte after fertilisation comprises both maternal and paternal chromosomes. After fertilisation, the oocyte remains in a double-haploid status for several hours, in mice for example for up to 18 hours after fertilisation. In accordance with the invention, the oocyte may be non-human.

In a more preferred embodiment of the method of the invention, the oocyte is a fertilised oocyte. The term "fertilised oocyte", as used herein, refers to an oocyte after fusion with the fertilizing sperm. For a period of many hours (such as up to 18 hours in mice) after fertilisation, the oocyte is in a double-haploid state, comprising one maternal haploid pronucleus and one paternal haploid pronucleus. After migration of the two pronuclei together, their membranes break down, and the two genomes condense into chromosomes, thereby reconstituting a diploid organism. Preferably, the mammalian or avian oocyte used in the method of the present invention is a fertilised mammalian or avian oocyte in the double-haploid state.

In the case of oocytes to be used as cells in the method of the invention the protein, fusion protein or the nucleic acid molecule encoding said protein or fusion protein is introduced into the oocyte by microinjection. Microinjection into the oocyte can be carried out by injection into the nucleus (before fertilisation), the pronucleus (after fertilisation) and/or by injection into the cytoplasm (both before and after fertilisation). When a fertilised oocyte is employed, injection into the pronucleus is carried out either for one pronucleus or for both pronuclei. Injection of the Tal-finger nuclease or of a DNA encoding the Tal-finger nuclease of step (a) of the method of modifying a target sequence of the present invention is preferably into the nucleus/pronucleus, while injection of an mRNA encoding the Tal-finger nuclease of step (a) is preferably into the cytoplasm. Injection of the nucleic acid molecule of step (b) is preferably into the nucleus/pronucleus. However, injection of the nucleic acid molecule of step (b) can also be carried out into the cytoplasm when said nucleic acid molecule is provided as a nucleic acid sequence having a nuclear localisation signal to ensure delivery into the nucleus/pronucleus. Preferably, the microinjection is carried out by injection into both the nucleus/pronucleus and the cytoplasm. For example, the needle can be introduced into the nucleus/pronucleus and a first amount of the Tal-finger nuclease and/or nucleic acid molecule are injected into the nucleus/pronucleus. While removing the needle from the oocyte, a second amount of the Tal-finger nuclease and/or nucleic acid molecule is injected into the cytoplasm.

Methods for carrying out microinjection are well known in the art and are described for example in Nagy et al. (Nagy A, Gertsenstein M, Vintersten K, Behringer R., 2003. Manipulating the Mouse Embryo. Cold Spring Harbour, N.Y.: Cold Spring Harbour Laboratory Press) as well as in the examples herein below.

Also preferred is that the nucleic acid molecule of step (b) of the method of the invention is (also) introduced into the cell by microinjection.

In another embodiment, the invention relates to method of producing a non-human vertebrate or mammal carrying a modified target sequence in its genome, the method comprising transferring a cell produced by the method of the invention into a pseudo pregnant female host.

In accordance with the present invention, the term "transferring a cell produced by the method of the invention into a pseudopregnant female host" includes the transfer of a fertilised oocyte but also the transfer of pre-implantation embryos of for example the 2-cell, 4-cell, 8-cell, 16-cell and blastocyst (70- to 100-cell) stage. Said pre-implantation embryos can be obtained by culturing the cell under appropriate conditions for it to develop into a pre-implantation embryo. Furthermore, injection or fusion of the cell with a blastocyst are appropriate methods of obtaining a pre-implantation embryo. Where the cell produced by the method of the invention is a somatic cell, derivation of induced pluripotent stem cells is required prior to transferring the cell into a female host such as for example prior to culturing the cell or injection or fusion of the cell with a pre-implantation embryo. Methods for transferring an oocyte or pre-implantation embryo to a pseudo pregnant female host are well known in the art and are, for example, described in Nagy et al., (Nagy A, Gertsenstein M, Vintersten K, Behringer R., 2003. Manipulating the Mouse Embryo. Cold Spring Harbour, N.Y.: Cold Spring Harbour Laboratory Press).

It is further envisaged in accordance with the method of producing a non-human vertebrate or mammal carrying a modified target sequence in its genome that a step of analysis of successful genomic modification is carried out before transplantation into the female host. As a non-limiting example, the oocyte can be cultured to the 2-cell, 4-cell or 8-cell stage and one cell can be removed without destroying or altering the resulting embryo. Analysis for the genomic constitution, e.g. the presence or absence of the genomic modification, can then be carried out using for example PCR or southern blotting techniques or any of the methods described herein above. Such methods of analysis of successful genotyping prior to transplantation are known in the art and are described, for example in Peippo et al. (Peippo J, Viitala S, Virta J, Raty M, Tammiranta N, Lamminen T, Aro J, Myllymaki H, Vilkki J.; Mol Reprod Dev 2007; 74:1373-1378).

Where the cell is an oocyte, the method of producing a non-human vertebrate or mammal carrying a modified target sequence in its genome comprises (a) modifying the target sequence in the genome of a vertebrate or mammalian oocyte in accordance with the method of the invention; (b) transferring the oocyte obtained in (a) to a pseudopregnant female host; and, optionally, (c) analysing the offspring delivered by the female host for the presence of the modification.

For this method of producing a non-human vertebrate or mammal, fertilisation of the oocyte is required. Said fertilisation can occur before the modification of the target sequence in step (a) in accordance with the method of producing a non-human vertebrate or mammal of the invention, i.e. a fertilised oocyte can be used for the method of modifying a target sequence in accordance with the invention. The fertilisation can also be carried out after the modification of the target sequence in step (a), i.e. a non-fertilised oocyte can be used for the method of modifying a target sequence in accordance with the invention, wherein the oocyte is subsequently fertilised before transfer into the pseudopregnant female host.

The step of analysing for the presence of the modification in the offspring delivered by the female host provides the necessary information whether or not the produced non-human vertebrate or mammal carries the modified target sequence in its genome. Thus, the presence of the modification is indicative of said offspring carrying a modified target sequence in its genome whereas the absence of the modification is indicative of said offspring not carrying the modified target sequence in its genome. Methods for analysing for the presence or absence of a modification have been detailed above.

The non-human vertebrate or mammal produced by the method of the invention is, inter alia, useful to study the function of genes of interest and the phenotypic expression/outcome of modifications of the genome in such animals. It is furthermore envisaged, that the non-human mammals of the invention can be employed as disease models and for testing therapeutic agents/compositions. Furthermore, the non-human vertebrate or mammal of the invention can also be used for livestock breeding.

In a preferred embodiment, the method of producing a non-human vertebrate or mammal further comprises culturing the cell to form a pre-implantation embryo or introducing the cell into a blastocyst prior to transferring it into the pseudo pregnant female host. Methods for culturing the cell to form a pre-implantation embryo or introducing the cell into a blastocyst are well known in the art and are, for example, described in Nagy et al., loc. cit.

The term "introducing the cell into a blastocyst" as used herein encompasses injection of the cell into a blastocyst as well as fusion of a cell with a blastocyst. Methods of introducing a cell into a blastocyst are described in the art, for example in Nagy et al., loc. cit.

The present invention further relates to a non-human vertebrate or mammalian animal obtainable by the above described method of the invention.

In a preferred embodiment of the methods of the invention, the cell is from a mammal selected from the group consisting of rodents, dogs, felides, primates, rabbits, pigs, or cows or the cell is from an avian selected from the group consisting of chickens, turkeys, pheasants, ducks, geese, quails and ratites including ostriches, emus and cassowaries or the cell is from a fish such as for example a zebrafish, salmon, trout, common carp or coi carp.

All of the mammals, avians and fish described herein are well known to the skilled person and are taxonomically defined in accordance with the prior art and the common general knowledge of the skilled person.

Non-limiting examples of "rodents" are mice, rats, squirrels, chipmunks, gophers, porcupines, beavers, hamsters, gerbils, guinea pigs, degus, chinchillas, prairie dogs, and groundhogs.

Non-limiting examples of "dogs" include members of the subspecies *canis* lupus familiaris as well as wolves, foxes, jackals, and coyotes.

Non-limiting examples of "felides" include members of the two subfamilies: the pantherinae, including lions, tigers, jaguars and leopards and the felinae, including cougars, cheetahs, servals, lynxes, caracals, ocelots and domestic cats.

The term "primates", as used herein, refers to all monkey including for example cercopithecoid (old world monkey) or platyrrhine (new world monkey) as well as lemurs, tarsiers, apes and marmosets (Callithrix jacchus).

As regards the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The figures show:

FIG. 1: TAL-Nuclease expression vectors.

The figure shows the structure and function of TAL-Nuclease fusion proteins, consisting of a sequence-specific DNA-binding domain and a nonspecific DNA cleavage (nuclease) domain. The DNA-binding domain can be assembled from the four types of 34 amino acid TAL peptide elements that exhibit binding specificity against one of the DNA nucleotides through the amino acid positions 12 and 13 (NI-A; HD-C; NG-T; NN-G). Upon binding of the TAL element domain to the selected target DNA sequence, the nuclease domain of the fusion protein comes into close contact to the DNA double-strand but does not cleave the DNA as a nuclease monomer. Only upon the binding of a second TAL-Nuclease fusion protein to a second DNA target sequence located downstream of the binding site of the first fusion protein, the DNA double strand is cleaved through cooperation of the two nuclease domains that are in close contact.

Figure 2:
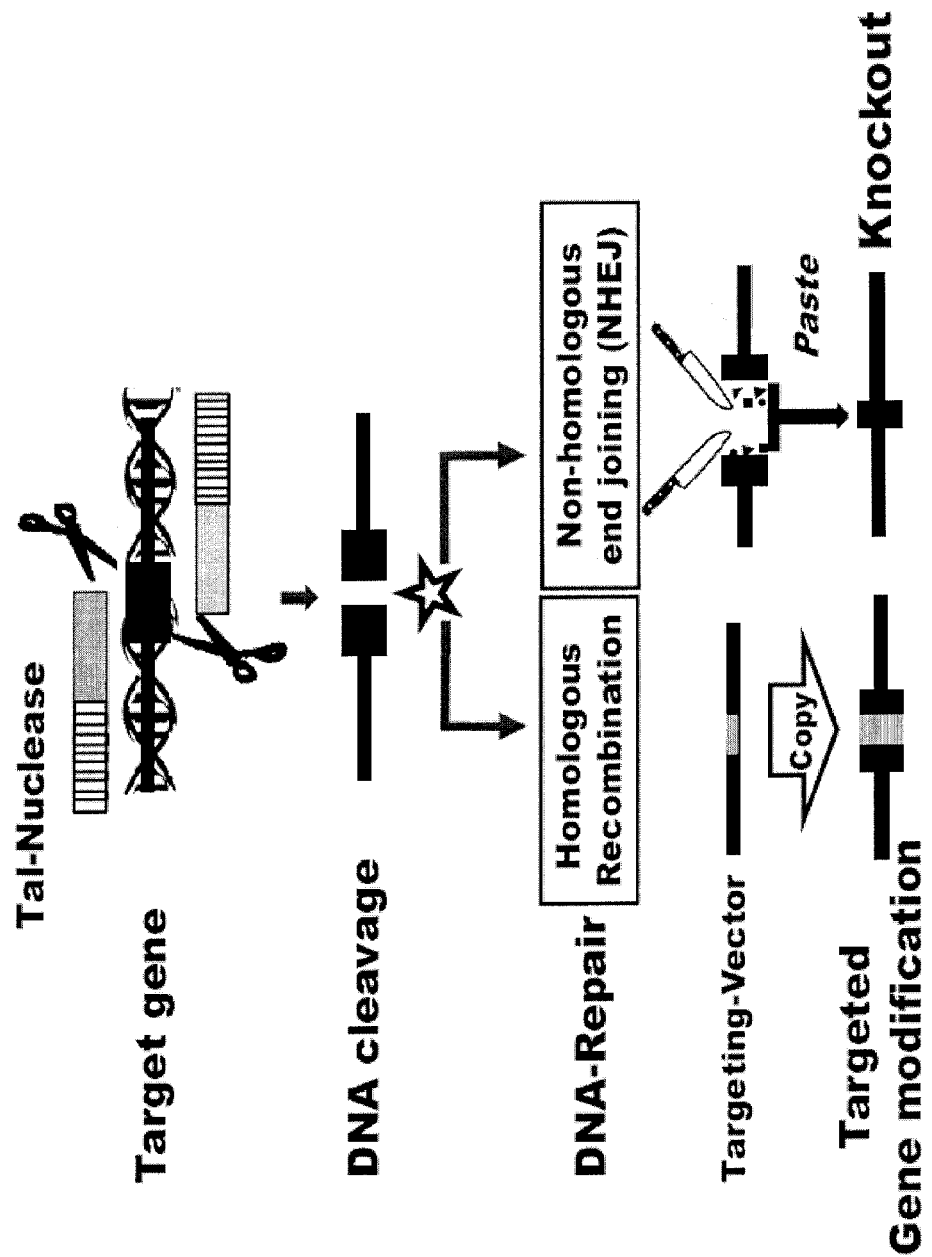

FIG. 2: TAL-Nuclease induced modification of genomic sequences.

The figure shows a pair of TAL-nuclease fusion proteins that bind up- and downstream of a selected target site within a genomic target gene. Upon the creation of a DNA double-strand break within the target site two competing DNA repair mechanisms are strongly activated in cells: i) by homologous recombination, in the presence of an externally introduced gene targeting vector that comprises two homology regions to the target gene and a predesigned genetic modification/mutation, the preplanned modification is copied from the targeting vector into the genome; by this route any targeted gene modification (e.g. knock-out, knock-in) can be placed into the genome, ii) by the non-homologous end joining repair pathway (NHEJ) the free DNA ends are closed by ligation without a repair template; by this route a variable number of nucleotides is frequently lost (knife symbol) before end ligation and results frequently into a knockout allele of the target gene.

Figure 3:
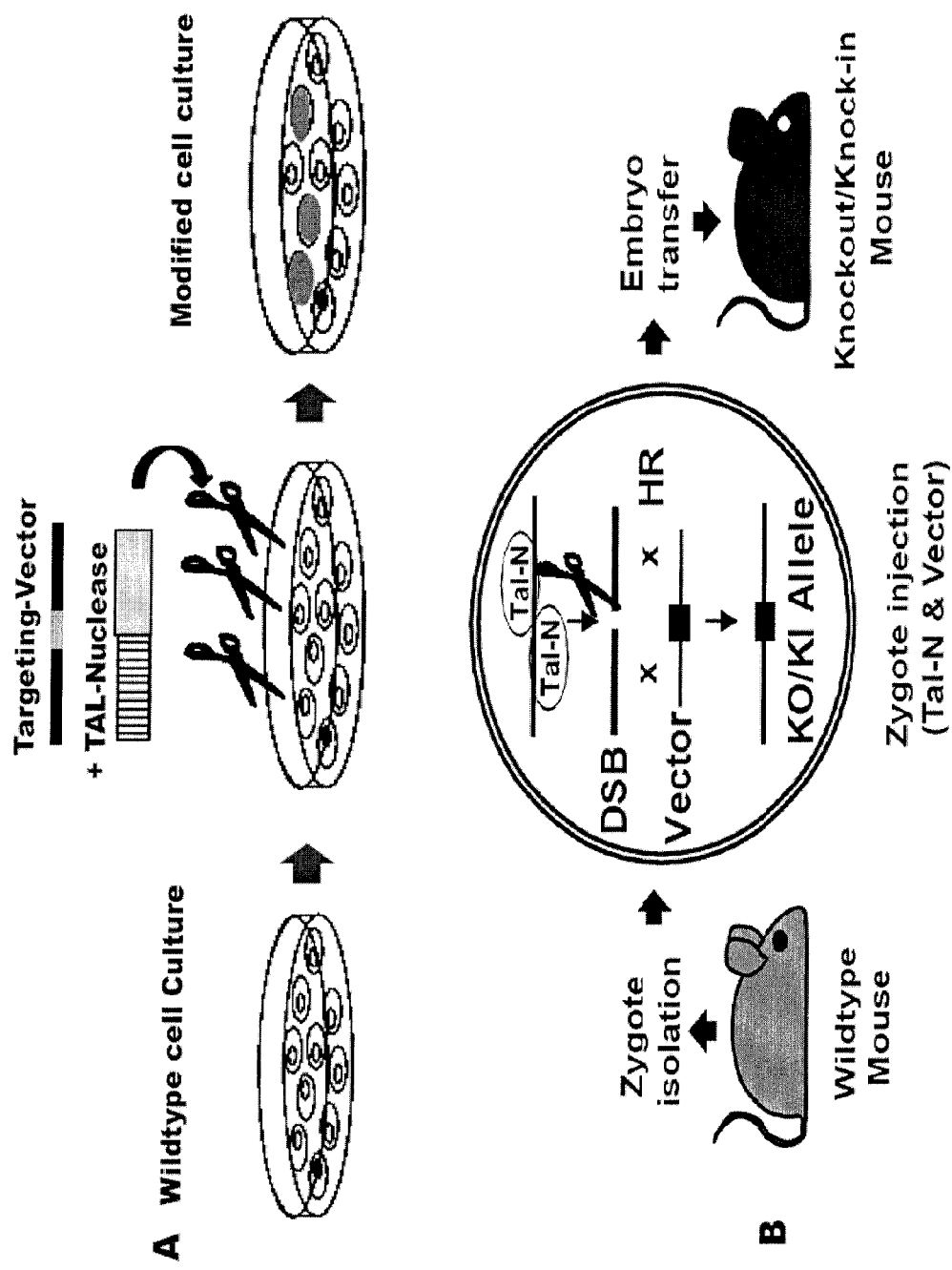

FIG. 3: Use of TAL-Nucleases for gene targeting in mammalian cell lines and zygotes.

A: For the generation of genetic modifications in mammalian cell lines TAL-nuclease expression vectors can be transfected, together with or without a specific gene targeting vector, into cultured cells. Upon nuclease expression and DNA repair a fraction of the treated cells contains the desired genetic alteration. These cells can be isolated and further cultured as a pure genetically modified cell line. B: Upon the microinjection of TAL-nuclease mRNA, together with or without a specific gene targeting vector, into fertilized mammalian oocytes (zygotes, isolated from wildtype female e.g. mice) a knockout (KO) or Knockin (KI) allele can be directly introduced into the genome of the one-cell embryo. Pseudopregnant females deliver live offspring from microinjected oocytes. The offspring is genotyped for the presence of the induced genetic modification. Positive animals are selected for further breeding to establish a gene targeted strain.

Figure 4:
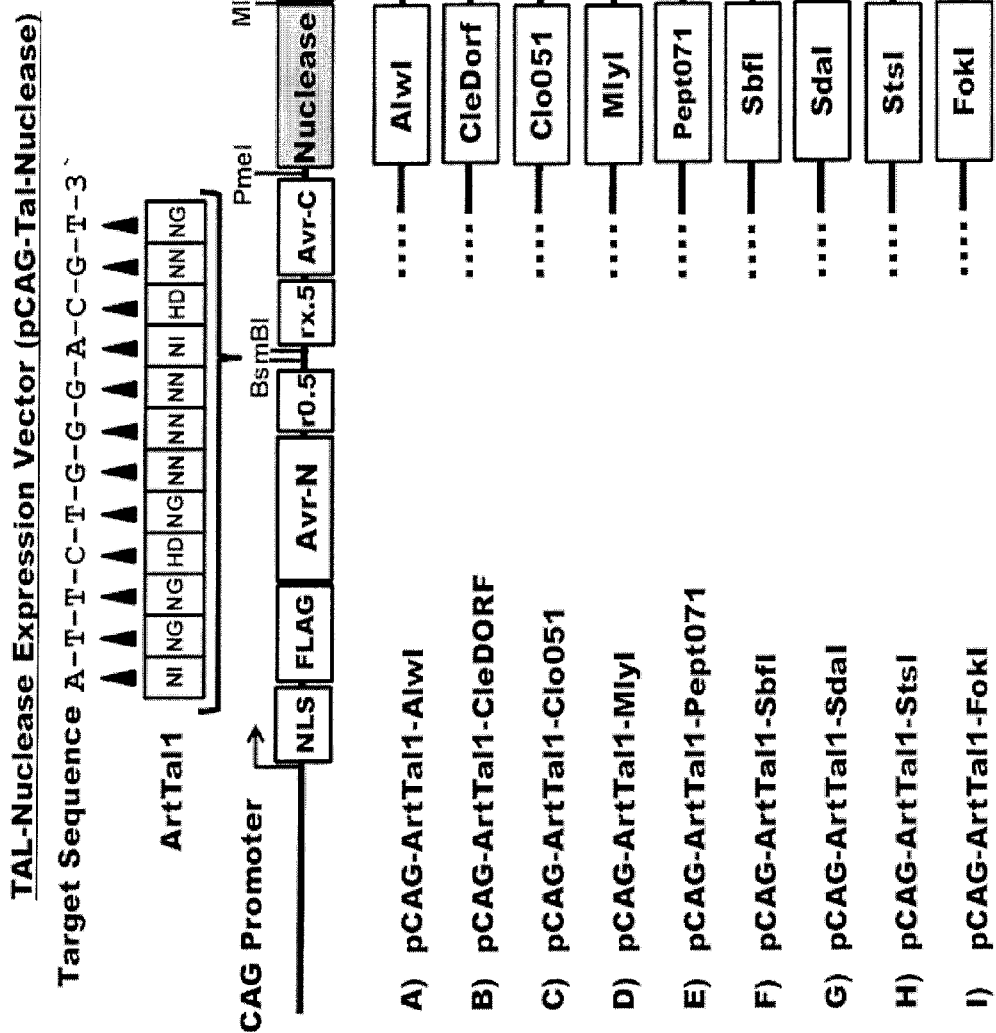

FIG. 4: TAL-Nuclease expression vectors.

The Tal nuclease expression vector pCAG-Tal-nuclease contains a CAG promoter region and a transcriptional unit comprising, upstream of a central pair of BsmBI restriction sites, an ATG start codon (arrow), a nuclear localisation sequence (NLS), a FLAG Tag sequence (FLAG), a linker sequence, a segment coding for 110 amino acids of the Tal protein AvrBs3 (AvrN) and its invariable N-terminal Tal repeat (r0.5). Downstream of the BsmBI sites the transcriptional unit contains an invariable C-terminal Tal repeat (rx.5), a segment coding for 44 amino acids derived from the Tal protein AvrBs3, a PmeI and MluI restriction site for the insertion of nuclease coding regions and a polyadenylation signal sequence (pA). DNA segments coding for TAL repeat elements can be inserted into the BsmBI sites of pCAG-Tal-nuclease for the expression of variable TAL-nuclease fusion proteins. To create ArtTal1-nuclease expression vectors the ArtTal1 array of TAL repeat elements, recognizing the specified 12 bp target sequence, was inserted into the BsmBI sites of pCAG-TAL-nuclease. Each 34 amino acid Tal repeat is drawn as a square indicating the repeat's amino acid code at positions 12/13 that confers binding to one of the DNA nucleotides of the target sequence (NI>A, NG>T, HD>C, NN>G) shown above. Next, synthetic nuclease domain coding regions were inserted into the PmeI and MluI sites of pCAG-ArtTal1-nuclease to obtain the expression vectors: A: pCAG-ArtTal1-Alw including the nuclease domain of the AlwI restriction endonuclease, B: pCAG-ArtTal1-CleDORF including the nuclease domain of the CleDORF gene, C: pCAG-ArtTal1-Clo051 including the nuclease domain of the Clo051 gene, D: pCAG-ArtTal1-Mly including the nuclease domain of the MlyI restriction endonuclease, E: pCAG-ArtTal1-Pept071 including the nuclease domain of the Pept071 gene, F: pCAG-ArtTal1-Sbf including the nuclease domain of the SbfI restriction endonuclease, G: pCAG-ArtTal1-Sda1 including the nuclease domain of the SdaI restriction endonuclease, H: pCAG-ArtTal1-Sst including the nuclease domain of the StsI restriction endonuclease, and I: pCAG-ArtTal1-Fok including the nuclease domain of the FokI restriction endonuclease FIG. 5: Amino acid sequence of the Clo051 protein Sequence of the 587 amino acid Clo051 protein in the single letter code. Indicated are the methionine at position 1 (M1), the tyrosine at position 587 (Y587) and the 199 residue nuclease domain between position E389 and Y587. Further highlighted are the positions D455, D472 and K474 that are characteristic for the conserved active site of the 'PD-(D/E) XK' superfamily of enzymes interacting with DNA.

Figure 6:
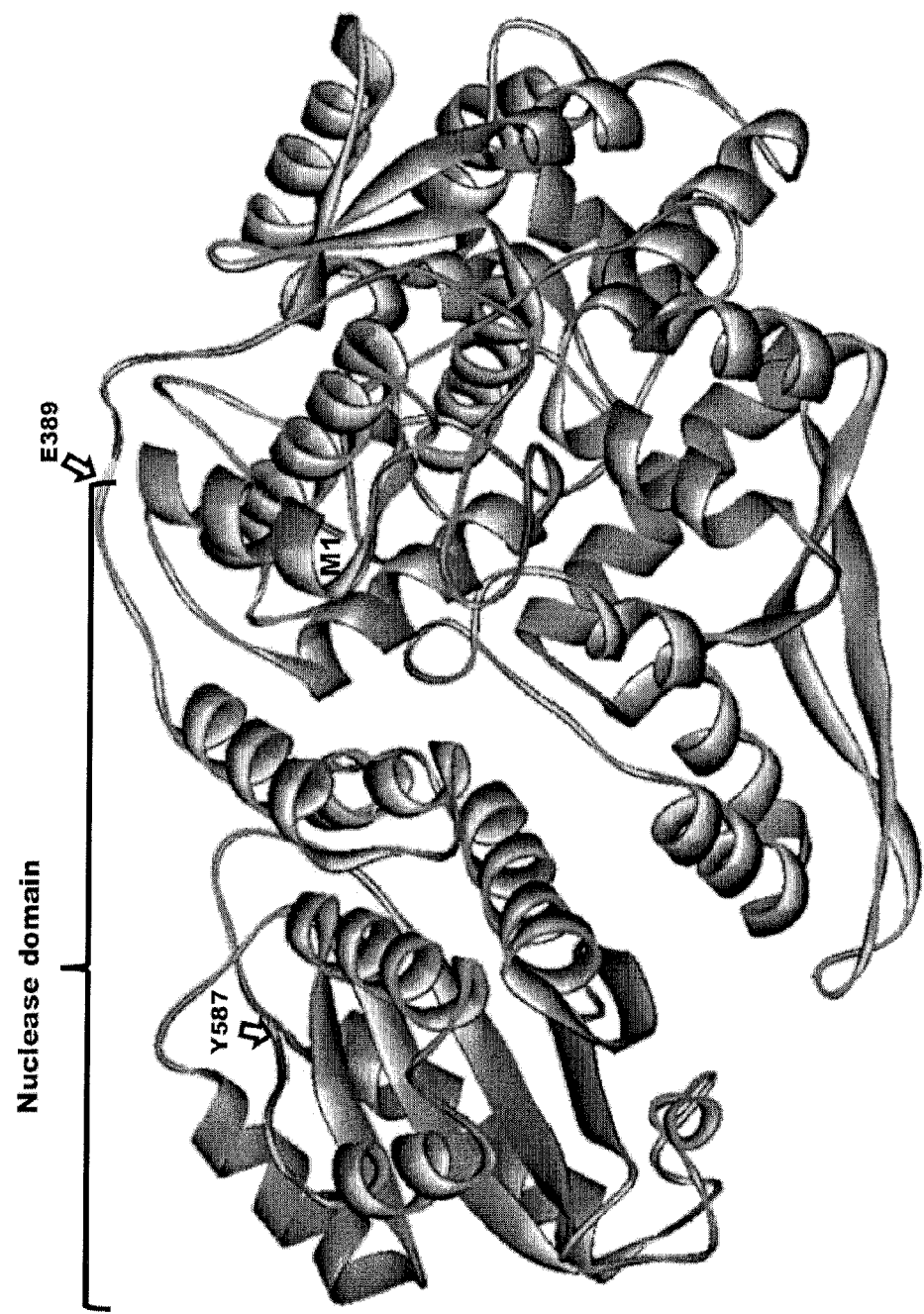

FIG. 6: Predicted structure of the Clo051 protein and its nuclease domain.

The tertiary structure of the Clo051 protein was predicted from its amino acid sequence (FIG. 5) using the I-TASSER software. The secondary structures are shown as alpha-helical and beta-stranded regions. Highlighted are the methionine at position 1 (M1), the glutamate residue 389 (E389) and tyrosine 587 (Y587). The protein chain between E389 and Y587 forms a separate folding domain that acts as a nuclease.

Figure 7:
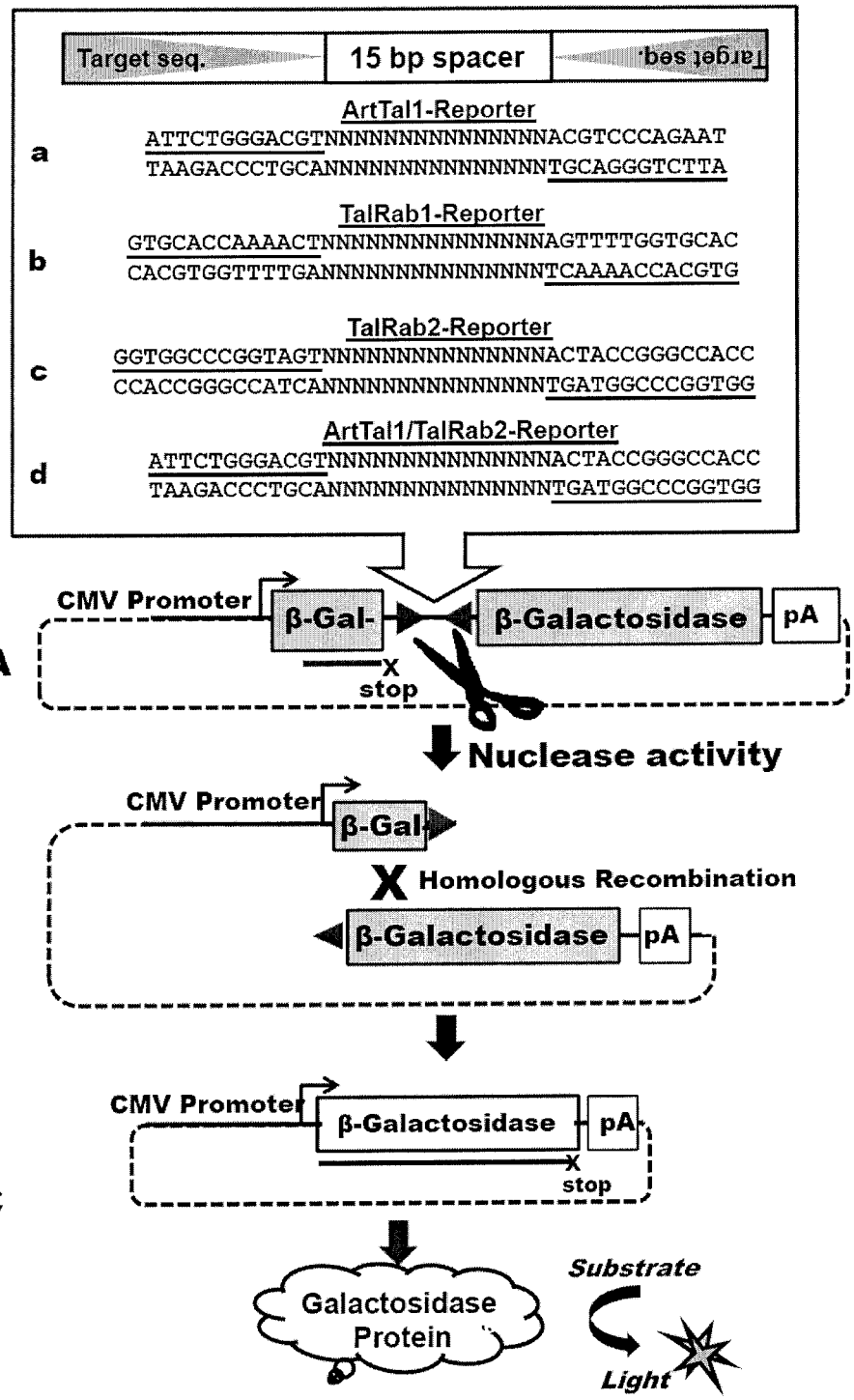

FIG. 7: TAL-Nuclease reporter plasmids and nuclease reporter assay.

A: TAL-nuclease reporter plasmids contain a CMV promoter region, a 400 bp sequence coding for the N-terminal segment of β-galactosidase and a stop codon. This unit is followed by a TAL binding target region consisting of two inverse oriented recognition sequences (underlined), separated by a 15 bp spacer region (NNN.), for the ArtTal1 array (a), the TalRab1 array (b), the TalRab2 array (c), or a hybrid binding region composed of one ArtTal1 and one TalRab2 recognition sequence (d). The TAL-nuclease target region is followed by the complete coding region for β-galactosidase and a polyadenylation signal (pA). To test for nuclease activity against the target sequence a TAL-nuclease expression vector (FIG. 4) is transiently cotransfected with its corresponding reporter plasmid into HEK 293 cells. Upon expression of the TAL-nuclease protein the reporter plasmid is opened by a nuclease-induced double-strand break within the TAL-nuclease target sequence (scissor symbol). B: The DNA regions adjacent to the double-strand break are identical over 400 bp and can be aligned and recombined (X) by homologous recombination DNA repair. C: Homologous recombination of an opened reporter plasmid results into a functional β-galactosidase expression vector that produces the β-galactosidase enzyme. After two days the transfected cells are lysed and the enzyme activity in the lysate is determined with a chemiluminescent reporter assay. The levels of the reporter catalysed light emission are measured and indicate TAL-nuclease activity in comparison to samples that were transfected with the reporter plasmid alone.

Figure 8:
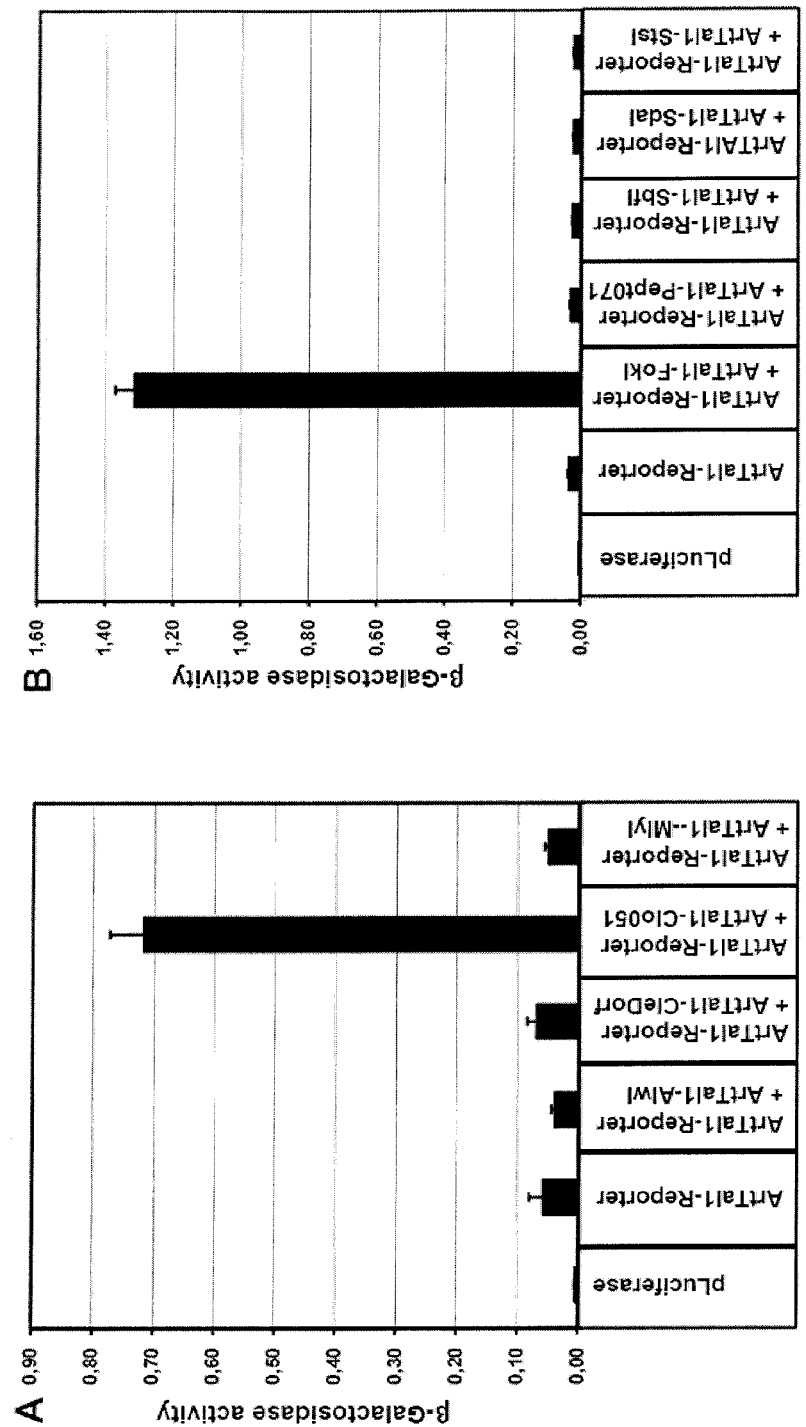

FIG. 8: Activity of Tal nuclease fusion proteins in HEK 293 cells.

To test for the nuclease activity of TAL-nuclease domain fusion proteins, expression vectors for the ArtTal1-Alwl, -CleDORF, -Clo051, -Mlyl, -Fokl, -Pept071, -Sbfl, -Sdal, and -Stsl proteins (FIG. 4) were transfected together with the ArtTal1 reporter plasmid (FIG. 7) into HEK 293 cells. Specific nuclease activity against the reporter plasmid's target sequence leads to homologous recombination and the expression of β-galactosidase. Two days after transfection the cell populations were lysed and the □ β-galactosidase activity determined with a chemiluminescent reporter assay. The levels of light emission were normalised in relation to the activity of a cotransfected Luciferase expression plasmid (pLuciferase) and are shown in comparison to the activity of a positive control β-galactosidase expression vector. The bar for each transfected sample represents the mean value and SD derived from three culture wells transfected side by side. A: The transfection of the ArtTal1 reporter plasmid without nuclease expression vector results in a low background level of β-galactosidase. The cotransfection of pCAG-ArtTal1-Alwl, -CleDORF, and -Mlyl with the ArtTal1 reporter plasmid did not lead to a significant increase of reporter expression, indicating that the ArtTal1-Alwl, -CleDORF, and -Mlyl fusion proteins do not exhibit nuclease activity. In contrast, the cotransfection of the ArtTal1 reporter and the pCAG-ArtTal1-Clo051 plasmids resulted in a strong increase of reporter expression, indicating that the ArtTal1-Clo051 fusion protein exhibits target specific nuclease activity in 293 cells. B: In an independent transfection experiment the cotransfection of pCAG-ArtTal1-Pept071, -Sbfl, -Sdal and -Sst with the ArtTal1 reporter plasmid did not lead to a significant increase of reporter expression, as compared to the ArtTal1 reporter plasmid alone, indicating that the ArtTal1-Pept071, -Sbfl, -Sdal, and -Stsl fusion proteins do not exhibit nuclease activity. In contrast, the cotransfection of the ArtTal1 reporter and the pCAG-ArtTal1-Fokl plasmids resulted in the increase of reporter expression, indicating the nuclease activity of the ArtTal1-Fokl fusion protein in 293 cells.

Figure 9:
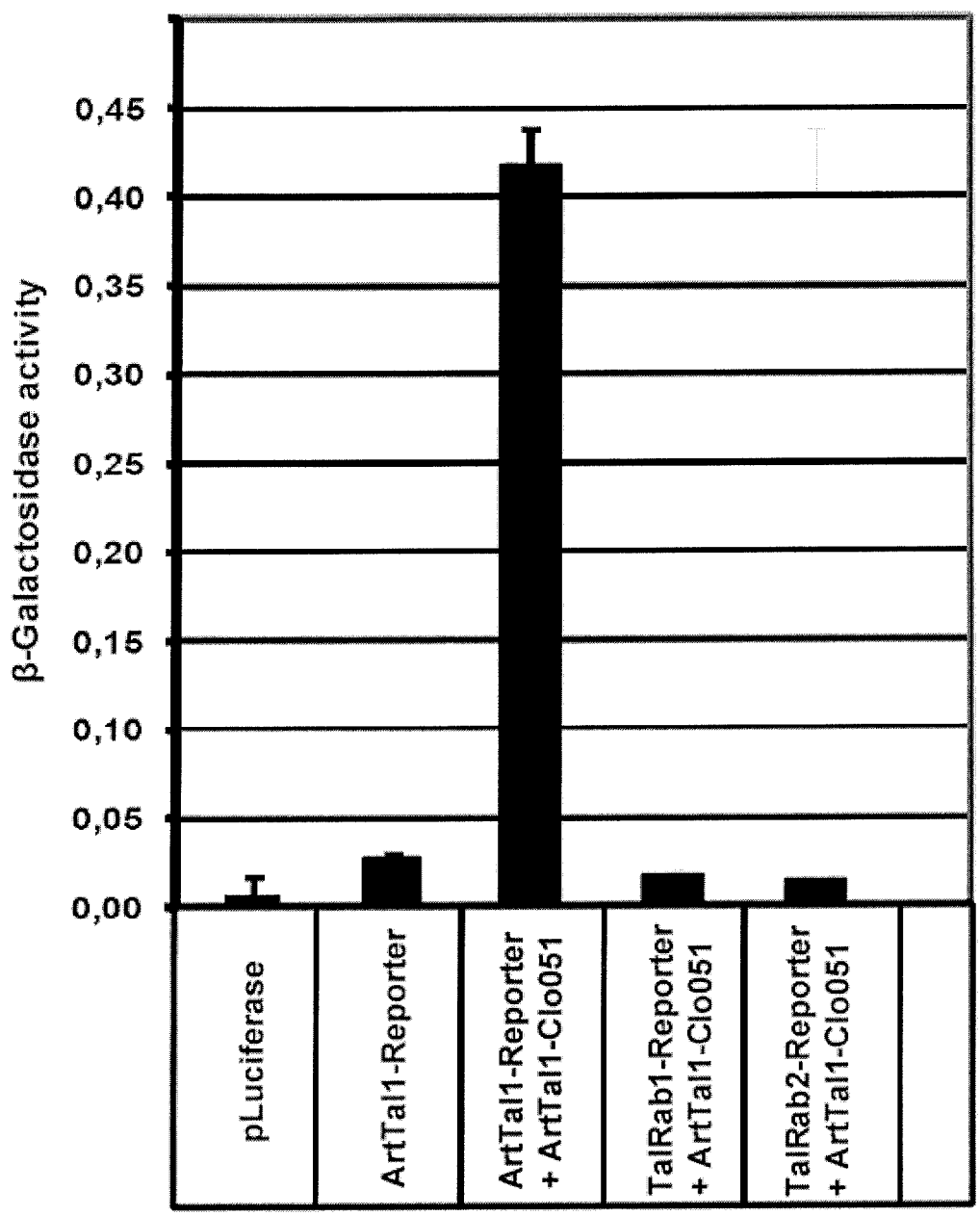

FIG. 9: Target sequence specificity of the ArtTal1-Clo051 nuclease.

To test for the specificity of the ArtTal1-Clo051 nuclease against the predesigned target sequence in comparison to unrelated DNA sequences, the pCAG-ArtTal1-Clo051 expression vector was cotransfected with the corresponding ArtTal1-reporter plasmid or with the TalRab1 or TalRab2 reporter plasmids (FIG. 7), which contain unrelated target sequences, into HEK 293 cells. Strong nuclease activity developed only in the specific combination of the ArtTal1-Clo051 expression vector together with the ArtTal1-reporter plasmid, indicating that the ArtTal1-Clo051 nuclease acts specifically against the predesigned target sequence.

Figure 10:
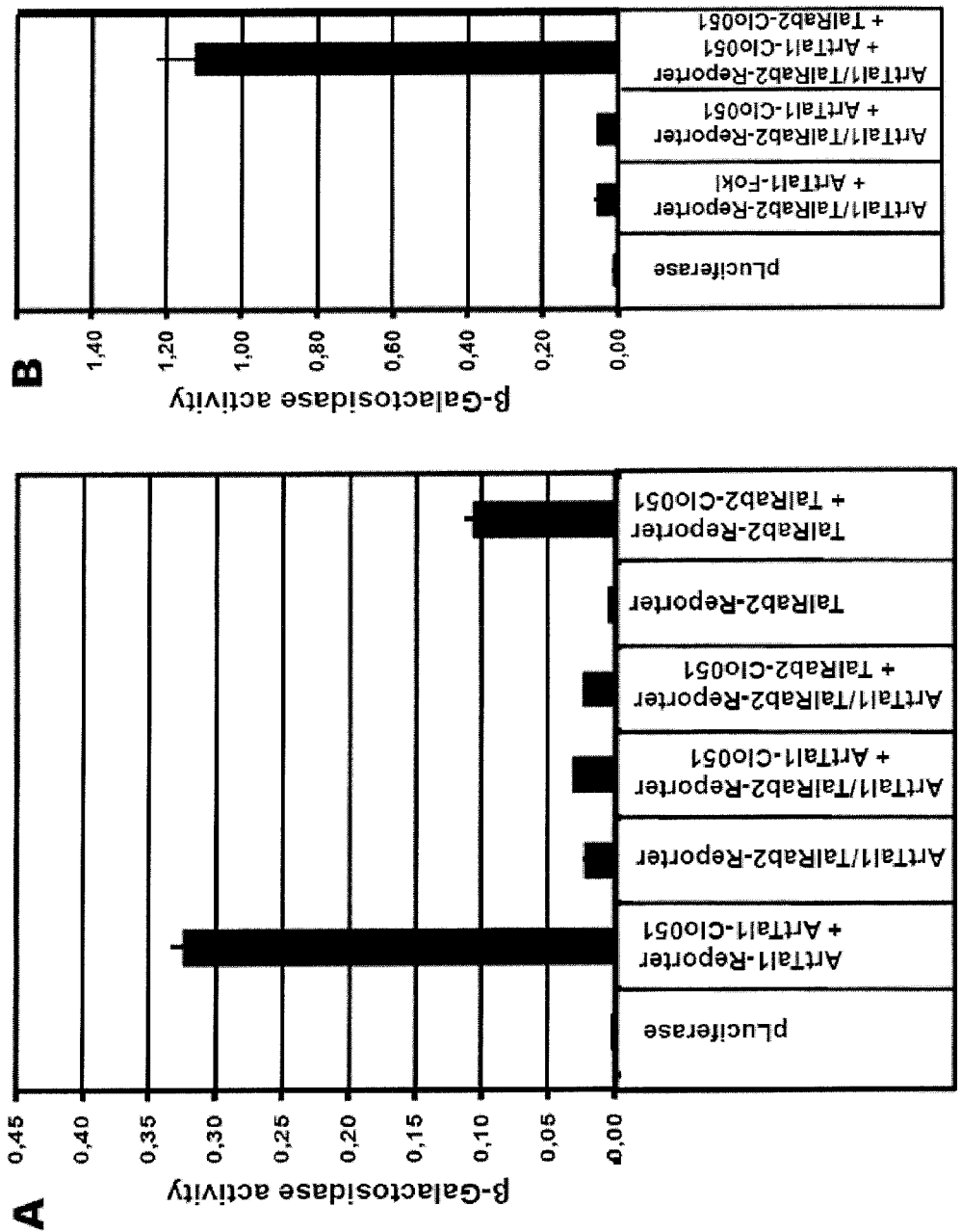

FIG. 10: Characterisation of the cooperativity of TAL-Clo051 nuclease fusion proteins A: To test for the cooperativity of the Clo051 nuclease domains of a pair of TAL-Clo051 fusion proteins, expression vectors for the ArtTal1-Clo051 or TalRab2-Clo051 fusion proteins were cotransfected with the corresponding ArtTal1- or TalRab2-reporter plasmid (FIG. 7) and compared to the cotransfection with the ArtTal1/TalRab2-reporter plasmid, that contains a hybrid target region (FIG. 7). Significant nuclease activity developed only in the combination of TAL-nuclease expression vectors with reporter plasmids that contain two identical, inverse copies of the corresponding TAL array target sequence, but not with the ArtTal1/TalRab2-reporter plasmid that contains only a single binding sequence of the ArtTal1-Clo051 and TalRab2-Clo051 fusion proteins. This result indicates that two Clo051 nuclease domains must cooperate to induce a DNA double-strand break, whereas a single Clo051 nuclease domain does not act as a nuclease. B: The cotransfection of the ArtTal1/TalRab2-reporter plasmid with both expression vectors for ArtTal1-Clo051 and TalRab2-Clo051, but not with ArtTal1-Clo051 or -Fok alone, results into strong nuclease activity, as compared to the transfection of the ArtTal1/TalRab2 reporter plasmid. This result indicates that nuclease activity and the induction of double-strand breaks in the target region occurs only upon the binding of two TAL-Clo051 fusion proteins and the interaction of a pair of Clo051 nuclease domains.

Figure 11:
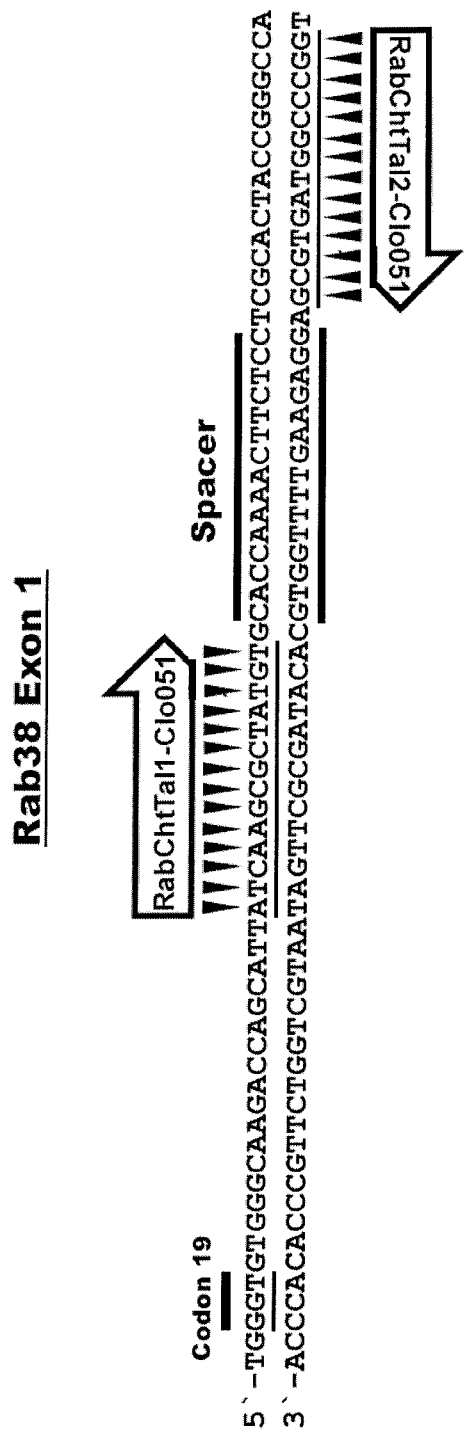

FIG. 11: Design of a TAL-Clo051 fusion protein pair in accordance with the present invention, recognizing the mouse Rab38 gene.

TAL nucleases recognizing a target sequence within exon 1 of the mouse Rab38 gene. The trinucleotide representing codon 19 is underlined. Indicated is each of a 14 nucleotide sequence that is recognised by one the indicated TAL-Clo051 fusion proteins RabChtTal1- and RabChtTal2-Clo051. The two 14 bp target sequences are flanking a central 15 bp spacer sequence that is cleaved by the Clo051 nuclease domains.

Figure 12:
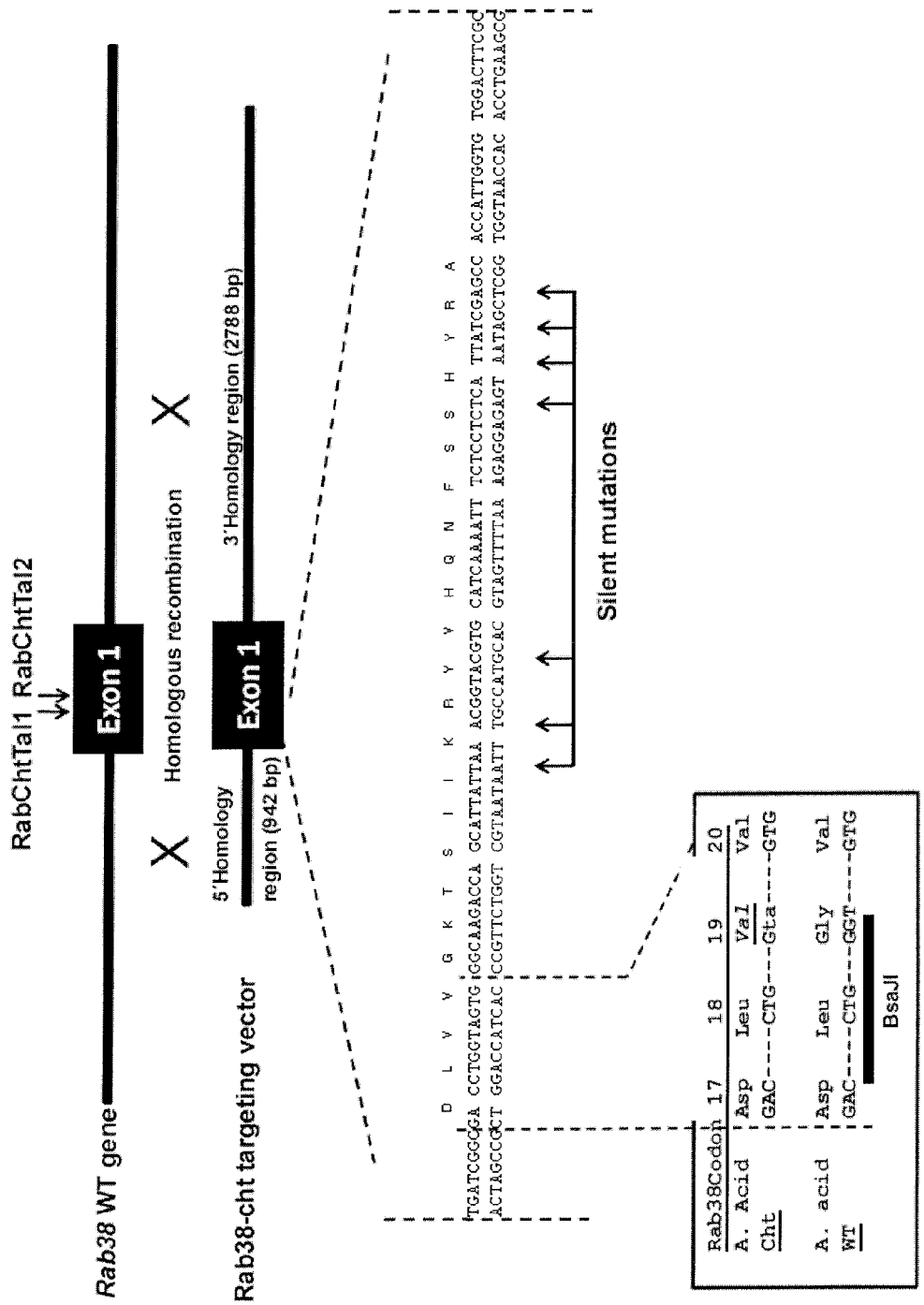

FIG. 12: Strategy for the modification of the mouse Rab38 gene in ES cells and zygotes using TAL-Clo051 fusion proteins.

Within exon 1 of the wildtype Rab38 gene (Rab38 WT) the position of the binding sites for the TAL nuclease pair RabChtTal1- and RabChtTal2-Clo051 are indicated. The Rab38-cht targeting vector contains a 942 bp 5'-homology region and a 2788 bp 3'-homology region flanking the Rab38 TAL recognition sites. Within exon1 two nucleotide changes within codon 19 (Gta) of Rab38 create a chocolate (cht) missense mutation coding for valine (Val) instead of the wildtype (WT) glycine (Gly), and remove a BsaJl restriction site. In each of the adjacent Rab38 TAL recognition sites several silent mutations were introduced to prevent the binding of Rab38 TAL proteins to the targeting vector. The induction of a double-strand break within the wildtype Rab38 gene by the RabCht-Tal protein pair stimulates homologous recombination with the Rab38-cht targeting vector and integrates the chocolate missense and the silent mutations into the genome.

FIG. 13: Isolation of hyperactive Clo051 nuclease mutants.

The figure shows the primary sequence of the Clo051 nuclease domain between the positions E389 and Y587. Indicated is the distribution of the positively charged arginine (R) and lysine (K) residues (filled squares) and of negatively charged glutamate (E) and aspartate (D) residues (open circles). Triangles indicate the positions S423 and R446. These residues constitute a three-dimensional framework of charges within the Clo051 domain that determines the unique tertiary structure of this nuclease, as modelled in the structure of FIG. 6. Certain replacements of polar versus non-polar residues or of non-polar residues against polar residues, e.g. at the positions 423 and 446, changes the three-dimensional structure of the protein chain and results into a more efficiently working nuclease activity.

Figure 14:
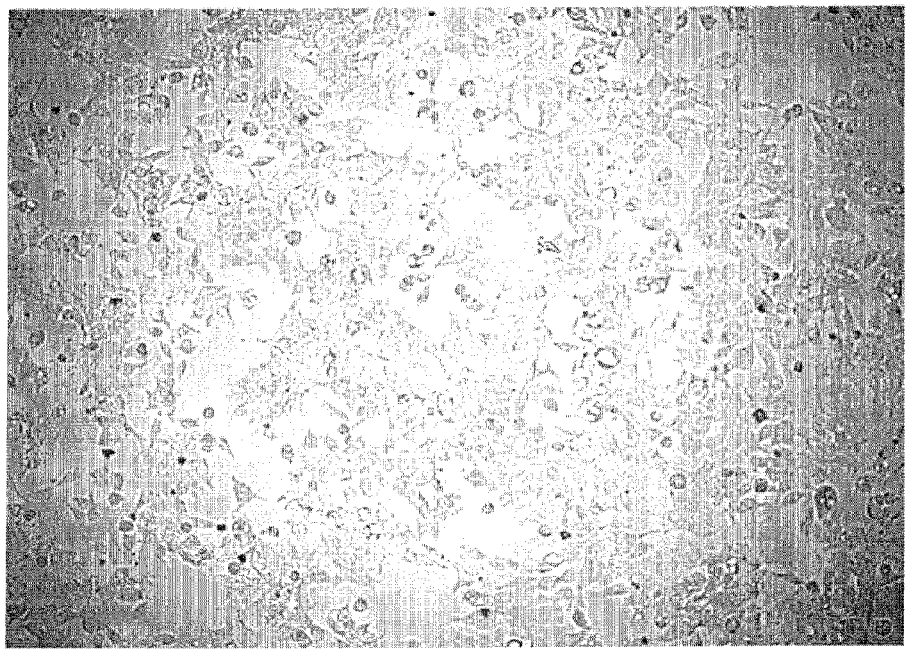
Figure 14:
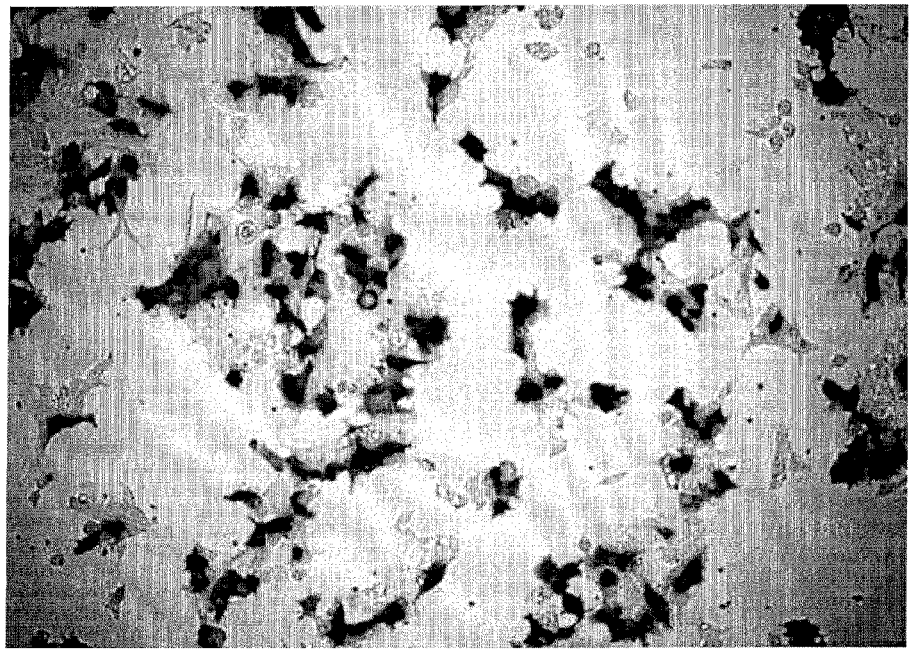

FIG. 14: Activity of ArtTal1-Clo051 nuclease on a genomic reporter in HEK 293 cells HEK293 cells harboring genomic integrated copies of the pCMV-Rab-Reporter(hygro) reporter construct were transfected with pBluescript or pCAG.ArtTal1-Clo051. Specific nuclease activity against the reporter's target sequence leads to homologous recombination and the expression of β-galactosidase. Two days after transfection the cell populations were fixed and the fraction of □β-galactosidase expressing cells was determined by histochemical X-Gal staining. A: X-Gal stained reporter cell culture upon transfection with pBluescript. B: X-Gal stained reporter cell culture upon transfection with pCAG-ArtTal1-Clo051 nuclease expression vector.

The examples illustrate the invention:

EXAMPLE 1

Construction of Expression and Reporter Vectors for Tal Nucleases and Detection of Specific Nuclease Activity Construction of TAL-Nuclease Expression Vectors For the expression of TAL-nucleases in mammalian cells we designed the generic expression vector pCAG-TAL-nuclease (SEQ ID NO: 3) (FIG. 4), that contains a CAG hybrid promoter region and a transcriptional unit comprising a sequence coding for a N-terminal peptide of 176 amino acids (SEQ ID NO: 4) of TAL nuclease fusion proteins, located upstream of a pair of BsmBl restriction sites. This N-terminal regions includes an ATG start codon, a nuclear localisation sequence, a FLAG Tag sequence, a glycine rich linker sequence, a segment coding for 110 amino acids of the Tal protein AvrBs3 and the invariable N-terminal Tal repeat of the Hax3 TAL effector. Downstream of the central BsmBl sites, the transcriptional unit contains 78 codons (SEQ ID NO: 5) including an invariable C-terminal TAL repeat (34 amino acids) and 44 residues derived from the TAL protein AvrBs3, followed by a Pmel and Mlul restriction site for the insertion of a nuclease coding region and by a polyadenylation signal sequence (pA). DNA segments coding for arrays of TAL repeats, designed to bind a TAL nuclease target sequence can be inserted into the BsmBl sites of pCAG-Tal-nuclease in frame with the up- and downstream coding regions for the expression of predesigned TAL-nuclease proteins.

To generate TAL-nuclease vectors for expression in mammalian cells we inserted a synthetic DNA segment with the coding region of an array of 12 Tal repeats, designated Art-Tal1 (SEQ ID NO: 6), into the BsmBl sites of pCAG-TAL-nuclease, to derive the plasmid pCAG-ArtTal1-nuclease (SEQ ID NO: 7). The TAL element array ArtTal1 recognises the artificial DNA target sequence 5'-ATTCTGGGACGT-3' (SEQ ID NO: 62) (FIG. 4), In another example we inserted a synthetic DNA segment with the coding region of an array of 14 Tal repeats, designated TalRab2 (SEQ ID NO: 8), into the BsmBI sites of pCAG-TAL-nuclease, to derive the plasmid pCAG-TalRab2-nuclease (SEQ ID NO: 9). The TAL element array TalRab2 recognises the DNA target sequence 5'-GGTGGCCCGGTAGT-3' (SEQ ID NO: 63) (FIG. 7) that occurs within the mouse Rab38 gene. The TAL target sequences were selected such that the binding regions of the TAL proteins are preceded by a T nucleotide. Following the sequence downstream of the initial T in the 5'>3' direction, specific TAL DNA-binding domains were combined together into arrays of 12 (ArtTal1) (FIG. 4), or 14 (TalRab2) TAL elements. Each TAL element motif consists of 34 amino acids, the position 12 and 13 of which determines the specificity towards recognition of A, G, C or T within the target sequence. To derive TAL element DNA-binding domains we used the TAL effector motif (repeat) #11 of the *Xanthomonas* Hax3 protein (GenBank accession No. AY993938.1 (LT-PEQVVAIASNIGGKQALETVQRLLPVLCQAHG) (SEQ ID NO: 64) with amino acids N12 and I13 to recognize A, the TAL effector motif (repeat) #5 (LTPQQVVAIASHDG-GKQALETVQRLLPVLCQAHG) (SEQ ID NO: 65) derived from the Hax3 protein with amino acids H12 and D13 to recognize C, and the TAL effector motif (repeat) #4 (LT-PQQWAIASNGGGKQALETVQRLLPVLCQAHG) (SEQ ID NO: 66) from the *Xanthomonas* Hax4 protein (Genbank accession No.: AY993939.1) with amino acids N12 and G13 to recognize T. To recognize a target G nucleotide we used the TAL effector motif (repeat) #4 from the Hax4 protein with replacement of the amino acids 12 into N and 13 into N (LTPQQWAIASNNGGKQALETVQRLLPVLCQAHG) (SEQ ID NO: 67).

Figure 5:
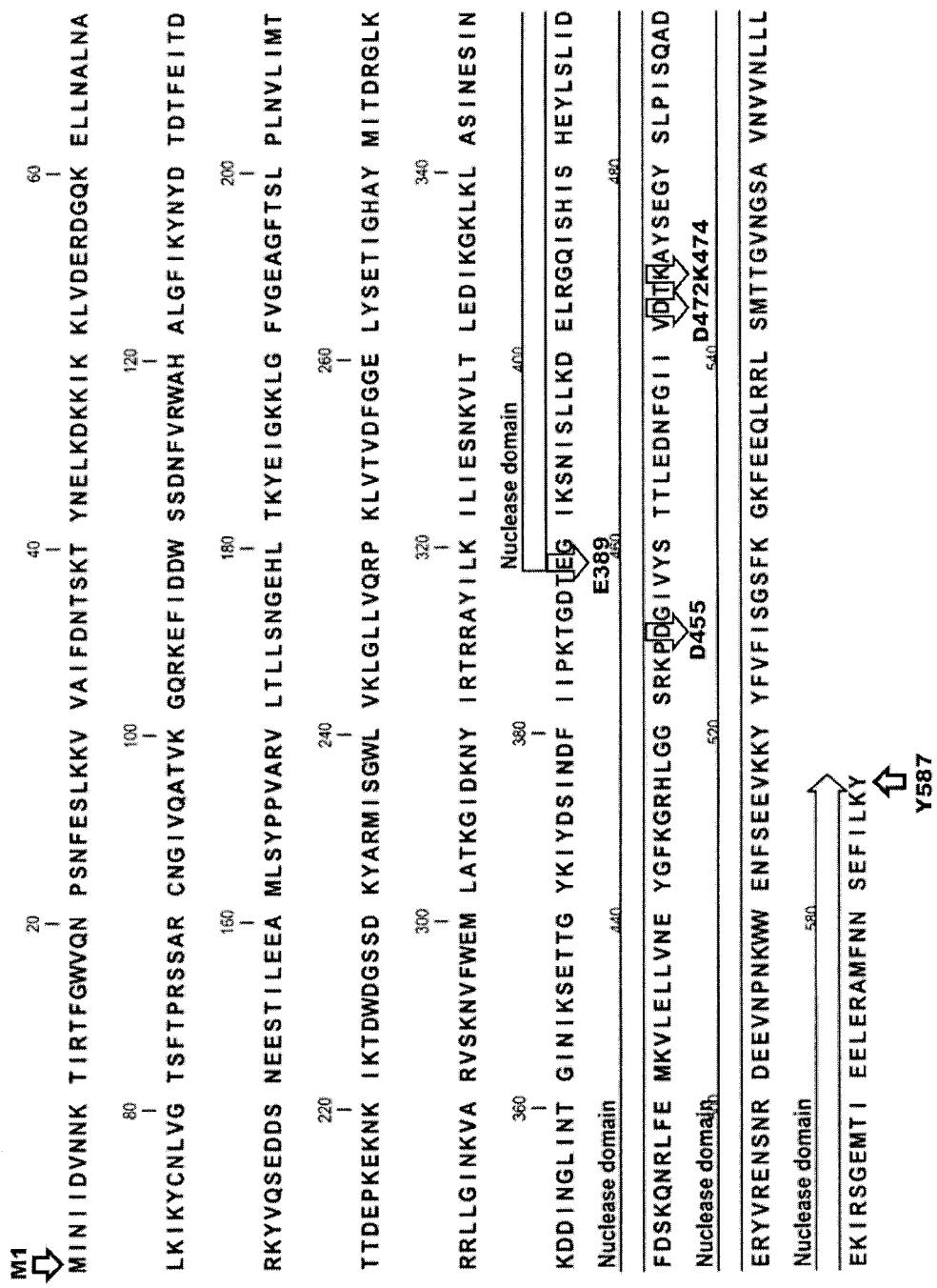

Next, we constructed fusion proteins of the ArtTal1 DNA binding domain with protein domains derived from known or putative nucleases and tested whether these TAL-nuclease fusion proteins are able to induce a double-strand break next to the DNA bound by the TAL recognition region. For this purpose we inserted synthetic DNA segments comprising the coding regions of eight putative nuclease domains and the known nuclease domain of FokI (SEQ ID NO: 10), into the Pmel and Mlul sites of the pCAG-ArtTal1-nuclease plasmid. Among the eight putative nuclease domains we selected domains from the five known restriction enzymes AlwI (SEQ ID NO: 11), MlyI (SEQ ID NO: 12), SbfI (SEQ ID NO: 13), SdaI (SEQ ID NO: 14) and StsI (SEQ ID NO: 15). In addition, we selected putative nuclease domains of three yet uncharacterised, hypothetical microbial genes, designated here as 'CleDORF' (SEQ ID NO: 16) (NCBI Reference Sequence: ZP_02080987.1, derived from the genome of *Clostridium leptum* DSM753), 'Clo051' (SEQ ID NO: 17) (NCBI Reference Sequence: ZP_05132802.1, derived from the genome of *Clostridium* spec. 7_2_43FAA) and 'Pept071' (SEQ ID NO: 18) (NCBI Reference Sequence: ZP_07399918.1, derived from the genome of *Peptoniphilus duerdenii* ATCC BAA-1640). These proteins were selected by characteristic sequence features that are compatible with the conserved active site of the 'PD-(D/E)XK' superfamily of enzymes (Kosinski, J., et al. (2005). BMC Bioinformatics, 6,172) interacting with DNA (see FIG. 6 for the Clo051 protein). In particular, the 587 residue Clo051 protein can be classified as a member of the PD-(D/E)XK protein family by the location of the amino acid pairs P454/D455 (PD motif) and D472/K474 (DXK motif) (FIG. 5). To elucidate whether the Clo051 protein contains a separate nuclease domain we performed a three-dimensional structural prediction from its primary amino acid sequence using the I-TASSER software (Roy, A. et al. (2010). Nat Protoc., 5(4):725-38). As shown in FIG. 6 the Clo051 protein is composed of two protein domains. The C-terminal domain of Clo051, approximately beginning with the residue E389, contains the PD-(D/E)XK family consensus motif and appears as a non specific nuclease domain.

For the expression of these protein domains in mammalian cells we used synthetic coding regions optimised according to the mammalian codon usage and inserted segments comprising the putative nuclease domains of Alwl (SEQ ID NO: 19), CleDORF (SEQ ID NO: 20), Clo051 (SEQ ID NO: 1), Mlyl (SEQ ID NO: 21), Pept071 (SEQ ID NO: 22), Sbfl (SEQ ID NO: 23), Sdal (SEQ ID NO: 24), Stsl (SEQ ID NO: 25) and the known nuclease domain of Fokl (SEQ ID NO: 26) into the Pmel and Mlul sites of the pCAG-ArtTal1-nuclease plasmid, to derive the expression vectors pCAG-ArtTal1-Alwl (SEQ ID NO: 27) (FIG. 4A), pCAG-ArtTal1-CleDORF (SEQ ID NO: 28) (FIG. 4B), pCAG-ArtTal1-Clo051 (SEQ ID NO: 29) (FIG. 4C), pCAG-ArtTal1-Mlyl (SEQ ID NO: 30) (FIG. 4D), pCAG-ArtTal1-Pept071 (SEQ ID NO: 31) (FIG. 4E), pCAG-ArtTal1-Sbfl (SEQ ID NO: 32) (FIG. 4F), pCAG-ArtTal1-Sdal (SEQ ID NO: 33) (FIG. 4G), pCAG-ArtTal1-Stsl (SEQ ID NO: 34) (FIG. 4H), and pCAG-ArtTal1-Fokl (SEQ ID NO: 35) (FIG. 4I). These expression vectors code for the TAL-fusion proteins designated as ArtTal1-Alwl (SEQ ID NO: 36), ArtTal1-CleDORF (SEQ ID NO: 37), ArtTal1-Clo051 (SEQ ID NO: 38), ArtTal1-Mlyl (SEQ ID NO: 39), ArtTal1-Pept071 (SEQ ID NO: 40), ArtTal1-Sbfl (SEQ ID NO: 41), ArtTal1-Sdal (SEQ ID NO: 42), ArtTal1-Stsl (SEQ ID NO: 43), and ArtTal1-Fokl (SEQ ID NO: 44).

Construction of TAL Nuclease Reporter Plasmids

To determine the activity and specificity of TAL nuclease domain fusion proteins in mammalian cells we constructed TAL nuclease reporter plasmids that contain two copies of a TAL DNA target sequence in inverse orientation, separated by a 15 nucleotide spacer region (FIG. 7a-d). This configuration enables to measure the activity of a single type of TAL nuclease that interacts as a homodimer of two protein molecules that are bound to the inverse pair of target sequences of the reporter plasmid. Upon DNA binding and interaction of two nuclease domains the reporter plasmid DNA is cleaved within the 15 bp spacer region and exhibits a double-strand break.

The TAL nuclease reporter plasmids contain a CMV promoter region, a 400 bp sequence coding for the N-terminal segment of (β-galactosidase and a stop codon. This unit is followed by the TAL nuclease target region (consisting of two inverse oriented recognition sequences separated by a 15 bp spacer region) for ArtTal1-fusion proteins in the plasmid ArtTal1-reporter (SEQ ID NO: 45)(FIG. 7 a), by the unrelated target sequence TalRab1 in the TalRab1-reporter plasmid (SEQ ID NO: 46) (FIG. 7 b), by the target region for TalRab2 fusion proteins in the TalRab2-reporter plasmid (SEQ ID NO: 47) (FIG. 8 c), or a hybrid target region containing one copy of the ArtTal1 and the TalRab2 recognition sequence in the ArtTal1/TalRab2-reporter plasmid (SEQ ID NO: 48) (FIG. 8 d).

Within these reporter plasmids the TAL nuclease target regions are followed by the complete coding region for (β-galactosidase and a polyadenylation signal (pA). To test for nuclease activity against the specific target sequence a TAL nuclease expression vector (FIG. 4) was transiently cotransfected with its corresponding reporter plasmid into mammalian cells. Upon expression of the TAL nuclease protein the reporter plasmid is opened by a nuclease-induced double-strand break within the TAL nuclease target sequence (FIG. 7 A). The DNA regions adjacent to the double-strand break are identical over 400 bp and can be aligned and recombined by homologous recombination DNA repair (FIG. 7 B). Homologous recombination of an opened reporter plasmid will subsequently result into a functional β-galactosidase coding region transcribed from the CMV promoter that leads to the production of β-galactosidase protein (FIG. 7 C). In lysates of transfected cells the enzymatic activity of β-galactosidase can be determined by chemiluminescense and reports the nuclease activity of the TAL fusion proteins.

Measurement of TAL-Nuclease Activity and Specificity in Human 293 Cells

To determine the activity and specificity of TAL nucleases in mammalian cells, we electroporated one million HEK 293 cells (ATCC #CRL-1573) (Graham F L, Smiley J, Russell W C, Nairn R., J. Gen. Virol. 36, 59-74, 1977) with 5 µg plasmid DNA of one of the TAL nuclease expression vectors (FIG. 4) together with 5 µg of one of the TAL nuclease reporter plasmids (FIG. 7). In addition, each sample received 5 µg of the firefly Luciferase expression plasmid pCMV-hLuc (SEQ ID NO: 49) and was adjusted to a total DNA amount of 20 µg with pBluescript (pBS) plasmid DNA (SEQ ID NO: 50). Upon transfection the cells were seeded in triplicate wells of a 6-well tissue culture plate and cultured for two days before analysis was started. For analysis the transfected cells of each well were lysed and the β-galactosidase and luciferase enzyme activities of the lysates were individually determined using chemiluminescent reporter assays following the manufacturer's instruction (Roche Applied Science, Germany) in a luminometer (Berthold Centro L B 960). As positive control we transfected 5 µg of the β-galactosidase expression plasmid pCMVβ(SEQ ID NO: 51) with 15 µg pBS, as negative control 5 µg pCMV-hLuc were transfected with 15 µg pBS or 5 µg pCMV-hLuc together with 5 µg of a TAL nuclease reporter plasmid and 10 µg pBS. The triplicate β-galactosidase values of each sample were normalised in relation to the levels of Luciferase activity and the mean value and standard deviation of β-galactosidase activity were calculated and expressed in comparison to the pCMVβ positive control. In this type of recombination assay the level of the β-galactosidase catalysed light emission reflects the cleavage and repair of the reporter plasmids and thereby indicates the activity of TAL nucleases.

As shown in FIG. 8 transfection of the ArtTal1-Reporter plasmid alone resulted in just background levels of β-galactosidase. The cotransfection of the ArtTal1-Reporter plasmid with the expression vectors pCAG-ArtTal1-Alwl, -CleDORF, -Mlyl, -Pept071, -Sbfl, -Sdal, and -Stsl did not reveal any significant nuclease activity of the encoded TAL fusion proteins (FIG. 8), indicating that the selected nuclease domains are unable to operate in combination with TAL DNA binding elements. In contrast, the cotransfection of the ArtTal1-Reporter plasmid with the expression vectors pCAG-ArtTal1-Clo051 (FIG. 8A) and -Fokl (FIG. 8b) resulted in significantly increased reporter activity, indicating that the selected Fokl and Clo051 protein domains are able to function as nuclease in fusion with TAL DNA binding elements.

Since in repeated assays TAL fusions with the Clo051 domain appeared more active as compared to fusions with the Fokl nuclease domain, we believe that the Clo051 domain is most suited for the construction of highly active TAL-nucleases.

In order to define whether the ArtTal1-Clo051 nuclease specifically recognizes its target sequence within the ArtTal1-reporter plasmid (FIG. 7a), pCAG-ArtTal1-Clo051 was cotransfected with the corresponding ArtTal1- or with the unrelated TalRab1- or TalRab2-reporter plasmids (FIG. 7b,c) into HEK 293 cells. As shown in FIG. 9 significantly increased reporter activity was detected only from the specific combination of the ArtTal-Clo051 nuclease with its corresponding promoter, whereas the cotransfection with unrelated reporter plasmids did not exhibit significant nuclease activity. These results indicate that the Clo051 nuclease domain in fusion with TAL DNA binding elements acts in a target sequence specific manner and that unrelated target sequences are not processed.

Next, we characterized whether the Clo051 nuclease domain induces recombinogenic double-strand breaks as a monomer, or whether the interaction of two nuclease domains as dimer is required. For this purpose we constructed the hybrid reporter plasmid ArtTal1/TalRab2-reporter (SEQ ID NO: 48) (FIG. 7d) that contains one ArtTal1 recognition sequence upstream of the spacer region and one TalRab2 recognition sequence downstream of the spacer region. The TalRab2 array (SEQ ID NO: 8) is composed of 14 TAL elements recognising the target sequence 5'-GGTGGCCCG-GTAGT-3' (SEQ ID NO: 63). The Clo051 nuclease domain was cloned as synthetic coding region into the PmeI and MluI sites of plasmid pCAG-TalRab2-nuclease (SEQ ID NO: 9) to derive the expression vector pCAG-TalRab2-Clo051 (SEQ ID NO: 52) for the expression of the TalRab2-Clo051 protein (SEQ ID NO: 53). As shown in FIG. 10A the cotransfection of pCAG-ArtTal1-Clo051 together with the ArtTal1-reporter plasmid resulted in significant reporter gene expression indicating specific nuclease activity of the ArtTal1-Clo051 fusion protein. Since the ArtTal1-reporter plasmids contains two inverse ArtTal1 binding sequences, the nuclease activity of ArtTal1-Clo051 may result from the action of a single fusion protein or the combined action of two molecules. To distinguish between these possibilities pCAGArtTal1-Clo051 was cotransfected with the ArtTal1/TalRab2-reporter plasmid that contains only one ArtTal1 binding sequence. As shown in FIG. 10A the ArtTal1-Clo051 nuclease did not exhibit significant nuclease activity on the ArtTal1/TalRab2-reporter, indicating that two Clo051 nuclease domains must interact as a dimer to induce a DNA double-strand break. These results were confirmed with the TalRab2-Clo051 nuclease that acted on its corresponding TalRab2-reporter but not on the hybrid ArtTal1/TalRab2-reporter plasmid (FIG. 10A). As expected, the ArtTal1-FokI fusion protein did likewise not exhibit nuclease activity on the ArtTal1/TalRab2-reporter (FIG. 10B).

Next, we studied whether two Clo051 nuclease domains, that are fused to different arrays of TAL DNA binding elements, are also able to interact and to induce double-strand breaks. For this purpose the expression vectors pCAG-Art-Tal1-Clo051 and pCAG-TalRab2-Clo051 were cotransfected together with the ArtTal1/TalRab2-reporter plasmid and the results compared to the cotransfection of pCAG-ArtTal1-Clo051 together with the ArtTal1/TalRab2-reporter. As shown in FIG. 10B, significant nuclease activity on the Art-Tal1/TalRab2-reporter developed only by the coexpression of the ArtTal1- and TalRab2-Clo051 nucleases, indicating that Clo051 nuclease domains fused with different TAL arrays are able to interact and to induce a DNA double-strand break within a hybrid target region containing the recognition sequences of two distinguished TAL DNA binding arrays.

EXAMPLE 2

Targeting of the Mouse Rab38 Gene in ES Cells and Zygotes with TAL-Clo051 Nucleases Construction of Rab38 specific TAL-Clo051 nucleases and a targeting vector To demonstrate the functionality of TAL effector DNA-binding domain—nuclease fusion proteins in mammalian cells we designed a pair of fusion proteins that recognizes a DNA target sequence within the mouse Rab38 gene (FIG. 11). The two TAL effector DNA-binding domain—nuclease fusion proteins are intended to bind together to the bipartite target DNA region and to induce a double strand break in the spacer region of the target region to stimulate homologus recombination at the target locus in mammalian cells.

The mouse Rab38 gene encodes the RAB38 protein that is a member of a family of proteins known to play a crucial role in vesicular trafficking. In chocolate (cht) mutant mice a single nucleotide exchange at position 146 (G>T mutation) within the first exon of Rab38 leads to the replacement of glycine by valine at codon 19 (Loftus, S. K., et al., Proc Natl Acad Sci USA, 2002. 99(7): p. 4471-6). This amino acid replacement is located within the conserved GTP binding domain of RAB38 and impairs the sorting of the tyrosinase-related protein 1 (TYRP1) into the melanosomes of Rab38$^{cht}$/Rab38$^{cht}$ melanocytes. TYRP1 is a melanosomal membrane glycoprotein, which functions both as a 5,6-Dihydroxyindol-2-carbonic-acid oxidase enzyme to produce melanin and as a provider of structural stability to tyrosinase in the melanogenic enzyme complex. TYRP1 is believed to transit from the trans-Golgi network to stage II melanosomes by means of clathrin-coated vesicles. The reduced amount of correctly located TYRP1 leads to an impairment of pigment production and the change of fur color from black to a chocolate-like brown color in Rab38$^{cht}$/Rab38$^{cht}$ mice. Since mutations of genes needed for melanocyte function are known to cause oculocutaneous albinism (OCD), such as Hermansky-Pudlak syndrome in man, the Rab38 gene is a candidate locus in OCD patients.

We aimed to introduce a phenocopy of the chocolate mutation at codon 19 of Rab38 using a pair of TAL-nucleases (RabChtTal1- and RabChtTal2-Clo051) that each recognise a 14 bp target sequence located up- and downstream of a central 15 bp spacer sequence within exon 1 of the Rab38 gene (FIG. 11). To derive expression vectors for the RabChtTal1- and RabChtTal2-Clo051 nucleases synthetic coding regions for the DNA binding domains RabChtTal1 and RabChtTal2 composed of 14 TAL elements and the Clo051 nuclease domain were inserted into the pCAG-TAL-nuclease vector. The resulting plasmid pCAG-RabChtTal1-Clo051 (SEQ ID NO: 54) encodes the RabChtTal1-Clo051 fusion protein (SEQ ID NO: 55), and the plasmid pCAG-RabChtTal2-Clo051 (SEQ ID NO: 56) encodes the RabChtTal2-Clo051 fusion protein (SEQ ID NO: 57).

For the modification of the Rab38 gene by homologous recombination in fertilised oocytes we constructed the gene targeting vector pRab38-chtTAL (FIG. 12) (SEQ ID NO: 58), comprised of two homology regions encompassing 942 and 2788 bp of genomic sequence flanking exon1 of the mouse Rab38 gene (SEQ ID NO: 59). For this purpose the vectors 5'- and 3'-homology arms were amplified from the genomic BAC clone RPCI-421G2 (derived from the C57BL/6J genome, Imagenes GmbH, Berlin) using specific PCR primers. Within the sequence of codon 19 we introduced two nucleotide changes that modify codon 19 from the wildtype sequence GGT, coding for glycine, into GTA, coding for valine. This new chocolate mutation can be distinguished from the natural chocolate mutation, which exhibits only a single nucleotide exchange within codon 19 (GTT) coding for valine (Loftus, S. K., et al., Proc Natl Acad Sci USA, 2002. 99(7): p. 4471-6). Both chocolate mutant alleles can be further distinguished from the wildtype allele by restriction analysis since the mutations in codon 19 remove a recognition site for the restriction endonuclease BsaJI (FIG. 12). The recognition region for the TAL-nucleases is located downstream of codon 19 (FIG. 11). For the construction of the targeting vector 3'-homology region each 14 bp TAL fusion protein recognition sequence was further modified by the introduction of silent nucleotide changes that do not alter the RAB38 protein sequence (FIG. 12), in order to avoid the potential processing of the targeting vector by the Rab38 specific TAL-nucleases.

For the modification of the Rab38 gene by homologous recombination in mouse ES cells we modified the gene targeting vector pRab38-chtTAL (FIG. 12) by the insertion of a neomycin resistance gene as selection marker into spacer region of the TAL-nuclease recognition region, to derive the targeting vector pRab38-chtTAL-neo (SEQ ID NO: 60).

Targeting of the Rab38 Gene in ES Cells and Zygotes

To demonstrate the utility of the RabChtTal1- and RabChtTal2-Clo051 proteins for gene targeting in mammalian cells (FIG. 3) we introduced the expression vectors or protein coding mRNA together with the pRab38-chtTAL-neo targeting vector into mouse ES cells or with the pRab38-chtTAL vector into fertilised mouse oocytes.

For targeting in ES cells we transfected IDG3.2 ES cells (Hitz, C. et al. Nucleic Acids Res. 35, e90, 2007) with linearised pRab38-chtTAL-neo targeting vector together with or without the TAL-nuclease expression plasmids pCAG-RabChtTal1- and pCAG-RabChtTal2-Clo051. The transfection, selection, expansion and genotyping of neomycin resistant ES cell clones was performed according to standard gene targeting procedures as described ((Nagy A, Gertsenstein M, Vintersten K, Behringer R., 2003. Manipulating the Mouse Embryo. Cold Spring Harbour, N.Y.: Cold Spring Harbour Laboratory Press). The analysis of resistant ES cell clones revealed that the expression of the TAL-nucleases lead to a significantly increased rate of homologous recombination at the Rab38 gene in ES cells. For microinjection into fertilised mouse oocytes the circular pRab38-chtTAL vector DNA was mixed with in vitro transcribed mRNA coding for RabChtTal1- and RabChtTal2-Clo051 proteins in injection buffer as described (Meyer, M., et al., Proc Natl Acad Sci USA. 107 (34): p. 15022-6). TAL-nuclease mRNA is prepared from the linearised expression plasmids pCAG-RabChtTAl1- and pCAG-RabChtTal2-Clo051 by in vitro transcription from the T7 promoter using the mMessage mMachine kit (Ambion) according to the manufacturers instructions. The mRNA is further modified by the addition of a poly-A tail using the Poly(A) tailing kit and purified with MegaClear columns from Ambion. Finally the mRNA is precipitated and resolved in injection buffer.

To isolate fertilised oocytes, males of the C57BL/6 strain are mated to super-ovulated females of the FVB strain. For super-ovulation three-week old FVB females are treated with 2.5 IU pregnant mares serum (PMS) 2 days before mating and with 2.5 IU Human chorionic gonadotropin (hCG) at the day of mating. Fertilised oocytes are isolated from the oviducts of plug positive females and microinjected in M2 medium (Sigma-Aldrich Inc Cat. No. M7167) with the TAL-nuclease mRNA and pRab38-chtTAL targeting vector preparation into one pronucleus and the cytoplasm following standard procedures (Nagy A, Gertsenstein M, Vintersten K, Behringer R., 2003. Manipulating the Mouse Embryo. Cold Spring Harbour, N.Y.: Cold Spring Harbour Laboratory Press).

Upon microinjection the TAL-nuclease mRNAs are translated into proteins that induce a double-strand break at one or both Rab38 alleles in one or more cells of the developing embryo. This event stimulates the recombination of the pRab38-chtTAL targeting vector with a Rab38 allele via the homology regions present in the vector and leads to the site-specific insertion of the mutant codon 19 into the genome, resulting into a Rab38$^{cht}$ allele bearing the chocolate mutation (FIG. 12). The microinjected zygotes were transferred into pseudopregnant females to allow their further development into live mice (Nagy A, Gertsenstein M, Vintersten K, Behringer R., 2003. Manipulating the Mouse Embryo. Cold Spring Harbour, N.Y.: Cold Spring Harbour Laboratory Press). From the resulting offspring genomic DNA was extracted from tail tips to analyse for the presence of the desired homologous recombination event at the Rab38 locus by PCR. This analysis was performed by the PCR amplification of the genomic region encompassing exon1. The presence of a Rab38$^{cht}$ allele can be recognised upon digestion of the PCR products with BsaJI, since the Rab38$^{cht}$ mutation at codon 19 leads to the removal of a BsaJI restriction site that is present in the wildtype sequence.

In one such experiment, mice derived from microinjected zygotes were analysed by a Rab38 PCR assay. Among this group most mice exhibited two alleles of the normal Rab38 wildtype genotype, whereas some individuals harboured one allele of the preplanned Rab38 chocolate mutation, as indicated by the absence of the BsaJI restriction site in exon 1

Taken together, it was possible to introduce a preplanned modification into the coding region of the Rab38 gene by TAL-Clo051 nuclease-assisted homologous recombination in mouse ES cells and fertilised oocytes.

EXAMPLE 3

Isolation of Hyperactive Clo051 Nuclease Mutants

As shown in FIG. 13 the primary sequence of the Clo051 nuclease domain between the positions E389 and Y587 exhibits a unique distribution of the positively charged arginine (R) and lysine (K) residues and of negatively charged glutamate (E) and aspartate (D) residues. These residues constitute a three-dimensional landscape of charges within the Clo051 domain that determines the unique tertiary structure of this nuclease, as shown in the structural model in FIG. 6. Certain replacements of polar versus non-polar residues or of non-polar residues against polar residues, e.g. at the positions 423 and 446, alter the three-dimensional structure of the protein chain and can result into an increase of the nuclease activity.

Such amino acid replacements may be made by trial and error or may follow specific hypotheses on the structural and functional impact on the Clo051 nuclease domain. Alternatively, a large number of randomly mutagenised variants of the Clo051 nuclease domain coding region can be assembled in a library by mutagenic PCR. This library of mutant molecules can be tested for the presence of hyperactive nuclease variants by a phenotypic screening assay in yeast, mammalian or E. coli cells that is coupled to a functional nuclease readout, e.g. as described for the improvement of the FLP recombinase (Buchholz et al., Nat. Biotechnol. 16, 657-62, 1998).

Such a functional screen for improved nuclease variants can result into the replacement of e.g. the residue 423 from a serine to a proline and of the residue 446 from an arginine to a glutamate. Such variant molecules can prove a superior nuclease activity as compared to the Clo051 wildtype form.

EXAMPLE 4

Clo051 Nuclease Induced Recombination of Genomic Substrates in Human Cells

The action of Clo051 nuclease was further tested in human HEK293 cells on a genomic integrated reporter construct. For this purpose the ArtTal1 reporter plasmid (FIG. 7) was modified by the insertion of a hygromycin resistance gene into the plasmid backbone. In addition the β-galactosidase reading frame was fused with the coding region of the neomycin resistance gene, resulting in the reporter plasmid pCMV-Rab-Reporter(hygro) (SEQ ID NO: 61). To generate a cell line harboring the reporter construct in its genome, linearized reporter plasmid DNA was electroporated into human HEK 293 cells (ATCC #CRL-1573) (Graham F L, Smiley J, Russell W C, Nairn R., J. Gen. Virol. 36, 59-74, 1977) and hygromycin resistant clones were selected and isolated. One of the resistant clones, that showed no background activity of the reporter gene, 293ArtTal-Rep#2, was chosen for further work.

Next, one million reporter cells were transfected with 5 µg plasmid DNA of the Tal nuclease expression vector pCAG-ArtTal1-Clo051 (FIG. 4) or with 5 µg of the unrelated cloning vector pBluescript as negative control. Upon transfection the cells were seeded in duplicate wells of a 6-well tissue culture plate and cultured for two days before analysis was started. For analysis the transfected cells of each well were fixed for 10 minutes with 4% formaldehyde and incubated for 4 hours with X-Gal staining solution (5 mM K3(FeIII(CN)6), 5 mM K4(FeIII(CN)6), 2 mM MgCl2, 1 mg/ml X-Gal (5-bromo-chloro-3-indoyl-β-D-galactopyranosid). Recombined cells that express the reporter gene are visualized by an intracellular blue staining and were quantified on photographic images using the ImageJ software's cell counter function (available at the website with the address http://imagej.nih.gov/ij). As shown in FIG. 14 A, transfection with the pBluescript control plasmid did not result in positive reporter cells (>0.1%, 0 positive cells of 1076 counted cells). In contrast, the transfection of pCAG-ArtTal-1 resulted into a substantial fraction of cells that recombined the reporter construct and express β-galactosidase (FIG. 14 B). As quantified from photographic images, 42.7% of the reporter cells (227 positive cells of 531 counted cells) showed successful recombination as indicated by expression of the reporter gene. In conclusion, this result indicates that ArtTal1-Clo051 nuclease protein can efficiently process a target sequence located within mammalian genomic DNA.

The invention claimed is:

1. A nucleic acid molecule encoding a fusion protein comprising a DNA-binding domain and
   (I) a polypeptide having the activity of an endonuclease, wherein the nucleic acid molecule is selected from the group consisting of:
   (a) a nucleic acid molecule encoding a polypeptide comprising or consisting of the amino acid sequence of SEQ ID NO: 1;
   (b) a nucleic acid molecule comprising or consisting of the nucleotide sequence of SEQ ID NO: 2;
   (c) a nucleic acid molecule encoding an endonuclease, the amino acid sequence of said endonuclease is at least 70% identical to the amino acid sequence of SEQ ID NO: 1;
   (d) a nucleic acid molecule comprising or consisting of a nucleotide sequence which is at least 50% identical to the nucleotide sequence of SEQ ID NO: 2;
   (e) a nucleic acid molecule which is degenerate with respect to the nucleic acid molecule of (d); and
   (f) a nucleic acid molecule corresponding to the nucleic acid molecule of any one of (a) to (e) wherein T is replaced by U;

or (II) a fragment of the polypeptide of (I) having the activity of an endonuclease.

2. The nucleic acid molecule of claim 1, wherein the amino acid residues P66, D67, D84 and/or K86 of SEQ ID NO: 1 are not modified in said endonuclease amino acid sequence (I)(c) that is at least 70% sequence identical to the amino acid sequence of SEQ ID NO: 1.

3. The nucleic acid molecule of claim 1, wherein the DNA-binding domain is a TAL effector motif of a TAL effector protein.

4. A vector comprising the nucleic acid molecule of claim 1.

5. An isolated host cell comprising the nucleic acid molecule of claim 1.

6. A method of modifying a target sequence in the genome of a eukaryotic cell, the method comprising the step of:
   (a) introducing into said cell the nucleic acid molecule of claim 1 or a vector comprising the nucleic acid molecule of claim 1.

7. The method of claim 6, wherein the modification of said target sequence is by homologous recombination with a donor nucleic acid sequence, further comprising the step:
   (b) introducing a nucleic acid molecule into said cell, wherein said nucleic acid molecule comprises said donor nucleic acid sequence, wherein said donor DNA sequence is flanked upstream by a first flanking element and downstream by a second flanking element, wherein said first and second flanking element are different and wherein each of said first and second flanking element are homologous to a continuous DNA sequence on either side of the double-strand break introduced in (a) of claim 6 within said target sequence in the genome of said eukaryotic cell.

8. The method of claim 6, wherein said cell is analysed for successful modification of said target sequence in the genome.

9. The method of claim 6, wherein the cell is selected from the group consisting of a mammalian or vertebrate cell, a plant cell or a fungal cell.

10. The method of claim 6, wherein the cell is an oocyte.

11. The method of claim 6, wherein the cell is selected from the group consisting of rodents, dogs, felides, primates, rabbits, pigs, cows, chickens, turkeys, pheasants, ducks, geese, quails, ostriches, emus, cassowaries and zebrafish.

12. An isolated host cell comprising the vector of claim 4.

* * * * *